United States Patent
Collins et al.

(10) Patent No.: US 7,557,103 B2
(45) Date of Patent: Jul. 7, 2009

(54) IMIDAZOPYRIDAZINE COMPOUNDS

(75) Inventors: Elizabeth Aaron Collins, Edinburgh, IN (US); Pablo Garcia-Losada, Madrid (ES); Chafiq Hamdouchi, Carmel, IN (US); Philip Arthur Hipskind, New Palestine, IN (US); Jianliang Lu, Fishers, IN (US); Takako Takakuwa, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 11/908,332

(22) PCT Filed: Apr. 3, 2006

(86) PCT No.: PCT/US2006/012072

§ 371 (c)(1),
(2), (4) Date: Sep. 11, 2007

(87) PCT Pub. No.: WO2006/107784

PCT Pub. Date: Oct. 12, 2006

(65) Prior Publication Data

US 2008/0153828 A1  Jun. 26, 2008

Related U.S. Application Data

(60) Provisional application No. 60/686,628, filed on Jun. 2, 2005.

(30) Foreign Application Priority Data

Apr. 5, 2005 (EP) ................... 05380063

(51) Int. Cl.
*A01N 43/60* (2006.01)

(52) U.S. Cl. .......... 514/248; 544/236; 549/52; 549/469

(58) Field of Classification Search ........ 514/248; 544/236; 549/52, 469
See application file for complete search history.

(56) References Cited

FOREIGN PATENT DOCUMENTS

| EP | 1 364 952 A | 11/2003 |
|----|----|----|
| EP | 1 466 527 A | 10/2004 |
| WO | WO 97/29109 A | 8/1997 |

OTHER PUBLICATIONS

Jordan, V. C. Nature Reviews: Drug Discovery, 2, 2003, p. 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
Moreau S et al: Synthesis and Anticonvulsant Properties of Triazolo- and Imidazopyridazinyl Carboxamides and Carboxylic Acids Bioorganic & Medicinal Chemistry, Elsevier Science Ltd, GB, vol. 6, No. 7, Jul. 1998, pp. 983-991, XP002991062.

* cited by examiner

*Primary Examiner*—James O Wilson
*Assistant Examiner*—Douglas M Willis
(74) *Attorney, Agent, or Firm*—R. Craig Tucker; Danica Hostettler

(57) ABSTRACT

The present invention relates to novel substituted imidazo[1,2-b]pyridazine compounds of Formula (I) pharmaceutical compositions thereof, and the use such compounds as corticotropin releasing factor 1 (CRF1) receptor antagonists in the treatment of psychiatric disorders and neurological diseases.

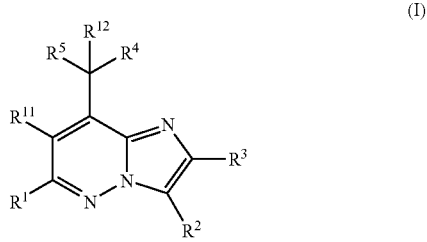

(I)

6 Claims, No Drawings

IMIDAZOPYRIDAZINE COMPOUNDS

This application is a 35 U.S.C. 371 National Stage Filing of PCT/US2006/012072 filed Apr. 3, 2006, which claims priority to European Provisional Application No. 05380063.7 filed Apr. 5, 2005 and U.S. Provisional Application No. 60/686,628 filed Jun. 2, 2005.

FIELD OF THE INVENTION

This invention relates to novel substituted imidazo[1,2-b]pyridazine compounds, pharmaceutical compositions thereof, and the use of such compounds as corticotropin releasing factor 1 (CRF1) receptor antagonists in the treatment of psychiatric disorders and neurological diseases.

BACKGROUND OF THE INVENTION

Corticotropin releasing factor (CRF) is a 41 amino acid peptide that is the primary physiological regulator of proopiomelanocortin (POMC) derived peptide secretion from the anterior pituitary gland [J. Rivier et al., Proc. Natl. Acad. Sci. (USA) 80:4851 (1983); W. Vale et al., Science 213:1394 (1981)]. In addition to its endocrine role at the pituitary gland, immunohistochemical localization of CRF has demonstrated that the hormone has a broad extrahypothalamic distribution in the central nervous system and produces a wide spectrum of autonomic, electrophysiological and behavioral effects consistent with a neurotransmitter or neuromodulator role in the brain [W. Vale et al., Rec. Prog. Horm. Res. 39:245 (1983); G. F. Koob, Persp. Behav. Med. 2:39 (1985); E. B. De Souza et al., J. Neurosci. 5:3189 (1985)]. There is also evidence that CRF plays a significant role in integrating the response in the immune system to physiological, psychological, and immunological stressors [J. E. Blalock, Physiological Reviews 69:1 (1989); J. E. Morley, Life Sci. 41:527 (1987)].

There is evidence that CRF has a role in psychiatric disorders and neurological diseases including depression, anxiety-related disorders and feeding disorders. A role for CRF has also been postulated in the etiology and pathophysiology of Alzheimer's disease, Parkinson's disease, Huntington's disease, progressive supranuclear palsy and amyotrophic lateral sclerosis, as they relate to the dysfunction of CRF neurons in the central nervous system [for a review, see: E. B. De Souze, Hosp. Practice 23:59 (1988)]. Furthermore, CRF is known to have a broad extrahypothalmic distribution in the CNS, contributing therein to a wide spectrum of autonomic behavioral and physiological effects [see, e.g., Vale et al., 1983; Koob, 1985; and E. B. De Souze et al., 1985]. For example, CRF concentrations are significantly increased in the cerebral spinal fluid of patients afflicted with affective disorder or major depression [C. B. Nemeroff et al., Science 226:1342 (1984); C. M. Banki et al., Am. J. Psychiatry 144:873 (1987); R. D. France et al., Biol. Psychiatry 28:86 (1988); M. Arato et al., Biol. Psychiatry 25:355 (1989)]. Moreover, excessive levels of CRF are known to produce anxiogenic effects in animal models [see, e.g., Britton et al., 1982; Berridge and Dunn, 1986 and 1987]. The density of CRF receptors is significantly decreased in the frontal cortex of suicide victims, consistent with a hypersecretion of CRF [C. B. Nemeroff et al., Arch. Gen. Psychiatry 45:577 (1988)]. In addition, there is a blunted adrenocorticotropin (ACTH) response to CRF (intravenously administered) observed in depressed patients [P. W. Gold et al., Am. J. Psychiatry 141:619 (1984); F. Holsboer et al., Psychoneuroendocrinology 9:147 (1984); P. W. Gold et al., New Engl. J. Med. 314:1129 (1986)]. Preclinical studies in rats and non-human primates provide additional support for the hypothesis that hypersecretion of CRF may be involved in the symptoms seen in human depression [R. M. Sapolsky, Arch. Gen. Psychiatry 46:1047 (1989)]. There is also preliminary evidence that tricyclic antidepressants can alter CRF levels and thus modulate the numbers of receptors in the brain [Grigoriadis et al., Neuropsychopharinacology 2:53 (1989)].

Neurochemical, endocrine and receptor binding studies have all demonstrated interactions between CRF and benzodiazepine anxiolytics, providing further evidence for the involvement of CRF in these disorders. Chlordiazepoxide attenuates the "anxiogenic" effects of CRF both in the conflict test [K. T. Britton et al., Psychopharmacology 86:170 (1985); K. T. Britton et al., Psychopharmacology 94:306 (1988)] and in the acoustic startle test [N. R. Swerdlow et al., Psychopharmacology 88:147 (1986)] in rats. The benzodiazepine receptor antagonist Ro 15-1788, which was without behavioral activity alone in the operant conflict test, reversed the effects of CRF in a dose-dependent manner while the benzodiazepine inverse agonist FG 7142 enhanced the actions of CRF [K. T. Britton et al., Psychopharmacology 94:396 (1988)]. Preliminary studies using the putative CRF receptor antagonist α-helical ovine CRF (9-41) in a variety of behavioral paradigms demonstrates that the antagonist produces "anxiolytic-like" effects that are qualitatively similar to the benzodiazepines [C. W. Berridge and A. J. Dunn, Horm. Behav. 21:393 (1987), Brain Research Reviews 15:71 (1990)].

CRF receptor subtypes, CRF1 and CRF2, have been identified and are distributed heterogeneously within the brain [D. T. Chalmers et al., TIPS 17:166-72 (1996)] thereby suggesting potential functional diversity [S. C. Heinrichs et al., Regul. Peptides 71:15 (1997)]. For example, widely distributed brain CRF1 receptors are strongly implicated in emotionality accompanying exposure to environmental stressors [G. Liebsch et al., Regul. Peptides 59: 229-39 (1995); D. W. Schulz, PNAS 93: 10477-82 (1996)]. Significantly, —CRF1, not CRF2, receptors appear to mediate select anxiogenic like behaviors [Heinrichs et al., 1997]. A more discrete septal/hypothalmic distribution [D. T. Chalmers et al., J. Neurosci. 15(10): 6340-50 (1995)] and the availability of alternative endogenous ligands [J. Vaughan et al., Nature 378: 287-92 (1995)] suggest an altogether different functional role for the CRF2 receptor [Heinrichs et al., 1997]. For example, a novel CRF-family neuropeptide with preferential affinity for CRF2 relative to CRF1 receptors is reported to suppress appetite without producing the profile of behavioral activation observed with selective CRF1 agonism (H. Tezval et al., PNAS 101(25): 9468-9473 (2004)]. In many cases, CRF2 agonism produces similar effects to those reported for CRF1 antagonists or CRF1 gene deletion [S. C. Heinrichs, Trends in Pharmacological Sciences 20(8):311-5 (1999)]. While CRF2 agonists have been proposed as antiobesity agents, CRF1 antagonists may be an important treatment for obesity as well [C. Contoreggi et al., Neuroendocrinology 80(2): 111-23 (2004)].

In view of the above, efficacious and selective antagonists of CRF1 are desired as potentially valuable therapeutic agents for the treatment of psychiatric disorders and neurological diseases. It is thus desirable to discover new CRF1 antagonists.

SUMMARY OF THE INVENTION

The compounds of the present invention include CRF1 receptor antagonists.

One embodiment of the present invention is a compound of Formula I:

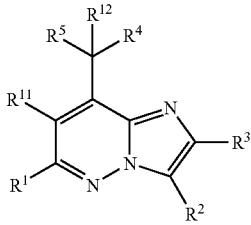

Formula I wherein:

R¹ and R³ are independently methyl, trifluoromethyl, or methoxy;

R² is selected from the group consisting of:

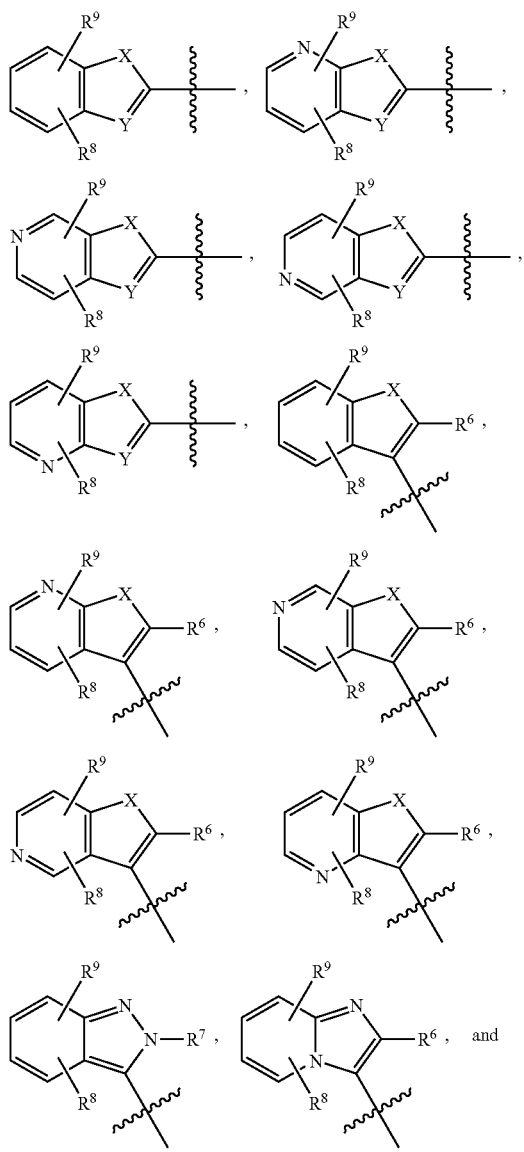

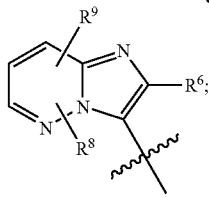

$R^4$ and $R^5$ are independently straight-chained $(C_2-C_4)$alkyl or straight-chained $(C_2-C_4)$ alkenyl;

$R^6$ is hydrogen, halo, cyano, $(C_1-C_3)$alkyl, or methoxy;

$R^7$ is hydrogen or $(C_1-C_3)$alkyl;

$R^8$ is hydrogen; halo; hydroxy; formyl; $(C_1-C_2)$alkoxy; $(C_1-C_7)$alkyl optionally substituted with one or two groups selected from hydroxy, $(C_1-C_2)$alkoxy, and cyclopropyl; $(C_2-C_3)$alkenyl; $(C_3-C_5)$cycloalkyl; $R^aR^bN$— or $R^{13}$—C(O)—;

$R^9$ is hydrogen, methyl, or trifluoromethyl;

$R^{11}$ is hydrogen;

$R^{12}$ is hydrogen, hydroxy, or halo;

$R^{13}$ is hydrogen, $(C_1-C_3)$alkyl, cyclopropyl, methoxy, or $R^aR^bN$—;

$R^a$ and $R^b$ are independently hydrogen, $(C_1-C_4)$alkyl, or methoxy;

X is —S—, —O—, or —NR⁷—; and

Y is N or CR⁶, with the proviso that when Y is N, X is —NR⁷—;

and pharmaceutically acceptable salts thereof.

Another embodiment of the present invention is a compound of Formula I wherein R¹ and R³ are methyl, R⁴ and R⁵ are ethyl, and R¹¹ and R¹² are hydrogen.

Yet another embodiment of the present invention is compound of Formula I wherein R² is selected from the group consisting of R

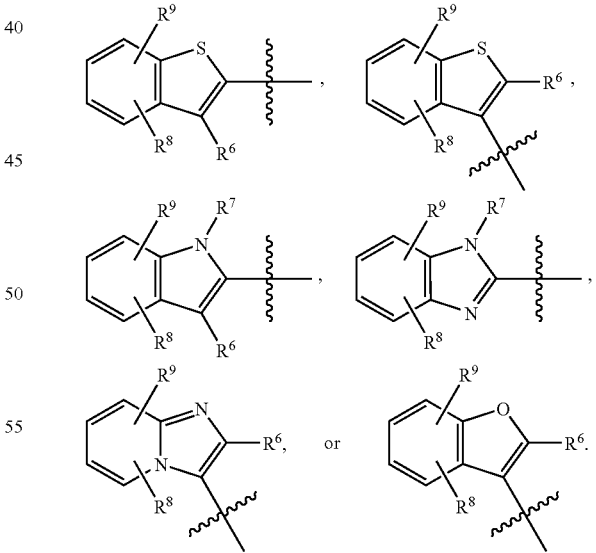

A further embodiment of the present invention is a compound of Formula I wherein R⁶ is hydrogen or methyl.

Another embodiment of the present invention is a compound of Formula I wherein R⁷ is methyl.

Yet another embodiment of the present invention is a compound of Formula I wherein R⁹ is hydrogen.

A further embodiment of the present invention is a compound of Formula I wherein $R^8$ is hydrogen, halo, $(C_1-C_5)$ alkyl, $(C_1-C_3)$alkoxy, or $(C_3)$alkyl substituted with hydroxy.

Another embodiment of the present invention is a pharmaceutical composition comprising a compound of Formula I, or a pharmaceutically acceptable salt thereof, and a pharmaceutically acceptable carrier, diluent or excipient.

Yet another embodiment of the present invention is a compound of Formula I for use as a medicament.

A further embodiment of the present invention is use of a compound of Formula I for the manufacture of a medicament for treating anxiety, depression, major depressive disorder, alcohol withdrawal symptoms, or irritable bowel syndrome in a mammal.

DETAILED DESCRIPTION OF THE INVENTION

As used above, and throughout the description of the invention, the following terms, unless otherwise indicated, shall be understood to have the following meanings:

"Alkoxy" means an alkyl-O— group, wherein the alkyl group is as herein described. Exemplary alkoxy groups include methoxy, ethoxy, n-propoxy, i-propoxy, and n-butoxy.

"Alkyl" means a saturated aliphatic hydrocarbon group, which may be straight or branched, having 1 to 7 carbon atoms in the chain.

"Alkenyl" means an unsaturated aliphatic hydrocarbon group, which may be straight or branched, having 2 to 4 carbon atoms in the chain.

"Cycloalkyl" means a monocyclic group, having 3 to 5 carbon atoms.

"Halo" means fluoro, chloro, bromo, or iodo.

"Pharmaceutically acceptable salts" refers to the relatively non-toxic, inorganic and organic acid addition salts, and base addition salts, of compounds of the present invention. These salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulphamates, malonates, salicylates, propionates, methylene-bis-β-hydroxynaphthoates, gentisates, isethionates, di-p-toluoyltartrates, methanesulphonates, ethanesulphonates, benzenesulphonates, p-toluenesulphonates, cyclohexylsulphamates and quinateslaurylsulphonate salts, and the like. See, for example S. M. Berge, et al., "Pharmaceutical Salts," *J. Pharm. Sci.*, 66, 1-19 (1977). Lists of suitable salts are found in Remington's Pharmaceutical Sciences, 17th ed., Mack Publishing. Company, Easton, Pa., 1985, p. 1418.

It will be understood that, as used herein, references to the compounds of Formula I are meant to also include the pharmaceutically acceptable salts thereof.

"Therapeutically effective amount" or "effective amount" means the amount of the compound of formula I of the present invention or pharmaceutical composition containing a compound of formula I of the present invention that will elicit the biological or medical response of or desired therapeutic effect on a tissue, system, animal or human that is being sought by the researcher, veterinarian, medical doctor or other clinician.

The terms "treatment," "treat," "treating," and the like, are meant to include both slowing or reversing the progression of a disorder. These terms also include alleviating, ameliorating, attenuating, eliminating, or reducing one or more symptoms of a disorder or condition, even if the disorder or condition is not actually eliminated and even if progression of the disorder or condition is not itself slowed or reversed. The term "treatment" and like terms also include preventive (e.g., prophylactic) and palliative treatment. Prevention of the disease is manifested by a prolonging or delaying of the onset of the symptoms of the disease.

The symbol "——" in a molecular structure indicates the position of attachment for that particular substituent.

When any variable occurs more than one time in any constituent or in formula I, its definition on each occurrence is independent of its definition at every other occurrence. Also, combinations of substituents and/or variables are permissible only if such combinations result in stable compounds. In choosing compounds of the present invention, one of ordinary skill in the art will recognize that the various substituents, i.e. $R^1$, $R^2$, etc., are to be chosen in conformity with well-known principles of chemical structure connectivity.

Under standard nomenclature used throughout this disclosure, the terminal portion of the designated side chain is described first, followed by the adjacent functionality toward the point of attachment. For example, an arylcarbonylaminoalkyl substituent is equivalent to aryl-C(O)—NH-alkyl-.

The present invention contemplates specific classes of compounds of Formula I. The following paragraphs describe such specific classes:

(a) $R^1$ is methyl;
(b) $R^3$ is methyl;
(c) $R^1$ and $R^3$ are methyl;
(d) $R^4$ is ethyl;
(e) $R^5$ is ethyl;
(f) $R^4$ and $R^5$ are ethyl;
(g) $R^6$ is hydrogen;
(h) $R^6$ is $(C_1-C_3)$alkyl;
(i) $R^6$ is methyl;
(j) $R^7$ is $(C_1-C_3)$alkyl;
(k) $R^7$ is methyl;
(l) $R^8$ is hydrogen, halo, $(C_1-C_5)$alkyl, $(C_1-C_2)$alkoxy, or $(C_3)$alkyl substituted with hydroxyl;
(m) $R^8$ is hydrogen, halo, methyl, methoxy, or propan-2-ol;
(n) $R^9$ is hydrogen or methyl;
(o) $R^9$ is hydrogen;
(p) $R^2$ is

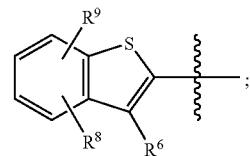

(q) $R^2$ is

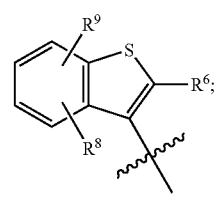

(r) $R^2$ is

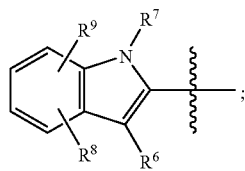

(s) $R^2$ is

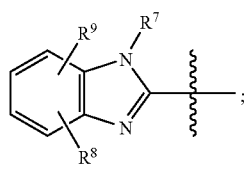

(t) $R^2$ is

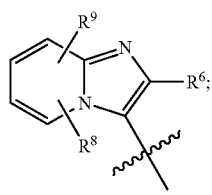

or (u) $R^2$ is

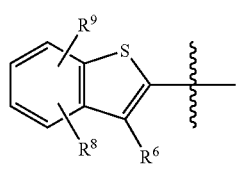

While all the compounds of Formula I are useful CRF1 receptor antagonists, certain classes of compounds are preferred. The following paragraphs describe such preferred classes:

(a) Each of $R^1$ and $R^3$ is methyl and each of $R^4$ and $R^5$ is ethyl;

(b) $R^1$ and $R^3$ are methyl, $R^4$ and $R^5$ are ethyl, and $R^{11}$ is hydrogen;

(c) $R^1$ and $R^3$ are methyl, $R^4$ and $R^5$ are ethyl, and $R^{11}$ and $R^{12}$ are hydrogen;

(d) $R^2$ is

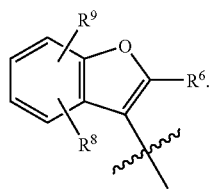

and $R^6$ is methyl;

(e) $R^2$ is

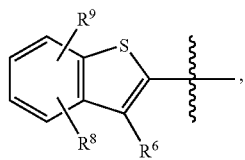

$R^6$ is methyl, and $R^9$ is hydrogen;

(f) $R^2$ is

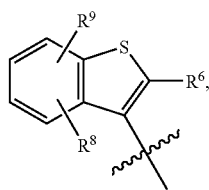

$R^6$ is methyl;

(g) $R^2$ is

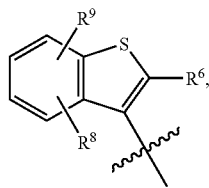

$R^6$ is methyl, and $R^9$ is hydrogen;

(h) $R^2$ is

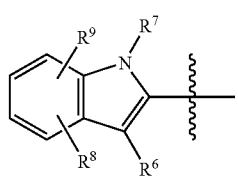

and $R^7$ is methyl;

(i) $R^2$ is

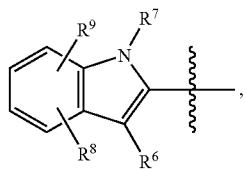

$R^7$ is methyl, and $R^9$ is hydrogen;

(j) R² is

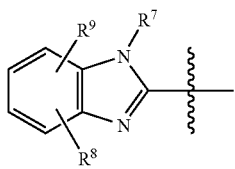

and R⁷ is methyl;

(k) R² is

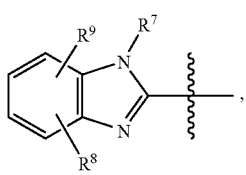

R⁷ is methyl, and R⁹ is hydrogen;

(l) R² is

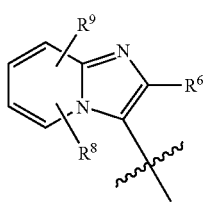

and R⁶ is methyl;

(m) R² is

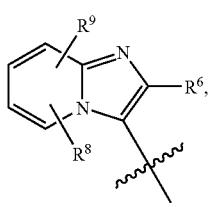

R⁶ is methyl, and R⁹ is hydrogen;

(n) R² is

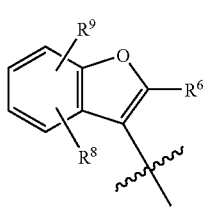

and R⁶ is methyl;

(o) R² is

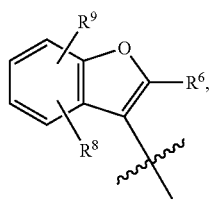

R⁶ is methyl, and R⁹ is hydrogen;

(p) R² is

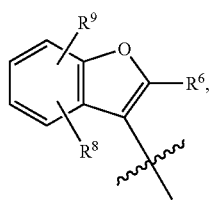

R⁶ is methyl, R⁸ is propan-2-ol, and R⁹ is hydrogen.

The following paragraphs describe even more specific classes of CRF1 receptor antagonists of the invention:

(a) R¹ and R³ are methyl, R⁴ and R⁵ are ethyl, and R¹¹ and R¹² are hydrogen, R² is

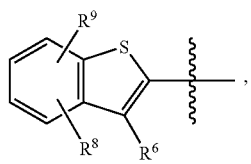

R⁶ is methyl, R⁸ is hydrogen, halo, (C₁-C₅)alkyl, (C₁-C₃)alkoxy, or (C₃)alkyl substituted with hydroxyl, and R⁹ is hydrogen;

(b) R¹ and R³ are methyl, R⁴ and R⁵ are ethyl, and R¹¹ and R¹² are hydrogen, R² is

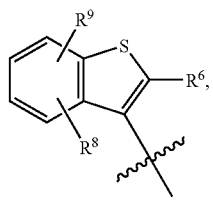

R⁶ is methyl, R⁸ is hydrogen, halo, (C₁-C₅)alkyl, (C₁-C₃)alkoxy, or (C₃)alkyl substituted with hydroxyl, and R⁹ is hydrogen;

(c) $R^1$ and $R^3$ are methyl, $R^4$ and $R^5$ are ethyl, and $R^{11}$ and $R^{12}$ are hydrogen, $R^2$ is

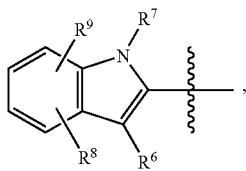

$R^6$ is hydrogen or methyl, $R^7$ is methyl, $R^8$ is hydrogen, halo, $(C_1-C_5)$alkyl, $(C_1-C_3)$alkoxy, or $(C_3)$alkyl substituted with hydroxyl, and $R^9$ is hydrogen;

(d) $R^1$ and $R^3$ are methyl, $R^4$ and $R^5$ are ethyl, and $R^{11}$ and $R^{12}$ are hydrogen, $R^2$ is

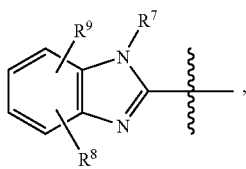

$R^7$ is methyl, $R^8$ is hydrogen, halo, $(C_1-C_5)$alkyl, $(C_1-C_3)$alkoxy, or $(C_3)$alkyl substituted with hydroxyl, and $R^9$ is hydrogen;

(e) $R^1$ and $R^3$ are methyl, $R^4$ and $R^5$ are ethyl, and $R^{11}$ and $R^{12}$ are hydrogen, $R^2$ is

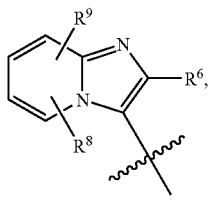

$R^6$ is methyl, $R^8$ is hydrogen, halo, $(C_1-C_5)$alkyl, $(C_1-C_3)$alkoxy, or $(C_3)$alkyl substituted with hydroxyl, and $R^9$ is hydrogen;

(f) $R^1$ and $R^3$ are methyl, $R^4$ and $R^5$ are ethyl, and $R^{11}$ and $R^{12}$ are hydrogen, $R^2$ is

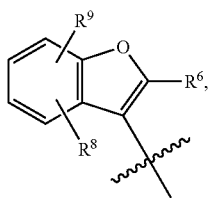

$R^6$ is methyl, $R^3$ is hydrogen, halo, $(C_1-C_5)$alkyl, $(C_1-C_3)$alkoxy, or $(C_3)$alkyl substituted with hydroxyl, and $R^9$ is hydrogen;

(g) $R^1$ and $R^3$ are methyl, $R^4$ and $R^5$ are ethyl, and $R^{11}$ and $R^{12}$ are hydrogen, $R^2$ is

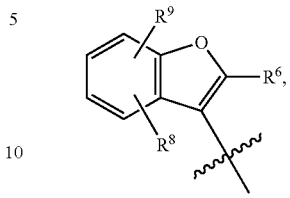

$R^6$ is methyl, $R^8$ is propan-2-ol, and $R^9$ is hydrogen.

Preferably compounds of the invention exhibit a Ki value for CRF1 binding of 10 micromolar or less, more preferably of 5 micromolar or less, and even more preferably 3 micromolar or less. Much more preferably, compounds of the invention exhibit a Ki value for CRF1 binding of 1 micromolar or less and even much more preferably 500 nanomolar or less. Even further preferred are compounds of the invention that exhibit a Ki value for CRF1 binding of 250 nanomolar or less, with 100 nanomolar or less being more further preferred. With even greater preference, compounds of the invention exhibit a Ki value for CRF1 binding of 30 nanomolar or less, while 15 nanomolar or less is even more greatly preferred. Compounds of the invention exhibiting a Ki value for CRF1 binding of 10 nanomolar or less are most preferred, while 5 nanomolar or less are most greatly preferred.

The present invention also provides a pharmaceutical composition comprising a compound of Formula I, or a pharmaceutically acceptable salt thereof and a pharmaceutically acceptable carrier, diluent, or excipient. A "pharmaceutically acceptable carrier, diluent, or excipient" is a medium generally accepted in the art for the delivery of biologically active agents to mammals, e.g., humans. Such carriers are generally formulated according to a number of factors well within the purview of those of ordinary skill in the art to determine and account for. These include, without limitation: the type and nature of the active agent being formulated; the subject to which the agent-containing composition is to be administered; the intended route of administration of the composition; and the therapeutic indication being targeted. Pharmaceutically acceptable carriers and excipients include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, well known to those of ordinary skill in the art. Descriptions of suitable pharmaceutically acceptable carriers, and factors involved in their selection, are found in a variety of readily available sources, e.g., Remington's Pharmaceutical Sciences, 17th ed., Mack Publishing Company, Easton, Pa., 1985, the contents of which are incorporated herein by reference.

These compounds of formula I may be administered orally, topically, parenterally, by inhalation or spray or rectally in dosage unit formulations containing conventional non-toxic pharmaceutically acceptable carriers, adjuvants and vehicles.

The pharmaceutical compositions containing compounds of general formula I may be in a form suitable for oral use, for example, as tablets, troches, lozenges, aqueous or oily suspensions, dispersible powders or granules, emulsion, hard or soft capsules, or syrups or elixirs.

Dosage forms suitable for administration generally contain from about 1 mg to about 100 mg of active ingredient per unit.

In these pharmaceutical compositions, the active ingredient will ordinarily be present in an amount of about 0.5 to 95% by weight based on the total weight of the composition. Appropriate coatings may be applied to increase palatability or delayed adsorption.

The compounds of formula I are antagonists at the CRF1 receptor and are useful in the treatment of anxiety disorders, depression, major depressive disorder, and stress related disorders. Anxiety disorders are a group of diseases, recognized in the art, that includes phobic disorders, anxiety states, post-traumatic stress disorder and atypical anxiety disorders [The Merck Manual of Diagnosis and Therapy, 16th edition (1992)]. Emotional stress is often a precipitating factor in anxiety disorders, and such disorders generally respond to medications that lower response to stress. The compounds are also useful in smoking cessation programs. The method of treatment involves administration to a mammal (e.g. a human) an effective amount of a compound of the invention. In particular, therapeutically effective amounts of the compounds of this invention are amounts effective to antagonize, or lower, levels of corticotropin releasing factor (CRF) in a mammal (e.g. a human), thereby alleviating in the mammal's conditions characterized by abnormally high levels of CRF expression.

As such, the present invention provides a method for treating a condition which is treatable by reducing CRF1 receptor stimulation, comprising administering to the mammal (e.g. a human) in need thereof a compound of Formula I, or a pharmaceutically acceptable salt thereof, in an amount effective to antagonize CRF1 receptor stimulation.

The present invention also provides use of a compound of Formula I for the manufacture of a medicament for treating a condition which is treatable by reducing CRF1 receptor stimulation.

The present invention also provides a method of antagonizing CRF1 receptors in a warm-blooded animal, comprising administering to the animal a compound of the invention at amount effective to antagonize CRF1 receptors. The warm-blooded animal is preferably a mammal, and more preferably a human.

The present invention also provides a method of treating a disorder in a warm-blooded animal, which disorder manifests hypersecretion of CRF, or the treatment of which disorder can be effected or facilitated by antagonizing CRF1 receptors, comprising administering to the animal a therapeutically effective amount of a compound of the invention. The warm-blooded animal is preferably a mammal, and more preferably a human.

Compounds of Formula I, or a pharmaceutically acceptable salt thereof, are useful for treating various disorders and conditions in a mammal (e.g. human) including social anxiety disorder; panic disorder; obsessive-compulsive disorder; major depressive disorder; anxiety with co-morbid depressive illness; affective disorder; anxiety; depression; irritable bowel syndrome; post-traumatic stress disorder; supranuclear palsy; immune suppression; gastrointestinal disease; anorexia nervosa, bulimia, or other feeding disorder; drug or alcohol withdrawal symptoms; substance abuse disorder (e.g., nicotine, cocaine, ethanol, opiates, or other drugs); inflammatory disorder; fertility problems; disorders the treatment of which can be effected or facilitated by antagonizing CRF, including but not limited to disorders induced or facilitated by CRF; a disorder selected from inflammatory disorders such as rheumatoid arthritis and osteoarthritis, pain, asthma, psoriasis and allergies; generalized anxiety disorder; panic; phobias; obsessive-compulsive disorder; sleep disorders induced by stress; stress-related illnesses; pain perception such as fibromyalgia; mood disorders such as depression, including major depression, major depressive disorder, single episode depression, recurrent depression, child abuse induced depression, and postpartum depression; dysthemia; bipolar disorders; cyclothymia; fatigue syndrome; chronic fatigue syndrome; stress-induced headache; headache; cancer; human immunodeficiency virus (HIV) infections; neurodegenerative diseases such as Alzheimer's disease, Parkinson's disease, Huntington's disease, senile dementia of the Alzheimer's type, and multiinfarct dementia; gastrointestinal diseases such as ulcers, irritable bowel syndrome, Crohn's disease, spastic colon, diarrhea, and post operative ilius and colonic hypersensitivity associated by psychopathological disturbances or stress; eating disorders such as anorexia and bulimia nervosa; hemorrhagic stress; stress-induced psychotic episodes; euthyroid sick syndrome; syndrome of inappropriate antidiarrhetic hormone (ADH); obesity; obesity and the metabolic syndrome; infertility; premature birth; head traumas; spinal cord trauma; ischemic neuronal damage (e.g., cerebral ischemia such as cerebral hippocampal ischemia); excitotoxic neuronal damage; epilepsy; cardiovascular and heart related disorders including hypertension, tachycardia and congestive heart failure; stroke; immune dysfunctions including stress induced immune dysfunctions (e.g., stress induced fevers, stress induced infections in humans and animals, porcine stress syndrome, bovine shipping fever, equine paroxysmal fibrillation, and dysfunctions induced by confinement in chickens, sheering stress in sheep or human-animal interaction related stress in dogs); muscular spasms; urinary incontinence; senile dementia of the Alzheimer's type; multiinfarct dementia; amyotrophic lateral sclerosis; chemical dependencies and addictions (e.g., dependences on alcohol, cocaine, heroin, benzodiazepines, or other drugs); drug and alcohol withdrawal symptoms; osteoporosis; psychosocial dwarfism and hypoglycemia.

A compound of this invention can be administered to treat the above disorders or abnormalities by means that produce contact of the active agent with the agent's site of action in the body of a mammal (e.g. human), such as by oral or parenteral administration using appropriate dosage forms. The compounds can be administered by any conventional means available for use in conjunction with pharmaceuticals either as individual therapeutic agent or in combination of therapeutic agents. It can be administered alone, but will generally be administered with a pharmaceutical carrier selected on the basis of the chosen route of administration and standard pharmaceutical practice.

The therapeutically effective amounts of the compounds of the invention for treating the diseases or disorders described above in a warm-blooded animal can be determined in a variety of ways known to those of ordinary skill in the art, e.g., by administering various amounts of a particular agent to an animal afflicted with a particular condition and then determining the effect on the animal. Typically, therapeutically effective amounts of a compound of this invention can be orally administered daily at a dosage of the active ingredient of 0.002 to 200 mg/kg of body weight. Ordinarily, a dose of 0.01 to 10 mg/kg in divided doses one to four times a day, or in sustained release formulation will be effective in obtaining the desired pharmacological effect. It will be understood, however, that the specific dose levels for any particular patient will depend upon a variety of factors including the activity of the specific compound employed, the age, body weight, general health, sex, diet, time of administration, route of administration, and rate of excretion, drug combination and the severity of the particular disease. Frequency of dosage may also vary depending on the compound used and the particular disease treated. However, for treatment of most CNS disorders, a dosage regimen of four-times daily or less is preferred. For the treatment of stress and depression, a dosage regimen of one or two-times daily is particularly preferred.

It will be appreciated that all combinations of specific and preferred embodiments discussed above and the examples discussed below are contemplated as being encompassed by the present invention, provided such combinations do not comprise inconsistent groupings. In addition, all examples described herein are for illustrative purposes, and are not intended to narrow the scope of the invention in any way.

Compounds of the invention can generally be prepared using the synthetic routes illustrated in the Schemes below. Starting materials can be prepared by procedures described in these schemes or by procedures that would be well known to one of ordinary skill in organic chemistry. The variables used in the schemes are as defined below or as in the claims.

The skilled artisan will appreciate that the introduction of certain substituents will create asymmetry in the compounds of Formula I. The present invention contemplates all enantiomers and mixtures of enantiomers and stereoisomers, that is, both the stereomerically pure form (e.g., geometrically pure, enantiomerically pure, or diastereomerically pure) and enantiomeric and stereoisomeric mixtures, including racemates. Enantiomeric and stereoisomeric mixtures can be resolved into their component enantiomers or stereoisomers by well known methods, such as chiral phase gas chromatography, chiral-phase high performance liquid chromatography, or crystallizing the compound as a chiral salt complex. Enantiomers and stereoisomers can also be obtained from stereomerically- or enantiomerically-pure intermediates, reagents, and catalysts by well known asymmetric synthetic methods.

Pharmaceutically acceptable salts are contemplated to be within the scope of the present invention. The compounds of the present invention are bases and salts of such compounds may be formed with acids, for example, a salt with inorganic acid such as hydrochloric acid or a salt with organic acid such as trifluoroacetic acid.

The compounds of this invention may be prepared by employing reactions as shown in the following schemes, in addition to other standard manipulations that are known in the literature or exemplified in the experimental procedures. These schemes, therefore, are not limited by the compounds listed nor by any particular substituents employed for illustrative purposes.

Scheme I:
Synthesis of Imidazole[1,2-b]pyridazine fragment

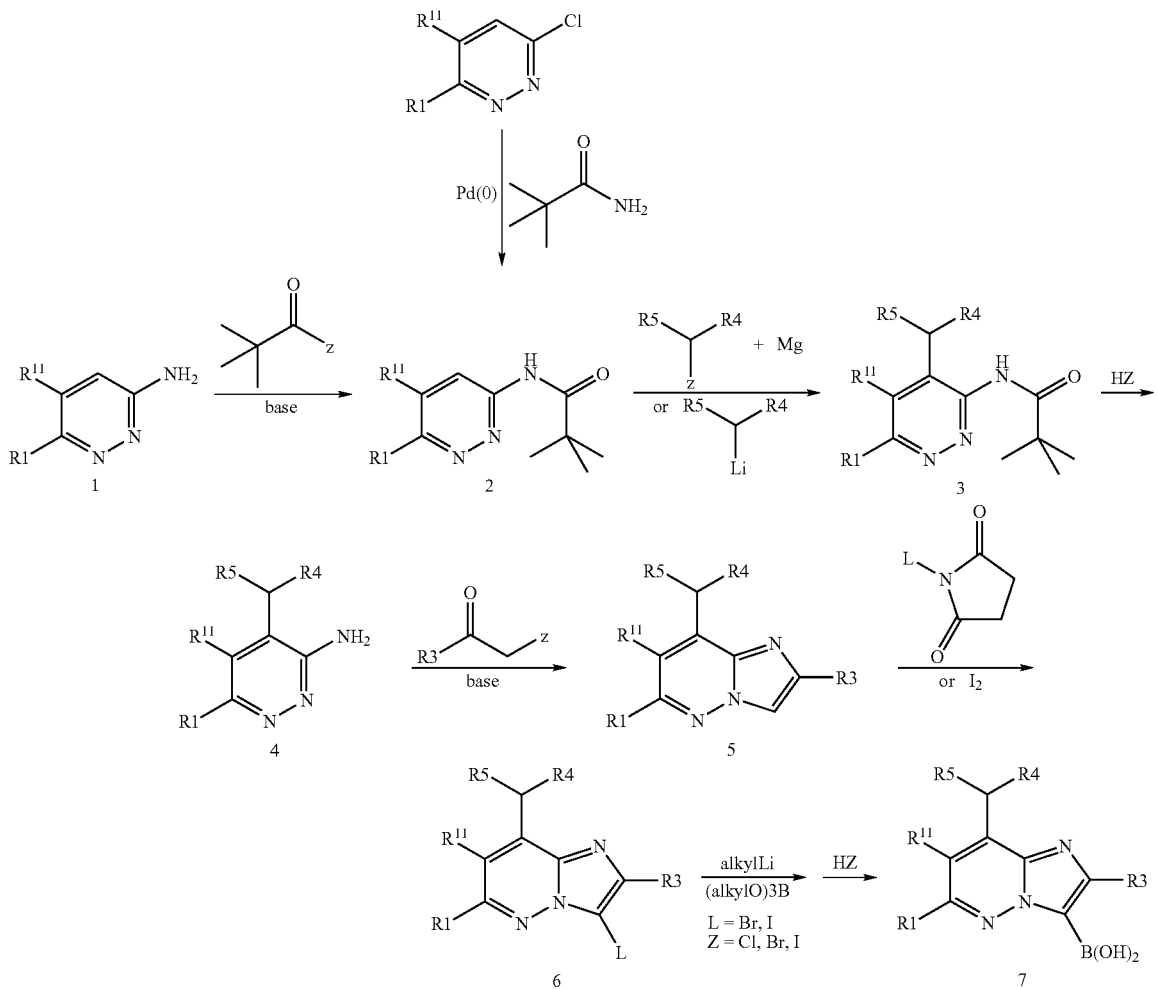

wherein $R^1$, $R^3$, $R^4$, $R^5$, and $R^{11}$ are defined supra.

In Scheme I, a substituted 3-amino-pyridazine 1 is acylated with pivaloyl halide in base in and a polar aprotic solvent at room temperature to the reflux temperature to give amide 2. Alternatively, a substituted 3-chloro-pyridazine is reacted with trimethylacetamide and a Palladium catalyst in the presence of base in THF to give the amide 2. Amide 2 is treated with a Grignard reagent or alkyllithium reagent in diethylether or THF to give the 4-substituted amide 3. Amide 3 is hydrolyzed with aqueous hydrogen halide at from room temperature to 110° C. then neutralized to provide free amine 4. Amine 4 is treated with an alpha-halo carbonyl ($R^3COCH_2$-Z) and base, e.g., sodium bicarbonate at from room temperature to 110° C. to give imidazopyridazine 5. Imidazopyridazine 5 is treated with a halogenating reagent (e.g., N-iodo or N-bromosuccinimide or iodine) in a polar aprotic solvent (e.g., acetonitrile) at from 0° C. to room temperature to give halide 6. Halide 6 is then treated with an alkyl lithium reagent in diethylether or THF at from −78° C. to room temperature, followed by treatment with a trialkylborate, e.g., trimethylborate to give an intermediate boronic ester, which is hydrolyzed upon workup with aqueous HCl to provide boronic acid 7.

Scheme II:
Synthesis of 5,6-bicycloaromatic-(2 or 3)-boronic acid/estersfor palladium catalyzed coupling.

Equation 1.

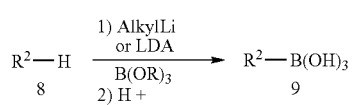

Where $R^2$—H of equation 1 Scheme II is:

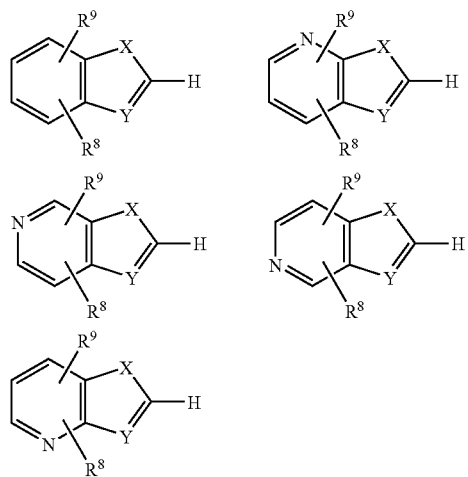

where X, Y, $R^8$, and $R^9$ have been defined previously.

Equation 2

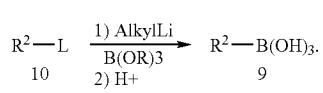

Where L has been previously defined and $R^2$—L is:

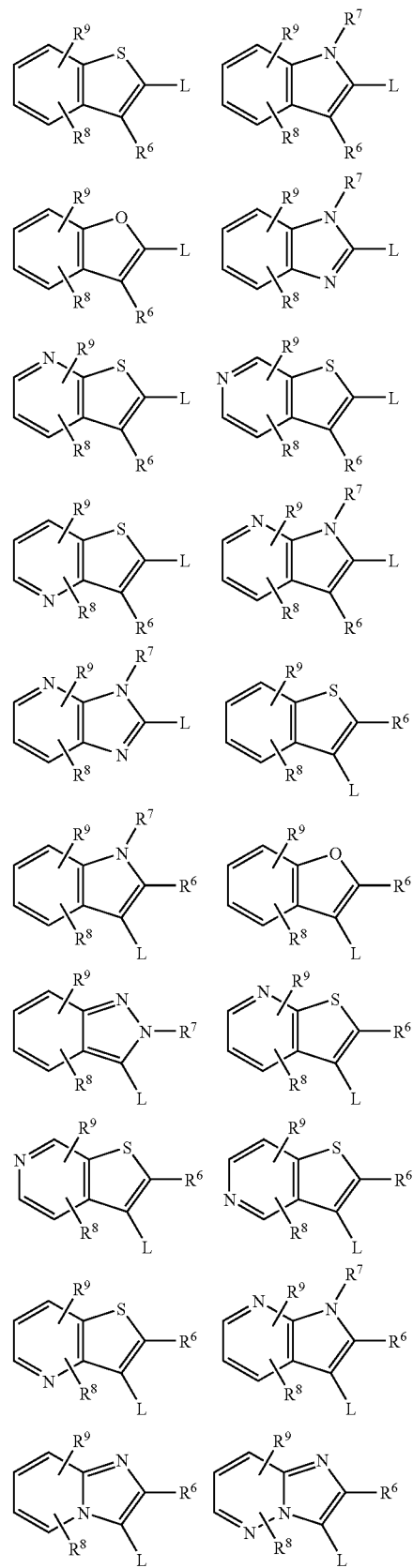

-continued

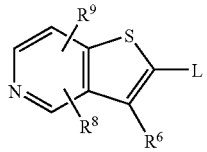

where $R^6$, $R^7$, $R^8$, and $R^9$ have been defined previously.

Equation 3

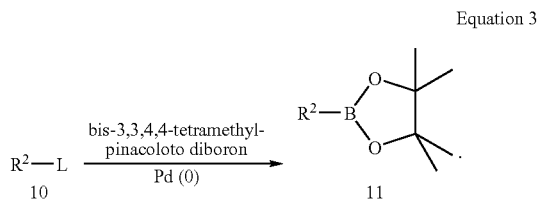

where $R^2$—L has been defined previously.

In Scheme II, Equation 1 shows, for example, that a benzo[b]thiophene-2-boronic acid 9 can be prepared by lithiating a 2-unsubstituted benzo[b]thiophene 8 with an alkyl lithium reagent, e.g., n-butyllithium or tert-butyllithium or lithium diisopropyl amine (0.9 to 3 equivalents) in THF or diethyl ether. The 5,6-bicycloaromatic lithium reagent that is formed in situ is then treated with a trialkyl boronate ester, e.g., trimethylborate. Upon workup from aqueous HCl, the trialkyl boronate ester is hydrolyzed to boronic acid 9. Other 5,6-bicycloaromatic-2-boronic acids 9 are obtained from the listed substituted 5,6-bicycloaromatic compounds 8 bearing a proton at the 2-position.

Equation 2 shows that 5,6-bicycloaromatic lithium reagents are generated by lithium-halogen exchange in THF or ether solvent at −65° C. by treating a lower alkyllithium reagent, e.g., n-, sec- or tert-butyllithium with a 5,6-bicycloaromatic 2- or 3-halide 10. The 5,6-bicycloaromatic lithium reagent that is formed in situ is then treated with a trialkyl boronate ester, e.g., trimethylborate. Upon workup from aqueous HCl, the trialkyl boronate ester is hydrolyzed to 5,6-bicycloaromatic 2- or 3-boronic acid 9.

Equation 3 shows the synthesis of 5,6-bicycloaromatic 2- or 3-boronic acid esters 11 by reacting a bis-pinacolato diboron reagent and 10 in the presence of a transition metal catalyst, e.g., [IR(OMe(COD)]2, tris-(dibenzylidene-acetone)dipalladium or palladium acetate/tricyclohexylphosphine at from 70-120° C. and in a solvent or mixture of solvents selected from DMF, DME, 1,4-dioxane, methanol and DME. Optionally, the boronate ester can be hydrolyzed to a boronic acid 9 with aqueous HCl.

If not commercially available, 5,6-bicycloaromatic 2-halides or 3-halides 10 or 2-boronic acids or 3-boronic acids 9 for coupling reactions shown in Scheme III below may be made by procedures which are selected from standard techniques of organic and heterocyclic chemistry, techniques that are analogous to the syntheses of known, structurally similar compounds and analogous to the procedures described in the preparations and examples of the present invention.

Additional procedures for preparing benzo[b]thiophene-(2 or 3)-boronic acid/esters are found in the following references: Journal of Organic Chemistry (1995), 60(23), 7508-10; PCT Int. Appl. (2003), WO 2003074533 A1 20030912; PCT Int. Appl. (2001), WO 2001036414 A1 20010525; U.S. (1999), Cont.-in-part of U.S. Ser. No. 467,444. U.S. Pat. No. 5,856,340 A 19990105; and PCT Int. Appl. (1996), WO 9630361 A1 19961003.

Additional procedures for preparing indole-(2 or 3)-boronic acid/esters are found in the following references: PCT Int. Appl. (2003), WO 2003074533 A1 20030912; PCT Int. Appl. (2003), WO 2003037252 A2 20030508; PCT Int. Appl. (2003), WO 2003024969 A1 20030327; PCT Int. Appl. (2003), WO 2003018555 A1 20030306; Recent Research Developments in Organic Chemistry (1997), 1 145-157; Synlett (1998), (9), 1025-1027; PCT Int. Appl. (2003), WO 2003000695 A1 20030103; Journal of Organic Chemistry (2002), 67(26), 9392-9396; Journal of the American Chemical Society (2002), 124(44), 13179-13184; PCT Int. Appl. (2002), WO 2002030895 A1 20020418; Heterocycles (1994), 37(3), 1761-72; Tetrahedron Letters (1993), 34(14), 2235-8; and Heterocycles (1990), 30(1, Spec. Issue), 627-33.

Halogenated benzimidazoles can be prepared by analogy to synthetic methods described in U.S.S.R. (1974), SU 443034 19740915 Patent written in Russian. Application: SU 72-1837202 19721013; Science of Synthesis (2002), 12 529-612; Organic Letters (2002), 4(25), 4543-4546; PCT Int. Appl. (2001), WO 2001002369 A2 2001011; and PCT Int. Appl. (2001) WO 2001053268 A2 20010726.

Where an N-alkylated benzimidazole is desired, the alkylation procedure which uses a base such as potassium carbonate and an alkylhalide in a polar aprotic solvent, e.g., acetonitrile at from room temperature to the reflux temperature of the mixture can be often performed either late or early in the synthetic sequences leading to Formula I whenever it is advantageous.

Additional procedures for preparing (5 or 6)-azabenzothiophene-(2 or 3)-boronic acid/esters are found in the following references: PCT Int. Appl. (2003), WO 2003059913 A1 20030724. Also, by analogy to synthetic references above, (5 or 6)-azabenzothiophene-(2 or 3)-boronic acids/esters are prepared 1) from the reaction of bis-pinacolotodiboron with palladium catalysis or 2) from the reaction of alkyllithiums followed by trialkylborate esters on 2- or 3-(bromo or iodo)-(5 or 6)-azabenzothiophenes. The synthesis of 2- or 3-(bromo or iodo)-(5 or 6)-azabenzothiophenes is effected by synthetic methods described in Bulletin des Societes Chimiques Belges (1970), 79 301-11; U.S. Pat. No. 6,492,383 B1 20021210 Application: US 2000-502129 20000210; Eur. Pat. Appl. (1988) EP 292051 A2 19881123; PCT Int. Appl. (2002), WO 2002100857 A1 20021219; PCT Int. Appl. (2002), WO 2002071827 A2 20020919; Arkiv foer Kemi (1970), 32(21), 249-68 [CAN 73:98840]; Arkiv foer Kemi (1970), 32(19), 217-27 [CAN 73:98839]; U.S. (1990), and U.S. Pat. No. 4,902,694 A 19900220 Application: US 88-231310 19880811.

By analogy to synthetic references above, (5 or 6)-azaindole-(2 or 3)-boronic acids/esters are prepared 1) from the reaction of bis-pinacolotodiboron with palladium catalysis or 2) from the reaction of alkyllithiums followed by trialkylborate esters on 2- or 3-(bromo or iodo)-(5 or 6)-azaindoles. The synthesis of 2- or 3-(bromo or iodo)-(5 or 6)-azaindoles is effected by synthetic methods described in Journal of Organic Chemistry (1991), 56(15), 4805-6; Khimiya Geterotsiklicheskikh Soedinenii (1972), (11), 1528-30. [CAN 78:43322]; Khimiya Geterotsiklicheskikh Soedinenii (1978), (4), 496-500. [CAN 89:43193]; and Tetrahedron Letters (2000), 41(6), 919-922.

Where an N-alkylated indole is desired, the alkylation procedure which uses a base such as potassium carbonate and an alkylhalide in a polar aprotic solvent, e.g., acetonitrile at from room temperature to the reflux temperature of the mixture can be often performed either late or early in the synthetic sequences leading to Formula I whenever it is advantageous.

Scheme III.
Synthesis of Compounds of Formula I by transition metal catalysis.

Equation 1:

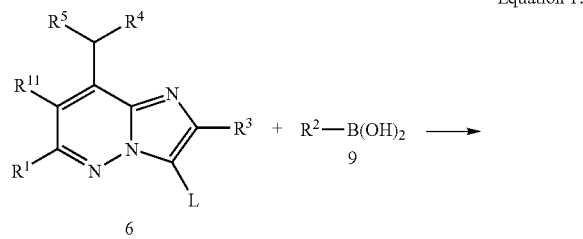
6
+ R²—B(OH)₂
9
⟶

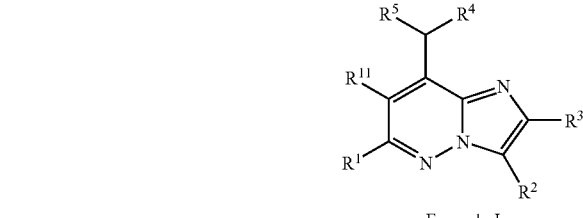
Formula I

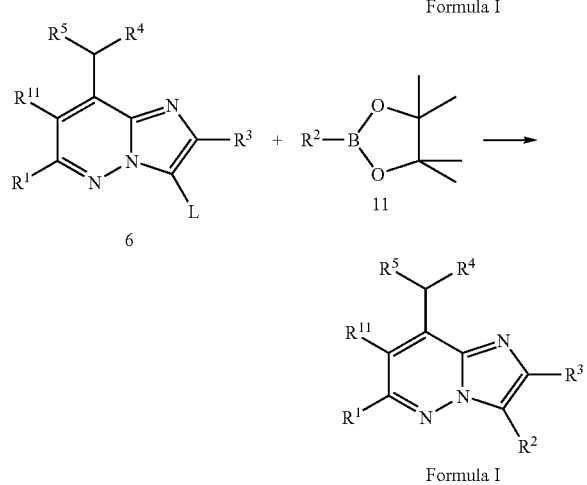

where reagents 6, 9, and 11 have been defined previously.

In Equation 1, halide 6 is used in a coupling reaction with a 5,6-bicycloaromatic boronic acid 9 or boronic ester 11 in the presence of palladium catalysis, e.g., tris-(dibenzylidene-acetone)dipalladium, palladium acetate/tricyclohexylphosphine or tetrakis-triphenylphosphine palladium (0) at from 70-120° C. and in a solvent or mixture of solvents selected from DMF, DME, 1,4-dioxane, methanol and DME to give a compound of Formula I.

Equation 2

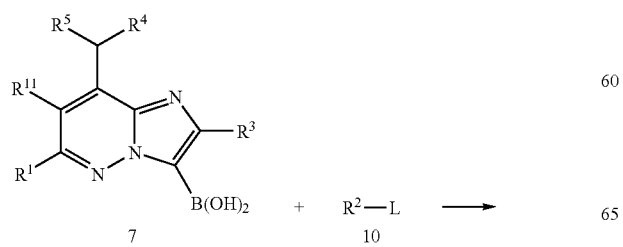

-continued

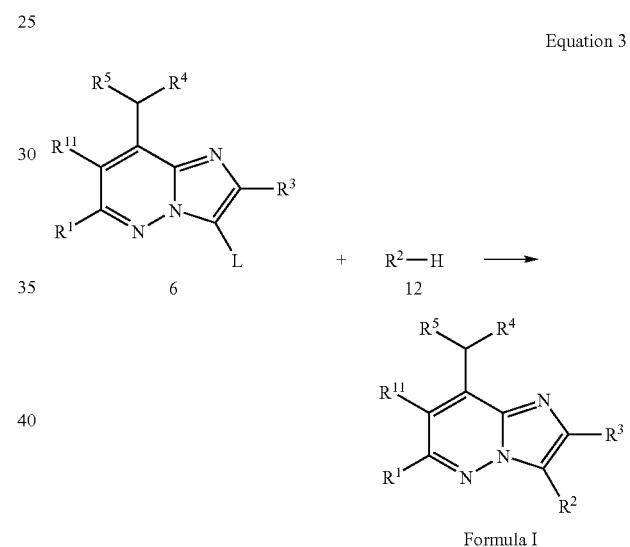
Formula I where reagents 7 and 10 have been defined previously.

In equation 2, boronic acid 7 is used in a coupling reaction with a 5,6-bicycloaromatic halide 10 and palladium catalysis, e.g., tris-(dibenzylidene-acetone)dipalladium, palladium acetate/tricyclohexylphosphine or tetrakis-triphenylphosphine palladium (0) at from 70-120° C. and in a solvent or mixture of solvents selected from DMF, DME, 1,4-dioxane, methanol and DME to give a compound of Formula I.

Equation 3 where reagent 6 has been defined previously and R²—H of equation 3 Scheme III is selected from the group consisting of:

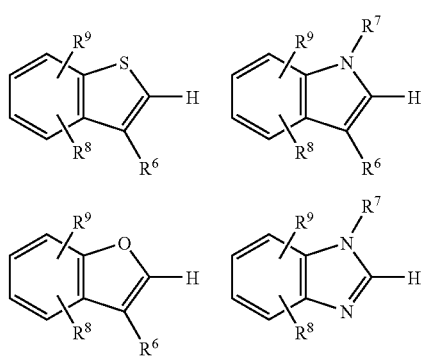

-continued

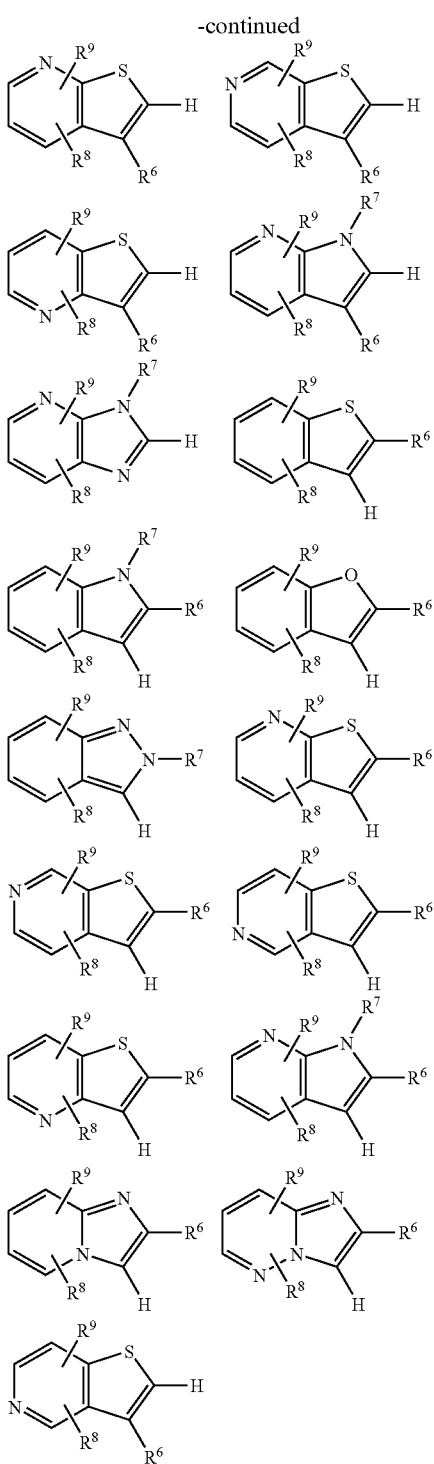

where $R^6$, $R^7$, $R^8$, and $R^9$ are defined supra.

In equation 3, halide 6 can be directly coupled with a 5,6-bicycloaromatic ring 12 that is unsubstituted in either or both the 2- or 3-position, i.e., from other $R^2$ fragments of Formula I bearing a proton in either or both the 2- or 3-position using transition metal catalysis, e.g., Pd(OAc)$_2$/PPh$_3$ or Pd$_2$dba$_3$ and base, e.g., Cs$_2$CO$_3$ at from 70-140° C. and in a solvent or mixture of solvents selected from DMF, DME, 1,4-dioxane, methanol and DME to give a compound of Formula I. Where both the 2-position and 3-position of $R^2$—H of equation 3 herein bears a proton, both 2- and 3-bicycloaromatic coupling products may be observed that may be separated by physical methods known to those skilled in the art.

Equation 4

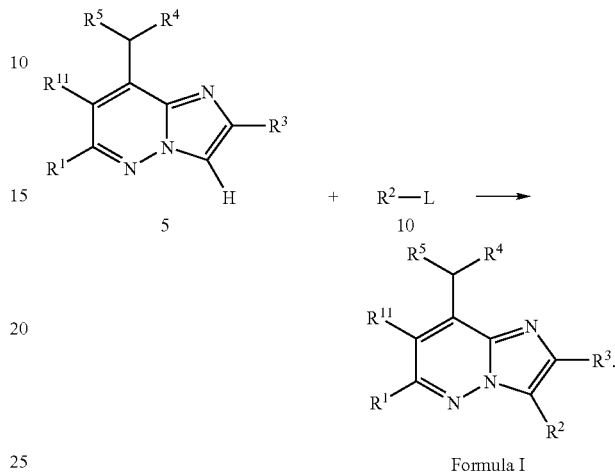

where reagents 5 and 10 have been previously described.

Alternately from equation 4, a 5,6-bicycloaromatic halide 10 can be directly coupled with imidazo[1,2-b]pyridazine 5 using transition metal catalysis, e.g., Pd(OAc)$_2$/PPh$_3$ or Pd$_2$dba$_3$ and base, e.g., Cs$_2$CO$_3$ at from 70-140° C. and in a solvent or mixture of solvents selected from DMF, DME, 1,4-dioxane, methanol and DME to give a compound of Formula I.

Equation 5

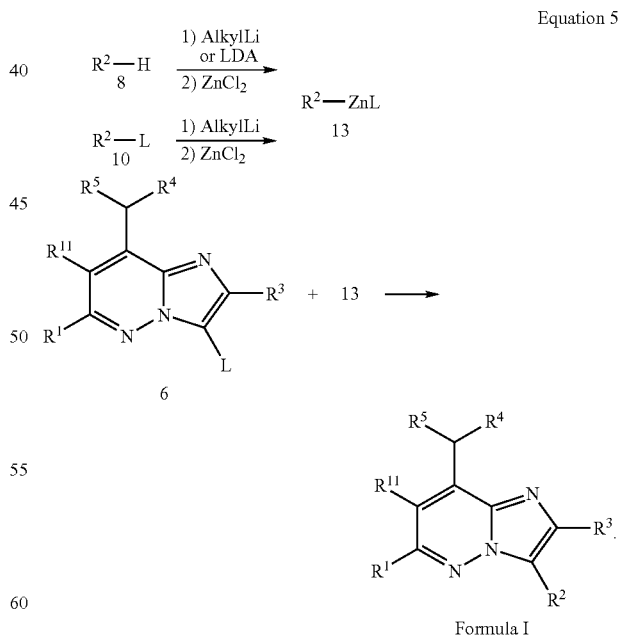

where reagents 6, 8, and 10 have been previously defined.

From equation 5, an in situ 5,6-bicycloaromatic zinc reagent 13 is prepared by either 1) treatment of 5,6-bicycloaromatic reagent 8 with an alkyllithium, e.g., n-, sec-, or tert-butyllithium or lithium diisopropylamide at −65 C followed by lithium-zinc exchange at room temperature to the organozinc reagent 13; or 2) treatment of 5,6-bicycloaromatic reagent 10 with an alkyllithium, e.g., n-, sec-, or tert-butyllithium at −65 C followed by lithium-zinc exchange at room temperature to the organozinc reagent 13. Reagent 13 is coupled with imidazo[1,2-b]pyridazine halide 6 in the presence of a palladium catalyst, e.g., tris-(dibenzylidene-acetone)dipalladium, palladium acetate/tricyclohexylphosphine or tetrakis-triphenylphosphine palladium (0) at from 70-120° C. and in a solvent or mixture of solvents selected from DMF, DME, 1,4-dioxane, methanol and DME to give a compound of Formula I.

Equation 6

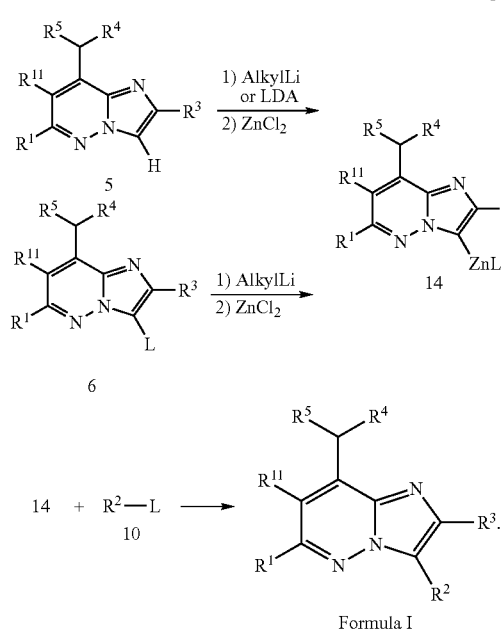

where reagents 5, 6, and 10 have been previously defined.

Alternately from equation 6, an in situ imidazo[1,2-b]pyridazine zinc reagent 14 is prepared by either 1) treatment of imidazo[1,2-b]pyridazine reagent 5 with an alkyllithium, e.g., n-, sec-, or tert-butyllithium or lithium diisopropylamide at −65 C followed by lithium-zinc exchange at room temperature to the organozinc reagent 14; or 2) treatment of imidazo[1,2-b]pyridazine reagent 6 with an alkyllithium, e.g., n-, sec-, or tert-butyllithium at −65 C followed by lithium-zinc exchange at room temperature to the organozinc reagent 14. Reagent 14 is coupled with 5,6-bicycloaromatic halide 6 in the presence of a palladium catalyst, e.g., tris-(dibenzylidene-acetone)dipalladium, palladium acetate/tricyclohexylphosphine or tetrakis-triphenylphosphine palladium (0) at from 70-120° C. and in a solvent or mixture of solvents selected from DMF, DME, 1,4-dioxane, methanol and DME to give a compound of Formula I.

Several 5,6-bicycloaromatic rings useful as starting materials for the synthesis of Formula I are commercially available, and several compounds of Formula I may also serve as useful intermediates in the preparation of other compounds of Formula I.

Scheme IV. Synthesis of substituted 4, 5, 6, and 7 aza-benzo[b]thiophenes

Equation 1.

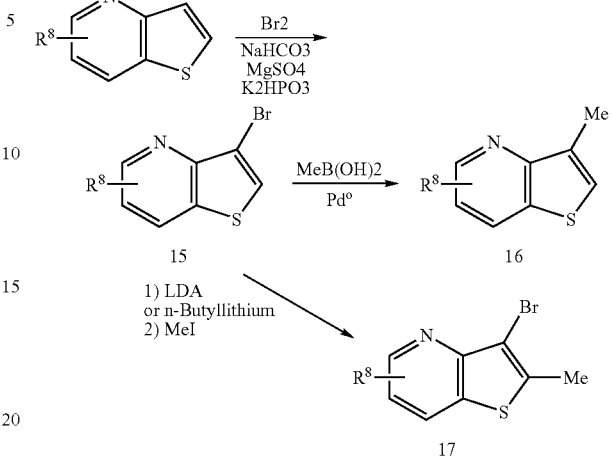

$R^8$ of this equation is limited to H or Cl

Equation 2.

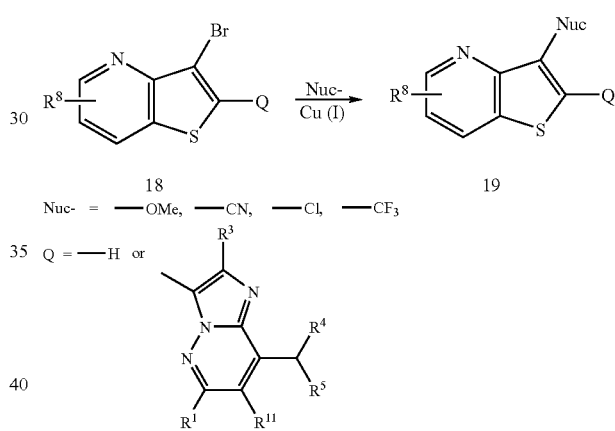

Nuc- = —OMe, —CN, —Cl, —CF$_3$

Q = —H or where $R^1$, $R^3$, $R^4$, $R^5$, $R^8$ and $R^{11}$ have been defined previously. Note that $R^8$ not only of this equation but also of Equation 3 Scheme IV below is not limited as in Equation 1 of Scheme IV.

Equation 3

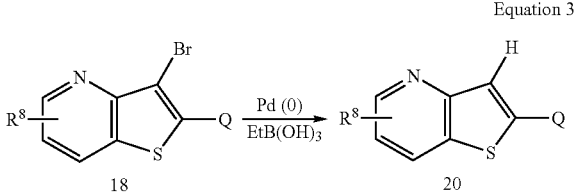

where Q has been defined in Equation 2 of Scheme IV.

From Equation 1, not only the illustrated 4-aza-benzo[b]thiophene but also 5, 6, or 7-aza-benzo[b]-thiophenes may be substituted with chlorine in a vacant 4, 5, 6, or 7 position, and they are brominated at the three position with elemental bromine and base, e.g., sodium bicarbonate and a phosphate buffer to produce compound 15 or the corresponding 5, 6, or 7-aza analogue of Compound 15. The defined analogues of compound 15 are coupled with methylboronic acid in the presence of palladium catalysis to give the 3-methyl derivative 16 or the corresponding 5, 6, or 7-aza analogue of Compound 16. Alternately, any 3-bromo-aza-benzo[b]thiophene 15 can be alkylated in the presence of a strong base, e.g., lithium diisopropylamide in THF and iodomethane to produce the 2-methyl derivative 17 or the corresponding 5, 6, or 7-aza analogue of Compound 17. As one skilled in the art will appreciate, intermediates such as 16 and 17 are further used as coupling partners, e.g., as either precursors to organozinc reagents or as brominated intermediates per se, to produce compounds of Formula I in the presence of palladium catalysis as described above.

From equation 2,3-bromo-4-aza-benzo[b]thiophenes 18, as intermediates or as substructures within Formula I, may be further elaborated by nucleophilic aromatic substitution of bromine at the three position in the presence of copper (I) catalysis and a nucleophile, such as, methoxy, cyano, and chloro or by a trifluoromethylanion species to give 19. One skilled in the art will also appreciate that other halides of $R^2$ (defined in its broadest sense) may be substrates for nucleophilic aromatic substitution if the ring carbon bearing the halide, e.g., fluoride or bromide is sufficiently electrophilic.

Further from equation 3,3-bromo-4-aza-benzo[b]thiophenes 18, as intermediates or as substructures within Formula I, can be reduced, i.e., debrominated with ethylboronic acid in the presence of palladium catalysis to give 20.

Scheme V

Scheme V further summarizes previously described methodologies for transition metal catalyzed coupling reactions but for imidazo[1,2-b]pyridazine compounds that have either no substituent at the 8-position (21) or a halogen at the 8-position (22) by treatment of 21 with a base such as nBuLi, PhLi, lithium di-isopropylamide or LiTMP in a solvent, e.g., THF in the presence of 12. Compounds 5', 6', and 7' are 8-unsubstituted counterparts to the previously described compounds 5, 6, and 7. Aryllithium reagents derived from 21 or 22 are used in condensation reactions with Weinrab amides or ketones to form ketones and carbinols, respectively leading to more complex $R^{12}$ substituents or precursors to alkenyl $R^4$ and/or $R^5$ substituents in Formula I via dehydration or dehydrohalogenation.

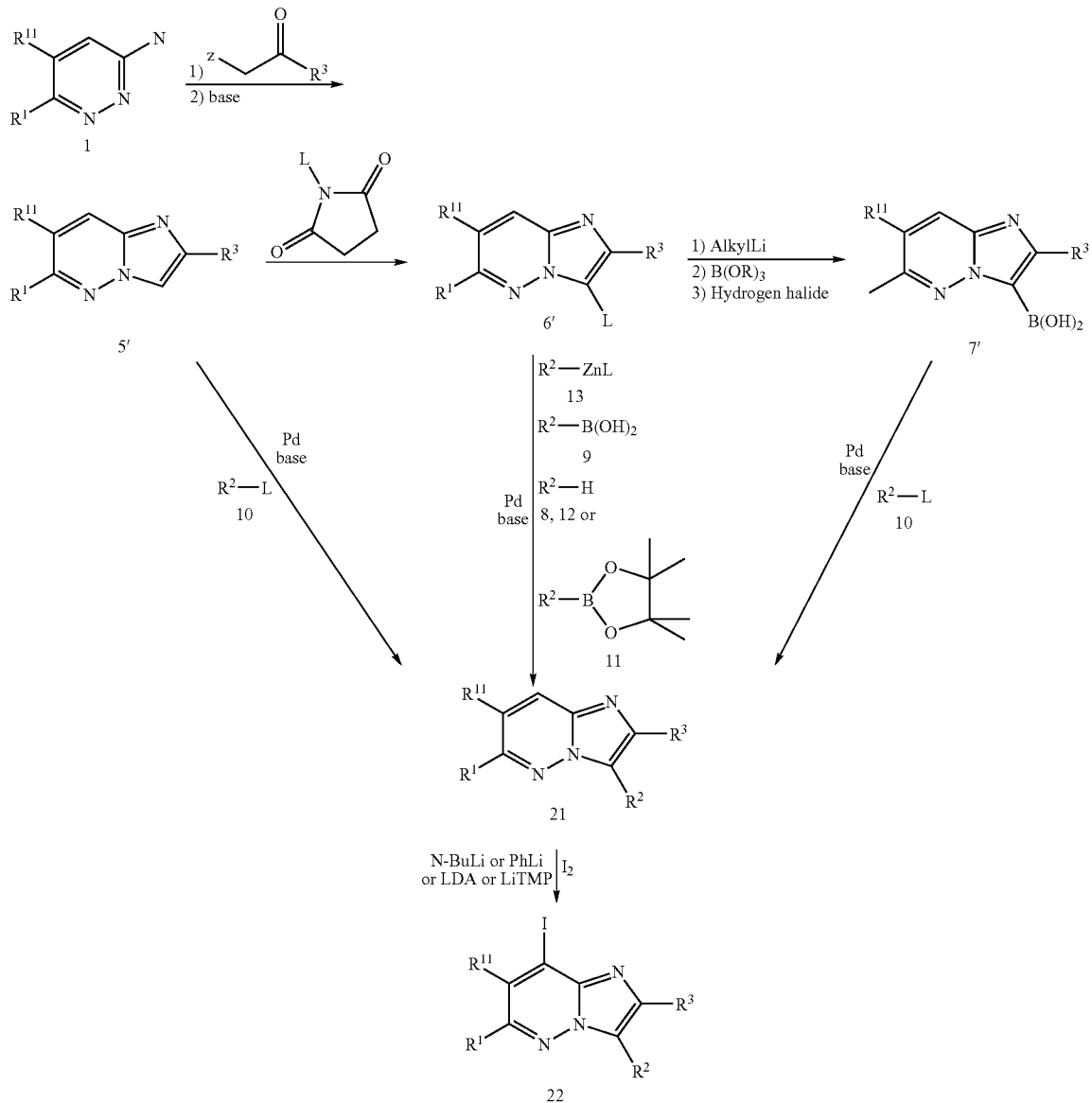

where $R^1$, $R^2$, $R^3$, $R^{11}$ and reagents 8, 9, 10, 11, 12, and 13 have been previously defined.

A skilled artisan would recognize that the order in which the assembly of compounds of Formula I may vary depending upon the availability of starting materials, the compatibility of substituents with reactions conditions, the necessity of performing functional group transformations, and the use of protection groups. Methods for introducing and removing nitrogen and oxygen protecting groups are well known in the art; see, for example, Greene and Wuts, *Protective Groups in Organic Synthesis*, $3^{rd}$ Ed., John Wiley and Sons, New York, Chapter 7 (1999).

Abbreviations

Dtbpy—2,6-Di-tert-butylpyridine

TBDMSCl or TBDMSiCl—tert-butyl-dimethylsilyl chloride

MS (ES)—Electrospray Mass spectrum

THF—tetrahydrofuran

DMSO—dimethylsulfoxide

DMF—dimethylformamide

DCM, $CH_2Cl_2$—dichloromethane

Dioxane—1,4-dioxane

N2—nitrogen gas

NIS—N-iodosuccinimide

NBS—N-bromosuccinimide

MeOH—methanol

EtOH—95% ethanol

RBF, RB—round bottom flask

RBSN—round bottom single neck flask

SiO2—silica gel

EtOAc, AcOEt—ethylacetate

HPLC—high pressure liquid chromatography on silica gel

ISCO—ISCO brand high pressure liquid chromatography on silica gel

AcCl—acetyl chloride

LDA—lithium diisopropylamine

KOAc—potassium acetate

TBABr—tetrabutyl ammonium bromide

NMP—N-methylpyrrolidinone

PPA—polyphosphoric acid

Pin2B2—bis-3,3,4,4-tetramethylpinacolato diboron $Pd_2dba_3$—Tris(dibenzylideneacetone)dipalladium PdCl2(dppf)—Dichloro[1,1'-bis(diphenylphosphino)ferrocene]palladium Tetrakis—tetrakis-(triphenylphosphine)-palladium.

Dppf—1,1'-Bis(diphenylphosphino)ferrocene.

LiTMP—Lithium 2,2,6,6-tetramethylpyridine r.t., RT—room temperature $[IrOMe(COD)]_2$—Bis(cyclooctadiene)bis(methoxy)diIridium $[IrCl(COD)]_2$—Bis(cyclooctadiene)-dichloro-diIridium

EXAMPLES

Without further elaboration, it is believed that one skilled in the art can, using the preceding description, practice the present invention to its fullest extent. The following examples are provided to describe the invention in further detail. They are intended to illustrate and not to limit the invention in any way whatsoever. Examples 1-132 provide exemplary compounds and illustrate the preparation thereof. Examples A-D illustrate various biological assays that can be used for determining the biological properties of the compounds of the inventions. Those skilled in the art will promptly recognize appropriate variations from the procedures described in the examples.

Example 1

Preparation of 8-(1-ethyl-propyl)-2,6-dimethyl-3-(5-fluoro-3-methyl-benzo[b]thiophen-2-yl)-imidazo[1,2-b]pyridazine

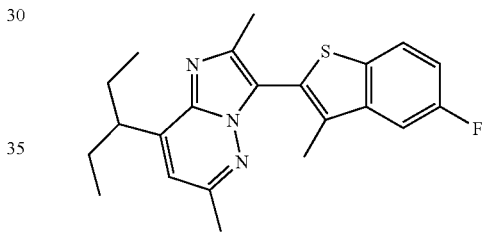

Method A.

A. 6-Methyl-pyridazin-3-ylamine

Dissolve 25.0 g (0.229 moles) of 3-chloro-6-methylpyridazine in 250 ml of $NH_4OH$ and heat to 170° C. in a sealed container for 24 h. Evaporate solvents. Triturate in methylene chloride and filter solid. Repeat with filtrate 4×. Combine all filtered solids and dry in vacuum oven over night to obtain product as off-white solid 4.32 g (0.040 moles, 20.4%). $H^1$NMR (DMSO-d6): δ 7.1 (d, J=8.9 Hz, 1H); 6.67 (d, J=6.67 Hz, 1H); 6.04 (s, br, 2H); 2.33 (s, 3H) ppm. ES+=110 (100%, M+1).

B. 2,2-Dimethyl-N-(6-methyl-pyridazine-3-yl)-propionamide

Method 1: To a dry flask is added 7.12 g of 6-methyl-pyridazin-3-ylamine in 170 ml dry methylene chloride. Next, 14.5 ml of triethylamine is added and the reaction is cooled to 0° C. Carefully add 2.7 ml (1.2 eq) of pivaloyl chloride, stir 10 minutes then removed bath. Stir 4 hours then add 200 ml of methylene chloride and wash 3 times with saturated aqueous sodium bicarbonate then brine. Dry over sodium sulfate, filter, and evaporate to an oil. Chromatograph using 6:1 hexanes:ethyl acetate, then 3:1, then 1:1, and flush with ethyl acetate. Combine and evaporate to give title compound 2, as white solid weighing 1.51 g (7.8 mmoles, 42.7%). $^1$H-NMR (DMSO-$d_6$): δ 10.39 (s, 1H); 8.11 (d, J=9.30 Hz, 1H); 7.51 (d, J=9.29 Hz, 1H); 2.54 (s, 3H); 1.23 (s, 9H) ppm. ES+=194 (70% mM+1); 102 (100%).

Method 2: To a dry pressure tube is added 200 mg (1.56 mol) of 3-chloro-5-methylpyridazine, 190 mg (1.87 mmol) of trimethylacetamide, 14.6 mg (0.023 mmol) of rac-2,2'-bis(diphenylphosphine)-1,1'-binaphthyl, tris(dibenzylideneacetone)-dipalladium (0), 762.4 mg (2.34 mmol) of cesium carbonate and 1.5 ml dry tetrahydrofuran. Purged flask with nitrogen and seal then heat to 100° C. overnight. Cooled, diluted with methylene chloride, and filter through celite. Evaporate solvents and chromatograph using 7:1 hexanes:ethyl acetate to 1:1 hexanes:ethyl acetate to obtain 91 mg (0.47 mmol), 30% as white solid.

C. N-[4-(1-Ethyl-propyl)-6-methyl-pyridazin-3-yl]-2,2-dimethyl-propionamide

To a dry 3 L flask fitted with a condenser and drop funnel is added 19.2 g (0.792 moles) of activated magnesium powder. Heat gun dry the entire apparatus under vacuum, allow to cool, add enough ether to cover the magnesium. To the addition funnel is added 100 g (0.662 mmol) of 3-bromopentane in 175 ml of diethyl ether. Add ⅓ of the bromopentane solution to the magnesium and stir under nitrogen until bubbling occurs, then drip in the rest at such a rate so that the bubbling continues gently. Stir 30 minutes longer after bubbling ceases. Next, drip in 21.3 g (0.110 mmol) of 2,2-dimethyl-N-(6-methyl-pyridazine-3-yl)-propionamide dissolved in 225 ml dry tetrahydrofuran. Stir 1 h. Carefully add over 1 L of saturated sodium tartrate and stir 30 minutes. Transfer to larger flask and add 2 L of ethyl acetate and stir 1 h. Separate layers and extract aqueous several times with ethyl acetate. Combine organic layers and evaporate solvents. Take up in 600 ml of methylene chloride and add 28 g (0.110 mol) of iodine and stir 2 h. Wash the organic phase once with aqueous solution of sodium sulfite then water. Dry over sodium sulfate, filter and evaporate to red oil. Chromatograph using 6:1 hexanes:ethyl acetate to 100% ethyl acetate. Combine product fractions, evaporate, and triturate residue in ethyl acetate and filter to obtain 12.0 g (45.6 mmol, 41.4%) of the title compound as a light tan solid. $^1$H-NMR (DMSO-$d_6$): δ 9.88 (s, 1H); 7.59 (s, 1H); 2.60 (s, 3H); 2.39-2.42 (m, 1H); 1.21-1.37 (m, 2H); 1.38-1.43 (m, 2H); 1.23 (s, 9H); 0.71 (t, J=7.49 Hz, 6H) ppm. MS/ES+=264.

D. 4-(1-Ethyl-propyl)-6-methyl-pyridazin-3-ylamine

Dissolve 12.0 g (45 mmol) of N-[4-(1-ethyl-propyl)-6-methyl-pyridazin-3-yl]-2,2-dimethyl-propionamide in 60 ml of concentrated hydrochloric acid. Heat to 95° C. in a sealed flask for 2 h. Work up by pouring over ice and extracting with ethyl acetate three times. Discard the organic and adjust pH of aqueous to basic using 2N sodium hydroxide. Extract basic solution with ethyl acetate five times. Dry over magnesium sulfate, filter, and evaporate to obtain 6.68 g (37 mmol, 81.0%) of the title compound as brownish oil. $^1$H-NMR (DMSO-$d_6$): δ 6.95 (s, 1H); 5.89 (s, br, 2H); 2.52-2.56 (m, 1H); 2.34 (s, 3H); 1.44-1.58 (m, 4H); 0.72 (t, J=7.04 Hz, 6H) ppm. MS/ES+=180 (100%, M+1).

E. 8-(1-Ethyl-propyl)-2,6-dimethyl-imidazo[1,2-b]pyridazine

Heat 850 mg (4.74 mmol) of 4-(1-ethyl-propyl)-6-methyl-pyridazin-3-ylamine and 0.415 ml (5.22 ml) of chloroacetone in 20 ml of ethanol in microwave at 110° C. for 35 minutes. Add 1.2 g (14.2 mmol) of sodium bicarbonate and heat in oil bath with reflux condensor at 100° C. overnight. Evaporate solvents, take up in ethyl acetate and wash 3 X's with brine. Dry over sodium sulfate, filter, and evaporate to a brown oil. Chromatograph using hexanes to 6:1 hex:ethyl acetate to ethyl acetate gradient. Collect title compound as oil weighing 3.69 g (17.0 mmol, 84.4%). $^1$H-NMR (DMSO-$d_6$): δ 7.34 (s, 1H); 6.84 (s, 1H); 2.85-3.10 (m, 1H); 2.43 (s, 3H); 2.32 (s, 3H); 1.70-1.80 (m, 4H); 0.712 (t, J=7.49 Hz, 6H) ppm. MS/ES+=219 (100%, M+2).

F. 8-(1-Ethyl-propyl)-3-iodo-2,6-dimethyl-imidazo[1,2-b]pyridazine

In nitrogen-purged flask is added 5.1 g (0.023 moles) of 8-(1-ethyl-propyl)-2,6-dimethyl-imidazo[1,2-b]pyridazine in 50 ml dry acetonitrile. Cool to 0° C. and add 5.54 g (0.025 moles) of NIS dissolved in 90 ml dry acetonitrile. Allow bath to come to room temperature and the reaction to stir overnight. Evaporate solvents, take up in ethyl acetate and wash two times with 50% aqueous solution of sodium sulfate then brine. Dry over sodium sulfate, filter and evaporate to a residue. Triturate in small amount of acetonitrile and filter solid. Repeat several times to obtain the title compound as light tan solid weighing 7.29 g (0.021 moles, 91.3%). $^1$H-NMR (DMSO-$d_6$): δ 6.96 (s, 1H); 3.0-3.3 (m, 1H); 2.51 (s, 3H); 2.35 (s, 3H); 1.71-1.80 (m, 4H); 0.71 (t, J=7.48 hz, 6H) ppm. MS/ES+=344 (100%, M+1).

G. Boronic Acid, 5-fluoro-3-methyl-benzo[b]thiophene-2-yl

In a dry flask is added 312.1 mg (1.88 mmol) of 5-fluoro-3-methyl-benzo[b]thiophene in 4 ml of dry THF. Cool to −78° C. and add 1.18 ml (1.90 mmol) of 1.6N n-butyllithium in hexanes. Stir 1.5 hrs at −78° C. then add 0.23 ml (2.02 mmol) of trimethylborate. After all is added, stir 3 hrs and allow bath to come to −20° C. then add 5N hydrochloric acid until acidic (pH=4). Dilute with water and extract three times with ethyl acetate. Combine organics and dry over sodium sulfate, filter and evaporate. Triturate in methylene chloride to obtain 258.3 mg (1.23 mmol, 65.4%) of a white solid of the title compound. Rf (1:1 hex:ethyl acetate)=0.085. MS/ES−=209 (M−1, 100%).

H. 8-(1-Ethyl-propyl)-2,6-dimethyl-3-(5-fluoro-3-methyl-benzo[b]thiophen-2-yl)-imidazo[1,2-b]pyridazine To a microwave pressure tube is added 3×0.200 g (1.75 mmol) of 8-(1-ethyl-propyl)-3-iodo-2,6-dimethyl-imidazo[1,2-b]pyridazine, 3×0.307 g (4.38 mmol) of boronic acid, 5-fluoro-3-methyl-benzo[b]thiophene-2-yl, 3×0.400 g (10.38 mmol) of Pd(PPh$_3$)$_4$, 3×0.730 mL (1.095 mmol) of 2M aqueous sodium carbonate, and 3×2 mL 7:3:2 DME:H$_2$O:EtOH and heated at 170 C for 60 min. The reaction mixture is partitioned between 150 mL of ethyl acetate and 150 mL of water. The layers are separated and the aqueous is extracted 3×100 mL of ethyl acetate, dried (MgSO$_4$), and concentrated under vacuum. The crude mixture is purified by chromatography using 2% Acetonitrile/Dichloromethane as a solvent system. The product containing fractions are combined to obtain 0.450 g of the title product, 67% yield. MS, ES+=382.1 (M+1); $^1$H NMR (DMSO-d6) δ 8.02-8.06 (m, 1H); 7.71 (d, J=2.31 Hz, 1H); 7.67 (d, J=2.31 Hz, 1H); 7.35 (d, J=6.26 Hz, 1H); 7.32 (d, J=2.63 Hz, 1H); 7.29 (m, 1H); 7.01 (s, 1H);

3.05-3.18 (m, 1H); 2.44 (s, 3H); 2.36 (s, 3H); 2.20 (s, 3H); 1.79-1.85 (m, 4H); 0.79 (t, J=7.26 Hz, 6H) ppm.
Method B.

A. 2-Bromo-5-fluoro-3-methylbenzo[b]thiophene

A mechanically-stirred solution of 5-fluoro-3-methyl-benzo[b]thiophene (50.32 g, 0.303 mol, 1.0 equiv) in acetonitrile (350 mL) is treated with NBS (56.32 g, 0.318 mol, 1.05 equiv). An initial endotherm reduces the reaction temperature to 17° C. A subsequent exotherm then increases the reaction temperature to 40° C. over a 10 min. period, at which time the reaction is cooled to 18-20° C. by application of an ice water bath. The reaction is stirred at RT for an additional 35 min. and the resultant slurry is slowly diluted with water (350 mL). The slurry is stirred for 10 min and the product is filtered, washed with 50:50 acetonitrile:water (100 mL) and dried to a colorless crystalline solid (65.56 g, 88%).

B. 8-(1-Ethyl-propyl)-2,6-dimethyl-3-(5-fluoro-3-methyl-benzo[b]thiophen-2-yl)-imidazo[1,2-b]pyridazine A mixture of 8-(1-ethyl-propyl)-2,6-dimethyl-imidazo[1,2-b]pyridazine (435 mg, 2.0 mmol, 1.0 equiv), 2-bromo-5-fluoro-3-methylbenzo[b]thiophene (564 mg, 2.3 mmol, 1.15 equiv), triphenylphosphine (100 mg, 0.38 mmol, 0.19 equiv), $Cs_2CO_3$ (1.37 g, 4.2 mmol, 2.1 equiv) and $Pd_2 dba_3$ (88 mg, 0.096 mmol, 0.048 equiv) in DMF (4.5 mL, degassed by sparging with nitrogen for 30 min. prior to use) is heated at 130° C. for 4 hr (magnetically-stirred under an atmosphere of $N_2$). The reaction is cooled and partitioned between MTBE (10 mL) and satd. $NH_4Cl$ solution (10 mL). The organic phase is washed with satd. $NH_4Cl$ solution (2×5 mL), dried ($Na_2SO_4$) and concentrated in vacuo to a brown film, which is adsorbed onto silica gel (1.0 g). Material is flash chromatographed (10 g of silica gel; heptane to 5% EtOAc in heptane to 10% EtOAc in heptane) and fractions containing pure product were combined and concentrated. The residue is stirred in warm heptane (6 mL) for 10 min. then refrigerated at −20° C. for 24 hr. Light yellow crystals are separated, washed with cold heptane and dried. The product is recrystallized from MeOH (3 mL) to provide the title compound as light yellow crystals (453 mg, 65%).

Example 2

Preparation of 8-(1-ethyl-propyl)-2,6-dimethyl-3-(3-methyl-benzo[b]thiophen-2-yl)-imidazo[1,2-b]pyridazine (Method A)

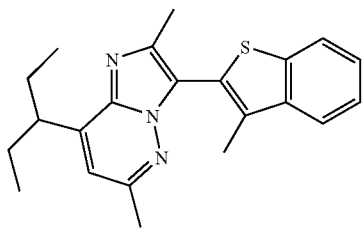

A. Boronic Acid, 3-methyl-benzo[b]thiophene-2-yl

By following a procedure analogous to Example 1G with 3-methyl-benzo[b]thiophene, the title compound (47.9% yield) is obtained as a white solid. Rf (iodine, 1:1 Hex:Ethyl acetate)=0.17. MS/ES−=191 (M−1, 100%).

B. 8-(1-Ethyl-propyl)-2,6-dimethyl-3-(3-methyl-benzo[b]thiophen-2-yl)-imidazo[1,2-b]pyridazine By following a procedure analogous to Example 1H, the title compound is obtained (38.3%). $^1$H-NMR (DMSO-d6): δ 7.95 (d, J=8.36 Hz, 1H); 7.89 (d, J=8.37 Hz, 1H); 7.41-7.51 (m, 2H); 7.05 (s, 1H); 3.08-3.13 (m, 1H); 2.43 (s, 3H); 2.38 (s, 3H); 2.21 (s, 3H); 1.78-1.87 (m, 4H); 0.74-0.85 (m, 6H) ppm. MS/ES+=364 (100%, M+1).

Preparation of 8-(1-ethyl-propyl)-2,6-dimethyl-3-(3-methyl-benzo[b]thiophen-2-yl)-imidazo[1,2-b]pyridazine (Method B)

A mixture of 8-(1-ethyl-propyl)-3-iodo-2,6-dimethyl-imidazo[1,2-b]pyridazine (0.145 mmol), 3-methyl-benzothiophene (7.25 mmol), $Pd_2 dba_3$ (0.0072 mmol), triphenylphosphine (0.029 mmol), and cesium carbonate (0.29 mmol) in previously degassed DMF (0.5 ml) is added to a pressure tube with a stirring bar. Mixture is degassed for 30 min. After heating for 16 h at 130° C., the reaction mixture is cooled, diluted with diethylether and washed with saturated aqueous ammonium chloride solution. The organic layer is dried over anhydrous magnesium sulfate, filtered, and the solvent is removed in vacuo. The residue is purified by silica gel column chromatography using mixtures of hexane-ethyl acetate as eluent to give the title compound (80%).

Example 3

Preparation of 8-(1-ethyl-propyl)-3-(5-methoxy-benzofuran-2-yl)-2,6-dimethyl-imidazo[1,2-b]pyridazine

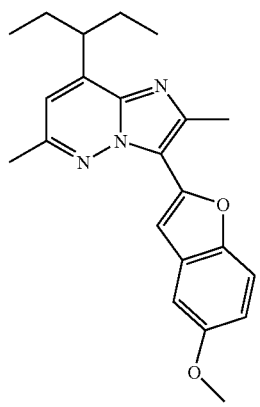

By following a procedure analogous to Example 1H, the title compound was obtained (47.0%) as a yellow solid. $^1$H-NMR (DMSO-d$_6$): δ 7.68 (s, 1H); 7.54 (d, J=8.81 Hz, 1H); 7.25 (s, 1H); 7.13 (s, 1H); 6.90 (d, J=6.16 Hz, 1H); 3.08-3.14 (m, 1H); 2.77 (s, 3H); 2.63 (s, 3H); 2.47 (s, 3H); 1.78-1.84 (m, 4H); 0.75 (t, J=7.26 Hz, 6H) ppm. MS/ES+= 364 (100%, M+1).

Example 4

Preparation of 3-(5-chloro-3-methyl-benzo[b]thiophen-2-yl)-8-(1-ethyl-propyl)-2,6-dimethyl-imidazo[1,2-b]pyridazine

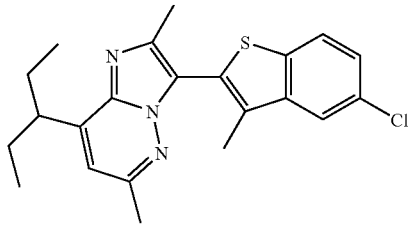

A. 2-Boronic Acid, 5-chloro-3-methyl-benzo[b]thiophene-2-yl

By following a procedure analogous to Example 1G with 5-chloro-3-methyl-benzo[b]thiophene, the title compound (37.1% yield) is obtained as a white solid. Rf (UV:1:1 hex:ethyl acetate)=0.08. MS/ES-=225 (M-1, 100%; 433, 50%).

A. 3-(5-Chloro-3-methyl-benzo[b]thiophen-2-yl)-8-(1-ethyl-propyl)-2,6-dimethyl-imidazo[1,2-b]pyridazine By following a procedure analogous to Example 1H, the title compound is obtained (23.6%) as yellow foam. $^1$H-NMR (DMSO-$d_6$): δ 8.04 (d, J=8.81 Hz, 1H); 7.94 (s, 1H); 7.46 (d, J=6.61 Hz, 1H); 7.02 (s, 1H); 3.08-3.13 (m, 1H); 2.43 (s, 3H); 2.35 (s, 3H); 2.21 (s, 3H); 1.77-1.86 (m, 4H); 0.77 (t, J=7.26 Hz, 6H) ppm. MS/ES+=398 (100%, M+1).

Example 5

Preparation of 8-(1-ethyl-propyl)-2,6-dimethyl-3-(4-chloro-1-methyl-indol-2-yl)-imidazo[1,2-b]pyridazine

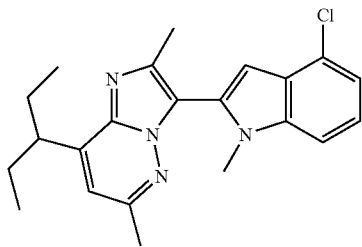

A. 4-Chloro-1-methyl-indole

In an oven dried, nitrogen purged, 3 neck, 50 mL round bottom flask, 0.794 mL (6.60 mmol) of 4-chloroindole in 10 mL of dry dimethylformamide is reacted with 0.260 g (6.60 mmol) of 60% sodium hydride dispersed in mineral oil at room temperature for 4 h. 0.411 mL (6.60 mmol) of iodomethane is added and the reaction is allowed to stir at room temperature 15 h. TLC (2:1 hexanes:ethyl acetate) indicates the starting material is gone and new less polar spot. The reaction is quenched with 50 mL of water, extracted 3×50 mL of ethyl acetate, dried (MgSO$_4$), and concentrated. The crude product is purified by chromatography using hexanes:ethyl acetate as a solvent system to obtain 0.785 g of the title compound, 72% yield. MS, ES=166.1 (M+1); $^1$H NMR (DMSO-$d_6$) δ 7.431-7.413 (m, 2H); 7.145-7.064 (m, 2H); 6.442-6.432 (m, 1H); 3.795 (s, 3H) ppm.

B. Boronic Acid, 4-chloro-1-methyl-indol-2-yl

In an oven dried, nitrogen purged, 3 neck, 50 mL round bottom flask, 0.785 g (4.74 mmol) of 4-chloro-1-methyl-indole in 10 mL of dry tetrahydrofuran is cooled to -78° C. 2.96 mL (4.74 mmol) of 1.6N n-butyllithium in hexanes is added and the mixture is stirred at -78° C. After 3 h, 0.638 mL (5.69 mmol) of trimethylborate is added. The mixture is allowed to stir overnight and the bath is allowed to expire. The reaction is quenched with 30 mL of dilute hydrochloric acid or until acidic. The layers are separated and the aqueous is extracted 3×50 mL of ethyl acetate, dried (MgSO$_4$), and concentrated under vacuum. The crude product is triturated in hexanes to obtain 0.480 g of the title compound, 48% yield. MS, ES=208.1 (M-1).

C. 8-(1-Ethyl-propyl)-2,6-dimethyl-3-(4-chloro-1-methyl-indol-2-yl)-imidazo[1,2-b]pyridazine To a microwave pressure tube is added 0.060 g (0.175 mmol) of 8-(1-ethyl-propyl)-3-iodo-2,6-dimethyl-imidazo[1,2-b]pyridazine, 0.092 g (0.437 mmol) of boronic acid, 4-chloro-1-methyl-indol-2-yl, 0.121 g (0.105 mmol) of Pd(PPh$_3$)$_4$, 0.218 mL (0.437 mmol) of 2M aqueous sodium carbonate, and 1.8 mL of 7:3:2 DME:H$_2$O:EtOH and heated at 150° C. for 30 minutes. The reaction mixture is partitioned between 20 mL of ethyl acetate and 20 mL of water. The layers are separated and the aqueous is extracted 3×25 mL of ethyl acetate, dried (MgSO$_4$), and concentrated under vacuum. The crude mixture is purified by chromatography using hexanes:ethyl acetate as a solvent system. The product containing fractions are combined to obtain 0.050 g of the title compound, 75% yield. MS, ES+=381.1 (M+1); $^1$H NMR (DMSO-d6) δ 7.664-7.659 (d, 1H); 7.578-7.556 (d, 1H); 7.233-7.206 (m, 1H); 7.018 (s, 1H); 6.654 (s, 1H); 3.526 (s, 1h); 2.430 (s, 3H); 2.372 (s, 3H); 1.853-1.792 (m, 4H); 0.801-0.782 (m 6h) ppm.

Example 6

Preparation of 8-(1-ethyl-propyl)-2,6-dimethyl-3-(5-chloro-1-methyl-indol-2-yl)-imidazo[1,2-b]pyridazine

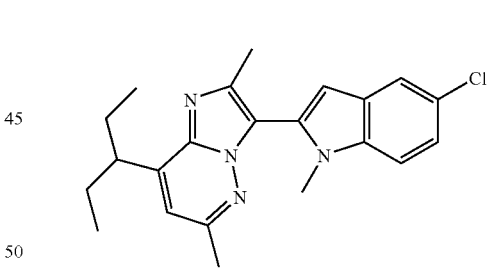

A. 5-Chloro-1-methylindole

In an oven dried, nitrogen purged, 3 neck, 50 mL round bottom flask, 1.00 g (6.60 mmol) of 5-chloroindole in 10 mL of dry dimethylformamide is reacted with 0.260 g (6.60 mmol) of 60% sodium hydride dispersed in mineral oil at room temperature for 4 h. 0.411 mL (6.60 mmol) of iodomethane is added and the reaction is allowed to stir at room temperature 15 h. The reaction is quenched with 50 mL of water, extracted 3×50 mL of ethyl acetate, dried (MgSO$_4$), and concentrated. The crude product is purified by chromatography using hexanes:ethyl acetate as a solvent system to obtain 0.545 g of the title compound, 50% yield. MS, ES=166.0 (M+1); $^1$H NMR (DMSO-d6) δ 7.567-7.564 (m, 1H); 7.453-7.431 (m, 1H); 7.381-7.374 (m, 1H); 7.131-7.105 (m, 1H); 6.393-6.386 (m, 1H); 2.768 (s, 3H) ppm.

B. Boronic Acid, 5-chloro-1-methyl-indol-2-yl

In an oven dried, nitrogen purged, 3 neck, 50 mL round bottom flask, 0.545 g (3.29 mmol) of 5-chloro-1-methylindole in 10 mL of dry tetrahydrofuran is cooled to −78° C. 2.06 mL (3.29 mmol) of 1.6M n-butyllithium in hexanes is added and the mixture is stirred at −78° C. After 3 h, 0.442 mL (3.95 mmol) of trimethylborate is added. The mixture is allowed to stir overnight and the bath is allowed to expire. Reaction is quenched with 30 mL of dilute hydrochloric acid or until acidic. The layers are separated and the aqueous is extracted 3×50 mL of ethyl acetate, dried (MgSO$_4$), and concentrated under vacuum. The crude product is triturated in hexanes to obtain 0.216 g of the title compound, 31% yield. MS, ES=208.1 (M−1).

C. 8-(1-Ethyl-propyl)-2,6-dimethyl-3-(5-chloro-1-methyl-indol-2-yl)-imidazo[1,2-b]pyridazine To a microwave pressure tube is added 0.060 g (0.175 mmol) of 8-(1-ethyl-propyl)-3-iodo-2,6-dimethyl-imidazo [1,2-b]pyridazine, 0.092 g (0.437 mmol) of boronic acid, 5-chloro-1-methyl-indol-2-yl, 0.120 g (0.105 mmol) of Pd(PPh$_3$)$_4$, 0.218 mL (0.437 mmol) of 2M aqueous sodium carbonate, and 1.6 mL of 7:3:2 DME:H$_2$O:EtOH and heated at 160° C. for 30 minutes and again at 160° C. for 10 minutes. The reaction mixture is partitioned between 20 mL of ethyl acetate and 20 mL of water. The layers are separated and the aqueous is extracted 3×25 mL of ethyl acetate, dried (MgSO$_4$), and concentrated under vacuum. The crude mixture is purified by chromatography using hexanes:ethyl acetate as a solvent system. The product containing fractions are combined to obtain 0.020 g of the title compound, 30% yield. MS, ES+=381.1 (M+1); $^1$H NMR (DMSO-d6) δ 7.547-7.526 (m, 2H); 7.216-7.172 (m, 1H); 7.020 (s, 1H); 6.679 (s, 1H); 3.535 (s, 3H); 3.105 (m, 1H); 2.423 (s, 3H); 2.379 (s, 3H); 1.847-1.769 (m, 4H); 0.797-0.759 (m, 6H) ppm.

Example 7

Preparation of 8-(1-ethyl-propyl)-2,6-dimethyl-3-(4-fluoro-1-methyl-indol-2-yl)-imidazo[1,2-b]pyridazine

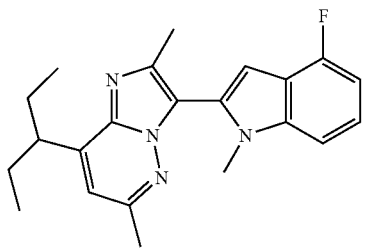

A. 4-Fluoro-1-methylindole

In an oven dried, nitrogen purged, 3 neck, 50 mL round bottom flask, 1.00 g (7.40 mmol) of 4-fluoroindole in 10 mL of dry dimethylformamide is reacted with 0.335 g (8.88 mmol) of 60% sodium hydride dispersed in mineral oil at room temperature for 4 h. 0.553 mL (8.88 mmol) of iodomethane is added and the reaction is allowed to stir at room temperature overnight, 15 h. The reaction is quenched with 50 mL of water, extracted 3×50 mL of ethyl acetate, dried (MgSO$_4$), and concentrated. The crude product is purified by chromatography using hexanes:ethyl acetate as a solvent system to obtain 0.675 g of the title compound, 61% yield. MS, ES+=150.1; $^1$H NMR (DMSO-d6) δ 7.358-7.350 (d, J=3.083, 1H); 7.279-7.258 (d, J=8.368, 1H); 7.126-7.073 (m, 1H); 6.806-6.760 (m, 1H); 6.459-6.452 (d, J=3.083, 1H); 3.787 (s, 1H) ppm.

B. Boronic Acid, 4-fluoro-1-methyl-indol-2-yl

In an oven dried, nitrogen purged, 3 neck, 50 mL round bottom flask, 0.675 g (4.53 mmol) of 4-fluoro-1-methylindole in 7 mL of dry tetrahydrofuran is cooled to −78° C. 5.66 mL (9.06 mmol) of 1.6M n-butyllithium in hexanes is added and the mixture is stirred at −78° C. After 3 h, 1.02 mL (9.06 mmol) of trimethylborate is added. The mixture is allowed to stir overnight and the bath is allowed to expire. Reaction is quenched with 30 mL of dilute hydrochloric acid or until acidic. The layers are separated and the aqueous is extracted 3×50 mL of ethyl acetate, dried (MgSO$_4$), and concentrated under vacuum. The crude product is triturated in hexanes to obtain 0.170 g of the title compound, 13% yield. MS, ES−=192.2 (M−1).

C. 8-(1-Ethyl-propyl)-2,6-dimethyl-3-(4-fluoro-1-methyl-indol-2-yl)-imidazo[1,2-b]pyridazine To a microwave pressure tube is added 0.060 g (0.175 mmol) of 8-(1-ethyl-propyl)-3-iodo-2,6-dimethyl-imidazo [1,2-b]pyridazine, 0.084 g (0.437 mmol) of boronic acid, 4-fluoro-1-methyl-indol-2-yl, 0.120 g (0.105 mmol) of Pd(PPh$_3$)$_4$, 0.218 mL (0.437 mmol) of 2M aqueous sodium carbonate, and 1.6 mL of 7:3:2 DME:H$_2$O:EtOH and heated at 160° C. for 30 minutes two times. The reaction mixture is partitioned between 20 mL of ethyl acetate and 20 mL of water. The layers are separated and the aqueous is extracted 3×25 mL of ethyl acetate, dried (MgSO$_4$), and concentrated under vacuum. The crude mixture is purified by chromatography using hexanes:ethyl acetate as a solvent system. The product containing fractions are combined to obtain 0.035 g of the title compound, 55% yield. MS, ES+=365.1 (M+1); $^1$H NMR (DMSO-d6) δ 7.392-7.371 (d, 1H); 7.219-7.167 (m, 1H); 7.016 (s, 1H); 6.895-6.850 (m, 1H); 6.721 (s, 1H); 3.526 (s, 3H); 3.102-3.089 (m, 1H); 2.424 (s, 3H); 2.375 (s, 3H); 1.882-1.752 (m, 4H); 0.795-0.757 (m, 6H) ppm.

Example 8

Preparation of 8-(1-ethyl-propyl)-2,6-dimethyl-3-(5-fluoro-1-methyl-indol-2-yl)-imidazo[1,2-b]pyridazine

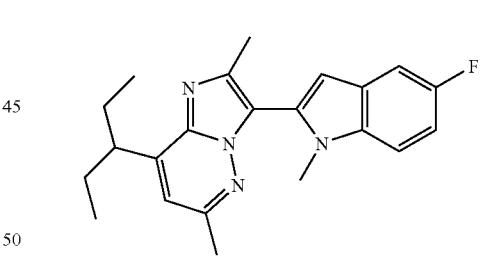

A. 5-Fluoro-1-methylindole

In an oven dried, nitrogen purged, 3 neck, 50 mL round bottom flask, 1.00 g (7.40 mmol) of 5-fluoroindole in 10 mL of dry dimethylformamide is reacted with 0.335 g (8.88 mmol) of 60% sodium hydride dispersed in mineral oil at room temperature for 4 h. 0.553 mL (8.88 mmol) of iodomethane is added and the reaction is allowed to stir at room temperature overnight, 15 h. The reaction is quenched with 50 mL of water, extracted 3×50 mL of ethyl acetate, dried (MgSO$_4$), and concentrated. The crude product is purified by chromatography using hexanes:ethyl acetate as a solvent system to obtain 1.00 g of the title compound, 91% yield. MS, ES+218.2 (M+1); $^1$H NMR (DMSO-d6) δ 7.428-7.366 (m, 1H); 7.293-7.262 (m, 1H); 6.988-6.937 (m, 1H); 6.384-6.376 (m, 1H); 3.766 (s, 3H) ppm.

B. Boronic Acid, 5-fluoro-1-methyl-indol-2-yl

In an oven dried, nitrogen purged, 3 neck, 50 mL round bottom flask, 1.00 g (6.70 mmol) of 5-fluoro-1-methylindole in 15 mL of dry tetrahydrofuran is cooled to −78° C. 8.38 mL (13.40 mmol) of 1.6M n-butyllithium in hexanes is added and the mixture is stirred at −78° C. After 3 h, 1.57 mL (14.07 mmol) of trimethylborate is added. The mixture is allowed to stir overnight and the bath is allowed to expire. Reaction is quenched with 30 mL of dilute hydrochloric acid or until acidic. The layers are separated and the aqueous is extracted 3×50 mL of ethyl acetate, dried (MgSO$_4$), and concentrated under vacuum. The crude product is triturated in hexanes to obtain 0.170 g of the title compound, 13% yield. MS, ES−=192.2 (M−1).

C. 8-(1-Ethyl-propyl)-2,6-dimethyl-3-(5-fluoro-1-methyl-indol-2-yl)-imidazo[1,2-b]pyridazine To a microwave pressure tube is added 0.060 g (0.175 mmol) of 8-(1-ethyl-propyl)-3-iodo-2,6-dimethyl-imidazo[1,2-b]pyridazine, 0.085 g (0.437 mmol) of boronic acid, 5-fluoro-1-methyl-indol-2-yl, 0.120 g (0.105 mmol) of Pd(PPh$_3$)$_4$, 0.218 mL (0.437 mmol) of 2M aqueous sodium carbonate, and 1.6 mL of 7:3:2 DME:H$_2$O:EtOH and heated at 160° C. for 30 minutes two times. The reaction mixture is partitioned between 20 mL of ethyl acetate and 20 mL of water. The layers are separated and the aqueous is extracted 3×25 mL of ethyl acetate, dried (MgSO$_4$), and concentrated under vacuum. The crude mixture is purified by chromatography using hexanes:ethyl acetate as a solvent system. The product containing fractions are combined to obtain 0.008 g of the title compound, 13% yield. MS, ES+=365.1 (M+1); $^1$H NMR (DMSO-d6) δ 7.559-7.522 (m, 1H); 7.388-7.351 (m, 1H); 7.098-7.052 (m, 1H); 7.013 (s, 1H); 6.644 (s, 1H); 3.520 (s, 3H); 3.110 (m, 1H); 2.428 (m, 3H); 2.369 (s, 3H); 1.891-1.682 (m, 4H); 0.799-0.763 (m, 6H) ppm.

Example 9

Preparation of 8-(1-ethyl-propyl)-2,6-dimethyl-3-(6-fluoro-1-methyl-indol-2-yl)-imidazo[1,2-b]pyridazine

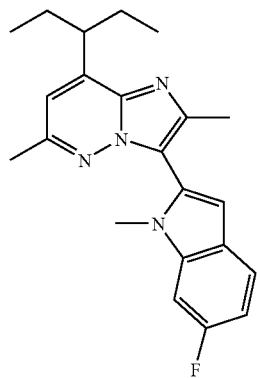

A. 6-Fluoro-1-methylindole

In an oven dried, nitrogen purged, 3 neck, 50 mL round bottom flask, 1.00 g (7.40 mmol) of 6-fluoroindole in 10 mL of dry dimethylformamide is reacted with 0.335 g (8.88 mmol) of 60% sodium hydride dispersed in mineral oil at room temperature for 4 h. 0.553 mL (8.88 mmol) of iodomethane is added and the reaction is allowed to stir at room temperature 15 h. The reaction is quenched with 50 mL of water, extracted 3×50 mL of ethyl acetate, dried (MgSO$_4$), and concentrated. The crude product is purified by chromatography using hexanes:ethyl acetate as a solvent system to obtain 0.525 g of the title compound, 48% yield. MS, ES−; $^1$H NMR (DMSO-d6) δ 7.523-7.488 (m, 1H); 7.300-7.292 (m, 2H); 6.852-6.825 (m, 1H); 6.411-6.409 (m, 1H); 3.767 (s, 3H) ppm.

C. Boronic Acid, 6-fluoro-1-methyl-indol-2-yl

In an oven dried, nitrogen purged, 3 neck, 50 mL round bottom flask, 0.525 g (3.52 mmol) of 6-fluoro-1-methylindole in 8 mL of dry THF is cooled to −78° C. 4.40 mL (7.04 mmol) of 1.6N n-butyllithium in hexanes is added and the mixture is stirred at −78° C. After 3 h, 0.828 mL (7.39 mmol) of trimethylborate is added. The mixture is allowed to stir overnight and the bath is allowed to expire. Reaction is quenched with 20 mL of dilute hydrochloric acid or until acidic. The layers are separated and the aqueous is extracted 3×25 mL of ethyl acetate, dried (MgSO$_4$), and concentrated under vacuum. The crude product is triturated in hexanes to obtain 0.127 g of the title compound, 19% yield. MS, ES+=194.1 (M+1) ES−=192.1 (M−1).

C. 8-(1-Ethyl-propyl)-2,6-dimethyl-3-(6-fluoro-1-methyl-indol-2-yl)-imidazo[1,2-b]pyridazine To a microwave pressure tube is added 0.060 g (0.175 mmol) of 8-(1-ethyl-propyl)-3-iodo-2,6-dimethyl-imidazo[1,2-b]pyridazine, 0.085 g (0.437 mmol) of boronic acid, 6-fluoro-1-methyl-indol-2-yl, 0.120 g (0.105 mmol) of Pd(PPh$_3$)$_4$, 0.218 mL (0.437 mmol) of 2M aqueous sodium carbonate, and 1.6 mL of 7:3:2 DME:H$_2$O:EtOH and heated at 160° C. for 30 minutes two times. The reaction mixture is partitioned between 20 mL of ethyl acetate and 20 mL of water. The layers are separated and the aqueous is extracted 3×25 mL of ethyl acetate, dried (MgSO$_4$), and concentrated under vacuum. The crude mixture is purified by chromatography using hexanes:ethyl acetate as a solvent system. The product containing fractions are combined to obtain 0.016 g of the title compound, 25% yield. MS, ES+=365.1 (M+1); $^1$H NMR (DMSO-d6) δ 7.423-7.402 (m, 2H); 7.017-6.968 (m, 3H); 6.724-6.718 (d, 1H); 3.647 (s, 3H); 3.114-3.084 (m, 1H); 2.433 (s, 3H); 2.368 (s, 3H); 1.879-1.750 (m, 4H); 0.790-0.754 (m, 6H) ppm.

Example 10

Preparation of 8-(1-ethyl-propyl)-2,6-dimethyl-3-(1,5,6-trimethyl-benzimidazol-2-yl)-imidazo[1,2-b]pyridazine

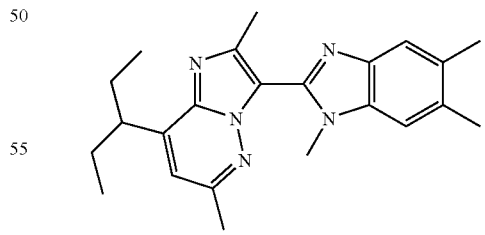

A. Boronic Acid, 8-(1-ethyl-propyl)-2,6-dimethyl-imidazo[1,2-b]pyridazine-3-yl In an oven dried nitrogen purged 3 neck 50 mL round bottom flask, 1.00 g (2.91 mmol) of 8-(1-ethyl-propyl)-3-iodo-2,6-dimethyl-imidazo[1,2-b]pyridazine in 60 mL of dry THF is cooled to −78° C. 4.12 mL (7.00 mmol) of 1.7M t-butyllithium in hexanes is added and reaction is stirred at −78° C. for 1 h. 0.818 mL (7.30 mmol) of trimethyl borate is added and reaction is followed by MS and TLC (1:1 hexane: ethylacetate) See indication of the title compound by MS. Allow to stir for an additional hour, quench with 1N hydrochloric acid, dilute with ethyl acetate, separate layers, extract aqueous 3×100 mL ethyl acetate, dry (MgSO$_4$), and concentrated. Triturate in hexanes and filter off solid to give the title compound 6.4 g (53%), MS, ES+=262.2 (M+1).

B. 1,5,6-Trimethylbenzimidazole

In an oven dried nitrogen purged 3 neck 50 mL round bottom flask, 5.00 g (34.20 mmol) of 5,6-dimethylbenzimidazole in 20 mL of dry dimethylformamide is reacted with 1.51 g (37.62 mmol) of sodium hydride at room temperature for 4 h. 2.34 mL (37.62 mmol) of iodomethane is added and reaction is allowed to stir at room temperature overnight. Reaction is quenched with water, layers are separated, extract aqueous 3×50 mL ethyl acetate, dry (MgSO$_4$), and concentrate. The crude mixture is purified by chromatography using dichloromethane: methanol as a solvent system. Product containing fractions are combined to obtain 3.75 g of the title compound, 68% yield. MS, ES+=161.1. H$^1$NMR (CDCl$_3$) δ 7.98 (s, 1H); 7.37 (s, 1H); 7.29 (s, 1H); 3.74 (s, 3H); 2.31 (s, 3H); 2.28 (s, 3H) ppm C. 1,5,6-Trimethyl-2-iodo-benzimidazole In an oven dried nitrogen purged 3 neck 50 mL round bottom flask, 1.00 g (0.624 mmol) of 1,5,6-trimethylbenzimidazole in 2 mL of dry tetrahydrofuran is cooled to −78° C. 0.881 mL (1.498 mmol) of 1.7 M t-butyllithium in hexanes is added and the reaction mixture is stirred at −78° C. for 1 h. 0.154 g (0.686 mmol) of NIS in 2 mL of dry tetrahydrofuran is added. Reaction is removed from bath and stirred at room temperature for 1 hour, quenched with saturated aqueous solution of ammonium chloride, and diluted with dichloromethane. The layers are separated, the aqueous is extracted 3×25 mL dichloromethane, dried (MgSO$_4$), and concentrated. The crude mixture is purified by chromatography using hexanes:ethyl acetate as a solvent system. The product containing fractions are combined to obtain 0.055 g of the title compound, 31% yield. MS, ES+=287.0 (M+1); $^1$H NMR (DMSO-d6) δ 7.337-7.324 (d, 2H); 3.684 (s, 3H); 2.309 (s, 3H); 2.275 (s, 3H) ppm.

D. 8-(1-Ethyl-propyl)-2,6-dimethyl-3-(1,5,6-trimethyl-benzimidazol-2-yl)-imidazo[1,2-b]pyridazine To a microwave pressure tube is added 0.100 g (0.383 mmol) of boronic acid, 8-(1-ethyl-propyl)-2,6-dimethyl-imidazo[1,2-b]pyridazine-3-yl, 0.025 g (0.087 mmol) of 1,5,6-Trimethyl-2-iodo-benzimidazole, 0.050 g (0.435 mmol) of Pd(PPh$_3$)$_4$, 0.109 mL (0.21 mmol) of 2M aqueous sodium carbonate, and 2.5 mL 7:3:2 DME:H$_2$O:EtOH and heated at 160° C. for 30 min. The reaction mixture is partitioned between 75 mL of ethyl acetate and 75 mL of water. The layers are separated and the aqueous is extracted 3×50 mL of ethyl acetate, dried (MgSO$_4$), and concentrated under vacuum. The crude mixture is purified by chromatography using 1% methanol:dichloromethane as a solvent system. The product containing fractions are combined to obtain 0.010 g of the title compound, 30% yield. MS, ES+=376.3 (M+1); $^1$H NMR (DMSO-d6) δ 7.491 (s, 1H); 7.416 (s, 1H); 7.063 (s, 1H); 3.586 (s, 3H); 3.117 (m, 1H); 2.450 (s, 3H); 2.401 (s, 3H); 2.378 (s, 3H); 2.338 (s, 3H); 1.858-1.783 (s, 4H); 0.803-0.766 (m, 6H) ppm.

Example 11

Preparation of 8-(1-ethyl-propyl)-2,6-dimethyl-3-(5-methoxy-1-methyl-benzimidazol-2-yl)-imidazo[1,2-b]pyridazine

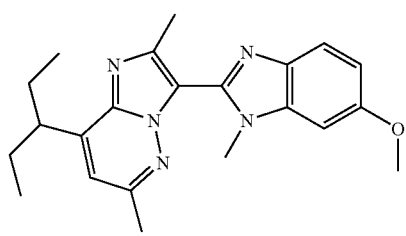

A. 5-Methoxy-1-methylbenzimidazole

In an oven dried nitrogen purged 3 neck 50 mL round bottom flask, 5.00 g (37.75 mmol) of 5-methoxybenzimidazole in 20 mL of dry dimethylformamide is reacted with 1.66 g (41.53 mmol) of sodium hydride at room temperature for 4 h. 2.58 mL (41.53 mmol) of iodomethane is added and reaction is allowed to stir at room temperature overnight. Reaction is quenched with water, layers are separated, extracted aqueous 3×50 mL ethyl acetate, dried (MgSO$_4$), and concentrated. The crude mixture is purified by chromatography using dichloromethane: methanol as a solvent system. Product containing fractions are combined to obtain 3.50 g of the title compound which is used as is, 57% yield.

B. 2-Iodo-5-methoxy-1-methylbenzimidazole

In an oven dried nitrogen purged 3 neck 50 mL round bottom flask, 0.500 g (1.75 mmol) of 5-methoxy-1-methyl-benzimidazole in 10 mL of dry THF is cooled to −78° C. 2.47 mL (4.20 mmol) of 1.7 M t-butyllithium in hexanes is added and the reaction mixture is stirred at −78° C. for 1 h. 0.472 g (2.1 mmol) of NIS in 10 mL of dry tetrahydrofuran is added. Reaction is removed from bath and stirred at room temperature for 1 hour, quenched with saturated aqueous solution of ammonium chloride, and diluted with dichloromethane. The layers are separated, the aqueous is extracted 3×50 mL dichloromethane, dried (MgSO$_4$), and concentrated. The crude mixture is purified by chromatography using hexanes: ethyl acetate as a solvent system. The product containing fractions are combined to obtain 0.125 g of the title compound, 25% yield. MS, ES+=289.0 (M+1); $^1$H NMR (DMSO-d$_6$) δ 7.439-7.417 (d, 1H); 7.147-7.141 (m, 1H); 6.771-6.743 (m, 1H); 3.794 (s, 3H); 3.707 (s, 3H) ppm.

C. 8-(1-Ethyl-propyl)-2,6-dimethyl-3-(5-methoxy-1-methyl-benzimidazol-2-yl)-imidazo[1,2-b]pyridazine To a microwave pressure tube is added 0.100 g (0.383 mmol) of boronic acid, 8-(1-ethyl-propyl)-2,6-dimethyl-imidazo[1,2-b]pyridazine-3-yl, 0.050 g (0.174 mmol) of 2-iodo-5-methoxy-1-methylbenzimidazole, 0.050 g (0.435 mmol) of Pd(PPh$_3$)$_4$, 0.109 mL (0.218 mmol) of 2M aqueous sodium carbonate, and 2.5 mL 7:3:2 DME:H$_2$O:EtOH and heated at 160° C. for 30 min. The reaction mixture is partitioned between 75 mL of ethyl acetate and 75 mL of water. The layers are separated and the aqueous is extracted 3×50 mL of ethyl acetate, dried (MgSO$_4$), and concentrated under vacuum. The crude mixture is purified by chromatography using 1% methanol/dichloromethane as a solvent system. The product containing fractions are combined to obtain 0.020 g of the title compound, 30% yield. MS, ES+=378.2 (M+1); $^1$H NMR (DMSO-d6) δ 7.607-7.587 (m, 1H); 7.205 (s, 1H); 7.065 (s, 1H); 6.895-6.872 (m, 1H); 3.846 (s, 3H); 3.603 (s, 3H); 3.121 (m, 1H); 2.454-2.456 (m, 3H); 2.405 (s, 3H); 1.843-1.784 (m, 4H); 0.806-0.769 (m, 6H) ppm.

Example 12

Preparation of 8-(1-ethyl-propyl)-2,6-dimethyl-3-(1-methyl-benzimidazol-2-yl)-imidazo[1,2-b]pyridazine

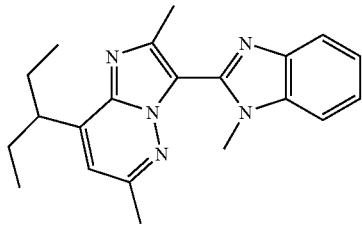

A. 2-Iodo-1-methylbenzimidazole

In an oven dried nitrogen purged 3 neck 100 mL round bottom flask, 1.00 g (7.57 mmol) of 1-methylbenzimidazole in 20 mL of dry tetrahydrofuran is cooled to –78° C. 10.69 mL (18.17 mmol) of 1.7 M t-butyllithium in hexanes is added and the reaction mixture is stirred at –78° C. for 1 h. 2.55 g (11.36 mmol) of NIS in 20 mL of dry tetrahydrofuran is added. Reaction is removed from bath and stirred at room temperature for 1 hour, quenched with saturated aqueous solution of ammonium chloride, and diluted with dichloromethane. The layers are separated, the aqueous is extracted 3×100 mL dichloromethane, dried (MgSO$_4$), and concentrated. The crude mixture is purified by chromatography using hexanes:ethyl acetate as a solvent system. The product containing fractions are combined to obtain 0.400 g of the title compound, 21% yield. MS, ES+=259.0 (M+1); $^1$H NMR (DMSO-d$_6$) δ 7.580-7.552 (m, 2H); 7.228-7.129 (m, 2H); 3.750 (s, 3H) ppm.

B. 8-(1-Ethyl-propyl)-2,6-dimethyl-3-(1-methyl-benzimidazol-2-yl)-imidazo[1,2-b]pyridazine To a microwave pressure tube is added 0.100 g (0.383 mmol) of boronic acid, 8-(1-ethyl-propyl)-2,6-dimethyl-imidazo[1,2-b]pyridazine-3-yl, 0.040 g (0.153 mmol) of 2-iodo-1-methylbenzimidazole, 0.106 g (0.092 mmol) of Pd(PPh$_3$)$_4$, 0.192 mL (0.383 mmol) of 2M aqueous sodium carbonate, and 2.5 mL 7:3:2 DME:H$_2$O:EtOH and heated at 160° C. for 40 min. The reaction mixture is partitioned between 75 mL of ethyl acetate and 75 mL of water. The layers are separated and the aqueous is extracted 3×50 mL of ethyl acetate, dried (MgSO$_4$), and concentrated under vacuum. The crude mixture is purified by chromatography using hexanes:ethyl acetate as a solvent system. The product containing fractions are combined to obtain 0.025 g of the title compound, 47% yield. MS, ES+=348.3 (M+1); $^1$H NMR (DMSO-d6) δ 7.740-7.647 (m, 2H); 7.357-7.256 (m, 2H); 7.081 (s, 1H); 3.652 (s, 3H); 3.123-3.110 (m, 1H); 2.456 (s, 3H); 2.425 (s, 3H); 1.897-1.771 (m, 4H); 0.808-0.771 (m, 6H) ppm.

Example 13

Preparation of 8-(1-ethyl-propyl)-2,6-dimethyl-3-(5-methoxy-3-methyl-benzo[b]thiophen-2-yl)-imidazo[1,2-b]pyridazine

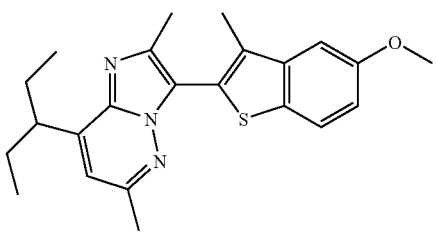

In an oven dried, nitrogen purged, 3 neck, 50 mL round bottom flask, 0.014 g (0.197 mmol) of potassium methoxide and 0.005 mL (0.013 mmol) of tris[2-(2-methoxyethoxy)ethyl]amine are heated at 150° C. and stirred vigorously for 5 minutes. 0.050 g (0.131 mmol) of 8-(1-ethyl-propyl)-2,6-dimethyl-3-(5-fluoro-3-methyl-benzo[b]thiophen-2-yl)-imidazo[1,2-b]pyridazine is added and the reaction is followed by TLC (2:1 Hexanes/Ethyl Acetate) and MS. After 4 h, the reaction mixture is diluted with 20 mL dichloromethane and 20 mL of water. The layers are separated and the aqueous is extracted 3×50 mL of dichloromethane, dried (MgSO$_4$), and concentrated under vacuum. The crude mixture is purified by chromatography using hexanes:ethyl acetate as a solvent system. Combined fractions to obtain 0.015 g of the title compound, 29% yield. MS, ES+=394.2 (M+1); H$^1$NMR (DMSO-d6) δ 7.863-7.842 (d, J=8.368, 1H); 7.327-7.321 (m, 1H); 7.076-7.049 (m, 1H); 6.991 (s, 1H); 3.857 (s, 3H); 3.094 (m, 1H); 2.477 (s, 3H); 2.350 (s, 3H); 2.180 (s, 3H); 1.853-1.760 (m, 4H); 0.793-0.757 (m, 6H) ppm.

Example 14

Preparation of 8-(1-ethyl-propyl)-2,6-dimethyl-3-(5-ethoxy-3-methyl-benzo[b]thiophen-2-yl)-imidazo[1,2-b]pyridazine

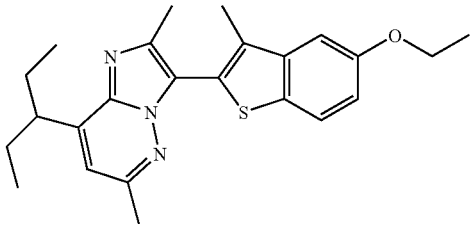

In an oven dried, nitrogen purged, 3 neck, 50 mL round bottom flask, 0.017 g (0.197 mmol) of potassium ethoxide and 0.021 mL (0.067 mmol) of tris[2-(2-methoxyethoxy)ethyl]amine are heated at 150° C. and stirred vigorously for 5 min. 0.050 g (0.131 mmol) of 8-(1-ethyl-propyl)-2,6-dimethyl-3-(5-fluoro-3-methyl-benzo[b]thiophen-2-yl)-imidazo[1,2-b]pyridazine is added and reaction is followed by TLC (5% acetonitrile:dichloromethane) and MS. After 15 h, the reaction mixture is diluted with 20 mL of dichloromethane and 20 mL of water. The layers are separated and the aqueous is extracted 3×50 mL of dichloromethane, dried (MgSO$_4$), and concentrated under vacuum. The crude mixture is purified by chromatography using acetonitrile:dichloromethane as solvent system. Combine fractions to obtain 0.003 g of the title compound, 6% yield. MS, ES+=408 (M+1); $^1$H NMR (DMSO-d6) δ 7.850 (d, J=8.367 Hz, 1H); 7.306 (s, 1H); 7.037 (d, 1H); 6.991 (s, 1H); 4.137-4.119 (m, 2H); 3.097 (m, 1H); 2.424 (s, 3H); 2.345 (s, 3H); 2.165 (s, 3H); 1.831-1.777 (m, 4H); 1.384-1.350 (m, 3H); 0.792-0.755 (m, 6H) ppm.

Example 15

Preparation of 8-(1-ethyl-propyl)-2,6-dimethyl-3-(5-fluoro-3-methyl-benzo[b]thiophen-2-yl)-imidazo[1,2-b]pyridazine, Methanesulfonate Salt 8-(1-Ethyl-propyl)-2,6-dimethyl-3-(5-fluoro-3-methyl-benzo[b]thiophen-2-yl)-imidazo[1,2-b]pyridazine (500.5 mg, 1.31 mmol, 1.0 equiv) is dissolved in EtOAc (4 mL, warming is required to obtain complete solution) and the solution is treated with methanesulfonic acid (85 μL, 1.31 mmol, 1.0 equiv) by syringe. The resultant solution is stirred magnetically at RT and is seeded with authentic 8-(1-ethyl-propyl)-2,6-dimethyl-3-(5-fluoro-3-methyl-benzo[b]thiophen-2-yl)-imidazo[1,2-b]pyridazine, methane-sulfonate salt, resulting in rapid precipitation of a solid. The mixture is stirred at RT for 3 h, and the white solid is filtered, washed with EtOAc and dried to provide the title compound as a white powder (609 mg, 95%).

Example 16

Preparation of 8-(1-ethyl-propyl)-2,6-dimethyl-3-{2,6-dimethyl-8-iodo-imidazo[1,2-b]pyridazin-3-yl}imidazo[1,2-b]pyridazine

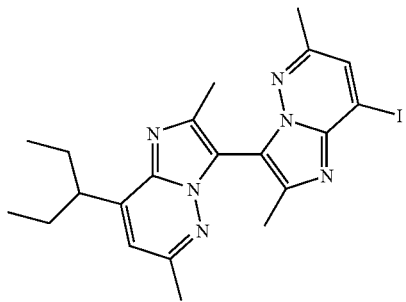

A. 2,6-Dimethyl-imidazo[1,2-b]pyridazine

A solution of 3-amino-6-methyl-pyridazine (4.53 g, 41.58 mmol) in EtOH (60 mL) is treated with chloroacetone (3.5 mL, 43.66 mmol). The reaction is refluxed overnight. While it is hot, NaHCO$_3$ (8.7 g, 103.9 mmol) is added in portions. The resulting mixture is refluxed for 2 h. It is cooled to rt and filtered through silical gel, washed with EtOAc, and concentrated. Purification of the crude material by chromatography gives the title compound (3.1 g, 21.11 mmol, 51%). $^1$H NMR (CDCl$_3$): δ 2.49 (s, 3H), 2.55 (s, 3H), 6.84 (d, J=9.3 Hz, 1H), 7.64 (s, 1H), 7.70 (d, J=9.3 Hz, 1H) ppm. ES-MS (m/z): calcd for C$_8$H$_9$N$_3$ (M+H)$^+$: 148.2. found: 148.1.

B. 8-(1-Ethyl-propyl)-2,6-dimethyl-3-{2,6-dimethyl-imidazo[1,2-b]pyridazin-3-yl}imidazo[1,2-b]pyridazine A mixture containing 2,6-dimethyl-imidazo[1,2-b]pyridazine (0.44 g, 2.99 mmol), 8-(1-ethyl-propyl)-3-iodo-2,6-dimethyl-imidazo[1,2-b]pyridazine (1.03 g, 2.99 mmol), Pd(OAc)$_2$ (34 mg, 0.15 mmol), PPh$_3$ (79 mg, 0.299 mmol), Cs$_2$CO$_3$ (1.95 g, 6.0 mmol) in DMF (50 mL) is stirred under N$_2$ at 130-140° C. overnight. The reaction mixture is cooled, diluted with EtOAc (300 mL), washed with H$_2$O (3×100 mL); dried (Na$_2$SO$_4$); filtered and concentrated. Purification of the resulting crude material by chromatography yields the title compound (0.37 g, 1.02 mmol, 34%). $^1$H NMR (CDCl$_3$): δ 0.92 (t, J=7.1 Hz, 6H), 1.80-1.95 (m, 4H), 2.43 (s, 3H), 2.44 (s, 3H), 2.46 (s, 3H), 2.50 (s, 3H), 3.35-3.43 (m, 1H), 6.69 (s, 1H), 6.92 (d, J=9.2 Hz, 1H), 7.82 (d, J=1H) ppm. ES-MS (m/z): calcd for C$_{21}$H$_{26}$N$_6$ (M+H)$^+$: 363.5. found: 363.3.

C. 8-(1-Ethyl-propyl)-2,6-dimethyl-3-{2,6-dimethyl-8-iodo-imidazo[1,2-b]pyridazin-3-yl}imidazo[1,2-b]pyridazine A solution of 8-(1-ethyl-propyl)-2,6-dimethyl-3-{2,6-dimethyl-imidazo[1,2-b]pyridazin-3-yl}imidazo[1,2-b]pyridazine (0.15 g, 0.43 mmol) in THF (5 mL) is cooled to –78 C. 2.0 M of LDA (0.26 mL, 0.51 mmol) is added dropwise. A solution of 12 (0.22 g, 0.85 mmol) in THF (3 mL) at –78 is then added to the reaction. It is than warmed to –50° C. gradually; quenched with sat. NH$_4$Cl$_4$ (4 mL), warmed to rt. It is diluted with H$_2$O (15 mL), extracted with EtOAc (3×25 mL); dried (Na$_2$SO$_4$), filtered and concentrated. Purification of the crude material by chromatography gives the title compound (55.8 mg, 0.11 mmol, 27%). $^1$H NMR (CDCl$_3$): δ 0.91 (t, J=7.5 Hz, 6H), 1.80-1.92 (m, 4H), 2.42 (s, 3H), 2.44 (s, 3H), 2.45 (s, 3H), 2.47 (s, 3H), 3.34-3.43 (m, 1H), 6.70 (s, 1H), 7.46 (s, 1H) ppm. ES-MS (m/z): calcd for C$_{21}$H$_{25}$IN$_6$ (M+H)$^+$: 489.5. found: 489.1.

Example 17

Preparation of 8-(1-ethyl-propyl)-2,6-dimethyl-3-{2,6-dimethyl-8-(1-methylethyl)-imidazo[1,2-b]pyridazin-3-yl}imidazo[1,2-b]pyridazine

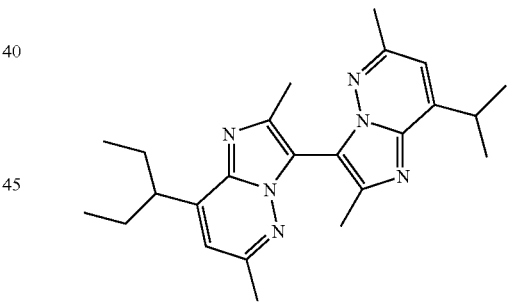

A. N-[4-(1-methylethyl)-6-methyl-pyridazin-3-yl]-2,2-dimethyl-propionamide

A solution of 2,2-dimethyl-N-(6-methyl-pyridazin-3-yl)-propionamide (4.00 g, 20.73 mmol) in THF (50 mL) is stirred at 0° C. 2.0 M iPrMgBr (46.6 mL, 93.26 mmol) is then added dropwise. The reaction is stirred at 0° C. for 30 min, then it is refluxed for 2 h. It is cooled to rt, poured into ice-H$_2$O; sat. NH$_4$Cl is added and extracted with EtOAc; dried with Na$_2$SO$_4$, filtered and concentrated. The crude material is dissolved in CH$_2$Cl$_2$ (100 mL), treated with 12 (5.8 g, 22.80 mmol) and stirred at rt for 2 h. The reaction is diluted with CH$_2$Cl$_2$ (100 mL), washed with 5% Na$_2$SO$_3$ (3×100 mL); dried with Na$_2$SO$_4$, filtered and concentrated. Purification of the crude material gives the title compound (1.38 g, 5.87 mmol, 28%). ES-MS (m/z): calcd for C$_{13}$H$_{21}$N$_3$O (M+H)$^+$: 236.3. found: 236.1.

B. 3-Amino-4-(1-methylethyl)-6-methyl-pyridazine

N-[4-(1-methylethyl)-6-methyl-pyridazin-3-yl]-2,2-dimethyl-propionamide (1.38 g, 5.87 mmol) is treated with HClO (10 mL), and refluxed for 3 h. It is cooled to rt, poured into ice-$H_2O$ (30 mL); extracted with EtOAc (2×30 mL). The aqueous layer is treated with 5 M NaOH to adjust the pH to 8-9. It is then extracted with EtOAc (3×50 mL); dried with $Na_2SO_4$, filtered and concentrated gives the title compound (0.59 g, 3.91 mmol, 67%). %). $^1$H NMR (CDCl$_3$): δ 1.28 (d, J=7.0 Hz, 6H), 2.51 (s, 3H), 2.72-2.83 (m, 1H), 5.95 (bs, 2H), 7.02 (s, 1H) ppm. ES-MS (m/z): calcd for $C_8H_{13}N_3$ (M+H)$^+$: 152.2. found: 152.1.

C. 8-(1-Methylethyl)-2,6-dimethyl-imidazo[1,2-b]pyridazine

Using a procedure analogous to Example 16A, from 3-amino-4-(1-methylethyl)-6-methyl-pyridazine (0.59 g, 3.91 mmol) gives the title compound (0.38 g, 2.02 mmol, 52%). $^1$H NMR (CDCl$_3$): δ 1.38 (d, J=7.1 Hz, 6H), 2.49 (s, 3H), 2.52 (s, 3H), 3.63-3.71 (m, 1H), 6.67 (s, 1H), 7.61 (s, 1H). ES-MS (m/z): calcd for $C_{11}H_{15}N_3$ (M+H)$^+$: 190.3; found: 190.1.

D. 8-(1-Ethyl-propyl)-2,6-dimethyl-3-{2,6-dimethyl-8-(1-methylethyl)-imidazo[1,2-b]pyridazin-3-yl}imidazo[1,2-b]pyridazine Using a procedure analogous to Example 16B, 8-(1-methylethyl)-2,6-dimethyl-imidazo[1,2-b]pyridazine (0.19 g, 1.01 mmol) and 8-(1-ethyl-propyl)-3-iodo-2,6-dimethyl-imidazo[1,2-b]pyridazine (0.40 g, 1.16 mmol) give the title compound (0.13 g, 0.32 mmol, 32%). $^1$H NMR (CDCl$_3$): δ 0.92 (t, J=7.5 Hz, 6H), 1.43 (d, J=1.4 Hz, 3H), 1.45 (d, J=1.4 Hz, 3H), 1.80-1.93 (m, 4H), 2.43 (s, 3H), 2.44 (s, 3H), 2.47 (s, 3H), 2.48 (s, 3H), 3.36-3.44 (m, 1H), 3.74-3.82 (m, 1H), 6.69 (s, 1H), 6.75 (s, 1H) ppm. ES-MS (m/z): calcd for $C_{24}H_{32}N_6$ (M+H)$^+$: 405.6. found: 405.3.

Example 18

Preparation of 8-(1-ethyl-propyl)-2,6-dimethyl-3-{2,6-dimethyl-8-ethyl-imidazo[1,2-b]pyridazin-3-yl}imidazo[1,2-b]pyridazine

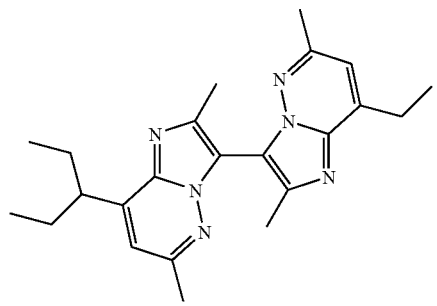

A. Preparation of N-(4-ethyl-6-methyl-pyridazin-3-yl)-2,2-dimethyl-propionamide Using a procedure analogous to Example 17A, 2,2-dimethyl-N-(6-methyl-pyridazin-3-yl)-propionamide (4.18 g, 21.65 mmol) and 3.0 M solution of EtMgBr (36 mL, 108.29 mmol) give the title compound (0.83 g, 3.76 mmol, 17%). $^1$H NMR (CDCl$_3$): δ 1.24 (t, J=7.5 Hz, 3H), 1.37 (s, 9H), 2.62 (q, J=7.5 Hz, 2H), 2.66 (s, 3H), 7.23 (s, 1H), 8.50 (s, 1H) ppm. ES-MS (m/z): calcd for $C_{12}H_{19}N_3O$ (M+H)$^+$: 222.3. found: 222.1.

B. 3-Amino-4-ethyl-6-methyl-pyridazine

Using a procedure analogous to Example 17B, N-(4-ethyl-6-methyl-pyridazin-3-yl)-2,2-dimethyl-propionamide (0.83 g, 3.76 mmol) gives the title compound 90.34 g, 2.47 mmol, 66%). $^1$H NMR (CDCl$_3$): δ 1.28 (d, J=7.0 Hz, 6H), 2.51 (s, 3H), 2.72-2.83 (m, 1H), 5.95 (bs, 2H), 7.02 (s, 1H) ppm. ES-MS (m/z): calcd for $C_8H_{13}N_3$ (M+H)$^+$: 152.2. found: 152.1.

C. 8-ethyl-2,6-dimethyl-imidazo[1,2-b]pyridazine

Using a procedure analogous to Example 16A, 3-amino-4-ethyl-6-methyl-pyridazine (0.33 g, 2.41 nmol) gives the title compound (0.31 g, 1.76 mmol, 73%). $^1$H NMR (CDCl$_3$): δ 1.32 (t, J=7.5 Hz, 3H), 2.42 (s, 3H), 2.44 (s, 3H), 2.96 (q, J=7.5 Hz, 2H), 6.59 (s, 1H), 7.54 (s, 1H). ES-MS (m/z): calcd for $C_{10}H_{13}N_3$ (M+H)$^+$: 176.2. found: 176.1.

D. 8-(1-Ethyl-propyl)-2,6-dimethyl-3-{2,6-dimethyl-8-ethyl-imidazo[1,2-b]pyridazin-3-yl}imidazo[1,2-b]pyridazine Using a procedure analogous to Example 16B, 8-ethyl-2,6-dimethyl-imidazo[1,2-b]pyridazine (0.30 g, 1.71 mmol) and 8-(1-ethyl-propyl)-3-iodo-2,6-dimethyl-imidazo[1,2-b]pyridazine (0.59 g, 1.71 mmol) give the title compound (0.25 g, 0.64 mmol, 38%). $^1$H NMR (CDCl$_3$): δ 0.90 (t, J=7.5 Hz, 6H), 1.43 (d, J=1.4 Hz, 3H), 1.78-1.92 (m, 4H), 2.42 (s, 3H), 2.43 (s, 3H), 2.44 (s, 3H), 2.45 (s, 3H), 3.11 (q, J=7.5 Hz, 2H), 3.34-3.42 (m, 1H), 6.67 (s, 1H), 6.74 (s, 1H) ppm. ES-MS (m/z): calcd for $C_{23}H_{30}N_6$ (M+H)$^+$: 391.5. found: 391.3.

Example 19

Preparation of 8-(1-ethyl-propyl)-2,6-dimethyl-3-{8-(1-ethylpropyl)-2-methyl-6-trifluoromethyl-imidazo[1,2-b]pyridazin-3-yl}imidazo[1,2-b]pyridazine

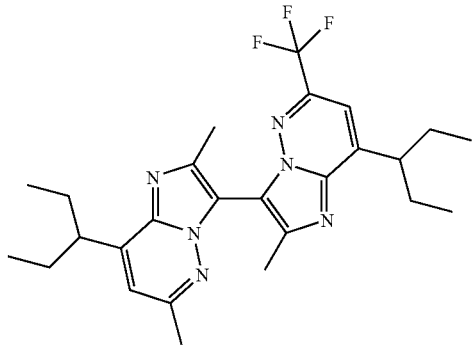

A. 2,2-Dimethyl-N-(6-trifluoromethyl-pyridazin-3-yl)-propionamideionamide

3-Chloro-6-trifluoromethyl-pyridazine (4.4 g, 24.18 mmol), prepared according to the lit. procedure (Goodman, A. J.; Stanforth, S. P.; Tarbit, B. Tetrahedron Lett. 1999, 55, 15067), is mixed with 2,2-dimethyl-propionamide (2.93 g, 29.01 mmol) in dioxane (100 mL). The mixture is treated with $Cs_2CO_3$ (11.82 g, 36.27 nmol) and BINAP (0.75 g, 1.21 mmol), then degassed with bubbling $N_2$ for 5 min. $Pd_2(dba)_3$ (1.11 g, 1.1 mmol) is added under $N_2$. The reaction is refluxed overnight. It is cooled to rt, filtered through silical gel; washed with EtOAc, and concentrated. Purification of the crude mixture by chromatography gives the title compound (1.09 g, 4.41 mmol, 18%). $^1$H NMR (CDCl$_3$): δ 1.39 (s, 9H), 7.09 (d, J=15.8 Hz, 1H), 8.68 (d, J=9.2 Hz, 1H) ppm. ES-MS (m/z): calcd for $C_{10}H_{12}F_3N_3O$ (M+H)$^+$: 248.2. found: 248.1.

B. N-[4-(1-ethyl-propyl)-6-trifluoromethyl-pyridazin-3-yl]-2,2-dimethyl-propionamide Using a procedure analogous to Example 17A, 2,2-dimethyl-N-(6-trifluoromethyl-pyridazin-3-yl)-propionamideionamide (1.00 g, 4.05 mmol) and 3-pentylmagnesium bromide (18.22 mmol), prepared from 3-pentylbromide (2.3 mL, 18.22 mmol) and Mg (0.49 g, 20.25 mmol), gives the title compound (0.60 g, 1.89 mmol, 47%). $^1$H NMR (CDCl$_3$): δ 0.84 (t, J=7.5 Hz, 6H), 1.40 (s, 9H), 1.71-1.80 (m, 4H), 2.54-2.62 (m, 1H), 7.64 (s, 1H), 8.14 (s, 1H) ppm. ES-MS (m/z): calcd for $C_{17}H_{22}F_3N_3O$ (M+H)$^+$: 318.4. found: 318.2.

C. 3-Amino-4-(1-ethyl-propyl)-6-trifluoromethyl-pyridazine

Using a procedure analogous to Example 17B, N-[4-(1-ethyl-propyl)-6-trifluoromethyl-pyridazin-3-yl]-2,2-dimethyl-propionamide (0.60 g, 1.90 mmol) gives the title compound (0.17 g, 0.73 mmol, 37%). $^1$H NMR (CDCl$_3$): δ 0.87 (t, J=7.5 Hz, 6H), 1.60-1.70 (m, 2H), 1.71-1.81 (m, 2H), 2.34-2.42 (m, 1H), 5.46 (bs, 2H), 7.28 (s, 1H) ppm. ES-MS (m/z): calcd for $C_{10}H_{14}F_3N_3$ (M+H)$^+$: 234.3. found: 234.0.

D. 8-(1-Ethyl-propyl)-2-methyl-6-trifluoromethyl-imidazo[1,2-b]pyridazine

Using a procedure analogous to Example 16A, 4-(1-ethyl-propyl)-6-trifluoromethyl-pyridazin-3-ylamine (0.17 g, 0.73 mmol) gives the title compound (0.18 g, 0.67 mmol, 92%). $^1$H NMR (CDCl$_3$): δ 0.86 (t, J=7.5 Hz, 6H), 1.78-1.92 (m, 4H), 2.55 (s, 3H), 3.35-3.41 (m, 1H), 7.02 (s, 1H), 7.03 (d, J=0.9 Hz, 1H). ES-MS (m/z): calcd for $C_{13}H_{16}F_3N_3$ (M+H)$^+$: 272.3. found: 272.1.

E. 8-(1-ethyl-propyl)-3-iodo-2-methyl-6-trifluoromethyl-imidazo[1,2-b]pyridazine A solution of 8-(1-ethyl-propyl)-2-methyl-6-trifluoromethyl-imidazo[1,2-b]pyridazine (0.18 g, 0.67 mmol) in CH$_3$CN (5 mL) is treated with NIS (0.18 g, 0.80 mmol), and stirred at rt overnight. It is diluted with EtOAc (50 mL), washed with 5% Na$_2$SO$_3$ (2×25 mL); dried (Na$_2$SO$_4$), filtered and concentrated to give the title compound (0.26 g, 0.65 mmol, 98%). $^1$H NMR (CDCl$_3$): δ 0.85 (t, J=7.0 Hz, 6H), 1.79-1.92 (m, 4H), 2.59 (s, 3H), 3.30-3.43 (m, 1H), 7.09 (s, 1H). ES-MS (m/z): calcd for $C_{13}H_{15}F_3IN_3$ (M+H)$^+$: 398.2. found: 398.1.

F. 8-(1-Ethyl-propyl)-2,6-dimethyl-3-{8-(1-ethylpropyl)-2-methyl-6-trifluoromethyl-imidazo[1,2-b]pyridazin-3-yl}imidazo[1,2-b]pyridazine Using a procedure analogous to Example 16B, 8-(1-ethyl-propyl)-3-iodo-2-methyl-6-trifluoromethyl-imidazo[1,2-b] pyridazine (0.15 g, 0.37 mmol) and 8-(1-ethyl-propyl)-2,6-dimethyl-imidazo[1,2-b]pyridazine (0.082 g, 0.37 mmol) give the title compound (0.096 g, 0.19 mmol, 53%). $^1$H NMR (CDCl$_3$): δ 0.89-0.97 (m, 12H), 1.80-1.97 (m, 8H), 2.47 (bs, 6H), 2.54 (s, 3H), 3.35-3.45 (m, 1H), 3.47-3.55 (m, 1H), 6.73 (s, 1H), 7.10 (s, 1H). ES-MS (m/z): calcd for $C_{26}H_{33}F_3N_6$ (M+H)$^+$: 487.6. found: 487.3.

Example 20

Preparation of 8-(1-ethyl-propyl)-2,6-dimethyl-3-{2,6-dimethyl-8-(1-ethylpropyl)-imidazo[1,2-b]pyridazin-3-yl}imidazo[1,2-b]pyridazine

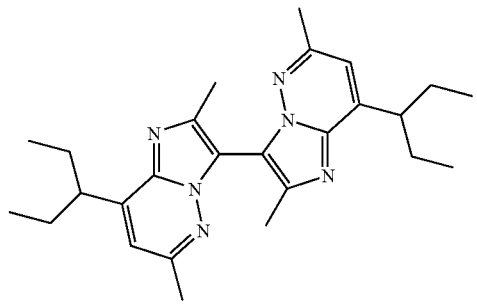

Using a procedure analogous to Example 16B, 8-(1-ethyl-propyl)-3-iodo-2,6-dimethyl-imidazo[1,2-b]pyridazine (0.10 g, 0.29 mmol) and 8-(1-ethyl-propyl)-2,6-dimethyl-imidazo[1,2-b]pyridazine (0.064 g, 0.29 mmol) give the title compound (0.054 g, 0.13 mmol, 43%). $^1$H NMR (CDCl$_3$): δ 0.91 (t, J=7.5 Hz, 6H), 0.92 (t, J=7.0 Hz, 6H), 1.80-1.93 (m, 8H), 2.43 (s, 6H), 2.47 (s, 6H), 3.36-3.44 (m, 2H), 6.68 (s, 2H). ES-MS (m/z): calcd for $C_{26}H_{36}N_6$ (M+H)$^+$: 433.6. found: 433.3.

Example 21

Preparation of 2-[8-(1-Ethyl-propyl)-2,6-dimethyl-imidazo[1,2-b]pyridazin-3-yl]-3-methyl-3H-imidazo[4,5-b]pyridine

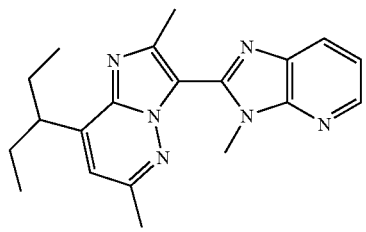

A mixture of 8-(1-ethyl-propyl)-3-iodo-2,6-dimethyl-imidazo[1,2-b]pyridazine (0.1 mol), 3-methyl-3H-imidazo[4,5-b]pyridine (0.12 mol), Pd$_2$dba$_3$ (1.45 mmol), triphenylphosphine (5.8 mmol), and cesium carbonate (0.06 mol) in previously degassed DMF (100 ml) were added to a pressure tube with a stirring bar. The mixture is degassed for 30 min. After heating for 16 h at 130° C., the reaction mixture is cooled, diluted with diethylether and washed with saturated aqueous ammonium chloride solution. The organic layer is dried over anhydrous magnesium sulfate, filtered, and solvent removed in vacuo. The residue is purified by silica gel column chromatography using mixtures of hexane-ethyl acetate to give the title compound Yield 50%. MS/ES+=349 (100%, M+1). $^1$H-NMR (CDCl$_3$): 8.48 (m, 1H); 8.15 (m, 1H); 7.25 (m, 1H); 6.84 (s, 1H); 3.82 (s, 3H); 3.34 (m, 1H); 2.61 (s, 3H); 2.50 (s, 3H); 1.82 (m, 4H); 0.81 (t, 6H) ppm.

Example 22

Preparation of 8-(1-ethyl-propyl)-2,6-dimethyl-3-(7-methyl-1H-indol-2-yl)-imidazo[1,2-b]pyridazine

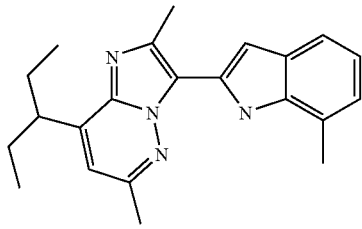

A. 7-methyl-2-(4,4,5,5-tetramethyl-[1,3,2]dioxaborolan-3-yl)-1H-indole

To a flask of IrCl(COD)₂ (0.051 g, 0.076 mmol), dtbpy (0.41 g, 0.15 mmol), and Pin₂B₂ (0.97 g, 3.81 mmol) is added octane (10 mL). After 10 minutes 7-methyl-1H-indole (0.50 g, 3.81 mmol) is added and the solution is heated at 80° C. overnight. The solution is concentrated and purified by ISCO (10%-40% EtOAc gradient) to furnish 0.46 g of material as a mixture of 2' and 3' isomers. The material is recrystallized from toluene (2 mL) and hexane (4 mL) to furnish the title compound (0.30 g, 1.17 mmol, 31%). ¹H NMR (CDCl₃), δ 1.38 (s, 12H), 2.49 (s, 3H), 7.01 (d, J=7.7 Hz, 1H), 7.11 (t, =7.7 Hz, 1H), 7.65 (d, J=2.3 Hz, 1H), 7.92 (d, J=7.9 Hz, 1H), 8.40 (bs, 1H). LC/MS (m/z): calcd. for $C_{15}H_2OBNO_2$ $(M+H)^+$: 257.2. found: 257.9.

B. 8-(1-Ethyl-propyl)-2,6-dimethyl-3-(7-methyl-1H-indol-3-yl)-imidazo[1,2-b]pyridazine A solution of 8-(1-ethyl-propyl)-3-iodo-2,6-dimethyl-imidazo[1,2-b]pyridazine (0.12 g, 0.35 mmol), 7-methyl-2-(4,4,5,5-tetramethyl-[1,3,2]dioxaborolan-3-yl)-1H-indole, Na₂CO₃ (0.60 g, 0.52 mmol), n-PrOH (1 mL), and water (0.1 mL) is degassed with nitrogen for 10 minutes. Pd(OAc)₂ (0.002 g, 0.007 mmol) and PPh₃ (0.006 g, 0.021 mmol) are added and the solution is heated at 88° C. overnight. The solution is diluted with EtOAc (15 mL), washed with water (10 mL), sat. NaHCO₃ (10 mL), dried over MgSO₄, filtered and concentrated. Purified by ISCO (5-50% EtOAc gradient) to furnish the title compound (0.040 g, 0.12 mmol, 33%). ¹H NMR (CDCl₃), δ 0.91 (t, J=7.5 Hz, 6H), 1.75-1.94 (m, 4H), 2.49 (s, 3H), 2.54 (s, 3H), 2.56 (s, 3H), 3.36-3.45 (m, 1H), 6.64 (s, 1H), 7.03-7.10 (m, 2H), 7.38 (dd, J=7.0, 1.7 Hz, 1H), 7.53 (d, J=2.6 Hz, 1H), 8.57 (bs, 1H). LC/MS (m/z): calcd. for $C_{22}H_{26}N_4$ $(M+H)^+$: 347.6. found: 347.2

Example 23

Preparation of 3-(1,7-dimethyl-1H-indol-2-yl)-8-(1-ethyl-propyl)-2,6-dimethyl-imidazo[1,2-b]pyridazine

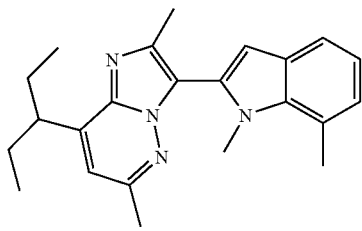

To a solution of 8-(1-ethyl-propyl)-2,6-dimethyl-3-(7-methyl-1H-indol-3-yl)-imidazo[1,2-b]pyridazine (0.037 g, 0.11 mmol) and DMF (2 mL) is added 60% NaH (0.005 g, 0.13 mmol). The solution is stirred for 30 minutes and MeI (0.008 mL, 0.13 mmol) is added. The solution is stirred for 1 h, diluted with EtOAc (20 mL), washed with water (2×10 mL), brine (10 mL), dried over MgSO₄, filtered and concentrated. The residue is purified by ISCO (30%-50% EtOAc gradient) to furnish the title compound (0.025 g, 0.069 mmol, 66%). ¹H NMR (CDCl₃), δ 0.91 (t, J=7.5 Hz, 6H), 1.77-1.95 (m, 4H), 2.48 (s, 3H), 2.53 (s, 3H), 2.83 (s, 3H), 3.35-3.44 (m, 1H), 4.17 (s, 3H), 6.62 (s, 1H), 6.94-7.01 (m, 2H), 7.25 (s, 1H), 7.30 (dd, J=7.6, 1.3 Hz, 1H). LC/MS (m/z): calcd. for $C_{23}H_{28}N_4$ $(M+H)^+$: 361.6. found: 361.2.

Example 24

Preparation of 8-(1-ethyl-propyl)-2,6-dimethyl-3-(1-methyl-1H-pyrrolo[2,3-b]pyridin-2-yl)-imidazo[1,2-b]pyridazine

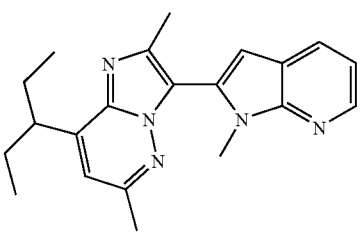

A. 1-Methyl-1H-pyrrolo[2,3-b]pyridine

To a solution of 1H-pyrrolo[2,3-b]pyridine (1.00 g, 8.46 mmol) and DMF (10 mL) is added 60% NaH (0.41 g, 10.16 mmol). After 30 min, MeI (0.63 mL, 10.16 mmol) is added and the solution stirred for 1 h. The solution is diluted with EtOAc (60 mL), washed with water (2×50 mL), brine (50 mL), dried aver MgSO₄, filtered and concentrated to furnish the title compound (1.10 g, 0.83 mmol, 99%). ¹H NMR (CDCl₃), δ 3.90 (s, 3H), 6.45 (d, J=3.5 Hz, 1H), 7.05 (dd, J=8.1, 4.6 Hz, 1H), 7.17 (d, J=3.5 Hz, 1H), 7.90 (d, J=7.7, 1.8 Hz, 1H), 8.40 (dd, J=4.8, 1.3 Hz, 1H). LC/MS (m/z): calcd. for $C_8H_8N_2$ $(M+H)^+$: 133.2. found.

B. 1-Methyl-2-(4,4,5,5-tetramethyl-[1,3,2]dioxaborolan-2-yl)-1H-pyrrolo[2,3-b]pyridine To a −78° C. solution of 1-methyl-1H-pyrrolo[2,3-b]pyridine (example Rupp-28) (1.17 g, 8.85 mmol) and THF (12 mL) is added 1.6M n-Bu—Li (6.6 mL, 10.62 mmol). The solution is heated to a reflux for 1 hour, cooled to ambient temperature, and 2-isopropoxy-4,4,5,5-tetramethyl-[1,3,2]dioxaborolane (3.60 mL, 17.70 mmol) is added. After 1 hour, the solution is diluted with CH₂Cl₂ (100 mL), washed with water (2×100 mL), brine (75 mL), dried over MgSO₄, filtered and concentrated. The residue is purified by ISCO (5%-15% EtOAc gradient) to furnish the title compound (0.25 g, 0.97 mmol, 11%). ¹H NMR (CDCl₃), δ 1.38 (s, 12H), 4.07 (s, 3H), 7.02 (dd, J=7.9, 4.7 Hz, 1H), 7.07 (s, 1H), 7.92 (d, J=7.9, 1.8 Hz, 1H), 8.39 (d, J=4.7, 1.8 Hz, 1H) ppm. LC/MS (m/z): calcd. for $C_{14}H_{19}BN_2O_2$ $(M+H)^+$: 259.2. found: 258.7.

C. 8-(1-Ethyl-propyl)-2,6-dimethyl-3-(1-methyl-1H-pyrrolo[2,3-b]pyridin-2-yl)-imidazo[1,2-b]pyridazine A solution of 8-(1-ethyl-propyl)-3-iodo-2,6-dimethyl-imidazo[1,2-b]pyridazine, 1-methyl-2-(4,4,5,5-tetramethyl-[1, 3,2]dioxaborolan-2-yl)-1H-pyrrolo[2,3-b]pyridine (0.23 g, 0.89 mmol), 2M Na$_2$CO$_3$ (0.72 mL, 1.45 mmol), and 7:3:2 DME:Water: EtOH (5 mL) is degassed with nitrogen for 15 minutes. Pd(PPh$_3$)$_4$ (0.051 g, 0.044 mmol) is added and the solution is heated at a reflux for three days. The solution is diluted with CH$_2$Cl$_2$ (50 mL), washed with 10% Na$_2$CO$_3$ (30 mL), water (30 mL), brine (30 mL), dried over MgSO$_4$, filtered and concentrated. The material is purified by ISCO (15%-30% EtOAc gradient) to furnish the title compound (0.12 g, 0.35 mmol, 48%). $^1$H NMR (CDCl$_3$), δ 0.90 (t, J=7.5 Hz, 6H), 1.78-1.95 (m, 4H), 2.50 (s, 3H), 2.53 (s, 3H), 3.32-3.40 (m, 1H), 3.74 (s, 3H), 6.64 (s, 1H), 6.72 (s, 1H), 7.11 (dd, J=8.3, 4.8 Hz, 1H), 7.96 (dd, J=8.3, 1.3 Hz, 1H), 8.40 (dd, J=4.8, 1.3 Hz, 1H) ppm. LC/MS (m/z): calcd. for C$_{21}$H$_{25}$N$_5$ (M+H)$^+$: 348.3. found: 348.2.

Example 25

Preparation of 3-(1,5-dimethyl-1H-indol-2-yl)-8-(1-ethyl-propyl)-2,6-dimethyl-imidazo[1,2-b]pyridazine

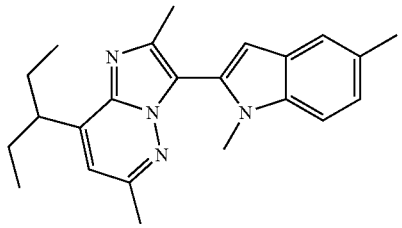

A. 1,5-Dimethyl-1H-indole-2-boronic Acid

To a 0° C. solution of 1,5-dimethyl-1H-indole (1.10 g, 7.58 mmol) and THF (15 mL) is added 1.6M n-Bu—Li (5.7 mL, 9.09 mmol) the solution is warmed to ambient temperature and stirred for 1 h. The solution is cooled to 0° C. and B(OMe)$_3$ (1.01 mL, 9.09 mmol) is added. The solution is warmed to ambient temperature and stirred overnight. 1M HCl (20 mL) is added and the pH adjusted to 7 with 1M NaOH. The aqueous phase is extracted with EtOAc (2×30 mL). The combined organic layers are washed with brine, dried over MgSO$_4$, filtered and concentrated. The solids are triturated with hexane, and recrystallized from toluene/hexane to furnish the title compound (0.17 g, 0.90 mmol, 12%). $^1$H NMR (CDCl$_3$), δ 2.38 (s, 3H), 4.08 (s, 3H), 6.91 (s, 1H), 6.99 (d, J=8.9 Hz, 1H), 7.29-7.38 (m, 2H) ppm. LC/MS (m/z): calcd. for C$_{10}$H$_{12}$BNO$_2$ (M+H)$^+$: 190.1. found: 146.1.

B. 3-(1,5-dimethyl-1H-indol-2-yl)-8-(1-ethyl-propyl)-2,6-dimethyl-imidazo[1,2-b]pyridazine A solution of 8-(1-ethyl-propyl)-3-iodo-2,6-dimethyl-imidazo[1,2-b]pyridazine (0.10 g, 0.29 mmol), 1,5-dimethyl-1H-indole-2-boronic acid (0.060 g, 0.32 mmol), 2M Na$_2$CO$_3$ (0.22 mL, 0.44 mmol), and n-PrOH (1.5 mL) is degassed with nitrogen for 10 minutes. Pd(OAc)$_2$ (0.0013 g, 0.0058 mmol), and PPh$_3$ (0.0046 g, 0.017 mmol) are added and the solution is heated at a reflux for two days. The solution is diluted with CH$_2$Cl$_2$ (50 mL), washed with 10% Na$_2$CO$_3$ (30 mL), water (30 mL), brine (30 mL), dried over MgSO$_4$, filtered and concentrated. The material is purified by ISCO (30%-50% EtOAc gradient) to furnish the title compound (0.010 g, 0.028 mmol, 10%). $^1$H NMR (CDCl$_3$), δ 0.90 (t, J=7.5 Hz, 6H), 1.75-1.95 (m, 4H), 2.48 (s, 3H), 2.49 (s, 3H), 2.51 (s, 3H), 3.32-3.41 (m, 1H), 3.58 (s, 3H), 6.59 (s, 1H), 6.70 (s, 1H), 7.12 (dd, J=8.4, 1.8 Hz, 1H), 7.31 (d, J=8.4 Hz, 1H), 7.47 (s, 1H) ppm. LC/MS (m/z): calcd. for C$_{23}$H$_{28}$N$_4$ (M+H)$^+$: 361.6; found: 361.2.

Example 26

Preparation of 8-(1-ethyl-propyl)-3-(7-fluoro-1H-indol-2-yl)-2,6-dimethyl-imidazo[1,2-b]pyridazine

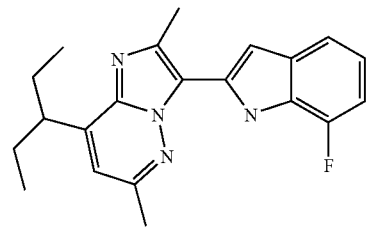

A. 7-fluoro-2-(4,4,5,5-tetramethyl-[1,3,2]dioxaborolan-2-yl)-1H-indole

To a mixture of 7-fluoro-1H-indole (0.50 g, 3.70 mmol), dtbpy (0.020 g, 0.074 mmol), Pin$_2$B$_2$ (0.94 g, 3.70 mmol) and hexane (20 mL) is added [Ir(OMe(COD)]$_2$ (0.027 g, 0.037 mmol). The solution is stirred over the weekend and concentrated. The residue is filtered thru a pad of silica gel eluting with 100% EtOAc and concentrated. The residue is recrystallized from hexane to furnish the title compound (0.53 g, 2.03 mmol, 55%). $^1$H NMR (CDCl$_3$), δ 1.39 (s, 12H), 6.90-7.04 (m, 2H), 7.13 (dd, =3.5, 2.2 Hz, 1H), 7.43 (d, J=7.9 Hz, 1H), 8.73 (s, 1H) ppm. LC/MS (m/z): calcd. for C$_{14}$H$_{17}$BFNO$_2$ (M+H)$^+$: 262.2. found: 262.0.

B. 8-(1-Ethyl-propyl)-3-(7-fluoro-1H-indol-2-yl)-2,6-dimethyl-imidazo[1,2-b]pyridazine Using the procedure analogous to Example 22B, from of 8-(1-ethyl-propyl)-3-iodo-2,6-dimethyl-imidazo[1,2-b]pyridazine (0.39 g, 0.1.81 mmol), 7-fluoro-2-(4,4,5,5-tetramethyl-[1,3,2]dioxaborolan-2-yl)-1H-indole (0.52 g, 1.99 mmol), 2M Na$_2$CO$_3$ (1.4 mL, 2.72 mmol), Pd(OAc)$_2$ (0.0081 g, 0.036 mmol), PPh$_3$ (0.028 g, 0.11 mmol), and n-PrOH (4 mL) is furnished the title compound (0.27 g, 0.77 mmol, 43%). $^1$H NMR (CDCl$_3$), δ 0.88 (t, J=7.5 Hz, 6H), 1.76-1.95 (m, 4H), 2.70 (s, 3H), 2.80 (s, 3H), 3.32-3.42 (m, 1H), 6.75 (s, 1H), 6.84-6.89 (m, 1H), 6.93 (dd, J=11.0, 7.9 Hz, 1H), 7.01-7.08 (m, 1H), 7.44 (d, J=7.9 Hz, 1H), 11.15 (s, 1H) ppm. LC/MS (m/z): calcd. for C$_{21}$H$_{23}$FN$_4$ (M+H)$^+$: 351.5. found: 351.2.

Example 27

Preparation of 8-(1-ethyl-propyl)-3-(7-fluoro-1-methyl-1H-indol-2-yl)-2,6-dimethyl-imidazo[1,2-b]pyridazine

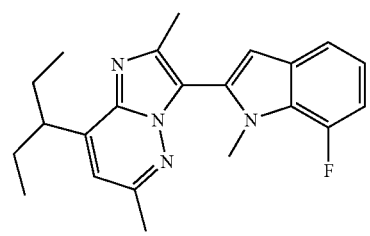

Using the procedure analogous to Example 23, from 8-(1-ethyl-propyl)-3-(7-fluoro-1H-indol-2-yl)-2,6-dimethyl-imidazo[1,2-b]pyridazine (0.060 g, 0.17 mmol), 60% NaH (0.013 g, 0.34 mmol), MeI (0.013 mL, 0.21 mmol), and DMF (1 mL) is furnished the title compound (0.60 g, 0.16 mmol, 97%). $^1$H NMR (CDCl$_3$), δ 0.91 (t, J=7.5 Hz, 6H), 1.78-1.95 (m, 4H), 2.51 (s, 3H), 2.53 (s, 3H), 3.32-3.42 (m, 1H), 4.79 (d, J=1.7 Hz, 3H), 6.68 (d, J=2.6 Hz, 1H), 6.73 (s, 1H), 6.90-6.96 (m, 1H), 6.99-7.05 (m, 1H), 7.42 (d, J=7.8 Hz, 1H). LC/MS (m/z): calcd. for $C_{22}H_{25}FN_4$ (M+H)$^+$: 365.3. found: 365.2.

Example 28

Preparation of 8-(1-ethyl-propyl)-3-(7-aza-3-methyl-benzo[b]thiophen-2-yl)-2,6-dimethyl-imidazo[1,2-b]pyridazine

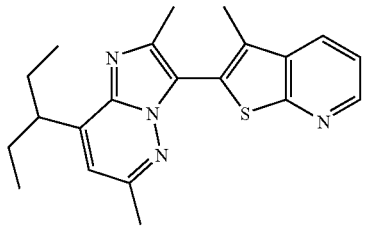

A. 7-Aza-3-methyl-benzo[b]thiophene

Three reaction vials are prepared. 214 mg of 3-Bromo-thieno[2,3-b]pyridine (1.0 mmol) and 180 mg of Methylboronic acid (3.0 mmol) are put in the each vial with 4 ml of DME/water/EtOH=7/3/1. 1.5 ml of 2 M Na$_2$CO$_3$ aq. (3.0 mmol) is added and N$_2$ gas is bubbled in for 15 min. 58 mg of Pd(PPh$_3$)$_4$ (0.05 mmol) is added and each vials are sealed. These vials are heated at 130° C. for 30 min in the microwave. All reaction mixtures are combined and water and CH$_2$Cl$_2$ are added. The CH$_2$Cl$_2$ layer are separated and dried over Na$_2$SO$_4$ and evaporated. The crude products are applied onto a silica-gel chromatography column (Hexane:AcOEt=5:1) to give 120 mg of the title compound. Yield 27%. mass spectrum (m/e): 150 (M+1); $^1$H-NMR (CDCl$_3$): 8.61 (dd, 1H, J=5.0 Hz, 1.4 Hz), 8.01 (dd, 1H, J=8.3 Hz, 1.4 Hz), 7.35 (dd, 1H, J=8.3 Hz, 5.0 Hz), 7.19 (d, 1H, J=1.3 Hz), 2.46 (d, 3H, J=1.3 Hz).

B. 8-(1-Ethyl-propyl)-3-(7-aza-3-methyl-benzo[b]thiophen-2-yl)-2,6-dimethyl-imidazo[1,2-b]pyridazine A mixture of 8-(1-ethyl-propyl)-3-iodo-2,6-dimethyl-imidazo[1,2-b]pyridazine (1.45 mmol), 7-aza-3-methyl-benzo[b]thiophene (7.25 mmol), Pd$_2$ dba$_3$ (0.072 mmol), triphenylphosphine (0.29 mmol), and cesium carbonate (2.9 mmol) in previously degassed DMF (5 ml) is added to a pressure tube with a stirring bar. The mixture is degassed for 30 min. After heating for 16 h at 130° C., the reaction mixture is cooled, diluted with diethylether and washed with saturated aqueous ammonium chloride solution. The organic layer is dried over anhydrous magnesium sulfate, filtered, and solvent is removed in vacuo. The residue is purified by silica gel column chromatography using mixtures of hexane-ethyl acetate as eluent to give the title compound (70%). $^1$H-NMR (CDCl$_3$): 8.50 (m, 1H); 7.95 (m, 1H); 7.28 (m, 1H); 6.61 (s, 1H); 3.27 (m, 1H); 2.41 (s, 6H); 2.24 (s, 3H); 1.79 (m, 4H); 0.78 (t, 6H). MS/ES+=365 (M+1).

Example 29

Preparation of 8-(1-ethyl-propyl)-3-(3,5-dimethyl-benzo[b]thiophen-2-yl)-2,6-dimethyl-imidazo[1,2-b]pyridazine (Method A)

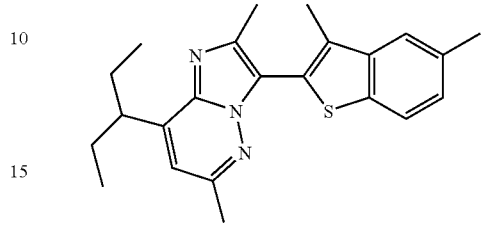

A mixture of 8-(1-ethyl-propyl)-3-iodo-2,6-dimethyl-imidazo[1,2-b]pyridazine (0.145 mmol), 3,5-dimethyl-benzothiophene-2-boronic acid (0.29 mmol), Pd$_2$ dba$_3$ (0.0072 mmol), triphenylphosphine (0.029 mmol), and barium hydroxide (0.435 mmol) in previously degassed mixture of DME/water [(2:1), 0.5 ml] is added to a pressure tube with a stirring bar. The mixture is degassed for 30 min. After heating for 16 h at 90° C., the reaction mixture is cooled, diluted with diethylether and washed with saturated aqueous ammonium chloride solution. The organic layer is dried over anhydrous magnesium sulfate, filtered, and the solvent is removed in vacuo. The residue is purified by silica gel column chromatography using mixtures of hexane-ethyl acetate as eluent to give the tile compound (90%). $^1$H-NMR (CDCl$_3$): 7.68 (m, 1H); 7.40 (m, 1H); 7.15 (m, 1H); 6.62 (s, 1H); 3.25 (m, 1H); 2.45 (s, 3H); 2.43 (s, 3H); 2.42 (s, 3H); 2.19 (s, 3H); 1.73 (m, 4H); 0.74 (t, 6H) ppm. MS/ES+=378 (M+1).

Preparation of 8-(1-ethyl-propyl)-3-(3,5-dimethyl-benzo[b]thiophen-2-yl)-2,6-dimethyl-imidazo[1,2-b]pyridazine (Method B)

A mixture of 8-(1-ethyl-propyl)-3-iodo-2,6-dimethyl-imidazo[1,2-b]pyridazine (0.145 mmol), 3-methyl-benzo[b]thiophene (7.25 mmol), Pd$_2$ dba$_3$ (0.0072 mmol), triphenylphosphine (0.029 mmol), and cesium carbonate (0.29 mmol) in previously degassed DMF (0.5 ml) is added to a pressure tube with a stirring bar. The mixture is degassed for 30 min. After heating for 16 h at 130° C., reaction mixture is cooled, diluted with diethylether and washed with saturated aqueous ammonium chloride solution. The organic layer is dried over anhydrous magnesium sulfate, filtered, and the solvent is removed in vacuo. The residue is purified by silica gel column chromatography using mixtures of hexane-ethyl acetate as eluent to give the title compound (85%).

General Procedure for the Preparation of 2- and 3-Indoyl Imidazopyridazines

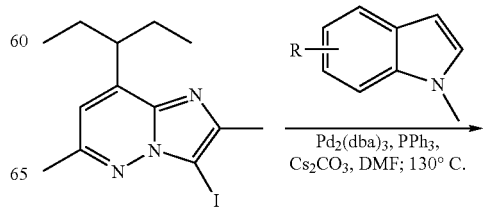

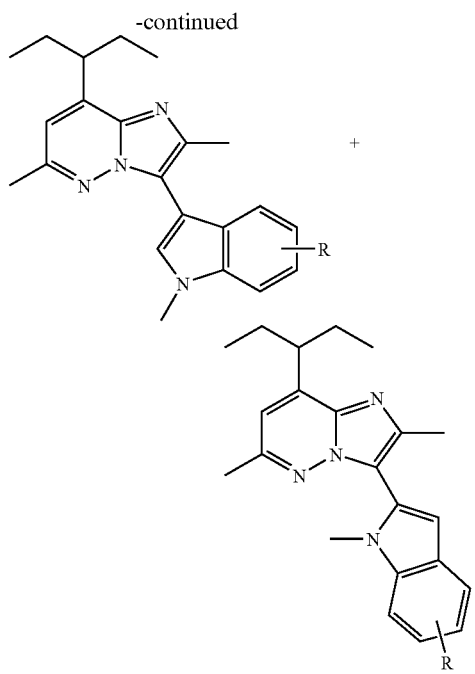

A mixture of 8-(1-ethyl-propyl)-3-iodo-2,6-dimethyl-imidazo[1,2-b]pyridazine (1 mmol), the substituted N-methylindole (1 to 3 mmol), $Pd_2dba_3$ (0.05 mmol), triphenyl-phosphine (0.2 mmol), and cesium carbonate (2 mmol) in previously degassed DMF (0.5 ml) is added to a pressure tube with a stirring bar. The mixture is degassed for 30 min. After heating for 16 h at 130° C., the reaction mixture is cooled, diluted with diethylether and washed with saturated aqueous ammonium chloride solution. The organic layer is dried over anhydrous magnesium sulfate, filtered, and the solvent is removed in vacuo. The residue is purified and the regioisomers separated by silica gel column chromatography using mixtures of hexane-ethyl acetate as eluent to yield the following compounds:

SPECIFIC EXAMPLES

|   | 3-isomer | | 2-isomer | |
| --- | --- | --- | --- | --- |
| R | Yield % | Example | Yield % | Example |
| 5-F | 10[a] | 30 | 20[a] | 8 |
| 4-F | — | — | 52[b] | 7 |
| 6-F | 8[b] | 31 | 50[b] | 9 |

[a] reaction is carried out with 1 eq of indole
[b] reaction is carried out with 3 eq of indole Data for Specific Examples Example 30

MS/ES+=365 (100%, M+1)
$^1$H-NMR: 7.30 (s, 1H); 7.25 (m, 1H); 7.10 (m, 1H); 6.90 (m, 1H); 6.55 (s, 1H); 3.82 (s, 3H); 3.29 (m, 1H); 2.44 (s, 3H); 2.40 (s, 3H); 1.77 (m, 4H); 0.79 (m, 6H) ppm.

Example 31

MS/ES+=365 (100%, M+1)
$^1$H-NMR: 7.32 (m, 1H); 7.25 (s, 1H); 6.98 (m, 1H); 6.82 (m, 1H); 6.54 (s, 1H); 3.77 (s, 3H); 3.28 (m, 1H); 2.44 (s, 3H); 2.40 (s, 3H); 1.74 (m, 4H); 0.82 (m, 6H) ppm.

Example 32

Preparation of 3-(1,7-dimethyl-1H-indol-2-yl)-8-(1-ethyl-propyl)-2,6-dimethyl-imidazo[1,2-b]pyridazine

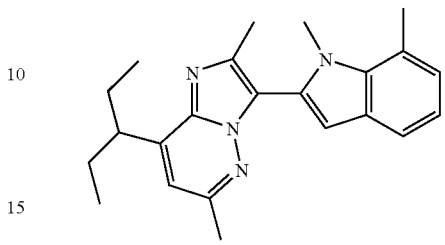

Using a procedure similar to Examples 30 and 31, 1,7-dimethyl-1H-indole gives the title compound Yield 63%. MS/ES+=361 (100%, M+1). $^1$H-NMR (CDCl$_3$): 7.43 (m, 1H); 6.90 (m, 2H); 6.61 (s, 1H); 6.55 (s, 1H); 3.71 (s, 3H); 3.26 (m, 1H); 2.41 (s, 3H); 2.40 (s, 3H); 1.74 (m, 4H); 0.80 (m, 6H) ppm.

Example 33

Preparation of 3-(6-chloro-1H-indol-2-yl)-8-(1-ethyl-propyl)-2,6-dimethyl-imidazo[1,2-b]pyridazine

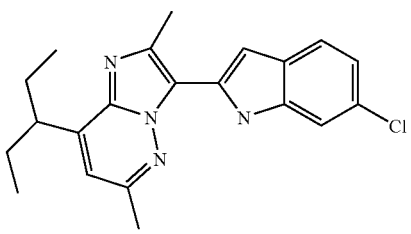

A. 6-Chloro-2-(4,4,5,5-tetramethyl-[1,3,2]dioxaborolan-2-yl)-1H-indole

Using the procedure analogous to Example 22A, from 6-chloro-1H-indole (1.0 g, 6.60 mmol), octane (20 mL), [IrCl(COD)]$_2$ (0.089 g, 0.13 mmol), dtbpy (0.071 g, 0.26 mmol), and Pin$_2$B$_2$ (2.51 g, 9.89 mmol) to furnish the title compound (0.31 g, 1.12 mmol, 17%) ppm. $^1$H NMR (CDCl$_3$), δ 1.37 (s, 12H), 7.14 (dd, J=8.4, 1.7 Hz, 1H), 7.38 (t, =1.7 Hz, 1H), 7.63 (d, J=2.4 Hz, 1H), 7.94 (d, J=8.4 Hz, 1H), 8.42 (bs, 1H) ppm. LC/MS (m/z): calcd. for $C_{14}H_{17}BClNO_2$ (M+H)$^+$: 277.1. found: 279.1.

B. 3-(6-Chloro-1H-indol-2-yl)-8-(1-ethyl-propyl)-2,6-dimethyl-imidazo[1,2-b]pyridazine Using the procedure analogous to example 22B, from 8-(1-ethyl-propyl)-3-iodo-2,6-dimethyl-imidazo[1,2-b]pyridazine (0.12 g, 0.35 mmol), 6-chloro-2-(4,4,5,5-tetramethyl-[1,3,2]dioxaborolan-2-yl)-1H-indole (0.31 g, 1.10 mmol), 2M Na$_2$CO$_3$ (0.41 mL, 0.83 mmol), n-PrOH (2 mL), Pd(OAc)$_2$ (0.0025 g, 0.0011 mmol) and PPh$_3$ (0.0087 g, 0.0033 mmol) to furnish an impure yellow solid. The material is chromatographed (19×300 Symmetry C18 7 μm, 40-65% ACN, 0.1% TFA) to furnish the title compound (0.055 g, 0.15 mmol, 28%) ppm. ¹H NMR (CDCl₃), δ 0.91 (t, J=7.5 Hz, 6H), 1.75-1.96 (m, 4H), 2.84 (s, 3H), 2.90 (s, 3H), 3.40-3.49 (m, 1H), 6.94 (dd, J=2.2, 0.9 Hz, 1H), 7.16 (d, J=1.8 Hz, 1H), 7.18 (d, J=1.8 Hz, 1H), 7.55 (d, J=1.8 Hz, 1H), 7.62 (d, J=8.4 Hz, 1H), 10.41 (bs, 1H) ppm. LC/MS (m/z): calcd. for $C_{21}H_{23}ClN_4$ (M+H)⁺: 366.2. found: 367.2

Example 34

Preparation of 3-(6-chloro-1-methyl-1H-indol-2-yl)-8-(1-ethyl-propyl)-2,6-dimethyl-imidazo[1,2-b]pyridazine

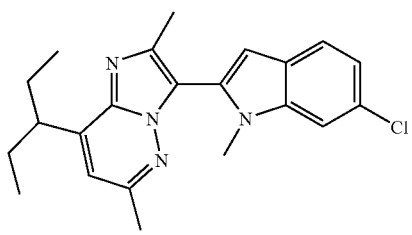

To a solution of 3-(6-chloro-1H-indol-2-yl)-8-(1-ethylpropyl)-2,6-dimethyl-imidazo[1,2-b]pyridazine (0.050 g, 0.14 mmol) and DMF (2 mL) is added 60% NaH (0.013 g, 0.33 mmol). The solution is stirred for 30 minutes and MeI (0.010 mL, 0.16 mmol) is added. The solution is stirred for 1 hour, diluted with EtOAc (20 mL), washed with water (2×10 mL), brine (10 mL), dried over MgSO₄, filtered and concentrated. The residue is purified by silica gel chromatography (30%-50% EtOAc gradient) to furnish the title compound (0.021 g, 0.055 mmol, 40%). ¹H NMR (CDCl₃), δ 0.90 (t, J=7.4 Hz, 6H), 1.75-1.95 (m, 4H), 2.49 (s, 3H), 2.51 (s, 3H), 3.31-3.40 (m, 1H), 3.57 (s, 3H), 6.65 (d, J=0.9 Hz, 1H), 6.72 (s, 1H), 7.12 (dd, J=8.4, 1.8 Hz, 1H), 7.40-7.42 (m, 1H), 7.58 (8.4 Hz, 1H) ppm. LC/MS (m/z): calcd. for $C_{22}H_{25}ClN_4$ (M+H)⁺: 380.2. found: 381.2.

Example 35

Preparation of 8'-cyclopropyl-8-(1-ethyl-propyl)-2,6,2',6'-tetramethyl-[3,3']bi[imidazo-[1,2-b]pyridazinyl]

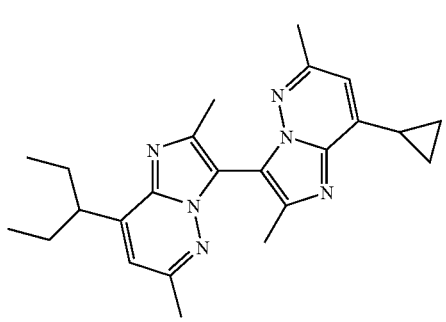

A. N-(4-Cyclopropyl-6-methyl-pyridazin-3-yl)-2,2-dimethyl-propionamide

Using a procedure analogous to Example 17A, from 2,2-dimethyl-N-(6-methyl-pyridazin-3-yl)-propionamide (4.825 g, 25.0 mmol) and 0.5 M solution of cyclopropylmagnesium bromide (200 mL, 100 mmol) to give the title compound (0.271 g, 1.17 mmol, 5%). ¹H NMR (CDCl₃): δ 0.70 (q, J=4.9, Hz, 2H), 1.08 (dq, J=4.9, 1.7 Hz, 2H), 1.36 (s, 9H), 1.89 (bs, 1H), 2.59 (s, 3H), 6.82 (s, 1H), 9.27 (bs, 1H) ppm. ES-MS (m/z): calcd for C13H19N3O (M+H)+: 234.3. found: 234.1.

B. 4-Cyclopropyl-6-methyl-pyridazin-3-ylamine

Using a procedure analogous to Example 17B, from N-(4-cyclopropyl-6-methyl-pyridazin-3-yl)-2,2-dimethyl-propionamide (0.27 g, 1.16 mmol) to give the title compound (0.17 g, 1.12 mmol, 96%). ¹H NMR (CDCl₃): δ0.74 (q, J=4.9 Hz, 2H), 1.14 (dq, J=4.9, 1.3 Hz, 2H), 1.64-1.73 (m, 1H), 2.49 (s, 3H), 6.40-6.80 (bs, 2H), 6.69 (s, 1H) ppm. ES-MS (m/z): calcd for C8H11N3 (M+H)+: 150.2. found: 150.1.

C. 8-Cyclopropyl-2,6-dimethyl-imidazo[1,2-b]pyridazine

Using a procedure analogous to Example 16A, 4-cyclopropyl-6-methyl-pyridazin-3-ylamine (0.17 g, 1.12 mmol) gives the title compound (76.5 mg, 0.41 mmol, 37%). ¹H NMR (CDCl₃): δ) 1.02 (dt, J=4.9, 4.4 Hz, 2H), 1.23 (dt, J=7.1, 4.4 Hz, 2H), 2.46 (s, 3H), 2.49 (s, 3H), 2.55-2.64 (m, 1H), 6.25 (s, 1H), 7.60 (s, 1H) ppm. ES-MS (m/z): calcd for C11H13N3 (M+H)+: 188.3. found: 188.1.

D. 8'-Cyclopropyl-8-(1-ethyl-propyl)-2,6,2',6'-tetramethyl-[3,3']bi[imidazo[1,2-b]pyridazinyl]

Using a procedure analogous to Example 16B, 8-cyclopropyl-2,6-dimethyl-imidazo[1,2-b]pyridazine (76.5 mg, 0.41 mmol) and 8-(1-ethyl-propyl)-3-iodo-2,6-dimethyl-imidazo[1,2-b]pyridazine (0.14 g, 0.41 mmol) give the title compound (71.6 mg, 0.18 mmol, 43%). ¹H NMR (CDCl₃): δ 0.91 (t, J=7.1 Hz, 6H), 1.05-1.11 (m, 2H), 1.24-1.30 (m, 2H), 1.75-1.93 (m, 4H), 2.41 (s, 3H), 2.42 (s, 3H), 2.44 (s, 3H), 2.45 (s, 3H), 2.65-2.75 (m, 1H), 3.33-3.45 (m, 1H), 6.64 (s, 1H), 6.67 (s, 1H) ppm. ES-MS (m/z): calcd for C24H30N6 (M+H)+: 403.6. found: 403.3.

Example 36

Preparation of 8'-cyclopentyl-8-(1-ethyl-propyl)-2,6,2',6'-tetramethyl-[3,3']bi-[imidazo[1,2-b]pyridazinyl]

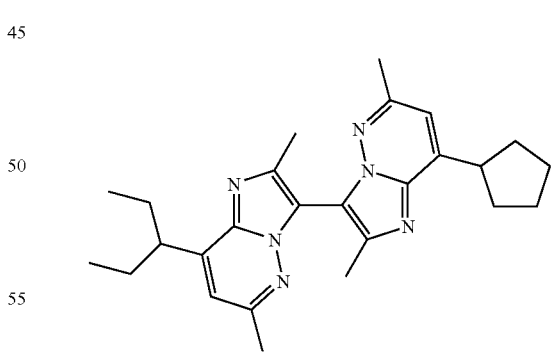

A. N-(4-Cyclopentyl-6-methyl-pyridazin-3-yl)-2,2-dimethyl-propionamide

Using a procedure analogous to Example 17A, 2,2-dimethyl-N-(6-methyl-pyridazin-3-yl)-propionamide (2.90 g, 15.0 mmol) and a 2.0 M solution of cyclopentylmagnesium bromide (30 mL, 60 mmol) gives the title compound (1.98 g, 7.6 mmol, 51%). ¹H NMR (CDCl₃): δ1.37 (s, 9H), 1.43-1.55

(m, 2H), 1.65-1.74 (m, 2H), 1.74-1.86 (m, 2H), 2.09-2.20 (2H), 2.66 (s, 3H), 3.00-3.15 (m, 1H), 7.25 (bs, 1H), 7.26 (s, 1H) ppm. ES-MS (m/z): calcd for C15H23N3O (M+H)+: 262.4. found: 262.2.

B. 4-Cyclopentyl-6-methyl-pyridazin-3-ylamine

Using a procedure analogous to Example 17B, N-(4-cyclopentyl-6-methyl-pyridazin-3-yl)-2,2-dimethyl-propionamide (1.98 g, 7.59 mmol) gives the title compound (1.21 g, 6.83 mmol, 90%). $^1$H NMR (CDCl$_3$): δ 1.58-1.68 (m, 2H), 1.70-1.86 (m, 4H), 2.03-2.13 (m, 2H), 2.53 (s, 3H), 2.80-2.90 (m, 1H), 4.77 (bs, 2H), 6.94 (s, 1H) ppm. ES-MS (m/z): calcd for C10H15N3 (M+H)+: 178.3. found: 178.1.

C. 8-Cyclopentyl-2,6-dimethyl-imidazo[1,2-b]pyridazine

Using a procedure analogous to Example 16A, 4-cyclopentyl-6-methyl-pyridazin-3-ylamine (1.20 g, 6.83 mmol) gives the title compound (1.02 g, 4.75 mmol, 70%). $^1$H NMR (CDCl$_3$): δ 1.61-1.74 (m, 2H), 1.74-1.91 (m, 4H), 2.19-2.28 (m, 2H), 2.49 (s, 3H), 2.51 (s, 3H), 3.66-3.78 (m, 1H), 6.68 (s, 1H), 7.61 (s, 1H) ppm. ES-MS (m/z): calcd for C13H17N3 (M+H)+: 216.3. found: 216.1.

D. 8'-Cyclopentyl-8-(1-ethyl-propyl)-2,6,2',6'-tetramethyl-[3,3']bi[imidazo[1,2-b]pyridazinyl]

Using a procedure analogous to Example 16B, 8-cyclopentyl-2,6-dimethyl-imidazo[1,2-b]pyridazine (0.41, 1.86 mmol) and 8-(1-ethyl-propyl)-3-iodo-2,6-dimethyl-imidazo[1,2-b]pyridazine (0.63 g, 1.86 mmol) give the title compound (0.43 g, 1.0 mmol, 54%). $^1$H NMR (CDCl$_3$): δ 0.92 (t, J=7.4 Hz, 6H), 1.70-1.96 (m, 10H), 2.25-2.35 (m, 2H), 2.43 (s, 3H), 2.44 (s, 3H), 2.47 (s, 6H), 3.35-3.48 (m, 1H), 3.78-3.90 (m, 1H), 6.68 (s, 1H), 6.76 (s, 1H) ppm. ES-MS (m/z): calcd for C26H34N6 (M+H)+: 431.6. found: 431.3.

Example 37

Preparation of 8-(1-Ethyl-propyl)-3-(5-fluoro-3-methyl-benzo[b]thiophen-2-yl)-6-methyl-2-trifluoromethyl-imidazo[1,2-b]pyridazine

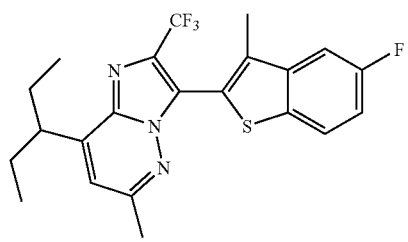

A. 8-(1-Ethyl-propyl)-6-methyl-2-trifluoromethyl-imidazo[1,2-b]pyridazine

To a dry 10 ml microwave reaction tube containing 4-(1-ethyl-propyl)-6-methyl-pyridazin-3-ylamine (500 mg, 2.79 mmol) in EtOH (2.0 ml) is added α-bromotrifluoroacetone (402 mg, 2.93 mmol). Heat the resulting mixture to 110° C. in microwave for 1 hr. Add NaHCO$_3$ (246.5 mg, 2.93 mmol) and mix well for 5 min then heat to 110° C. in microwave for 1 h. Remove EtOH via reduced pressure and dilute with EtOAc (30 ml); wash with H$_2$O (3×10 ml); extract aqueous layer with EtOAc (2×20 ml); dry (Na$_2$SO$_4$), filter and purify by silica gel chromatography to give the title compound (29.5 mg, 0.068 mmol, 9.8%). 1 HNMR (CDCl$_3$): 0.869 (t, J=7.6 Hz, 6H), 1.863 (m, 4H), 2.597 (s, 3H), 3.30 (m, 1H), 6.799 (s, 1H), 8.137 (s, 1H) ppm. ES-MS (m/z): calcd for C13H16F3N3 (M+H)$^+$: 271.29. found: 272.2

B. 8-(1-Ethyl-propyl)-3-(5-fluoro-3-methyl-benzo[b]thiophen-2-yl)-6-methyl-2-trifluoromethyl-imidazo[1,2-b]pyridazine To a dry 10 ml round bottom flask with reflux condenser containing 8-(1-ethyl-propyl)-6-methyl-2-trifluoromethyl-imidazo[1,2-b]pyridazine (150 mg, 0.690 mmol), 2-bromo-5-fluoro-3-methyl-benzo[b]thiophene (186.1 mg, 0.759 mmol), and Cs$_2$CO$_3$ (472 mg, 1.45 mmol) in NMP (1.1 ml). The mixture is degassed with bubbling N$_2$ for 15 min. Then add Pd$_2$(dba)$_3$ (32 mg, 0.0345 mmol) and PPh$_3$ (36.2 mg, 0.138 mmol). Heat the reaction mixture at 130° C. and stir overnight. Dilute with H$_2$O; extract with EtOAc (3×20 ml); dried (Na$_2$SO$_4$), filter and purify by HPLC to give title compound (29.5 mg, 0.068 mmol, 10%). $^1$H NMR (CDCl$_3$): 0.931 (t, J=7.6 Hz, 6H), 1.912 (m, 4H), 2.286 (s, 3H), 2.552 (s, 3H), 3.386 (m, 1H), 6.877 (s, 1H), 7.224 (td, J=2.4, 9.0 Hz, 1H), 7.50 (dd, J=2.9, 9.8 Hz, 1H), 7.842 (dd, J=4.9, 9.0 Hz, 1H) ppm. ES-MS (m/z): calcd for C22H21F4N3S (M+H)$^+$: 435.39. found: 436.2.

Example 38

Preparation of 3-[8-(1-ethyl-propyl)-2,6-dimethyl-imidazo[1,2-b]pyridazin-3-yl]-2-methyl-imidazo[1,2-a]pyridine-8-carboxaldehyde

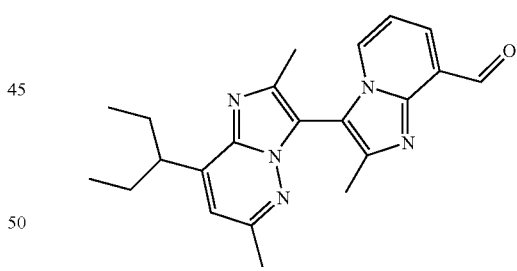

A. 8-Diethoxymethyl-2-methyl-imidazo[1,2-a]pyridine

Using a procedure analogous to Example 16 A, from 2-amino-pyridine-3-carboxaldehyde (prepared according to a literature procedure, Rivera, N. R.; Hsiao, Y.; Cowen, J. A.; McWilliams, C.; Amstrong, J.; Yasuda, N.; Hughes, D. L. Synthe. Commun. 2001, 31, 1573), (4.0 g, 32.79 mmol) to give the title compound (1.71 g, 7.31 mmol, 22%). $^1$H NMR (CDCl$_3$): δ. 1.26 (t, J=6.9 Hz, 6H), 2.49 (s, 3H), 3.65-3.81 (m, 4H), 6.12 (s, 1H), 6.76 (m, 1H), 7.35 (s, 1H), 7.40 (d, J=7.0 Hz), 8.00 (dd, J=7.0, 0.8 Hz, 1H) ppm. ES-MS (m/z): calcd for C13H18N2O2 (M+H)+: 235.3. found: 235.1.

B. 3-(8-Diethoxymethyl-2-methyl-imidazo[1,2-a]pyridin-3-yl)-8-(1-ethyl-propyl)-2,6-dimethyl-imidazo[1,2-b]pyridazine Using a procedure analogous to Example 16B, 8-diethoxymethyl-2-methyl-imidazo[1,2-a]pyridine (1.70 g, 7.26 mmol) and 8-(1-ethyl-propyl)-3-iodo-2,6-dimethyl-imidazo[1,2-b]pyridazine (2.49 g, 7.26 mmol) give the title compound (2.34 g, 5.21 mmol, 72%). $^1$H NMR (CDCl$_3$): δ. 0.92 (t, J=7.5 Hz, 3H), 0.93 (t, J=7.5 Hz, 3H), 1.31 (t, J=7.1 Hz, 3H), 1.33 (t, J=7.1 Hz, 3H), 1.79-1.93 (m, 4H), 2.14 (s, 3H), 2.44 (s, 6H), 3.34-3.42 (m, 1H), 3.67-3.94 (m, 4H), 6.26 (s, 1H), 6.73 (s, 1H), 6.73-6.80 (m, 1H), 7.44-7.54 (m, 2H) ppm. ES-MS (m/z): calcd for C26H35N5O2 (M+H)+: 450.6. found: 450.3.

C. 3-[8-(1-Ethyl-propyl)-2,6-dimethyl-imidazo[1,2-b]pyridazin-3-yl]-2-methyl-imidazo[1,2-a]pyridine-8-carboxaldehyde A solution of 3-(8-diethoxymethyl-2-methyl-imidazo[1,2-a]pyridin-3-yl)-8-(1-ethyl-propyl)-2,6-dimethyl-imidazo[1,2-b]pyridazine (2.33 g, 5.20 mmol) in acetone (25 mL) is treated with 5 M HCl (1.0 mL, 5 mmol) and the resulting solution is refluxed for 4 h. The organic solvent is removed in vacuo; the residue is diluted with H$_2$O (100 mL), the pH is adjusted to 8-9 using sat. NaHCO$_3$; the mixture is extracted with EtOAc (2×100 mL); dried with Na$_2$SO$_4$; filtered and concentrated, and purification of the crude material by silica gel chromatography gives the title compound (1.39 g, 3.72 mmol, 71%). $^1$H NMR (CDCl$_3$): δ. 0.92 (t, J=7.5 Hz, 3H), 0.93 (t, J=7.5 Hz, 3H), 1.81-1.95 (m, 4H), 2.43 (s, 3H), 2.44 (s, 3H), 2.51 (s, 3H), 3.30-3.42 (m, 1H), 6.76 (s, 1H), 6.91 (t, J=7.0 Hz, 1H), 7.74 (dd, J=7.0, 1.3 Hz, 1H), 7.78 (dd, J=7.0, 1.3 Hz, 1H), 10.84 (s, 1H) ppm. ES-MS (m/z): calcd for C22H25N5O (M+H)+: 376.5. found: 376.2.

Example 39

Preparation of {3-[8-(1-ethyl-propyl)-2,6-dimethyl-imidazo[1,2-b]pyridazin-3-yl]-2-methyl-imidazo[1,2-a]pyridin-8-yl}-methanol

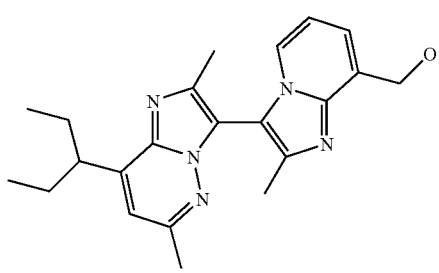

A solution of 3-[8-(1-ethyl-propyl)-2,6-dimethyl-imidazo[1,2-b]pyridazin-3-yl]-2-methyl-imidazo[1,2-a]pyridine-8-carboxaldehyde (0.33 g, 0.89 mmol) in CH$_3$OH 910 ml) is treated with NaBH4 (37 mg, 0.98 mmol), and stirred at RT for 30 min. It is quenched with sat. NH$_4$Cl (5 mL), the organic solvent is removed in vacuo, and the residue is diluted with H$_2$O (10 mL) ppm. The aqueous layer is extracted with EtOAC (2×30 mL); the combined organic layers is dried with Na$_2$SO$_4$; filtered and concentrated to give the title compound (0.29 g, 0.78 mmol, 87%). $^1$H NMR (CDCl$_3$): δ. 0.90 (t, J=7.0 Hz, 3H), 0.91 (t, J=7.0 Hz, 3H), 1.78-1.98 (m, 4H), 2.42 (s, 3H), 2.43 (s, 3H), 2.45 (s, 3H), 3.36-3.42 (m, 1H), 4.39 (bs, 1H), 5.11 (s, 2H), 6.73 (d, J=5.7 Hz, 1H), 6.73 (s, 1H), 7.17 (d, J=6.6 Hz, 1H), 7.46 (d, J=6.6 Hz, 1H) ppm. ES-MS (m/z): calcd for C$_{22}$H$_{27}$N$_5$O (M+H)+: 378.5. found: 378.3.

Example 40

Preparation of 8-(1-ethyl-propyl)-3-(8-methoxymethyl-2-methyl-imidazo[1,2-a]pyridin-3-yl)-2,6-dimethyl-imidazo[1,2-b]pyridazine

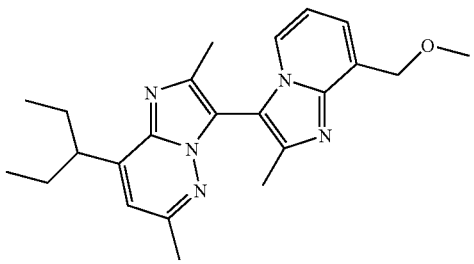

A solution of {3-[8-(1-ethyl-propyl)-2,6-dimethyl-imidazo[1,2-b]pyridazin-3-yl]-2-methyl-imidazo[1,2-a]pyridin-8-yl}-methanol (0.23 g, 0.60 mmol) in THF (10 mL) is treated with 60% NaH (29 mg, 0.73 mmol) at 0° C., and the resulting mixture is stirred at 0° C. for 30 min. CH$_3$I (56 μL, 0.91 mmol) is added and the reaction is stirred at 0° C. for 2 h, and at RT overnight. It is quenched with sat. NH$_4$Cl (10 mL), diluted with H$_2$O (20 mL), and extracted with EtOAc (2×20 ml). The combined organic layers are dried with Na$_2$SO$_4$, filtered and concentrated to give the title compound (0.22 g, 0.55 mmol, 91%). $^1$H NMR (CDCl$_3$): δ 0.91 (t, J=7.3 Hz, 3H), 0.93 (t, J=7.3 Hz, 3H), 1.79-1.95 (m, 4H), 2.41 (s, 3H), 2.43 (s, 3H), 2.44 (s, 3H), 3.32-3.42 (m, 1H), 3.59 (s, 3H), 4.96 (d, J=13.6 Hz, 1H), 5.01 (d, J=13.6 Hz, 1H), 6.73 (s, 1H), 6.76 (t, J=6.7 Hz, 1H), 7.31 (d, J=6.6 Hz, 1H), 7.46 (d, J=6.6 Hz, 1H) ppm. ES-MS (m/z): calcd for C23H29N5O (M+H)+: 392.5. found: 392.3.

Example 41

Preparation of 1-{3-[8-(1-Ethyl-propyl)-2,6-dimethyl-imidazo[1,2-b]pyridazin-3-yl]-2-methyl-imidazo[1,2-a]pyridin-8-yl}-ethanol

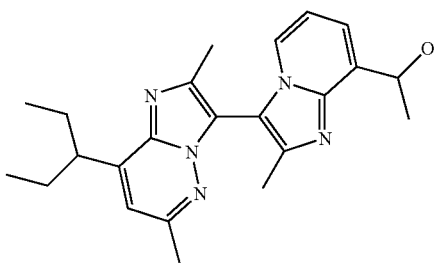

A solution of 3-[8-(1-ethyl-propyl)-2,6-dimethyl-imidazo[1,2-b]pyridazin-3-yl]-2-methyl-imidazo[1,2-a]pyridine-8-carboxaldehyde (1.07 g, 2.84 mmol) in THF (30 mL) is cooled at 0° C., treated with 3.0 M CH$_3$MgBr (1.1 mL, 3.41 mmol). The reaction is stirred at 0° C. for 30 min. It is then quenched with sat. NH₄Cl (15 mL), diluted with H₂O (15 mL), extracted with EtOAc (2×30 mL). The combined organic layers is dried with Na₂SO₄, filtered and concentrated. Purification of the crude material by silica gel chromatography gives the title compound (0.93 g, 2.38 mmol, 83%). ¹H NMR (CDCl₃): δ 0.91 (t, J=7.1 Hz, 3H), 0.92 (t, J=7.1 Hz, 3H), 1.75 (d, J=6.6 Hz, 3H), 1.79-1.94 (m, 4H), 2.41 (s, 6H), 2.45 (s, 3H), 3.32-3.42 (m, 1H), 5.17 (m, 1H), 5.39 (m, 1H), 6.72 (t, J=7.0 Hz, 1H), 6.73 (s, 1H), 7.13 (d, J=7.1 Hz, 1H), 7.43 (d, J=7.1 Hz, 1H) ppm. ES-MS (m/z): calcd for C23H29N5O (M+H)+: 392.5. found: 392.3.

Example 42

Preparation of 8-(1-ethyl-propyl)-3-[8-(1-methoxy-ethyl)-2-methyl-imidazo[1,2-a]pyridin-3-yl]-2,6-dimethyl-imidazo[1,2-b]pyridazine

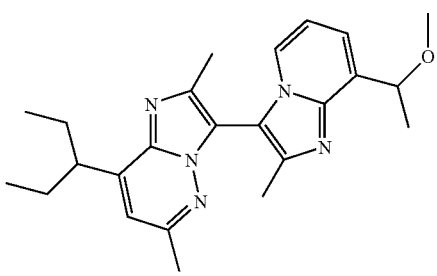

Using a procedure analogous to Example 40, 1-{3-[8-(1-ethyl-propyl)-2,6-dimethyl-imidazo[1,2-b]pyridazin-3-yl]-2-methyl-imidazo[1,2-a]pyridin-8-yl}-ethanol (73.5 mg, 0.18 mmol) gives the title compound (63.5 mg, 0.17 mmol, 83%). ¹H NMR (CDCl₃): δ 0.92 (t, J=7.4 Hz, 3H), 0.93 (t, J=7.4 Hz, 3H), 1.65 (dd, J=6.2, 2.2 Hz, 3H), 1.80-1.95 (m, 4H), 2.40-2.49 (m, 9H), 3.35-3.46 (m, 4H), 5.24 (q, J=6.2 Hz, 1H), 6.73 (d, J=1.7 Hz, 1H), 6.77 (t, J=7.0 Hz, 1H), 7.31 (d, J=6.5 Hz, 1H), 7.45 (d, J=6.5 Hz, 1H) ppm. ES-MS (m/z): calcd for C24H31N5O (M+H)+: 406.6. found: 406.3.

Example 43

Preparation of 1-{3-[8-(1-Ethyl-propyl)-2,6-dimethyl-imidazo[1,2-b]pyridazin-3-yl]-2-methyl-imidazo[1,2-a]pyridin-8-yl}-ethanone

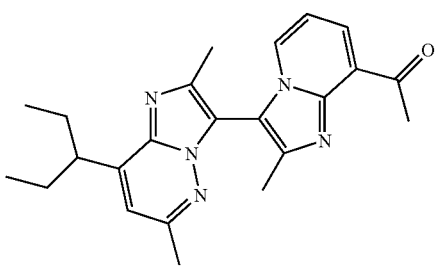

A solution of 1-{3-[8-(1-ethyl-propyl)-2,6-dimethyl-imidazo[1,2-b]pyridazin-3-yl]-2-methyl-imidazo[1,2-a]pyridin-8-yl}-ethanol (0.77 g, 1.96 mmol) dissolved in CH₂Cl₂ (20 mL) is cooled to 0° C., treated with NMO (0.34 g, 2.94 mmol) and TPAP (34 mg, 0.098 mmol). The reaction is stirred at 0° C. for 10 min, then at RT for 4 h. It is filtered through silica gel, washed with EtOAc. Purification of the crude material by silica gel chromatography gives the title compound (0.63 g, 1.61 mmol, 82%) as a yellow solid. ¹H NMR (CDCl₃): δ 0.92 (t, J=7.5 Hz, 3H), 0.93 (t, J=7.5 Hz, J=7.5 Hz, 3H), 1.80-1.95 (m, 4H), 2.43 (s, 3H), 2.45 (s, 3H), 2.48 (s, 3H), 3.12 (s, 3H), 3.34-3.46 (m, 1H), 6.75 (s, 1H), 6.83 (t, J=7.0 Hz, 1H), 7.67 (dd, J=7.1, 1.4 Hz, 1H), 7.91 (dd, J=7.1, 1.4 Hz, 1H) ppm. ES-MS (m/z): calcd for C23H27N5O (M+H)+: 390.5. found: 390.2.

Example 44

Preparation of 2-{3-[8-(1-ethyl-propyl)-2,6-dimethyl-imidazo[1,2-b]pyridazin-3-yl]-2-methyl-imidazo[1,2-a]pyridin-8-yl}-propan-2-ol

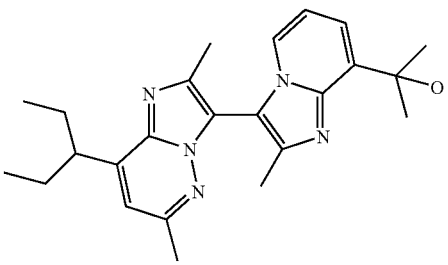

A suspension of CeCl₃ (0.37 g, 2.22 mmol) in THF (10 mL) is stirred at RT for 2 h. It is then cooled to 0° C., and treated with 3.0 M CH₃MgBr (0.74 mL, 2.22 mmol). The mixture is stirred at 0° C. for 2 h. A solution of 1-{3-[8-(1-ethyl-propyl)-2,6-dimethyl-imidazo[1,2-b]pyridazin-3-yl]-2-methyl-imidazo[1,2-a]pyridin-8-yl}-ethanone (0.57 g, 1.48 mmol) in THF (5 mL) is added to the mixture at 0° C. The reaction is stirred at 0° C. for 30 min and at RT for 2 h. It is finally quenched with sat. NH₄Cl (10 mL), diluted with H₂O (50 mL); extracted with EtOAc (3×100 mL). The combined organic layers is dried with Na₂SO₄, filtered and concentrated. Purification of the crude material by silica gel chromatography gives the title compound (0.36 g, 0.90 mmol, 61%). ¹H NMR (CDCl₃): δ 0.92 (t, J=7.5 Hz, 3H), 0.93 (t, J=7.5 Hz, 3H), 1.80 (s, 6H), 1.80-1.95 (m, 4H), 2.41 (s, 3H), 2.42 (s, 3H), 2.45 (s, 3H), 3.31-3.41 (m, 1H), 6.67-6.74 (m, 1H), 6.73 (s, 1H), 6.92 (bs, 1H), 7.09 (bs, 1H), 7.41 (d, J=5.6 Hz, 1H) ppm. ES-MS (m/z): calcd for C24H31N5O (M+H)+: 406.6. found: 406.3.

Example 45

Preparation of 8-(1-Ethyl-propyl)-2,6-dimethyl-3-(2-methyl-imidazo[1,2-a]pyridin-3-yl)-imidazo[1,2-b]pyridazine

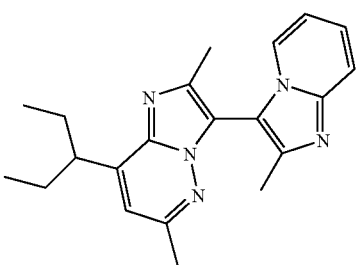

Using a procedure analogous to Example 16B, 2-methyl-imidazo[1,2-a]pyridine (Chem. Ber. 1926; 59, 2054), (0.38 g, 2.92 mmol) and 8-(1-ethyl-propyl)-3-iodo-2,6-dimethyl-imidazo[1,2-b]pyridazine (1.00 g, 2.92 mmol) give the title compound (0.21 g, 0.60 mmol, 21%). $^1$H NMR (CDCl$_3$): δ 0.91 (t, J=7.5 Hz, 3H), 0.92 (t, J=7.5 Hz, 3H), 1.80-1.95 (m, 4H), 2.42 (s, 3H), 2.43 (s, 3H), 2.45 (s, 3H), 3.34-3.42 (m, 1H), 6.73 (s, 1H), 6.74 (dt, J=6.6, 0.9 Hz, 1H), 7.21-7.25 (m, 1H), 7.52 (d, J=6.6 Hz, 1H), 7.64 (d, J=6.6 Hz, 1H) ppm. ES-MS (m/z): calcd for C$_{21}$H$_{25}$N$_5$ (M+H)+: 348.5. found: 348.2.

Example 46

Preparation of 3-(2,8-dimethyl-imidazo[1,2-a]pyridin-3-yl)-8-(1-ethyl-propyl)-2,6-dimethyl-imidazo[1,2-b]pyridazine

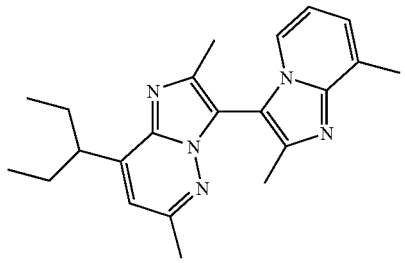

Using a procedure analogous to Example 16B, 2,8-dimethyl-imidazo[1,2-a]pyridine (J. Chem. Soc. 1951; 2411, 2415), (0.30 g, 2.06 mmol) and 8-(1-ethyl-propyl)-3-iodo-2,6-dimethyl-imidazo[1,2-b]pyridazine (0.71 g, 2.06 mmol) give the title compound (0.48 g, 1.33 mmol, 65%). $^1$H NMR (CDCl$_3$): δ 0.92 (t, J=7.5 Hz, 3H), 0.93 (t, J=7.5 Hz, 3H), 1.81-1.95 (m, 4H), 2.41 (s, 3H), 2.44 (s, 3H), 2.45 (s, 3H), 2.70 (s, 3H), 3.35-3.43 (m, 1H), 6.65 (t, J=6.6 Hz, 1H0, 6.72 9s, 1H), 7.03 (d, J=6.6 Hz, 1H), 7.40 9d, J=6.6 Hz, 1) ppm. ES-MS (m/z): calcd for C$_{22}$H$_{27}$N$_5$ (M+H)+: 362.5. found: 362.2.

Example 47

Preparation of 3-[8-(1-ethyl-propyl)-2,6-dimethyl-imidazo[1,2-b]pyridazin-3-yl]-2-methyl-benzo[b]thiophene-7-carboxylic acid methyl ester

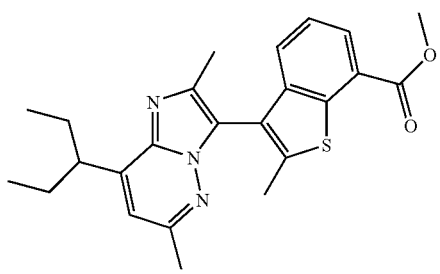

A. 2-Methyl-benzo[b]thiophene-7-carboxylic Acid Methyl Ester

A mixture of 7-bromo-2-methyl-benzo[b]thiophene (Acheson, R. M.; Cooper, M. W. J. Chem. Soc., Perkin Trans 11980, 1185), (0.88 g, 3.89 mmol), with Pd(OAc)$_2$ (176.4 mg), dppf (637.2 mg), Et$_3$N (3.0 mL) and CH$_3$OH (17 mL) in DMSO (26 mL) is reacted at 80° C./1100 psi of CO for 24 h. The crude reaction mixture is diluted with EtOAc (100 mL), washed with 0.1 M HCl (3×30 mL); dried with Na$_2$SO$_4$; filtered and concentrated. Purification of the crude material by silica gel chromatography to give the title compound (0.66 g, 3.19 mmol, 82%). $^1$H NMR (CDCl$_3$): δ 2.63 (s, 3H), 4.02 (s, 3H), 7.04 (q, J=0.9 Hz, 1H), 7.38 (t, J=7.9 Hz, 1H), 7.84 (d, J=8.0 Hz, 1H), 8.01 (dd, J=8.0, 1.3 Hz, 1H) ppm. ES-MS (m/z): calcd for C$_{11}$H$_{10}$O$_2$S (M+NH$_4$)$^+$: 224.3. found: 224.1.

B. 3-Bromo-2-methyl-benzo[b]thiophene-7-carboxylic Acid Methyl Ester

A solution of 2-methyl-benzo[b]thiophene-7-carboxylic acid methyl ester (0.50 g, 2.44 mmol) in CHCl$_3$ (10 mL) is cooled to 0° C., treated with a solution of Br$_2$ (0.13 mL, 2.44 mmol) in CHCl$_3$ (5 mL). The reaction is stirred at 0° C. for 30 min, then at RT overnight. The reaction is diluted with CH$_2$Cl$_2$ (50 mL), washed with 10% Na$_2$S$_2$O$_3$ (2×20 mL); dried with Na$_2$SO$_4$, filtered and concentrated to give the title compound (0.69 g, 2.43 mmol, 100%). $^1$H NMR (CDCl$_3$): δ 2.58 (s, 3H), 4.02 (s, 3H), 7.50 (t, J=7.9 Hz, 1H), 7.92 (d, J=7.9 Hz, 1H), 8.08 (d, J=7.5 Hz, 1H).

C. 3-[8-(1-Ethyl-propyl)-2,6-dimethyl-imidazo[1,2-b]pyridazin-3-yl]-2-methyl-benzo[b]thiophene-7-carboxylic Acid Methyl Ester Using a procedure analogous to Example 16B, from 3-bromo-2-methyl-benzo[b]thiophene-7-carboxylic acid methyl ester (0.51 g, 1.79 mmol) and 8-(1-ethyl-propyl)-2,6-dimethyl-imidazo[1,2-a]pyridine (0.39 g, 1.79 mmol) to give the title compound (0.23 g, 0.55 mmol, 31%). $^1$H NMR (CDCl$_3$): δ 0.91 (t, J=7.5 Hz, 6H), 1.79-1.95 (m, 4H), 2.37 (s, 3H), 2.43 (s, 3H), 2.45 (s, 3H), 3.35-3.41 (m, 1H), 4.04 (s, 3H), 6.67 (s, 1H), 7.35 (t, J=7.9 Hz, 1H), 7.42 (d, J=7.5 Hz, 1H), 8.06 (d, J=7.5 Hz, 1H).) ppm. ES-MS (m/z): calcd for C$_{24}$H$_{27}$N$_3$O$_2$S (M+H)+: 422.6. found: 422.3.

Example 48

Preparation of 2-{3-[8-(1-Ethyl-propyl)-2,6-dimethyl-imidazo[1,2-b]pyridazin-3-yl]-2-methyl-benzo[b]thiophen-7-yl}-propan-2-ol

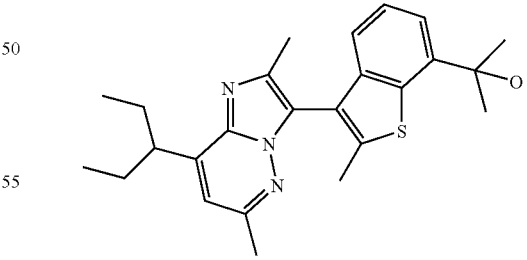

A solution of 3-[8-(1-ethyl-propyl)-2,6-dimethyl-imidazo[1,2-b]pyridazin-3-yl]-2-methyl-benzo[b]thiophene-7-carboxylic acid methyl ester (0.22 g, 0.52 mmol) in THF (10 mL) is cooled to 0° C. It is treated with 3.0 M CH$_3$MgBr (0.44 mL, 1.31 mmol) and the reaction is stirred at 0° C. for 10 min, then refluxed for 2 h. It is quenched with sat. NH$_4$Cl at 0° C., then diluted with H$_2$O (20 mL); and extracted with EtOAc (2×30 mL). The combined organic layers is dried with Na$_2$SO$_4$, filtered and concentrated. Purification of the crude material by silica gel chromatography gives the title compound (0.19 g, 0.45 mmol, 85%). $^1$H NMR (CDCl$_3$): δ 0.91 (t, J=7.5 Hz, 3H), 0.92 (t, J=7.5 Hz, 3H), 1.79 (s, 6H), 1.70-1.95 (m, 4H), 2.37 (s, 3H), 2.41 (s, 3H), 2.44 (s, 3H), 3.35-3.41 (m, 1H), 6.63 (s, 1H), 7.13 (t, J=3.5 Hz, 1H), 7.20-7.26 (m, 2H) ppm. ES-MS (m/z): calcd for C$_{25}$H$_{31}$N$_3$OS (M+H)+: 422.6. found: 422.3.

Example 49

Preparation of 8-(1-ethyl-propyl)-3-(7-isopropenyl-2-methyl-benzo[b]thiophen-3-yl)-2,6-dimethyl-imidazo[1,2-b]pyridazine

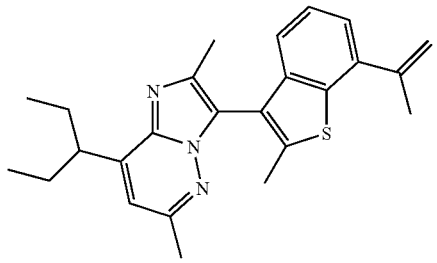

A. 2-(3-Bromo-2-methyl-benzo[b]thiophen-7-yl)-propan-2-ol

Using a procedure analogous to Example 48, from 3-bromo-2-methyl-benzo[b]thiophene-7-carboxylic acid methyl ester (8.3 g, 29.12 mmol) and 3.0 M CH$_3$MgBr (24.3 mL, 72.81 mmol) to give the title compound (7.65 g, 26.87 mmol, 92%). $^1$H NMR (CDCl$_3$): δ 1.73 (s, 6H), 1.90 (bs, 1H), 2.54 (s, 3H), 7.25 (s, 1H), 7.38 (t, J=7.5 Hz, 1H), 7.65 (d, J=7.9 Hz, 1H).

B. 3-Bromo-7-isopropenyl-2-methyl-benzo[b]thiophene

A solution of 2-(3-bromo-2-methyl-benzo[b]thiophen-7-yl)-propan-2-ol (0.98 g, 3.45 mmol) in CH$_2$Cl$_2$ 910 mL) is treated with Et$_3$N (0.72 mL, 5.18 mmol) and MsCl (0.29 mL, 3.80 mmol) at) 0° C. The reaction is stirred at 0° C. for 10 min, and at RT overnight. It is diluted with EtOAc (50 mL), washed with 0.1 M HCl (10 m), H$_2$O (20 mL); dried with Na$_2$SO$_4$, filtered and concentrated. Purification of the crude material by silica gel chromatography gives the title compound (0.36 g, 1.35 mmol, 39%). $^1$H NMR (CDCl$_3$): δ) 2.23 (s, 3H), 2.56 (s, 3H), 5.40 (s, 1H), 5.49 (s, 1H), 7.28 (s, 1H), 7.41 (t, J=7.1 Hz, 1H), 7.64 (d, J=7.9 Hz, 1H) ppm.

C. 8-(1-Ethyl-propyl)-3-(7-isopropenyl-2-methyl-benzo[b]thiophen-3-yl)-2,6-dimethyl-imidazo[1,2-b]pyridazine Using a procedure analogous to Example 16B, from 3-bromo-7-isopropenyl-2-methyl-benzo[b]thiophene (0.36 g, 1.35 mmol) and 8-(1-ethyl-propyl)-2,6-dimethyl-imidazo[1,2-a]pyridine (0.30 g, 1.35 mmol) to give the title compound (0.37 g, 0.91 mmol, 67%). $^1$H NMR (CDCl$_3$): δ 0.91 (t, J=7.0 Hz, 3H), 0.92 (t, J=7.0 Hz, 3H), 1.75-1.95 (m, 4H), 2.28 (s, 3H), 2.38 (s, 3H), 2.41 (s, 3H), 2.44 (s, 3H), 3.34-3.45 (m, 1H), 5.43 (s, 1H), 5.58 (s, 1H), 6.67 (s, 1H), 7.13 (d, J=7.5 Hz, 1H), 7.22-7.29 (m, 2H) ppm. ES-MS (m/z): calcd for C$_{25}$H$_{29}$N$_3$S (M+H)+: 404.6. found: 404.3.

Example 50

Preparation of 8-(1-ethyl-propyl)-3-(7-isopropyl-2-methyl-benzo[b]thiophen-3-yl)-2,6-dimethyl-imidazo[1,2-b]pyridazine

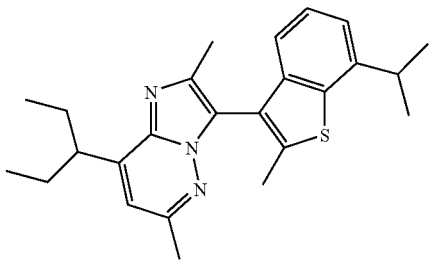

A solution of 8-(1-ethyl-propyl)-3-(7-isopropenyl-2-methyl-benzo[b]thiophen-3-yl)-2,6-dimethyl-imidazo[1,2-b]pyridazine (33 mg, 0.08 mmol) in CH$_3$OH (25 mL) is hydrogenated at 30 psi/RT/1 h using 10% Pd—C (99 mg). The reaction mixture is filtered through celite, washed with EtOAc and concentrated to give the title compound (13.6 mg, 0.03 mmol, 41%). $^1$H NMR (CDCl$_3$): δ 0.92 (t, J=7.5 Hz, 6H), 1.42 (d, J=2.6 Hz, 3H), 1.44 (d, J=2.6 Hz, 3H), 1.75-1.95 (m, 4H), 2.40 (s, 3H), 2.41 (s, 3H), 2.45 (s, 3H), 3.20-3.30 (m, 1H), 3.35-3.50 (m, 1H), 6.69 (s, 1H), 7.07 (d, J=7.5 Hz, 1H), 7.18 (d, J=7.0 Hz, 1H), 7.26 (t, J=7.9 Hz, 1H) ppm. ES-MS (m/z): calcd for C$_{25}$H$_{31}$N$_3$S (M+H)+: 406.6. found: 406.3.

Example 51

Preparation of 8-(1-ethyl-propyl)-2,6-dimethyl-3-[2-methyl-7-(1-methyl-cyclopropyl)-benzo[b]thiophen-3-yl]-imidazo[1,2-b]pyridazine

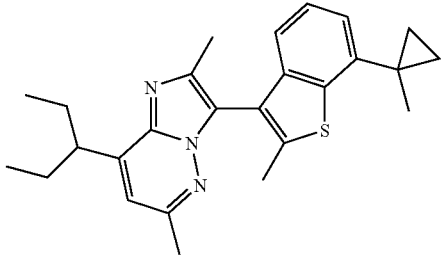

A solution of 8-(1-ethyl-propyl)-3-(7-isopropenyl-2-methyl-benzo[b]thiophen-3-yl)-2,6-dimethyl-imidazo[1,2-b]pyridazine (97 mg, 0.24 mmol) in CH$_2$Cl$_2$ (5 mL) is cooled to 0° C., treated with 1.0 M Et$_2$Zn (1.2 mL, 1.2 mmol) and ClCH$_2$I (176 μL, 2.4 mmol). The reaction is stirred at 0° C. for 30 min, then at RT for 1 h. The reaction is cooled to 0° C., quenched with sat. NH$_4$Cl (10 mL); diluted with H$_2$O (15 mL); extracted with EtOAc (3×30 mL); dried with Na$_2$SO$_4$, filtered and concentrated. The crude material is subjected to the same condition to ensure the conversion is completed. Purification of the crude material using silica gel chromatography gives the title compound (12.4 mg, 0.03 mmol, 12%). $^1$H NMR (CDCl$_3$): δ 0.80-0.84 (m, 2H), 0.92 (t, J=6.9 Hz, 6H), 0.97-1.11 (m, 2H), 1.51 (s, 3H), 1.79-1.94 (m, 4H), 2.41 (s, 3H), 2.43 (s, 3H), 2.46 (s, 3H), 3.22-3.54 (m, 1H), 6.69 (s, 1H), 7.07 (d, J=7.5 Hz, 1H), 7.21 (t, J=7.5 Hz, 1H), 7.26 (d, J=7.5 Hz, 1H) ppm. ES-MS (m/z): calcd for $C_{26}H_{31}N_3S$ (M+H)+: 418.6. found: 418.3.

Example 52

Preparation of 2-{3-[8-(1-ethyl-propyl)-2,6-dimethyl-imidazo[1,2-b]pyridazin-3-yl]-2-methyl-benzo[b]thiophen-7-yl}-propan-1-ol

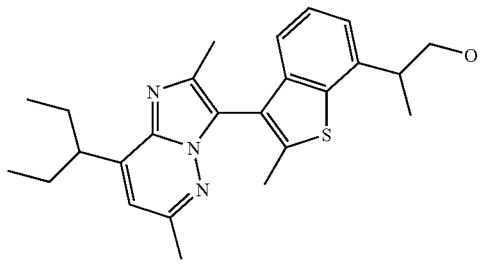

A solution of 8-(1-ethyl-propyl)-3-(7-isopropenyl-2-methyl-benzo[b]thiophen-3-yl)-2,6-dimethyl-imidazo[1,2-b]pyridazine (0.58 g, 1.45 mmol) in THF (20 mL) is cooled to −78° C., and treated with 2.0 M $BH_3.SMe_2$ (2.2 mL, 4.3 mmol). The reaction is stirred in the cooling bath, allowed to warm up gradually to RT and stirred at RT overnight. It is cooled to 0° C., treated with $CH_3OH$ (10 mL), 5 M NaOH (10 mL), and 30% $H_2O_2$ (10 mL). The resulting mixture is stirred at 0° C. for 15 ml, and then at RT for 4 h. It is diluted with $H_2O$ (100 mL); extracted with EtOAc (3×100 mL). The combined organic layers is washed with 5% $Na_2SO_3$ (100 mL), $H_2O$ (100 mL); dried with $Na_2SO_4$; filtered and concentrated. Purification of the crude material by silica gel chromatography gives the title compound (0.35 g, 0.83 mmol, 57%). $^1H$ NMR ($CDCl_3$): δ 0.91 (t, J=7.0 Hz, 3H), 0.92 (t, J=7.0 Hz, 3H), 1.44 (d, J=3.5 Hz, 1.5H), 1.46 (d, J=3.5 Hz, 1.5 Hz), 1.75-1.95 (m, 4H), 2.38 (s, 3H), 2.42 (s, 3H), 2.44 (s, 3H), 3.25-3.40 (m, 1H), 3.40 (bs, 1H), 3.82-4.03 (m, 2H), 6.68 (s, 1H), 7.11 (d, J=7.5 Hz, 1H), 7.19 (d, J=7.5 Hz, 1H), 7.27 (t, J=7.5 Hz, 1H) ppm. ES-MS (m/z): calcd for $C_{25}H_{31}N_3OS$ (M+H)+: 422.6. found: 422.3.

Example 53

Preparation of 8-(1-ethyl-propyl)-3-[7-(2-methoxy-1-methyl-ethyl)-2-methyl-benzo[b]thiophen-3-yl]-2,6-dimethyl-imidazo[1,2-b]pyridazine

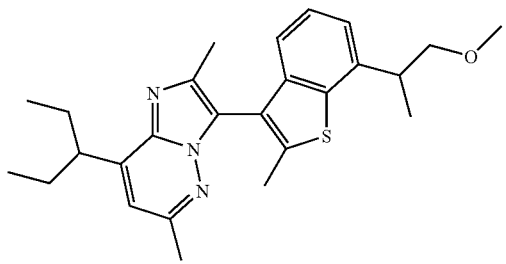

Using a procedure analogous to Example 40, from 2-{3-[8-(1-ethyl-propyl)-2,6-dimethyl-imidazo[1,2-b]pyridazin-3-yl]-2-methyl-benzo[b]thiophen-7-yl}-propan-1-ol (0.17 g, 0.41 mmol) to give the title compound (0.17 g, 0.39 mmol, 96%). $^1H$ NMR ($CDCl_3$): δ 0.91 (t, J=7.5 Hz, 3H), 0.92 (t, J=7.5 Hz, 3H), 1.46 (dd, J=6.6, 4.0 Hz, 3 Hz), 1.75-1.95 (m, 4H), 2.38 (s, 3H), 2.42 (s, 3H), 2.44 (s, 3H), 3.32-3.44 (m, 1H), 3.40 (s, 3H), 3.59 (dq, J=7.4, 4.0 Hz, 1H), 3.75 (dd, J=9.3, 6.2 Hz, 1H), 6.67 (s, 1H), 7.09 (d, J=7.0 Hz, 1H), 7.16 (d, J=7.0 Hz, 1H), 7.25 (t, J=7.0 Hz, 1H) ppm. ES-MS (m/z): calcd for $C_{26}H_{33}N_3OS$ (M+H)+: 435.6. found: 436.3.

Example 54

8-(1-ethyl-propyl)-2,6-dimethyl-3-(3-methyl-thieno[3,2-b]pyridin-2-yl)-imidazo[1,2-b]pyridazine

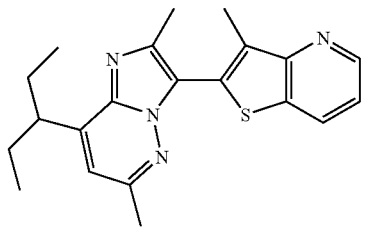

A 7-Bromo-thieno[3,2-b]pyridine 5.00 g of [3,2-b]pyridin-7-ol (33 mmol) and 50 g of phosphorus oxybromide (174 mmol) are put in a flask and heated at 110° C. for 3 h. The hot reaction mixture is poured into mixture of ice and 5N NaOH and extracted with $CHCl_2$, dried over $Na_2SO_4$ and evaporated. The crude product is applied onto a silica-gel chromatography column (Hexane:AcOEt=3:1) to give 4.19 g of the title compound. Yield 59%. mass spectrum (m/e): 215 (M+1); $^1H$-NMR ($CDCl_3$): 8.55 (d, 1H, J=4.3 Hz), 7.86 (d, 1H, J=5.7 Hz), 7.69 (d, 1H, J=5.7 Hz), 7.49 (d, 1H, J=4.3 Hz) ppm.

B. Thieno[3,2-b]pyridine 3.69 g of 7-Bromo-thieno[3,2-b]pyridine (17 mmol) is dissolved in 20 ml of dry THF and cooled to −78° C. 21.2 ml of n-BuLi 1.6M in hexane (34 mmol) is added slowly to the mixture at −78° C. and stirred at −78° C. for 20 min, and 20 ml of $MeOH/H_2O$=1/1 is added and stirred at room temperature for 1 h. The reaction mixture is extracted with CHCl2. The separated $CH_2Cl_2$ layer is washed with sat. NaCl, dried over $Na_2SO_4$ and evaporated. The crude product is applied onto a silica-gel chromatography column (Hexane→Hexane:AcOEt=−10:1) to give 1.44 g of the title compound. Yield 62%. mass spectrum (m/e): 136 (M+1); $^1H$-NMR ($CDCl_3$): 8.73 (m, 1H), 8.22 (m, 1H), 7.79 (m, 1H), 7.61 (m, 1H), 7.29 (m, 1H) ppm.

C. 3-Bromo-thieno[3,2-b]pyridine 3.45 g of Thieno[3,2-b]pyridine (25.6 mmol), 2.15 g of sodium bicarbonate (25.6 mmol), 6.69 g of K2HPO4 (38.4 mmol) and 4.01 g of $MgSO_4$ (33.3 mmol) are placed in the flask with 60 ml of CHCl3. The mixture is stirred under reflux and 1.57 ml of Br2 (30.7 mmol) is added slowly. The reaction mixture is stirred under reflux overnight. Additional 0.7 ml of bromine is added and stirred under reflux for 4 h and cooled to room temperature. Water is added and extracted with CHCl3. The separated CHCl3 is washed by sat. Na2S2O3 and sat. NaCl and dried over $Na_2SO_4$ and evaporated. The title compound is recrystallized from Hexane/$CH_2Cl_2$. 3.94 g, Yield 72%. mass spectrum (m/e): 215 (M+1); $^1$H-NMR (CDCl$_3$): 8.86 (d, 1H, J=5.2 Hz), 8.24 (d, 1H, J=8.2 Hz), 7.82 (s, 1H), 7.38 (dd, 1H, J=8.2 Hz, 5.2 Hz) ppm.

D. 3-Methyl-thieno[3,2-b]pyridine 3 reaction vials are prepared: 214 mg of 3-bromo-thieno [3,2-b]pyridine (1.0 mmol) and 180 mg of methylboronic acid (3.0 mmol) are put in the each vial with 4 ml of DME/ water/EtOH=7/3/1. 1.5 ml of 2 M Na$_2$CO aq. (3.0 mmol) is added and N$_2$ gas is bubbled in for 15 min. 58 mg of Pd(PPh$_3$)$_4$ (0.05 mmol) is added and each vials are sealed. These vials are heated at 130° C. for 30 min in the microwave. All reaction mixtures are combined, and water and CH$_2$Cl$_2$ are added. The CH$_2$Cl$_2$ layer are separated and dried over Na$_2$SO$_4$ and evaporated. The crude products are applied onto a silica-gel chromatography column (Hexane: AcOEt: 2 M NH$_3$ in MeOH=20:4:1) to give 193 mg of the title compound. Yield 43%. mass spectrum (m/e): 150 (M+1); $^1$H-NMR (CDCl$_3$): 8.76 (dd, 1H, J=4.7 Hz, 1.5 Hz), 8.20 (dd, 1H, J=8.2 Hz, 1.5 Hz), 7.43 (d, 1H, J=1.2 Hz), 7.29 (dd, 1H, J=8.2 Hz, 4.7 Hz), 2.58 (d, 3H, J=1.2 Hz) ppm.

8-(1-ethyl-propyl)-2,6-dimethyl-3-(3-methyl-thieno [3,2-b]pyridin-2-yl)-imidazo[1,2-b]pyridazine 190 mg of 3-Methyl-thieno[3,2-b]pyridine (1.28 mmol) is dissolved in 3.0 ml of dry THF and cooled to −78° C. 0.62 ml of n-BuLi 2.5M in hexane (1.54 mmol) is added at −78° C. and stirred at −78° C. for 10 min and room temperature for 10 min. The reaction vessel is cooled to −78° C. again and 3.3 ml of 0.5 M ZnCl$_2$ in THF (1.66 mmol) is added at −78C and stirred at room temperature for 15 min. 343 mg of 8-(1-ethyl-propyl)-3-iodo-2,6-dimethyl-imidazo[1,2-b]pyridazine (1.0 mmol) and 41 mg of PdCl$_2$(pddf) (0.05 mmol) are added and the tube is capped. The tube is heated at 80° C. for overnight. The reaction is quenched by NH4Claq. and extracted by CH$_2$Cl$_2$, dried over Na$_2$SO$_4$ and evaporated. The crude product is applied onto a silica-gel chromatography column (Hexane:AcOEt:2 M NH3 in MeOH=10:3:1) to give 127 mg of the title compound. Yield 35%. mass spectrum (m/e): 365 (M+1); $^1$H-NMR (CDCl$_3$): 8.79 (dd, 1H, J=4.8 Hz, 1.4 Hz), 8.21 (dd, 1H, J=7.9 Hz, 1.4 Hz), 7.33 (dd, 1H, J=7.9 Hz, 4.8 Hz), 6.76 (s, 1H), 3.38 (m, 1H), 2.55 (s, 6H), 2.47 (s, 3H), 1.89 (m, 4H), 0.92 (t, 6H, J=7.5 Hz) ppm.

Example 55

8-(1-Ethyl-propyl)-2,6-dimethyl-3-(2-methyl-thieno [3,2-b]pyridin-3-yl)-imidazo[1,2-b]pyridazine

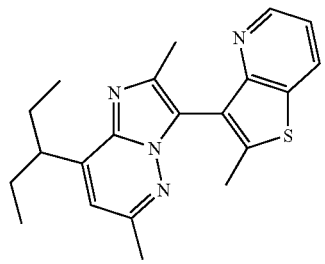

A. 3-Bromo-2-methyl-thieno[3,2-b]pyridine 674 mg of 3-Bromo-thieno[3,2-b]pyridine (3.15 mmol) is dissolved in 12 ml of dry THF and cooled to −78° C. 2.3 ml of LDA-mono-tetrahydrofuran (1.5 M) solution in cyclohexane (3.46 mmol) is added to the mixture at −78° C. and stirred at −78° C. for 20 min. 0.22 ml of methyliodide (3.46 mmol) is added to the mixture and stirred at −78° C.→room temperature for 2 h. the reaction mixture is quenched by sat. NH$_4$Cl and extracted with CH$_2$Cl$_2$. The separated CH$_2$Cl$_2$ is dried over Na$_2$SO$_4$ and evaporated. The crude product is applied onto a silica-gel chromatography column (Hexane:AcOEt:2 M NH3 in MeOH=20:4:1) to give 618 mg of the title compound. Yield 86%. mass spectrum (m/e): 230 (M+1); $^1$H-NMR (CDCl$_3$): 8.78 (dd, 1H, J=4.8 Hz, 1.4 Hz), 8.10 (dd, 1H, J=8.2 Hz, 1.4 Hz), 7.30 (dd, 1H, J=8.2 Hz, 4.8 Hz), 2.67 (s, 3H).

B. 8-(1-Ethyl-propyl)-2,6-dimethyl-3-(2-methyl-thieno[3,2-b]pyridin-3-yl)-imidazo[1,2-b]pyridazine 380 mg of 3-Bromo-2-methyl-thieno[3,2-b]pyridine (1.66 mmol) is placed into the vial with 3.56 ml of Reiki Zn, suspension in THF (2.50 mmol) and capped and heated at 100C for 2 h. The excess Zinc is allowed to settle down and the solution is transferred to the vial containing 250 mg of 8-(1-ethyl-propyl)-3-iodo-2,6-dimethyl-imidazo[1,2-b]pyridazine (0.72 mmol) and 48 mg of PdCl$_2$(pddf) (0.06 mmol) in 2 ml of dry THF. The vial is capped by Teflon cap and heated at 80C for overnight. The reaction mixture is quenched by sat.NH4Claq. and extracted by CH$_2$Cl$_2$, dried over Na$_2$SO$_4$ and evaporated. The crude product is applied onto a silica-gel chromatography column (Hexane: AcOEt: 2 M NH3 in MeOH=20:4:1) to give 24.2 mg of the title compound. Yield 9.2%. mass spectrum (m/e): 365 (M+1); $^1$H-NMR (CDCl$_3$): 8.66 (dd, 1H, J=4.7 Hz, 1.4 Hz), 8.16 (dd, 1H, J=8.1 Hz, 1.4 Hz), 7.25 (dd, 1H, J=8.1 Hz, 4.7 Hz), 6.68 (s, 1H), 3.43 (m, 1H), 2.50 (s, 3H), 2.47 (s, 3H), 2.46 (s, 3H), 1.88 (m, 4H), 0.93 (m, 6H) ppm.

Example 56

8-(1-Ethyl-propyl)-2,6-dimethyl-3-(2-methyl-thieno [3,2-c]pyridin-3-yl)-imidazo[1,2-b]pyridazine

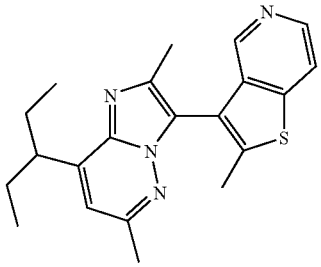

A. 3-Bromo-thieno[3,2-c]pyridine 1.46 g of Thieno[3,2-c]pyridine (10.8 mmol), 907 mg of NaHCO$_3$ (10.8 mmol), 2.82 g of K$_2$HPO$_4$ (16.2 mmol) and 1.69 g of MgSO$_4$ (14.04 mmol) are placed into the flask with 40 ml of chloroform. The reaction mixture is stirred under reflux. 0.72 ml of bromine (14.04 mmol) is added slowly to the mixture and kept stirring for overnight. CH$_2$Cl$_2$ and water are added to the cooled reaction mixture and separated CH$_2$Cl$_2$ layer is dried over Na$_2$SO$_4$ and evaporated. The crude product is applied onto a silica-gel chromatography column (Hexane: AcOEt=5:1→Hexane:AcOEt:2 M NH3 in MeOH=10:3:1) to give 660 mg of the title compound. Yield 29%. mass spectrum (m/e): 215 (M+1); $^1$H-NMR (CDCl$_3$): 9.17 (m, 1H), 8.59 (m, 1H), 7.83 (d, 1H, J=5.2 Hz), 7.52 (s, 1H) ppm.

B. 3-Bromo-2-methyl-thieno[3,2-c]pyridine 291 mg of 3-Bromo-thieno[3,2-c]pyridine (1.36 mmol) is dissolved in 3 ml of dry THF and cooled to −78° C. 1.00 ml of lithium diisopropylamine mono(tetrahydrofuran) 1.5M solution in cyclohexane (1.5 mmol) is added to the mixture at −78° C. and stirred at −78° C. for 20 min. 213 mg of methyl iodide (1.5 mmol) is added to the mixture and stirred at −78° C.→room temperature for 1 h. The reaction mixture is quenched by sat. NH$_4$Cl and extracted with CH$_2$Cl$_2$. The separated CH$_2$Cl$_2$ is dried over Na$_2$SO$_4$ and evaporated. The crude product is applied onto a silica-gel chromatography column (Hexane:AcOEt:2 M NH$_3$ in MeOH=20:4:1) to give 225 mg of the title compound. Yield 72%. mass spectrum (m/e): 230 (M+1); 1H-NMR (CDCl$_3$): 9.01 (s, 1H), 8.52 (d, 1H, J=5.5 Hz), 7.72 (d, 1H, J=5.5 Hz), 2.61 (s, 3H) ppm.

C. 8-(1-Ethyl-propyl)-2,6-dimethyl-3-(2-methyl-thieno[3,2-c]pyridin-3-yl)-imidazo[1,2-b]pyridazine 225 mg of 3-Bromo-2-methyl-thieno[3,2-c]pyridine (0.98 mmol) is placed into the vial with 2.14 ml of Reiki Zn, suspension in THF (1.50 mmol) and capped and heated at 100° C. for 2 h. The excess Zinc is allowed to settle down and the solution is transferred to the vial containing 200 mg of 8-(1-ethyl-propyl)-3-iodo-2,6-dimethyl-imidazo[1,2-b]pyridazine (0.58 mmol) and 41 mg of PdCl2(pddf) (0.05 mmol) in 3 ml of dry THF. The vial is capped with a Teflon cap and heated at 80° C. for 2 days. The reaction mixture is quenched by sat. NH$_4$Cl and extracted by CH$_2$Cl$_2$, dried over Na$_2$SO$_4$ and evaporated. The crude product is applied onto a silica-gel chromatography column (Hexane:AcOEt:2 M NH3 in MeOH=20:4:1) to give 12.8 mg of the title compound. Yield 4%. Mass spectrum (m/e): 365 (M+1); $^1$H-NMR (CDCl$_3$): 8.54 (m, 1H), 8.46 (m, 1H), 7.80 (m, 1H), 6.74 (s, 1H), 3.41 (m, 1H), 2.51 (s, 3H), 2.47 (s, 3H), 2.44 (s, 3H), 1.89 (m, 4H), 0.94 (m, 6H) ppm.

Example 57

8-(1-Ethyl-propyl)-2,6-dimethyl-3-(2-methyl-thieno[2,3-b]pyridin-3-yl)-imidazo[1,2-b]pyridazine

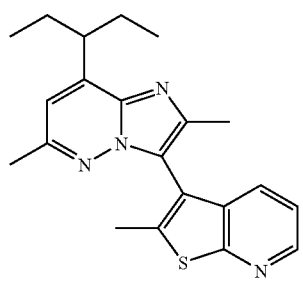

A. 3-Bromo-thieno[2,3-b]pyridine 2.30 g of Thieno[2,3-b]pyridine (17 mmol), 1.43 g of NaHCO$_3$ (17 mmol), 4.44 g of K$_2$HPO$_4$ (25.5 mmol) and 2.66 g of MgSO$_4$ (22.1 mmol) are placed into the flask with 80 ml of dichloromethane. The reaction mixture is stirred under reflux. 1.05 ml of bromine (20.4 mmol) is added slowly to the mixture and is stirred overnight. CH$_2$Cl$_2$ and water are added to the cooled reaction mixture and separated. The CH$_2$Cl$_2$ layer is dried over Na$_2$SO$_4$ and evaporated. The crude product is applied onto a silica-gel chromatography column (Hexane:AcOEt=3:1) to give 1.76 g of the title compound. Yield 48%. mass spectrum (m/e): 215 (M+1); $^1$H-NMR (CDCl$_3$): 8.67 (m, 1H), 8.13 (m, 1H), 7.59 (s, 1H), 7.45 (m, 1H) ppm.

B. 3-Bromo-2-methyl-thieno[2,3-b]pyridine 500 mg of 3-Bromo-thieno[2,3-b]pyridine (3.70 mmol) is dissolved in 3 ml of dry THF and cooled to −78° C. 2.71 ml of lithium diisopropylamine mono (tetrahydrofuran) 1.5 M solution in cyclohexane (4.07) is added to the mixture at −78° C. and stirred at −78° C. for 20 min. 0.25 ml of methyl iodide (43.7 mmol) is added to the mixture and stirred at −78° C.→room temperature for 1 h. The reaction mixture is quenched with sat. NH$_4$Cl and extracted with CH$_2$Cl$_2$. The separated CH$_2$Cl$_2$ is dried over Na$_2$SO$_4$ and evaporated. The crude product is applied onto a silica-gel chromatography column (Hexane:AcOEt=3:1) to give 382 mg of the title compound. Yield 45%. mass spectrum (m/e): 230 (M+1); $^1$H-NMR (CDCl$_3$): 8.56 (dd, 1H, J=4.7 Hz, 1.5 Hz), 7.97 (dd, 1H, J=8.5 Hz, 1.5 Hz), 7.37 (dd, 1H, J=8.5 Hz, 4.7 Hz), 2.62 (s, 3H) ppm.

C. 8-(1-Ethyl-propyl)-2,6-dimethyl-3-(2-methyl-thieno[2,3-b]pyridin-3-yl)-imidazo[1,2-b]pyridazine 382 mg of 3-Bromo-2-methyl-thieno[2,3-b]pyridine (1.67 mmol) is placed into the vial with 2.5 ml of Reiki Zn, suspension in THF (1.75 mmol) and capped and heated at 100° C. for 2 h. The excess Zinc is allowed to settle down and the solution is transferred to the vial containing 200 mg of 8-(1-ethyl-propyl)-3-iodo-2,6-dimethyl-imidazo[1,2-b]pyridazine (0.58 mmol) and 41 mg of PdCl2(pddf) (0.05 mmol) in 3 ml of dry THF. The vial is capped with a Teflon cap and heated at 80° C. for 2 days. The reaction mixture is quenched with sat. NH$_4$Cl and extracted by CH$_2$Cl$_2$, dried over Na$_2$SO$_4$ and evaporated. The crude product is applied onto a silica-gel chromatography column (Hexane:AcOEt=8:1) to give 22 mg of the title compound. Yield 4%. mass spectrum (m/e): 365 (M+1).

Example 58

8-(1-Ethyl-propyl)-2,6-dimethyl-3-(2-methyl-thieno[2,3-c]pyridin-3-yl)-imidazo[1,2-b]pyridazine

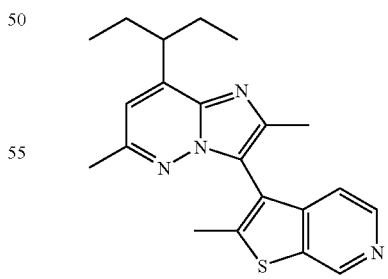

A. 3-Bromo-thieno[2,3-c]pyridine

The title compounds is prepared essentially as described in synthesis of 3-bromothieno[3,2-c]pyridine using thieno[2,3-c]pyridine. mass spectrum (m/e): 215 (M+1).

B. 3-Bromo-2-methyl-thieno[2,3-c]pyridine 428 mg of 3-Methyl-thieno[2,3-c]pyridine (2.0 mmol) is dissolved in 10 ml of dry THF and cooled to −78° C. 1.46 ml of lithium diisopropylamine mono(tetrahydrofuran) 1.5M solution in cyclohexane (2.2 mmol) is added at −78° C. and stirred at −78° C. for 15 min. 0.136 ml of methyl iodide (2.2 mmol) is added and stirred at room temperature for 30 min. Saturated NH$_4$Cl is added to quench the reaction, and the mixture is extracted with CH$_2$Cl$_2$. The separated CH$_2$Cl$_2$ layer is washed with brine, dried over Na$_2$SO$_4$ and evaporated. The crude product is applied onto a silica-gel chromatography column (Hexane:AcOEt=3:1) to give 419 mg of the title compound. Yield 91%. mass spectrum (m/e): 230 (M+1); $^1$H-NMR (CDCl$_3$): 9.02 (s, 1H), 8.59 (d, 1H, J=5.0 Hz), 7.62 (d, 1H, J=5.0 Hz), 2.66 (s, 3H) ppm.

C. 8-(1-Ethyl-propyl)-2,6-dimethyl-3-(2-methyl-thieno[2,3-c]pyridin-3-yl)-imidazo[1,2-b]pyridazine 190 mg of 3-Bromo-2-methyl-thieno[2,3-c]pyridine (0.83 mmol) is placed into the vial with 1.78 ml of Reiki Zn, suspension in THF (1.25 mmol) and capped and heated at 100° C. for 2 h. The excess Zinc is allowed to settle down and the solution is transferred to the vial containing 172 mg of 8-(1-ethyl-propyl)-3-iodo-2,6-dimethyl-imidazo[1,2-b]pyridazine (0.5 mmol) and 24 mg of PdCl$_2$(pddf) (0.03 mmol) in 3 ml of dry THF. The vial is capped with a Teflon cap and heated at 80° C. overnight. The reaction mixture is quenched with sat. NH$_4$Cl, extracted with CH$_2$Cl$_2$, dried over Na$_2$SO$_4$ and evaporated. The crude product is applied onto a silica-gel chromatography column (Hexane:AcOEt:2 M NH3 in MeOH=20:5:1) to give 28 mg of the title compound. Yield 15%. mass spectrum (m/e): 365 (M+1).

Example 59

8-(1-Ethyl-propyl)-2,6-dimethyl-3-(3-methyl-thieno[2,3-c]pyridin-2-yl)-imidazo[1,2-b]pyridazine

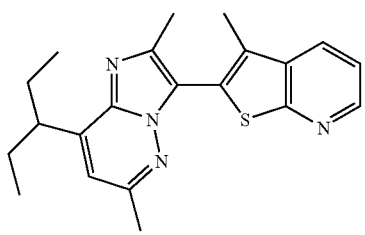

A. 3-Methyl-thieno[2,3-c]pyridine(NC7-A07062-092)

642 mg of 3-Bromo-thieno[2,3-c]pyridine (3.0 mmol), 540 mg of methylboronic acid (9.0 mmol) are placed into flask with 10 ml of DME/water/EtOH=7:3:1. The air is replaced with N$_2$ gas and 174 mg of Pd(PPh3)$_4$ (0.15 mmol) is added. The reaction mixture is stirred under reflux for overnight. To the reaction mixture is added water and CH$_2$Cl$_2$. The separated CH$_2$Cl$_2$ layer is washed by brine, dried over Na$_2$SO$_4$ and evaporated. The crude product is applied onto a silica-gel chromatography column (Hexane:AcOEt:2 M NH3 in MeOH=20:4:1) to give 131 mg of the title compound. Yield 29%. mass spectrum (m/e): 150 (M+1); $^1$H-NMR (CDCl$_3$): 9.16 (d, 1H, J=0.8 Hz), 8.56 (d, 1H, J=5.2 Hz), 7.64 (dd, 1H, J=5.2 Hz, 0.8 Hz), 7.37 (d, 1H, J=1.2 Hz), 2.50 (d, 3H, J=1.2 Hz) ppm.

B. 8-(1-Ethyl-propyl)-2,6-dimethyl-3-(3-methyl-thieno[2,3-c]pyridin-2-yl)-imidazo[1,2-b]pyridazine 149 mg of 3-Methyl-thieno[2,3-c]pyridine (1.0 mmol) is dissolved in 3.0 ml of dry THF and cooled to −78° C. 0.48 ml of n-BuLi 2.5M in hexane (1.2 mmol) is added at −78° C. and stirred at −78° C. for 10 min and room temperature for 10 min. The reaction vessel is cooled to −78° C. again and 2.6 ml of 0.5M ZnCl$_2$ in THF (1.3 mmol) is added at −78° C. and stirred at room temperature for 15 min. 274 mg of 8-(1-ethyl-propyl)-3-iodo-2,6-dimethyl-imidazo[1,2-b]pyridazine (2151431) (0.8 mmol) and 41 mg of PdCl$_2$(pddf) (0.05 mmol) are added and the tube is capped. The tube is heated at 80° C. for 3 days. The reaction is quenched by NH$_4$Claq. and extracted by CH$_2$Cl$_2$, dried over Na$_2$SO$_4$ and evaporated. The crude product is applied onto a silica-gel chromatography column (Hexane:AcOEt:2 M NH3 in MeOH=20:4:1) to give 131 mg of the title compound. Yield 45%. mass spectrum (m/e): 365 (M+1).

Example 60

8-(1-Ethyl-propyl)-2,6-dimethyl-3-(2-methyl-benzo[b]thiophen-3-yl)-imidazo[1,2-b]pyridazine

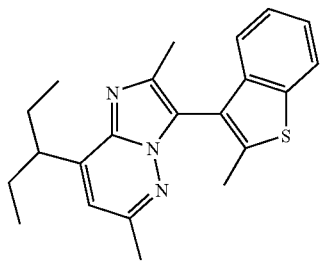

A. 3-Bromo-2-methyl-benzo[b]thiophene 1.06 g of 3-Bromo-benzo[b]thiophene (5.0 mmol) is dissolved in 10 ml of dry tetrahedrofuran and cooled to −78° C. and 3.67 ml of lithium diisopropylamine 1.5M in cyclohexane (5.5 mmol) is added slowly and stirred at −78° C. for 15 min. 0.35 ml of Methyl iodide (5.6 mmol) is added and the reaction mixture is stirred at room temperature for 1 h, sat. NH$_4$Cl is added, and the mixture is extracted with CH$_2$Cl$_2$, dried over Na$_2$SO$_4$ and evaporated. The crude product is applied onto a silica-gel chromatography column (Hexane:AcOEt=10:1) to give the title compound. 835 mg (74%). $^1$H-NMR (CDCl$_3$): 7.76 (t, 2H, J=7.7 Hz), 7.46 (t, 1H, J=7.7 Hz), 7.37 (t, 1H, J=7.7 Hz), 2.60 (s, 3H)

B. 8-(1-Ethyl-propyl)-2,6-dimethyl-3-(2-methyl-benzo[b]thiophen-3-yl)-imidazo[1,2-b]pyridazine 217 mg of 8-(1-Ethyl-propyl)-2,6-dimethyl-imidazo[1,2-b]pyridazine (11.0 mmol), 227 mg of 3-bromo-2-methyl-benzo[b]thiophene (1.0 mmol), 26.2 mg of triphenylphosphine (0.1 mmol) and 650 mg of cesium carbonate (2.0 mmol) are placed into a reaction vial with 3 ml of dry DMF. N$_2$ gas is bubbled in for 10 min and 34 mg of palladium acetate (0.05 mmol) is added. The reaction vial is capped with a Teflon cap and heated at 130° C. overnight. The reaction mixture is concentrated and applied onto a silica-gel chromatography column (Hexane:AcOEt:2M NH3 in MeOH=10:2:1) to give the title compound 119 mg (33%). mass spectrum (m/e): 364; $^1$H-NMR (CDCl$_3$): 7.86 (m, 1H), 7.31 (m, 3H), 6.72 (s, 1H), 3.44 (m, 1H), 2.47 (s, 3H), 2.42 (s, 3H), 1.90 (m, 4H), 0.95 m, 6H) ppm.

Example 61

3-(3-Bromo-thieno[3,2-b]pyridin-2-yl)-8-(1-ethyl-propyl)-2,6-dimethyl-imidazo[1,2-b]pyridazine

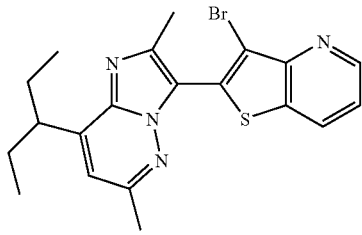

428 mg of 3-Bromo-thieno[3,2-b]pyridine (2.0 mmol) is dissolved in 2.0 ml of dry THF and cooled to −78° C. and 0.88 ml of n-BuLi 2.5M in hexane (2.2 mmol) is added slowly and the mixture is stirred at −78° C. for 15 min. 4.4 ml of ZnCl$_2$ 0.5M in THF (2.2 mmol) is added and stirred at room temperature for 20 min. 617 mg of 8-(1-ethyl-propyl)-3-iodo-2,6-dimethyl-imidazo[1,2-b]pyridazine (1.8 mmol) and 66 mg of PdCl$_2$(dppf) (0.08 mmol) are added. The reaction vial is capped with a Teflon cap and heated at 80° C. overnight. Water and CH$_2$Cl$_2$ are added, and the separated CH$_2$Cl$_2$ layer is dried over Na$_2$SO$_4$ and evaporated. The crude product is applied onto a silica-gel chromatography column (Hexane:AcOEt=5:1) to produce the title compound 171 mg (22%), mass spectrum (m/e): 430; $^1$H-NMR (CDCl$_3$): 8.84 (dd, 1H, J=4.5 Hz, 1.4 Hz), 8.20 (dd, 1H, J=8.4 Hz, 1.4 Hz), 7.37 (dd, 1H, J=8.4 Hz, 4.5 Hz), 6.75 (s, 1H), 3.34 (m, 1H), 2.56 (s, 3H), 2.51 (s, 3H), 1.85 (m, 4H), 0.89 (t, 6H, J=7.4 Hz) ppm.

Example 62

3-(3-Chloro-thieno[3,2-b]pyridin-2-yl)-8-(1-ethyl-propyl)-2,6-dimethyl-imidazo[1,2-b]pyridazine

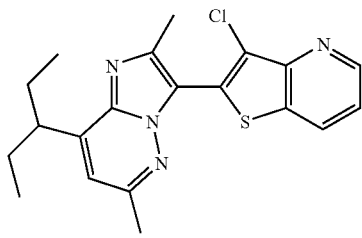

A. 3-Chloro-thieno[3,2-b]pyridine 250 mg of 3-Bromo-thieno[3,2]pyridine (1.16 mmol) and 68 mg of copper (I) chloride (1.39 mmol) are placed into 4 ml vial with 3.0 ml of dry DMF. The reaction vial is capped with a Teflon cap and heated at 120° C. overnight. The reaction mixture is applied onto a silica-gel chromatography column (Hexane:AcOEt:2M NH$_3$ in MeOH=20:4:1) to give 47 mg of the title compound (24%). mass spectrum (m/e): 170; $^1$H-NMR (CDCl$_3$): 8.82 (m, 1H), 8.20 (m, 1H), 7.66 (s, 1H), 7.35 (dd, 1H, J=4.6 Hz, 8.4 Hz) ppm.

B. 3-(3-Chloro-thieno[3,2-b]pyridin-2-yl)-8-(1-ethyl-propyl)-2,6-dimethyl-imidazo[1,2-b]pyridazine 80 mg of 3-Chloro-thieno[3,2-b]pyridine (0.47 mmol) is dissolved in 3.0 ml of dry THF and cooled to −78° C. 0.19 ml of n-BuLi (0.47 mmol) is added slowly and stirred at −78° C. for 10 min. 0.94 ml of 0.5M ZnCl$_2$ in THF (0.47 mmol) is added at −78° C. and stirred at room temperature for 10 min. 161 mg of 8-(1-ethyl-propyl)-3-iodo-2,6-dimethyl-imidazo[1,2-b]pyridazine (0.47 mmol) and 22 mg of PdCl$_2$(dppf) (0.03 mmol) are added and the vial is capped with a Teflon cap and heated at 80° C. overnight. The reaction mixture is concentrated and applied onto a silica-gel chromatography column (Hexane:AcOEt:2M NH$_3$ in MeOH=20:4:1) to give 84 mg of the title compound (47%). mass spectrum (m/e): 385; $^1$H-NMR (CDCl$_3$): 8.84 (d, 1H, J=4.7 Hz), 8.20 (d, 1H, J=8.3 Hz), 7.38 (dd, 1H, J=4.7 Hz, 8.3 Hz), 6.76 (s, 1H), 3.34 (m, 1H), 2.56 (s, 3H), 2.52 (s, 3H), 1.85 (m, 4H), 0.89 (t, 6H, J=7.4 Hz) ppm.

Example 63

2-[8-(1-Ethyl-propyl)-2,6-dimethyl-imidazo[1,2-b]pyridazin-3-yl]-thieno[3,2-b]pyridine-3-carbonitrile

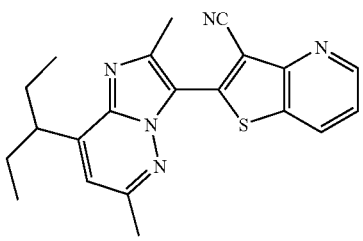

50 mg of 3-(3-Bromo-thieno[3,2-b]pyridin-2-yl)-8-(1-ethyl-propyl)-2,6-dimethyl-imidazo[1,2-b]pyridazine (0.12 mmol) and 32 mg of copper (I) cyanide (0.36 mmol) are placed into a reaction vial with 2.0 ml of dry DMF. The vial is capped with a Teflon cap and heated at 120° C. overnight. The reaction mixture is applied onto a silica-gel chromatography column (1$^{st}$ column; Hexane:AcOEt=5:1, 2$^{nd}$ column; Hexane:AcOEt:2M NH3 in MeOH=20:4:1) to give 7.2 mg of the title compound (16%). mass spectrum (m/e): 376; $^1$H-NMR (CDCl$_3$): 8.86 (m, 1H), 8.22 (m, 1H), 7.40 (dd, 1H, J=8.2 Hz, 4.6 Hz), 6.83 (s, 1H), 3.32 (m, 1H), 2.73 (s, 3H), 2.60 (s, 3H), 1.85 (m, 4H), 0.88 (t, 6H, J=7.5 Hz) ppm.

Example 64

8-(1-Ethyl-propyl)-3-(3-methoxy-thieno[3,2-b]pyridin-2-yl)-2,6-dimethyl-imidazo[1,2-b]pyridazine

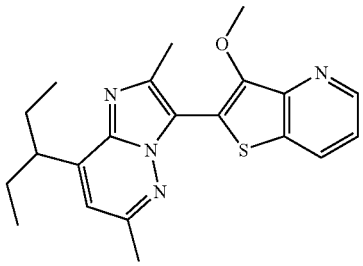

50 mg of 3-(3-Bromo-thieno[3,2-b]pyridin-2-yl)-8-(1-ethyl-propyl)-2,6-dimethyl-imidazo[1,2-b]pyridazine (0.12 mmol) and 13 mg of sodium methoxide (0.24 mmol) and 22 mg of copper (I) iodide (0.12 mmol) are placed into 4 ml reaction vial with 3.0 ml of dry MeOH. The reaction vial is capped with a Teflon cap and heated at 120° C. overnight. The reaction mixture is filtered, and water and $CH_2Cl_2$ are added. The separated $CH_2Cl_2$ is dried over $Na_2SO_4$ and evaporated. The crude product is applied onto a silica-gel chromatography column ($1^{st}$ column; Hexane:AcOEt:2M $NH_3$ in MeOH=20:4:1, $2^{nd}$ column; $CH_2Cl_2$:Hexane:Acetnitrile=5: 4:1) to give the title compound 20 mg (45%). mass spectrum (m/e): 381; $^1$H-NMR ($CDCl_3$): 8.72 (m, 1H), 8.10 (m, 1H), 7.29 (dd, 1H, J=4.6 Hz, 8.3 Hz), 6.72 (s, 1H), 4.03 (s, 3H), 3.34 (m, 1H), 2.55 (s, 3H), 2.54 (s, 3H), 1.84 (m, 4H), 0.88 (t, 6H, J=7.6 Hz) ppm.

Example 65

1-Ethyl-propyl)-2,6-dimethyl-3-thieno[3,2-b]pyridin-2-yl-imidazo[1,2-b]pyridazine

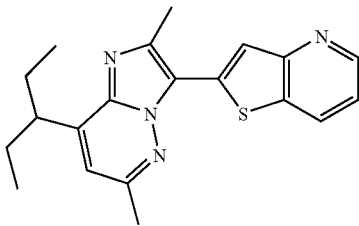

35 mg of 3-(3-Bromo-thieno[3,2-b]pyridin-2-yl)-8-(1-ethyl-propyl)-2,6-dimethyl-imidazo[1,2-b]pyridazine (0.08 mmol), 18 mg of ethylboronic acid (0.24 mmol) and 0.12 ml of 2M $Na_2CO_3$. (0.24 mmol) are placed into microwave reaction vial with 3.0 ml of DME/water/EtOH=7/3/1. $N_2$ gas is bubbled in for 10 min and 12 mg of Pd(PPh$_3$)$_4$ (0.01 mmol) is added. The reaction vial is sealed and heated at 150° C. for 30 min in the microwave. Water and $CH_2Cl_2$ are added. The separated $CH_2Cl_2$ layer is dried over $Na_2SO_4$ and evaporated. The crude product is applied onto a silica-gel chromatography column (Hexane:AcOEt=3:1) to give the title compound 19 mg (71%). mass spectrum (m/e): 351; $^1$H-NMR ($CDCl_3$): 8.70 (m, 1H), 8.23 (m, 1H), 8.20 (m, 1H), 7.24 (m, 1H), 6.77 (s, 1H), 3.34 (m, 1H), 2.83 (s, 3H), 2.67 (s, 3H), 1.83 (m, 4H), 0.86 (t, 6H, J=7.4 Hz) ppm.

Examples 66 & 67

3-(3-Bromo-thieno[2,3-b]pyridin-2-yl)-8-(1-ethyl-propyl)-2,6-dimethyl-imidazo[1,2-b]pyridazine and 8-(1-Ethyl-propyl)-2,6-dimethyl-3-thieno[2,3-b]pyridin-2-yl-imidazo[1,2-b]pyridazine

66

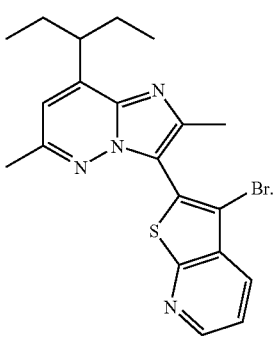

67

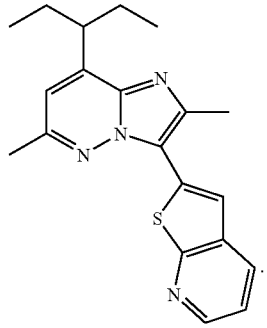

214 mg of 3-Bromo-thieno[2,3-b]pyridine (1.0 mmol) is dissolved in 1.5 ml of dry THF and cooled to −78° C. 0.44 ml of n-butyl lithium 2.5M in hexane is added slowly and stirred at −78° C. for 10 min. 2.2 ml of 0.5 M $ZnCl_2$ in THF (1.1 mmol) is added and stirred at room temperature for 20 min. 274 mg of 8-(1-ethyl-propyl)-3-iodo-2,6-dimethyl-imidazo [1,2-b]pyridazine (0.8 mmol) and 33 mg of PdCl$_2$(dppf) (0.04 mmol) are added. The reaction vial is capped and heated at 80° C. for 3 days. The reaction is filtered and applied onto a silica-gel chromatography column (Hexane: AcOEt=8:1) to give 49 mg of the 3-(3-bromo-thieno[2,3-b]pyridin-2-yl)-8-(1-ethyl-propyl)-2,6-dimethyl-imidazo[1,2-b]pyridazine (11%) and 33 mg of reduced compound, 8-(1-ethyl-propyl)-2,6-dimethyl-3-thieno[2,3-b]pyridin-2-yl-imidazo[1,2-b]pyridazine, (9%).

3-(3-Bromo-thieno[2,3-b]pyridin-2-yl)-8-(1-ethyl-propyl)-2,6-dimethyl-imidazo[1,2-b]pyridazine; mass spectrum (m/e): 430; $^1$H-NMR ($CDCl_3$): 8.65 (dd, 1H, J=4.6 Hz, 1.7 Hz), 8.14 (dd, 1H, J=8.1 Hz, 1.7 Hz), 7.44 (dd, 1H, J=8.1 Hz, 4.6 Hz), 6.74 (s, 1H), 3.33 (m, 1H), 2.55 (s, 3H), 2.52 (s, 3H), 1.85 (m, 4H), 0.89 (t, 6H, J=7.4 Hz) ppm.

8-(1-Ethyl-propyl)-2,6-dimethyl-3-thieno[2,3-b]pyridin-2-yl-imidazo[1,2-b]pyridazine; mass spectrum (m/e): 351; $^1$H-NMR ($CDCl_3$): 8.54 (dd, 1H, J=4.5 Hz, 1.5 Hz), 8.09 (dd, 1H, J=8.1 Hz, 1.5 Hz), 7.89 (s, 1H), 7.31 (dd, 1H, J=8.1 Hz, 4.5 Hz), 6.76 (s, 1H), 3.33 (m, 1H), 2.81 (s, 3H), 266 (s, 3H), 1.84 (m, 4H), 0.86 (t, 6H, J=7.6 Hz) ppm.

Example 68

3-(3-Chloro-thieno[2,3-b]pyridin-2-yl)-8-(1-ethyl-propyl)-2,6-dimethyl-imidazo[1,2-b]pyridazine

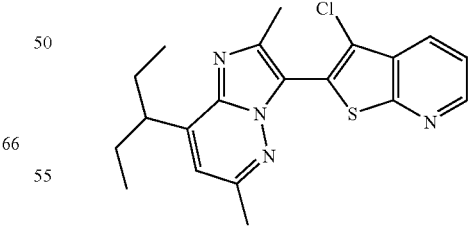

A. 3-Chloro-thieno[2,3-b]pyridine 500 mg of 3-Bromo-thieno[2,3-b]pyridine (2.3 mmol) and 136 mg of copper chloride (I) (2.78 mmol) are placed into reaction vial with 3.0 ml of dry DMF. The vial is capped with a Teflon cap and heated at 130° C. overnight. The reaction mixture is poured into $CH_2Cl_2$ and washed with $NaHCO_3$, brine and dried over $Na_2SO_4$. The solvents are removed and the residue applied onto a chromatography silica-gel column (Hexane:AcOEt=10:1) to give 280 mg of the title compound (71%); mass spectrum (m/e): 170; ¹H-NMR (CDCl₃): 8.53 (m, 1H), 8.11 (m, 1H), 7.41 (m, 2H) ppm.

B. 3-(3-Chloro-thieno[2,3-b]pyridin-2-yl)-8-(1-ethyl-propyl)-2,6-dimethyl-imidazo[1,2-b]pyridazine 250 mg of 3-Chloro-thieno[2,3-b]pyridine (1.5 mmol) is dissolved in 2.0 ml of dry THF and cooled to −78° C. 0.59 ml of n-butyl lithium 2.5 M in hexane (1.5 mmol) is added slowly and stirred at room temperature for 3 min and cooled to −78° C. 3.0 ml of 0.5 M ZnCl₂ in THF (1.5 mmol) is added and stirred at room temperature for 20 min. 343 mg of 8-(1-ethyl-propyl)-3-iodo-2,6-dimethyl-imidazo[1,2-b]pyridazine (1.0 mmol) and 41 mg of PdCl₂(dppf) (0.05 mmol) are added and the reaction vial is capped with a Teflon cap and heated at 80° C. overnight. The reaction mixture is concentrated and applied onto a chromatography silica-gel column (Hexane:AcOEt=3:1); mass spectrum (m/e): 385; ¹H-NMR (CDCl₃): 8.66 (dd, 1H, J=4.5 Hz, 1.5 Hz), 8.10 (dd, 1H, J=8.1 Hz, 1.5 Hz), 7.44 (1H, J=8.1 Hz, 4.5 Hz), 6.74 (s, 1H), 3.33 (m, 1H), 2.55 (s, 3H), 2.53 (s, 3H), 1.85 (m, 4H), 0.89 (t, 6H, J=7.5 Hz) ppm.

Example 69 & 70

3-(3-Bromo-5-chloro-thieno[3,2-b]pyridin-2-yl)-8-(1-ethyl-propyl)-2,6-dimethyl-imidazo[1,2-b]pyridazine and 3-(5-chloro-thieno[3,2-b]pyridin-3-yl)-8-(1-ethyl-propyl)-2,6-dimethyl-imidazo[1,2-b]pyridazine

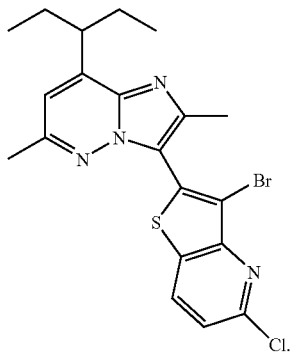

69

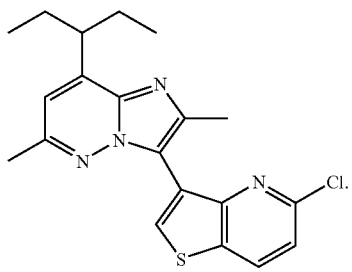

70

A. 3-Bromo-5-chloro-thieno[3,2-b]pyridine 1.00 g of 5-Chloro-thieno[3,2-b]pyridine (5.91 mmol), 497 mg of sodium bicarbonate (5.91 mmol), 1.54 g of potassium hydrogenphosphate (8.87 mmol) and 1.07 g of magnesium sulfate (8.87 mmol) are placed in a flask with 50 ml of chloroform. The reaction mixture is stirred under reflux for 30 min. 0.55 ml of Bromine (10.82 mmol) is added and stirred under reflux overnight. 0.55 ml of Additional bromine (10.82 mmol) is added and stirred under reflux for 1 day. The reaction mixture is cooled to room temperature and water and CH₂Cl₂ are added. Organic layer is separated. The water layer is adjusted to pH=14 with 5N NaOH and extracted with CH₂Cl₂. All organic layers are combined together and dried over Na₂SO₄ and evaporated. The crude product is applied onto a silica-gel chromatography column (Hexane:AcOEt=5:1) to give 796 mg of the title compound (54%). ¹H-NMR (CDCl₃): 8.12 (d, 1H, J=7.9 Hz), 7.81 (s, 1H), 7.36 (d, 1H, J=7.9 Hz) ppm.

B. 3-(3-Bromo-5-chloro-thieno[3,2-b]pyridin-2-yl)-8-(1-ethyl-propyl)-2,6-dimethyl-imidazo[1,2-b]pyridazine and 3-(5-Chloro-thieno[3,2-b]pyridin-3-yl)-8-(1-ethyl-propyl)-2,6-dimethyl-imidazo[1,2-b]pyridazine 248 g of 3-Bromo-5-chloro-thieno[3,2-b]pyridine (1.0 mol) is dissolved in 2.0 l of dry THF and cooled to −78° C. 0.4 l of n-BuLi 2.5M in hexane (1.0 mol) is added slowly and stirred at −78° C. for 15 in. 2.0 l of 0.5M ZnCl₂ in THF (1.0 mol) is added and stirred at room temperature for 20 in. 343 g of 8-(1-ethyl-propyl)-3-iodo-2,6-dimethyl-imidazo[1,2-b]pyridazine (1.0 mol) and 37 g of PdCl₂(dppf) (0.05 mol) are added and the reaction vial is capped with a Teflon cap. The vial is heated at 80° C. overnight. The reaction mixture is filtered and applied onto a silica-gel chromatography column (1ˢᵗ column; hexane AcOEt=10:1, 2ⁿᵈ column; CH₃CN:CH₂Cl₂:Hexane=1:5:4) to give 16 mg of 3-(3-bromo-5-chloro-thieno[3,2-b]pyridin-2-yl)-8-(1-ethyl-propyl)-2,6-dimethyl-imidazo[1,2-b]pyridazine (3%) and 9 mg of 3-(5-chloro-thieno[3,2-b]pyridin-3-yl)-8-(1-ethyl-propyl)-2,6-dimethyl-imidazo[1,2-b]pyridazine (2%).

3-(3-Bromo-5-chloro-thieno[3,2-b]pyridin-2-yl)-8-(1-ethyl-propyl)-2,6-dimethyl-imidazo[1,2-b]pyridazine: mass spectrum (m/e): 463; ¹H-NMR (CDCl₃): 8.12 (d, 1H, J=8.5 Hz), 7.38 (d, 1H, J=8.5 Hz), 6.75 (s, 1H), 3.33 (m, 1H), 2.55 (s, 3H), 2.51 (s, 3H), 1.85 (m, 4H), 0.89 (t, 6H, J=7.7 Hz) ppm.

3-(5-Chloro-thieno[3,2-b]pyridin-3-yl)-8-(1-ethyl-propyl)-2,6-dimethyl-imidazo[1,2-b]pyridazine: mass spectrum (m/e): 385; ¹H-NMR (CDCl₃): 8.15 (s, 1H), 8.11 (d, 1H, J=8.6 Hz), 7.24 (d, 1H, J=8.6 Hz), 6.79 (s, 1H), 3.33 (m, 1H), 2.82 (s, 3H), 2.67 (s, 3H), 1.84 (m, 4H), 0.85 (t, 6H, J=7.5 Hz) ppm.

Example 71

Preparation of 8-(1-butyl-pentyl)-3-(5-fluoro-3-methyl-benzo[b]thiophen-2-yl)-2,6-dimethyl-imidazo[1,2-b]pyridazine

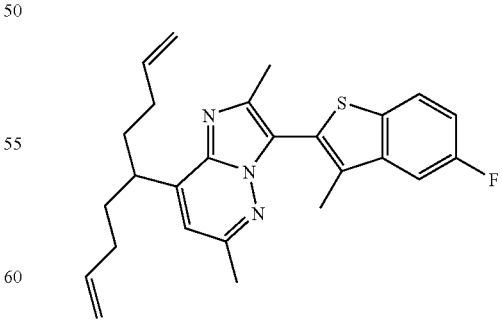

Using a procedure similar to example 133, from 8-(1-but-3-enyl-penta-1,4-dienyl)-3-(5-fluoro-3-methyl-benzo[b]thiophen-2-yl)-2,6-dimethyl-imidazo[1,2-b]pyridazine (0.50 g, 0.12 mmol) to give the title compound (0.045 g, 90%). ¹H NMR (CDCl₃): δ 7.8 (dd, J=4.8, 8.5 Hz, 1H), 7.5 (dd, J=2.5, 9.7 Hz, 1H), 7.2 (m, 1H), 6.7 (s, 1H), 3.4 (m, 1H), 2.5 (s, 3H), 2.49 (s, 3H), 2.3 (s, 3H), 1.78 (m, 4H), 1.25 (m, 4H), 1.18 (m, 4H), 0.85 (t, J=5.7, 6H) ppm. Mass spectrum (m/e): 438 (M+1).

Example 72

8-(1-ethyl-propyl)-2,6-dimethyl-3-(1-methyl-1H-pyrrolo[2,3-b]pyridin-2-yl)-imidazo[1,2-b]pyridazine

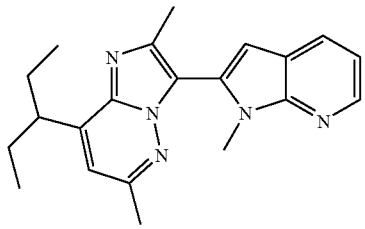

A solution of 8-(1-ethyl-propyl)-3-iodo-2,6-dimethyl-imidazo[1,2-b]pyridazine 1-methyl-2-(4,4,5,5-tetramethyl-[1,3,2]dioxaborolan-2-yl)-1H-pyrrolo[2,3-b]pyridine (example Rupp-30) (0.23 g, 0.89 mmol), 2M $Na_2CO_3$ (0.72 mL, 1.45 mmol), and 7:3:2 DME:Water:EtOH (5 mL) is degassed with nitrogen for 15 minutes. $Pd(PPh_3)_4$ (0.051 g, 0.044 mmol) is added and the solution is heated at a reflux for three days. The solution is diluted with $CH_2Cl_2$ (50 mL), washed with 10% $Na_2CO_3$ (30 mL), water (30 mL), brine (30 mL), dried over $MgSO_4$, filtered and concentrated. The material is purified by ISCO (15%-30% EtOAc gradient) to furnish the title compound (0.12 g, 0.35 mmol, 48%). $^1$H NMR (CDCl$_3$), δ 0.90 (t, J=7.5 Hz, 6H), 1.78-1.95 (m, 4H), 2.50 (s, 3H), 2.53 (s, 3H), 3.32-3.40 (m, 1H), 3.74 (s, 3H), 6.64 (s, 1H), 6.72 (s, 1H), 7.11 (dd, J=8.3, 4.8 Hz, 1H), 7.96 (dd, J=8.3, 1.3 Hz, 1H), 8.40 (dd, J=4.8, 1.3 Hz, 1H) ppm. LC/MS (m/z): calcd. for $C_{21}H_{25}N_5$ (M+H)$^+$: 348.3. found: 348.2.

Example 73

3-(1,5-Dimethyl-1H-indol-2-yl)-8-(1-ethyl-propyl)-2,6-dimethyl-imidazo[1,2-b]pyridazine

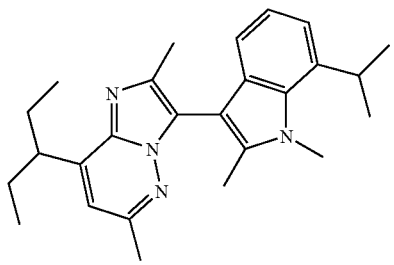

A. 7-isopropyl-2-methyl-1H-indole

To a solution of (2-isopropyl-phenyl)-hydrazine 7.60 g, 0.0506 mol) (Asselin et al., *J. Med. Chem.* 1976, 19, 787-792) and acetone (100 mL) is added 1M HCl in EtOH (2 drops). The solution is heated at a reflux overnight. The solution is concentrated, dissolved in toluene (100 mL) and concentrated. The residue is dissolved in o-xylene (100 mL) and $ZnCl_2$ (8.3 g) is added. The solution is heated at 140° C. for 2 hours, cooled to ambient temperature, diluted with EtOAc (200 mL), washed with sat. $NH_4Cl$, dried over $Na_2SO_4$, filtered and concentrated. The residue is purified by ISCO (5%-15% EtOAc gradient to furnish the title compound (1.76 g, 10.16 mmol, 20%). $^1$H NMR (CDCl$_3$), δ 1.43 (d, J=7.0 Hz, 6H), 2.50 (s, 3H), 3.17-3.29 (m, 1H), 6.24-6.27 (m, 1H), 7.02 (d, J=7.1 Hz, 1H), 7.07 (dd, J=7.5, 7.1 Hz, 1H), 7.39 (d, J=7.5 Hz, 1H), 7.85 (bs, 1H) ppm. LC/MS (m/z): calcd. for $C_{12}H_{15}N$ (M+H)$^+$: 174.1. found: 174.1.

B. 7-isopropyl-1,2-dimethyl-1H-indole

To a solution of 7-isopropyl-2-methyl-1H-indole (0.75 g, 4.33 mmol) and DMF (2 mL) is added 60% NaH (0.19 g, 4.76 mmol). After 30 minutes iodomethane (0.30 mL, 4.76 mmol) is added and the solution stirred for 1 hour. The solution is diluted with $Et_2O$ (30 mL), washed with water (2×20 mL), brine (20 mL) dried over $MgSO_4$, filtered and concentrated. The residue is purified by ISCO (2%-5% EtOAc gradient) to furnish the title compound (0.33 g, 1.76 mmol, 41%). $^1$H NMR (CDCl$_3$), δ 1.42 (d, J=6.5 Hz, 6H), 2.43 (s, 3H), 3.84-3.91 (m, 1H), 6.24-6.27 (m, 1H), 3.93 (s, 1H), 6.29 (s, 1H), 7.01-7.14 (m, 1H), 7.38 (d, J=7.5 Hz, 1H) ppm. LC/MS (m/z): calcd. for $C_{13}H_{17}N$ (M+H)$^+$: 188.2. found: 188.1.

C. 3-(1,5-Dimethyl-1H-indol-2-yl)-8-(1-ethyl-propyl)-2,6-dimethyl-imidazo[1,2-b]pyridazine A solution of 8-(1-ethyl-propyl)-3-iodo-2,6-dimethyl-imidazo[1,2-b]pyridazine (0.30 g, 0.87 mmol), 7-isopropyl-1,2-dimethyl-1H-indole (0.33 g, 1.76 mmol), $Cs_2CO_3$ (0.57 g, 1.75 mmol), and DMF (5 mL), is degassed with $N_2$ for 20 minutes. $Pd_2(dba)_3$ (0.040 g, 0.044 mmol is added and the solution is heated at 130° C. overnight. The solution is diluted EtOAc (30 mL) washed with water (2×30 mL), brine (30 mL) dried over $MgSO_4$, filtered and concentrated. The residue is purified by ISCO (20%-30% EtOAc gradient) to furnish the title compound (0.017 g, 0.042 mmol, 4.8%). $^1$H NMR (CDCl$_3$), δ 1.14-1.46 (m, 6H), 1.76-1.95 (m, 4H), 2.30 (s, 3H), 2.42 (s, 3H), 2.45 (s, 3H), 3.38-3.48 (m, 1H), 3.86-3.97 (m, 1H), 4.04 (s, 3H), 6.64 (s, 1H), 6.99-7. LC/MS (m/z): calcd. for $C_{26}H_{34}N_4$ (M+H)$^+$: 403.3. found: 403.4.

Example 74

Preparation of 8-(1-ethyl-propyl)-2,6-dimethyl-3-(6-methyl-1H-indol-2-yl)-imidazo[1,2-b]pyridazine

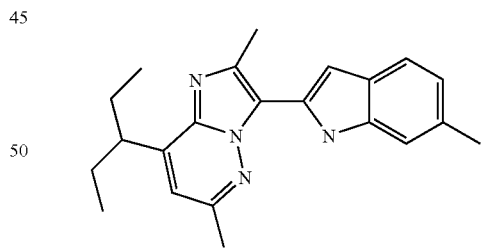

A. 6-Methyl-2-(4,4,5,5-tetramethyl-[1,3,2]dioxaborolan-2-yl)-1H-indole

Using a procedure analogous to Example 22A., from 6-methyl-1H-indole (0.50 g, 3.81 mmol), dtbpy (0.041 g, 0.15 mmol), $Pin_2B_2$ (1.45 g, 5.72 mmol), hexane (10 mL) and [Ir(OMe(COD)]$_2$ (0.051 g, 0.076 mmol), to furnish the title compound (0.51 g, 1.98 mmol, 52%). $^1$H NMR (CDCl$_3$), δ 1.40 (s, 12H), 2.47 (s, 3H), 7.03 (dd, J=8.3, 1.3, 1H), 7.13 (t, J=0.9 Hz, 1H), 7.54 (d, J=2.6 Hz, 1H), 7.94 (d, J=8.2 Hz, 1H), 8.38 (bs, 1H) ppm. LC/MS (m/z): calcd. for $C_{15}H_{20}BNO_2$ (M+H)$^+$: 258.2. found: 258.0.

B. 8-(1-ethyl-propyl)-2,6-dimethyl-3-(6-methyl-1H-indol-2-yl)-imidazo[1,2-b]pyridazine Using the procedure analogous to Example 22B., from of 8-(1-ethyl-propyl)-3-iodo-2,6-dimethyl-imidazo[1,2-b]pyridazine (0.12 g, 0.55 mmol), 6-methyl-2-(4,4,5,5-tetramethyl-[1,3,2]dioxaborolan-2-yl)-1H-indole (0.17 g, 0.66 mmol), 2 M Na$_2$CO$_3$ (0.41 mL, 0.83 mmol), Pd(OAc)$_2$ (0.0025 g, 0.011 mmol), PPh$_3$ (0.0087 g, 0.0033 mmol), and n-PrOH (2 mL) is furnished the title compound (0.048 g, 0.14 mmol, 25%). $^1$H NMR (CDCl$_3$), δ 0.91 (t, J=7.4 Hz, 6H), 1.76-1.94 (m, 4H), 2.49 (s, 6H), 2.56 (s, 3H), 3.35-3.45 (m, 1H), 6.64 (s, 1H), 6.98 (dd, J=8.4, 0.9 Hz, 1H), 7.41 (s, 1H), 7.42-7.44 (m, 2H), 8.62 (bs, 1H) ppm.

Example 75

Preparation of 3-(1-ethyl-7-fluoro-1H-indol-2-yl)-8-(1-ethyl-propyl)-2,6-dimethyl-imidazo[1,2-b]pyridazine

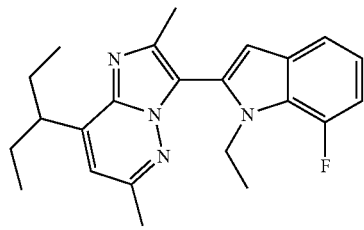

Using the procedure analogous to Example 23, from 8-(1-ethyl-propyl)-3-(7-fluoro-1H-indol-2-yl)-2,6-dimethyl-imidazo[1,2-b]pyridazine (0.060 g, 0.17 mmol), DMF (1 mL), 60% NaH (0.013 g, 0.34 mmol), and iodoethane (0.016 mL, 0.21 mmol) to furnish the title compound (0.025 g, 0.066 mmol, 39%). $^1$H NMR (CDCl$_3$), δ 0.91 (t, J=7.5 Hz, 6H), 1.25 (t, J=6.9 Hz, 3H), 1.76-1.96 (m, 4H), 2.48 (s, 3H), 2.49 (s, 3H), 3.33-3.43 (m, 1H), 3.99-4.42 (m, 2H), 6.65 (d, J=2.3 Hz, 1H), 6.72 (s, 1H), 6.69-6.98 (m, 1H), 6.99-7.06 (m, 1H), 7.43 (d, J=7.8 Hz, 1H) ppm. LC/MS (m/z): calcd. for C$_{23}$H$_{27}$FN$_4$ (M+H)$^+$: 379.3. found: 379.2.

Examples 76 & 77

Preparation of 8-(1-ethyl-propyl)-3-(7-fluoro-1-isopropyl-1H-indol-2-yl)-2,6-dimethyl-imidazo[1,2-b]pyridazine and 8-(1-ethyl-propyl)-3-(7-fluoro-1,3-diisopropyl-1H-indol-2-yl)-2,6-dimethyl-imidazo[1,2-b]pyridazine

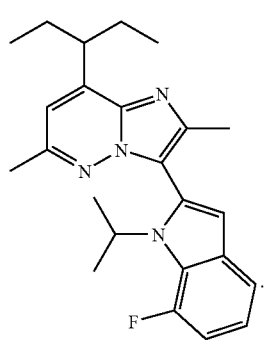

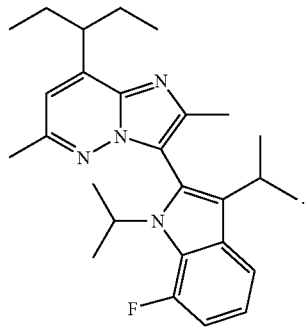

Using the procedure analogous to Example 23, from 8-(1-ethyl-propyl)-3-(7-fluoro-1H-indol-2-yl)-2,6-dimethyl-imidazo[1,2-b]pyridazine (0.060 g, 0.17 mmol), DMF (1 mL), 60% NaH (0.013 g, 0.34 mmol), and 2-iodo-propane (0.020 mL, 0.21 mmol) to furnish the title compounds example 76 (0.012 g, 0.031 mmol, 18%) and example 77 (6.09 mg, 0.014, 9.1%).

Example 76

$^1$H NMR (CDCl$_3$), δ 0.83-1.02 (m, 6H), 1.41 (d, J=6.5 Hz, 3H), 1.66 (d, J=6.2 Hz, 3H), 1.77-1.95 (m, 4H), 2.47 (s, 6H), 3.31-3.45 (m, 1H), 4.10-4.27 (m, 1H), 6.61 (d, J=2.6 Hz, 1H), 6.73 (s, 1H), 6.94-7.02 (m, 1H), 7.02-7.09 (m, 1H), 7.45 (d, J=7.9 Hz, 1H) ppm. LC/MS (m/z): calcd. C$_{24}$H$_{29}$FN$_4$ (M+H)$^+$: 393.3. found: 393.3.

Example 77

$^1$H NMR (CDCl$_3$), δ 0.89-0.98 (m, 6H), 1.25 (d, J=7.0 Hz, 3H), 1.30 (d, J=7.0 Hz, 3H), 1.40 (d, J=6.1 Hz, 3H), 1.49 (d, J=6.7 Hz, 3H), 1.77-1.97 (m, 4H), 2.41 (s, 3H), 2.44 (s, 3H), 3.33-3.47 (m, 1H), 4.10-4.27 (m, 1H), 6.71 (s, 1H), 6.92-7.00 (m, 1H), 7.00-7.07 (m, 1H), 7.60 (d, J=7.9 Hz, 1H) ppm. LC/MS (m/z): calcd C$_{27}$H$_{35}$FN$_4$ (M+H)$^+$: 435.3. found: 435.3.

Example 78

Preparation of 3-[8-(1-Ethyl-propyl)-2,6-dimethyl-imidazo[1,2-b]pyridazin-3-yl]-2-methyl-benzofuran-7-carboxylic Acid Methyl Ester

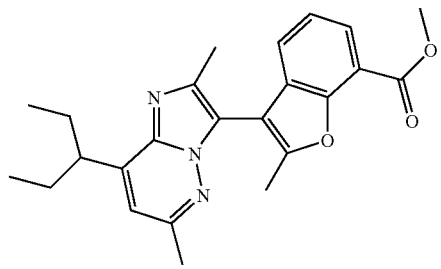

A. 3-Bromo-2-methyl-benzofuran-7-carboxylic Acid Methyl Ester

A solution of 2-methyl-benzofuran-7-carboxylic acid methyl ester (0.55 g, 2.87 mmol), prepared according to a literature procedure (Ishikawa, T.; Nagai, K.; Ohkubo, N.; Ishii, H. Heterocycles 1994, 39, 371), in CH$_2$Cl$_2$ (15 mL) at 0° C. is treated with bromine (147 µL, 2.87 mmol). The reaction is stirred at 0° C. for 30 min, then at RT overnight. The reaction is diluted with EtOAc 960 mL); washed with 5%

Na$_2$S$_2$O$_3$ (2×20 mL); brine (20 mL); dried with Na$_2$SO$_4$, filtered and concentrated gives the title compound (0.79 g, 2.87 mmol, 100%). $^1$H NMR (CDCl$_3$): δ 2.55 (s, 3H), 4.00 (s, 3H), 7.33 (t, J=7.5 Hz, 1H), 7.63 (dd, J=7.9, 0.9 Hz, 1H), 7.93 (dd, J=7.9, 0.9 Hz, 1H) ppm.

B. 3-[8-(1-Ethyl-propyl)-2,6-dimethyl-imidazo[1,2-b]pyridazin-3-yl]-2-methyl-benzofuran-7-carboxylic Acid Methyl Ester Using a procedure analogous to Example 16B, from 3-bromo-2-methyl-benzofuran-7-carboxylic acid methyl ester (0.77 g, 2.86 mmol) and 8-(1-ethyl-propyl)-2,6-dimethyl-imidazo[1,2-a]pyridine (0.63 g, 2.86 mmol) gives the title compound (74.1 mmg, 0.18 mmol, 6%). $^1$H NMR (CDCl$_3$): δ 0.89 (t, J=7.5 Hz, 3H), 0.90 (t, J=7.5 Hz, 3H), 1.75-1.94 (m, 4H), 2.45 (s, 3H), 2.46 (s, 3H), 2.51 (s, 3H), 3.30-3.44 (m, 1H), 4.04 (s, 3H), 6.69 (s, 1H), 7.24 (t, J=7.3 Hz, 1H), 7.45 (d, J=7.5 Hz, 1H), 7.92 (d, J=7.5 Hz, 1H) ppm. ES-MS (m/z): calcd for C$_{24}$H$_{27}$N$_3$O$_3$ (M+H)+: 406.5. found: 406.2.

Example 79

8-(1-Ethyl-propyl)-2,6-dimethyl-3-(3-trifluoromethyl-thieno[3,2-b]pyridin-2-yl)-imidazo[1,2-b]pyridazine

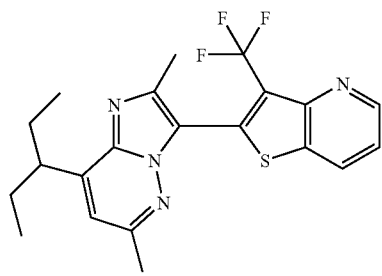

90 mg of 3-(3-Bromo-thieno[3,2-b]pyridin-2-yl)-8-(1-ethyl-propyl)-2,6-dimethyl-imidazo[1,2-b]pyridazine (0.21 mmol), 57 mg of CF$_3$CO$_2$Na (0.42 mmol) and 80 mg of CuI (0.42 mmol) are placed into microwave vessel with 3 ml of DMF/toluene=2/1. The vial is capped and heated at 210° C. for 60 min in microwave. The reaction mixture is applied onto silica-gel column (Hexane:AcOEt=8:1) directly to produce the tile compound. 27 mg (31%) mass spectrum (m/e): 419 (M+1); $^1$H-NMR (CDCl$_3$): 8.88 (dd, 1H, J=4.9 Hz, 1.4 Hz), 8.22 (dd, 1H, J=7.8 Hz, 1.4 Hz), 7.4 (dd, 1H, J=7.8 Hz, 4.9 Hz), 6.74 (s, 1H), 3.31 (m, 1H), 2.53 (s, 3H), 2.79 (s, 3H), 1.85 (m, 4H), 0.88 (t, 6H, J=7.4 Hz).

Example 80

Preparation of 3-(2-methyl-2H-indazol-3-yl)-8-(1-ethyl-propyl)-2,6-dimethyl-imidazo[1,2-b]pyridazine

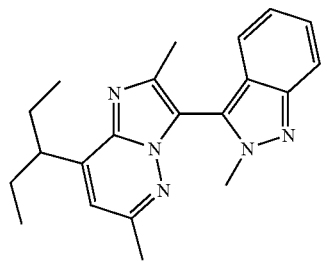

8-(1-ethyl-propyl)-3-iodo-2,6-dimethyl-imidazo[1,2-b]pyridazine (300 mg, 0.87 mmol), 2-methyl-2H-indazole (ref. J. Org. Chem. 2003, 68, 4093-4095, 230 mg, 1.76 mmol) and cesium carbonate (570 mg, 1.75 mmol) stirred in DMF (5 ml) and degassed by bubbling a stream of nitrogen through the mixture. PdCl$_2$(PPh$_3$)$_2$ added and the mixture heated to 100° C. overnight. The mixture is added to water and extracted twice with ether. The combined organic extracts are washed with brine, dried over Na$_2$SO$_4$, filtered and concentrated. The crude product is purified by chromatography using a hexane-ethyl acetate gradient (100% hexane to 50% ethyl acetate in hexane) to give the title compound (85 mg, 28% yield).

ES-MS (m/z): calc'd for C$_{21}$H$_{25}$N$_5$: 347.5. found 348.2 (M+H)+

$^1$H NMR (400 mHz, CDCl$_3$): δ 7.81 (d, 1H), 7.45 (d, 1H), 7.29 (t, 1H), 7.17 (t, 1H), 6.80 (bs, 1H), 4.15 (s, 3H), 3.42 (s, 1H), 3.33 (m, 1H), 2.50 (s, 6H), 2.45 (s, 3H), 1.90 (m, 4H), 0.95 (t, 6H) ppm.

Example 81

Preparation of 8-(1-Ethyl-propyl)-2,6,2',6'-tetramethyl-8'-(1-propyl-butyl)-[3,3']bi[imidazo[1,2-b]pyridazinyl]

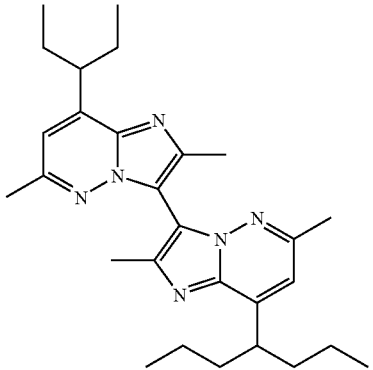

Using a procedure analogous to Example 16B, from 3-iodo-2,6-dimethyl-8-(1-propyl-butyl)-imidazo[1,2-b]pyridazine 0.36 g, 0.97 mmol), and 8-(1-ethyl-propyl)-2,6-dimethyl-imidazo[1,2-b]pyridazine (0.22 g, 0.97 mmol) gives the title compound (0.34 g, 0.74 mmol, 76%). $^1$H NMR (CDCl$_3$): δ 0.86-0.96 (m, 12H), 1.20-1.44 (m, 4H), 1.75-1.95 (m, 8H), 2.44 (s, 6H), 2.47 (s, 3H), 2.48 (s, 3H), 3.35-3.46 (m, 1H), 3.50-3.57 (m, 1H), 6.89 (s, 2H) ppm. ES-MS (m/z): calcd for C$_{28}$H$_{40}$N$_6$ (M+1)$^+$: 461.7. found: 461.3.

Example 82

Preparation of 3-(4-methoxy-3-methyl-benzofuran-2-yl)-8-(1-ethyl-propyl)-2,6-dimethyl-imidazo[1,2-b]pyridazine

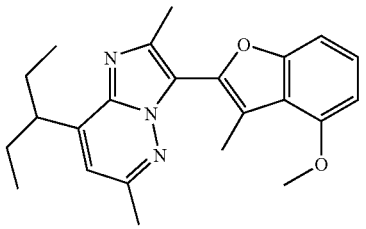

A. (2-Acetyl-3-hydroxy-phenoxy)-acetic Acid

Sodium hydroxide (6.0 g, 150.5 mmol) is dissolved in water (60 ml) followed by the addition of chloroacetic acid (8.0 g, 84.3 mmol) and 2-hydroxy-6-methoxy-acetophenone (5.0 g, 30.1 mmol). The resulting solution is heated to 90° C. for 3.5 hours. After cooling, the solution is acidified with HCl (concentrated) and extracted with ethyl acetate. The combined organic extracts are extracted with sodium bicarbonate (sat'd), the aqueous layer acidified with HCl (concentrated) and extracted twice with ethyl acetate. The combined organic extracts are washed with brine, dried over $Na_2SO_4$, filtered and concentrated to a yellow solid. This solid is washed with hexane, filtered and air dried to give the title compound (4.0 g, 60% yield).

$^1$H NMR (400 mHz, DMSO): δ 7.29 (t, 1H), 6.72 (d, 1H), 6.62 (d, 3H), 4.73 (s, 2H), 3.76 (s, 3H), 2.41 (s, 3H) ppm.

B. 4-Methoxy-3-methyl-benzofuran (2-Acetyl-3-hydroxy-phenoxy)-acetic acid (2.0 g, 8.9 mmol) is added to acetic anhydride (60 ml) followed by sodium acetate (10.0 g, 122.0 mmol). The mixture is stirred and heated to 110° C., under a nitrogen atmosphere, for 5 hrs. then cooled to 0° C. Water (100 ml) is added slowly, stirred while warming to ambient temperature and continued stirring overnight. The solution is extracted twice with ethyl acetate and the combined organic extracts are washed twice with sodium hydroxide (1N), then brine, dried over $Na_2SO_4$, filtered and concentrated. The crude product is purified by chromatography using a hexane-ethyl acetate gradient (100% hexane to 25% ethyl acetate in hexane) to give the title compound (1.2 g, 83% yield).

$^1$H NMR (400 mHz, $CDCl_3$): δ 7.29 (s, 1H), 7.21 (t, 1H), 7.10 (d, 1H), 6.65 (d, 1H), 3.94 (s, 3H), 2.40 (s, 3H) ppm.

C. 3-(4-Methoxy-3-methyl-benzofuran-2-yl)-8-(1-ethyl-propyl)-2,6-dimethyl-imidazo[1,2-b]pyridazine 4-Methoxy-3-methyl-benzofuran (240 mg, 1.50 mmol) added to THF (6 ml) and cooled to −72° C. n-Butyl lithium (1.0 ml, 1.60 mmol) added and stirred for 5 minutes, warmed to ambient temperature for 10 minutes and cooled again to −72° C. Zinc chloride (0.5 N in THF, 3.2 ml, 1.6 mmol) added, stirred for 5 minutes then warmed to ambient temperature and stirred for 10 minutes. 8-(1-ethyl-propyl)-3-iodo-2,6-dimethyl-imidazo[1,2-b]pyridazine (240 mg, 0.69 mmol) and $PdCl_2$(dppf)-$CH_2Cl_2$ complex (Aldrich, 64 mg, 0.08 mmol) are added. The mixture is heated to 60° C. for 4 hrs, cooled to ambient temperature, added to HCl (1N) and extracted twice with EtOAc. The combined organic extracts are dried over $Na_2SO_4$, filtered and concentrated. The crude product is purified by chromatography using a hexane-ethyl acetate gradient (100% hexane to 30% ethyl acetate in hexane) to give the title compound (54 mg, 21% yield). ES-MS (m/z): calc'd for $C_{23}H_{27}N_3O_2$: 377.5. found 378.1 (M+H)+
$^1$H NMR (400 mHz, $CDCl_3$): δ 7.27 (t, 1H), 7.18 (d, 1H), 6.74 (s, 1H), 6.70 (d, 1H), 3.99 (s, 3H), 3.39 (bs, 1H), 2.55 (s, 3H), 2.54 (s, 3H), 2.41 (s, 3H), 1.87 (m, 4H), 0.91 (t, 6H) ppm.

Example 83

Preparation of 8-(1-ethyl-propyl)-3-(5-fluoro-3-methyl-benzofuran-2-yl)-2,6-dimethyl-imidazo[1,2-b]pyridazine

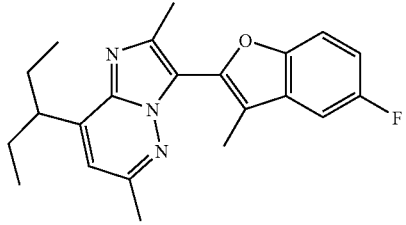

A. (2-Acetyl-4-fluoro-phenoxy)-acetic Acid 5-fluoro-2-hydroxy-acetophenone (Aldrich, 5.12 g, 33.2 mmol) is suspended in $H_2O$ (60 mL) and treated with NaOH (6.7 gm, 167.5 mmol) followed by chloroacetic acid (9.4 gm, 100 mmol). The resulting mixture is refluxed for 3.5 hr then cooled to room temperature. The aqueous solution is decanted from a dark colored solid that formed then acidified by the addition of concentrated HCl. The mixture is refrigerated overnight to complete the precipitation of the product. The precipitate is collected by filtration then recrystallized from toluene to give the title compound (1.88 gm, 27% yield). ES-MS (m/z): calc'd for $C_{10}H_9FO_4$: 212.05. found 213.1 (M+H)+$^1$H NMR (400 mHz, DMSO): δ 13.16 (br s, 1H), 7.42-7.34 (m, 2H), 7.18-7.15 (m, 1H), 4.86 (s, 2H), 2.64 (s, 3H) ppm.

B. 5-Fluoro-3-methyl-benzofuran (2-Acetyl-4-fluoro-phenoxy)-acetic acid (1.87 gm, 8.8 mmol) is dissolved in acetic anhydride (60 mL) and treated with sodium acetate (10 gm, 0.12 mol). The resulting mixture is heated to 110° C. for 5 hr, then cooled to 0° C. $H_2O$ (100 mL) is added and the solution is stirred overnight at room temperature. The aqueous solution is then extracted into $Et_2O$ (2×75 mL). The combined organic extracts are washed with 3% aqueous KOH (2×75 mL), $H_2O$ (2×75 mL) and brine (1×75 mL), then dried over $Na_2SO_4$, filtered and concentrated. The crude product is purified by chromatography using hexane to give the title compound (1.07 gm, 81% yield).

$^1$H NMR (400 mHz, $CDCl_3$): δ 7.47 (s, 1H), 7.43-7.39 (m, 1H), 7.21 (dd, J=2.6 Hz, 8.8 Hz, 1H), 7.04 (dt, J=2.6 Hz, 8.8 Hz, 1H), 2.25 (s, 3H) ppm.

C. 8-(1-Ethyl-propyl)-3-(5-fluoro-3-methyl-benzofuran-2-yl)-2,6-dimethyl-imidazo[1,2-b]pyridazine A THF solution (6 mL) of 5-fluoro-3-methyl-benzofuran (187.0 mg, 1.25 mmol) is cooled to −78° C. under $N_2$ then treated with nBuLi (1.6 M in hexane, 1.0 mL, 1.6 mmol). After 10 min at −78° C., $ZnCl_2$ (Aldrich, 0.5 M in THF, 3.0 mL, 1.5 mmol) is added. The resulting mixture is warmed to room temperature and treated with 8-(1-ethyl-propyl)-3-iodo-2,6-dimethyl-imidazo[1,2-b]pyridazine (212.4 mg, 0.62 mmol) and $PdCl_2$(dppf)-$CH_2Cl_2$ complex (Aldrich, 60 mg, 0.073 mmol). The mixture is heated to 65° C. for 18 hours, then poured into $H_2O$, acidified with 1 N HCl then extracted with ethyl acetate. The organic extract is ished with aq. brine, dried over $Na_2SO_4$, filtered, and concentrated. The crude product is purified by chromatography using hexane-ethyl acetate gradient (100% hexane to 20% ethyl acetate in hexane) to give the title compound as a solid (121.7 mg, 54% yield).

ES-MS (m/z): calc'd for $C_{22}H_{24}FN_3O$: 365.19. found 366.1 (M+H)+

$^1$H NMR (400 mHz, $CDCl_3$): δ 7.48 (dd, J=4.0 Hz, 8.8 Hz, 1H), 7.28 (dd, J=2.6 Hz, 8.4 Hz, 1H), 7.08 (dt, J=2.6 Hz, 8.8 Hz, 1H), 6.76 (s, 1H), 3.40-3.33 (m, 1H), 2.56 (s, 6H), 2.28 (s, 3H), 1.94-1.80 (m, 4H), 0.91 (t, J=7.5 Hz, 6H) ppm.

Example 84

Preparation of 3-[3-(5-fluoro-3-methyl-benzo[b]thiophen-2-yl)-2,6-dimethyl-imidazo[1,2-b]pyridazin-8-yl]-pentan-3-ol

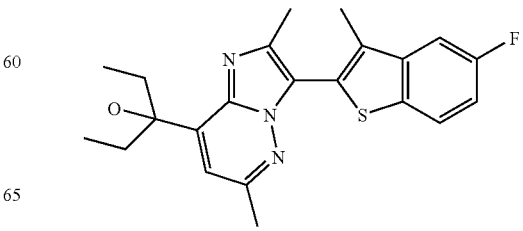

A. 2,6-Dimethyl-imidazo[1,2-b]pyridazine

A 3 neck 1 L round bottom flask is charged with 6-methyl-pyridazin-3-ylamine (20 g, 0.18 moles), ethanol 2B (200 mL), and chloroacetone (23.7 g, 20.4 mL, 0.256 moles, 1.4 equiv). The reaction mixture is heated at 70° C. overnight. NaHCO$_3$ (23.2 g, 0.276 moles, 1.5 equiv) is added portion wise. After most of bubbling subsides, the reaction is heated at 100° C. overnight. The solvents are removed in vacuo and the residue is taken up in dichloromethane and filtered through a filter paper. The solvent is again removed in vacuo. The residue is purified using silica gel chromatography with a hexanes:ethyl acetate gradient to obtain the title compound (15.5 g, 57%). $^1$H-NMR (DMSO-d$_6$), δ 2.34 (s, 3H), 2.47 (s, 3H), 7.03, (d, J=10 Hz, 1H), 7.85 (d, J=10 Hz, 1H), 7.91 (s, 1H) ppm. MS (APCI): 148 (M+1).

B. 2-Bromo-5-fluoro-3-methyl-benzo[b]thiophene

A 3 neck 2 L round bottom flask is fitted with a septum, a mechanical stirrer, and stopper. The flask is charged with 5-fluoro-3-methylbenzothiophene (55.4 g, 0.311 moles) and acetonitrile (350 mL). The mixture is stirred with a mechanical stirrer and the reaction temperature is monitored. NBS is added portion wise. The reaction temperature rises slightly, and the reaction is cooled with ice water bath. A solid crashes out of solution. The solid is filtered and rinsed 2 times with a 1:1 mixture of acetonitrile and water (100 mL). The solid is dried in a vacuum oven overnight at room temperature to obtain the title product (69 g, 95%). $^1$H-NMR (DMSO-d$_6$), δ 2.41 (s, 3H), 7.34 (td, J=10, 2 Hz, 1H), 7.69 (dd, J=10, 2 Hz, 1H), 8.04 (dd, J=9, 5 Hz, 1H) ppm.

C. 3-(5-Fluoro-3-methyl-benzo[b]thiophen-2-yl-2,6-dimethyl-imidazo[1,2,-b]pyridazine A 1 L round bottom flask is charged with 2,6-dimethyl-imidazo[1,2-b]pyridazine (15.5 g, 0.105 moles, 1.0 equiv), 2-bromo-5-fluoro-3-methyl-benzo[b]thiophene (29.6 g, 0.121 moles, 1.15 equiv), anhydrous dimethylformamide (440 mL), triphenylphosphine (5.24 g, 0.020 moles, 0.19 equiv), Cs$_2$CO$_3$ (71.8 g, 0.220 moles, 2.1 equiv), and Pd$_2$(dba)$_3$ (4.62 g, 0.0050 mol, 0.048 equiv). Nitrogen is bubbled through the reaction mixture for 20 minutes. The reaction is heated for 8 hours at 130° C. The progress of the reaction is monitored by TLC (1:1 hexanes:ethyl acetate). The reaction is partitioned between t-butyl methyl ether and a sat. NH$_4$Cl solution. The aqueous layer is extracted twice more with t-butyl methyl ether. The combined organic extracts are washed twice with a sat. NH$_4$Cl solution, dried over Na$_2$SO$_4$, filtered, and concentrated to obtain a crude product (63 g). The crude material is purified via silica gel chromatography using a hexanes:ethyl acetate gradient to obtain the title compound (21.4 g, 65%). $^1$H-NMR (CDCl$_3$), δ 2.26 (s, 3H), 2.51 (s, 3H), 2.54 (s, 3H), 6.99 (d, J=9 Hz, 1H), 7.16 (td, J=9, 3 Hz, 1H), 7.45 (dd, J=10, 3 Hz, 1H), 7.79 (dd, J=9, 5 Hz, 1H), 7.86 (d, J=9 Hz, 1H) ppm. MS (APCI): 312 (M+1).

D. 3-(5-Fluoro-3-methyl-benzo[b]thiophen-2-yl-8-iodo-2,6-dimethyl-imidazo[1,2,-b]pyridazine A round bottom flask is charged with 3-(5-fluoro-3-methyl-benzo[b]thiophen-2-yl-2,6-dimethyl-imidazo[1,2,-b]pyridazine, dry tetrahydrofuran (33 mL), and iodine (16.8 g, 0.066 mol, 4.0 equiv). The reaction mixture is cooled to –78° C. on a dry ice/acetone bath. A solution of freshly prepared LDA in THF (33 mL) and hexanes (42 mL) is added to the reaction mixture dropwise. The temperature of the reaction is kept under –70° C. during the addition. After the LDA addition, the reaction is quenched with methanol. The reaction is partitioned between ethyl acetate and a sat. Na$_2$S$_2$O$_3$ solution. The aqueous layer is extracted once more with ethyl acetate. The organic extracts are combined, washed with a sat. Na$_2$S$_2$O$_3$ solution again, dried over Na$_2$SO$_4$, filtered and concentrated to obtain a brown foam. The crude material is purified via silica gel chromatography using a hexanes:ethyl acetate gradient to obtain the title compound (1.60 g, 22%). $^1$H-NMR (CDCl$_3$), δ 2.24 (s, 3H), 2.48 (s, 3H), 2.52 (s, 3H), 7.16 (td, J=9, 3 Hz, 1H), 7.44 (dd, J=9 Hz, 3 Hz, 1H), 7.49 (s, 1H), 7.78 (dd, J=9, 5 Hz, 1H) ppm. MS (APCI): 438 (M+1).

E. 3-(5-Fluoro-3-methyl-benzo[b]thiophen-2-yl)-2,6-dimethyl-imidazo[1,2-b]pyridazine-8-carboxylic Acid Methyl Ester Using a procedure analogous to Example 47A, from 3-(5-fluoro-3-methyl-benzo[b]thiophen-2-yl)-8-iodo-2,6-dimethyl-imidazo[1,2-b]pyridazine (453.5 mg, 1.04 mmol) gives the title compound (0.13 g, 0.34 mmol, 33%). $^1$H NMR (CDCl$_3$): δ 2.23 (s, 3H), 2.57 (s, 3H), 2.59 (s, 3H), 4.11 (s, 3H), 7.16 (dt, J=8.8, 2.6 Hz, 1H), 7.45 (dd, J=9.3, 1.8 Hz, 1H), 7.53 (s, 1H), 7.79 (dd, J=8.8, 4.8 Hz, 1H) ppm. ES-MS (m/z): calcd for C$_{19}$H$_{16}$FN$_3$O$_2$S (M+1)$^+$: 370.4. found: 370.2.

F. 3-[3-(5-Fluoro-3-methyl-benzo[b]thiophen-2-yl)-2,6-dimethyl-imidazo[1,2-b]pyridazin-8-yl]-pentan-3-ol A solution of 3-(5-fluoro-3-methyl-benzo[b]thiophen-2-yl)-2,6-dimethyl-imidazo[1,2-b]pyridazine-8-carboxylic acid methyl ester (0.12 g, 0.32 mmol) in THF (10 mL) is treated with 3.0 M EtMg Br (0.32 mL, 0.96 mmol). The resulting solution is stirred at rt for 10 min and then refluxed overnight. It is cooled to 0° C., quenched with sat. NH$_4$Cl (5 mL); diluted with H$_2$O (10 mL); extracted with EtOAc (3×20 mL). The combined organic layers are dried with Na$_2$SO$_4$, filtered and concentrated. Purification of crude material by chromatography gives the title compound (8.0 mg, 0.02 mmol, 6%). $^1$H NMR (CDCl$_3$): δ 0.91 (t, J=7.4 Hz, 6H), 1.95-2.13 (m, 4H), 2.27 (s, 3H), 2.49 (s, 3H), 2.54 (s, 3H), 6.19 (bs, 1H), 6.75 (s, 1H), 7.16 (dt, J=8.8, 2.2 Hz, 1H), 7.45 (dd, J=9.7, 2.2 Hz, 1H), 7.79 (dd, J=8.8, 4.8 Hz, 1H) ppm. ES-MS (m/z): calcd for C$_{22}$H$_{24}$FN$_3$OS (M+1)$^+$: 398.5. found: 398.3.

Example 85

Preparation of 8-(1-ethyl-propyl)-2,6,2',6',8'-pentamethyl-[3,3']bi[imidazo[1,2-b]pyridazinyl]

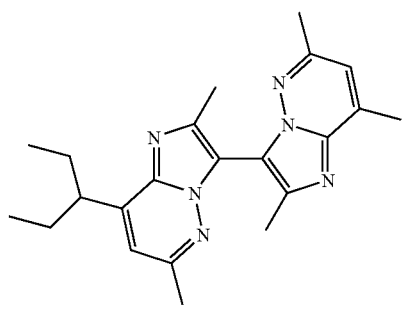

A. N-(4,6-dimethyl-pyridazin-3-yl)-2,2-dimethyl-propionamide

Using a procedure analogous to Example 17A, from 2,2-dimethyl-N-(6-methyl-pyridazin-3-yl)-propionamide (1.70 g, 8.80 mmol) and CH3Mg Br (3.0 M, 16.1 mL, 48.5 mmol)

gives the title compound (0.43 g, 2.08 mmol, 24%). ¹H NMR (CDCl₃): δ 1.35 (s, 9H), 2.23 (s, 3H), 2.62 (s, 3H), 7.19 (s, 1H), 9.00 (bs, 1H) ppm. ES-MS (m/z): calcd for $C_{11}H_{17}N_3O$ (M+1)⁺: 208.3. found: 208.1.

B. 4,6-dimethyl-pyridazin-3-ylamine

Using a procedure analogous to Example 17B, from N-(4,6-dimethyl-pyridazin-3-yl)-2,2-dimethyl-propionamide (0.43 g, 2.09 mmol) gives the title compound (49.8 g, 0.40 mmol, 19%). ES-MS (m/z): calcd for $C_6H_9N_3$ (M+1)⁺: 124.2. found: 124.2.

C. 2,6,8-trimethyl-imidazo[1,2-b]pyridazine

Using a procedure analogous to Example 17C., from 4,6-dimethyl-pyridazin-3-ylamine (49.8 mg, 0.40 mmol) gives the title compound (44.3 mg, 0.28 mmol, 69%). ¹H NMR (CDCl₃): δ 2.49 (s, 3H), 2.50 (s, 3H), 2.61 (s, 3H), 6.68 (s, 1H), 7.61 (s, 1H) ppm. ES-MS (m/z): calcd for $C_9H_{11}N_3$ (M+1)⁺: 162.2. found: 162.1.

D. 8-(1-ethyl-propyl)-2,6,2',6',8'-pentamethyl-[3,3']bi[imidazo[1,2-b]pyridazinyl]

Using a procedure analogous to Example 16B, from 8-(1-ethyl-propyl)-2,6,2',6',8'-pentamethyl-[3,3']bi[imidazo[1,2-b]pyridazinyl] (44.3 mg, 0.28 mmol) and 8-(1-ethyl-propyl)-3-iodo-2,6-dimethyl-imidazo[1,2-b]pyridazine (94 mg, 0.28 mmol) gives the title compound (38.9 mg, 0.10 mmol, 39%). ¹H NMR (CDCl₃): δ 0.91 (t, J=7.5 Hz, 6H), 1.79-1.89 (m, 4H), 2.43 (s, 3H), 2.44 (s, 3H), 2.45 (s, 3H), 2.46 (s, 3H), 2.68 (s, 3H), 3.34-3.44 (m, 1H), 6.68 (s, 1H), 6.75 (s, 1H) ppm. ES-MS (m/z): calcd for $C_{22}H_{28}N_6$ (M+1)⁺: 377.5. found: 377.3.

Example 86

Preparation of 8-(1-ethyl-propyl)-2,6,2',6'-tetramethyl-8'-propyl-[3,3']bi[imidazo[1,2-b]pyridazinyl]

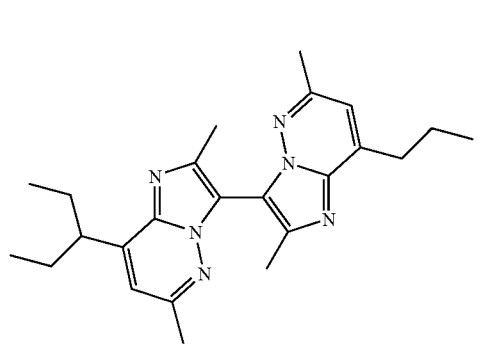

A. 2,2-Dimethyl-N-(6-methyl-4-propyl-pyridazin-3-yl)-propionamide

Using a procedure analogous to Example 17A., from 2,2-dimethyl-N-(6-methyl-pyridazin-3-yl)-propionamide (1.91 g, 9.89 mmol) and isopropyl MgBr (2.0 M, 22.2 mL, 54.4 mmol) gives the title compound (1.90 g, 8.09 mmol, 82%). ES-MS (m/z): calcd for $C_{13}H_{21}N_{30}$ (M+1)⁺: 236.3. found: 236.1.

B. 6-Methyl-4-propyl-pyridazin-3-ylamine

Using a procedure analogous to Example 17B., from 2,2-dimethyl-N-(6-methyl-4-propyl-pyridazin-3-yl)-propionamide (1.90 g, 8.09 mmol) gives the title compound (1.17 g, 7.72 mmol, 95%). ¹H NMR (CDCl₃): δ 1.02 (t, J=7.0 Hz, 3H), 1.64-1.75 (m, 2H), 2.39 (t, J=7.9 Hz, 2H), 2.53 (s, 3H), 4.65 (bs, 2H), 6.90 (s, 1H) ppm. ES-MS (m/z): calcd for $C_8H_{13}N_3$ (M+1)⁺: 152.2. found: 152.2.

C. 2,6-Dimethyl-8-propyl-imidazo[1,2-b]pyridazine

Using a procedure analogous to Example 17C, from 6-methyl-4-propyl-pyridazin-3-ylamine (1.16 g, 7.68 mmol) gives the title compound (1.11 g, 5.89 mmol, 77%). ¹H NMR (CDCl₃): δ 1.02 (t, J=7.0 Hz, 3H), 1.77-1.88 (m, 2H), 2.49 (s, 3H), 2.51 (s, 3H), 2.96 (t, J=7.5 Hz, 2H), 6.66 9s, 1H), 7.60 (s, 1H) ppm. ES-MS (m/z): calcd for $C_{11}H_{15}N_3$ (M+1)⁺: 190.3. found: 190.1.

D. 8-(1-ethyl-propyl)-2,6,2',6'-tetramethyl-8'-propyl-[3,3']bi[imidazo[1,2-b]pyridazinyl]

Using a procedure analogous to Example 16B, from 2,6-dimethyl-8-propyl-imidazo[1,2-b]pyridazine (0.31 g, 1.68 mmol) and 8-(1-ethyl-propyl)-3-iodo-2,6-dimethyl-imidazo[1,2-b]pyridazine (0.57 g, 1.68 mmol) gives the title compound (0.17 g, 0.43 mmol, 26%). ¹H NMR (CDCl₃): δ 0.91 (t, J=7.3 Hz, 6H), 1.09 (t, J=7.1 Hz, 3H), 1.78-1.95 (m, 6H), 2.43 (s, 3H), 2.44 (s, 3H), 2.46 (s, 6H), 3.05 (t, J=7.5 Hz, 2H), 3.35-3.43 (m, 1H), 6.68 (s, 1H), 6.74 (s, 1H) ppm. ES-MS (m/z): calcd for $C_{24}H_{32}N_6$ (M+1)⁺: 405.6. found: 405.3.

Example 87

Preparation of 8-(1-ethyl-propyl)-2,6-dimethyl-3-(3-methyl-benzofuran-2-yl)-imidazo[1,2-b]pyridazine

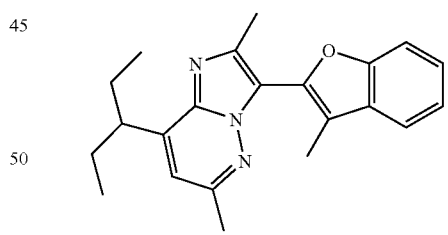

A THF solution (6 mL) of 3-methyl-benzofuran (200 mg, 1.51 mmol) is cooled to −78° C. under N₂ then treated with nBuLi (1.6 M in hexane, 1.0 mL, 1.6 mmol). After 5 min at −78° C., the solution is warmed to 0° C. for 10 minutes, then to room temperature for 10 min. The mixture is then cooled to −78° C. and treated with ZnCl₂ (Aldrich, 0.5 M in THF, 3.2 mL, 1.6 mmol). The resulting mixture is warmed to room temperature and treated with 8-(1-ethyl-propyl)-3-iodo-2,6-dimethyl-imidazo[1,2-b]pyridazine (235.3 mg, 0.69 mmol) and PdCl₂(dppf)-CH₂Cl₂ complex (Aldrich, 64 mg, 0.078 mmol). The mixture is heated to 60° C. for 4 hours, then poured into 1 N HCl (60 mL) and extracted with ethyl acetate (2×60 mL). The organic extract is washed with aq. brine, dried over Na$_2$SO$_4$, filtered, and concentrated. The crude product is purified by chromatography using hexane-ethyl acetate gradient (100% hexane to 20% ethyl acetate in hexane) to elute the product. Obtained is 8-(1-ethyl-propyl)-2,6-dimethyl-3-(3-methyl-benzofuran-2-yl)-imidazo[1,2-b]pyridazine as a solid (143.8 mg, 60% yield). ES-MS (m/z): calc'd for C$_{22}$H$_{25}$N$_3$O: 347.20. found 348.5 (M+H)+$^1$H NMR (400 mHz, CDCl$_3$): δ 7.65 (d, J=8.4 Hz, 1H), 7.57 (d, J=7.9 Hz, 1H), 7.41-7.31 (m, 2H), 6.76 (br s, 1H), 3.38 (br s, 1H), 2.56 (s, 6H), 2.32 (s, 3H), 1.94-1.81 (m, 4H), 0.91 (t, J=7.5 Hz, 6H) ppm.

Example 88

A. 2-{3-[8-(1-ethyl-propyl)-2,6-dimethyl-imidazo[1,2-b]pyridazin-3-yl]-2-methyl-benzofuran-7-yl}-propan-2-ol

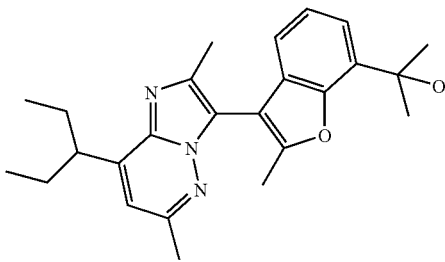

Using a procedure analogous to Example 48, from 3-[8-(1-ethyl-propyl)-2,6-dimethyl-imidazo[1,2-b]pyridazin-3-yl]-2-methyl-benzofuran-7-carboxylic acid methyl ester, Example 78, (0.5685 g, 1.40 mmol) and CH$_3$MgBr gives the title compound (0.5276 g, 1.30 mmol, 93%). $^1$H NMR (CDCl$_3$): δ 0.90 (t, J=7.5 Hz, 3H), 0.91 (t, J=7.5 Hz, 3H), 1.76-1.94 (m, 4H), 1.82 (s, 6H), 2.46 (s, 6H), 2.48 (s, 3H), 2.62 (bs, 1H), 3.32-3.43 (m, 1H), 6.68 (s, 1H), 7.14-7.18 (m, 2H), 7.31-7.36 (m, 1H) ppm. ES-MS (m/z): calcd for C$_{25}$H$_{31}$N$_3$O$_2$ (M+1)$^+$: 406.5. found: 406.3.

Example 89

Preparation of Hydrochloride Salt of 2-{3-[8-(1-ethyl-propyl)-2,6-dimethyl-imidazo[1,2-b]pyridazin-3-yl]-2-methyl-benzofuran-7-yl}-propan-2-ol, Hydrochloride Salt

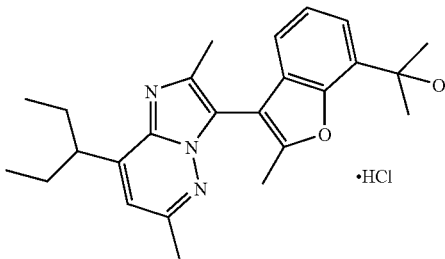

2-{3-[8-(1-ethyl-propyl)-2,6-dimethyl-imidazo[1,2-b]pyridazin-3-yl]-2-methyl-benzofuran-7-yl}-propan-2-ol 9105 mg, 0.2593 mmol) is dissolved in CH$_3$OH (5 mL), reacted with 21 μL of acetyl chloride (0.28 mmol) at rt for 5 min. The excess organic solvent is removed in vacuo gives the title compound (108 mg, 100%). $^1$H NMR (CD$_3$OD): δ 0.96 (t, J=7.5 Hz, 3H), 0.97 (t, J=7.5 Hz, 3H), 1.77 (s, 3H), 1.78 (s, 3H), 1.84-2.02 (m, 4H), 2.49 (s, 3H), 2.58 (s, 3H), 2.62 (s, 3H), 3.07-3.17 (m, 1H), 7.16-7.24 (m, 2H), 7.50 (dd, J=7.1, 1.2 Hz, 1H), 7.68 (s, 1H) ppm.

Example 90

Preparation of 8-(1-ethyl-propyl)-3-(7-isopropenyl-2-methyl-benzofuran-3-yl)-2,6-dimethyl-imidazo[1,2-b]pyridazine

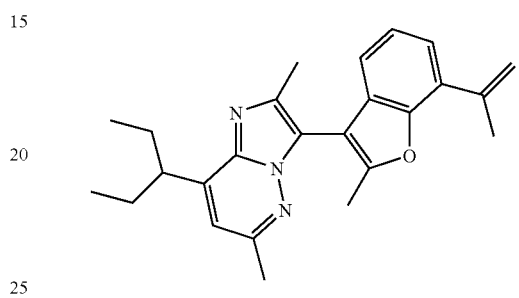

Using a procedure analogous to Example 49B., from 2-{3-[8-(1-ethyl-propyl)-2,6-dimethyl-imidazo[1,2-b]pyridazin-3-yl]-2-methyl-benzofuran-7-yl}-propan-2-ol. (0.32 g, 0.79 mmol), methanesulfonyl chloride (67 μL, 0.97 mmoL) and Et$_3$N (0.28 mL, 1.98 mmol) gives the title compound (0.14 g, 0.36 mmol, 46%). $^1$H NMR (CDCl$_3$): δ 0.90 (t, J=7.5 Hz, 3H), 0.91 (t, J=7.5 Hz, 3H), 1.77-1.95 (m, 4H), 2.34 (s, 3H), 2.45 (s, 3H), 2.47 (s, 3H), 2.48 (s, 3H), 3.32-3.46 (m, 1H), 5.41 (t, J=1.4 Hz, 1H), 5.84 (s, 1H), 6.70 (s, 1H), 7.16 (s, 1H), 7.17 (s, 1H), 7.27 (t, J=4.4 Hz, 1H) ppm. ES-MS (m/z): calcd for C$_{25}$H$_{29}$N$_3$O (M+1)$^+$: 388.5. found: 388.3.

Example 91

Preparation of 8-(1-ethyl-propyl)-3-(7-isopropyl-2-methyl-benzofuran-3-yl)-2,6-dimethyl-imidazo[1,2-b]pyridazine

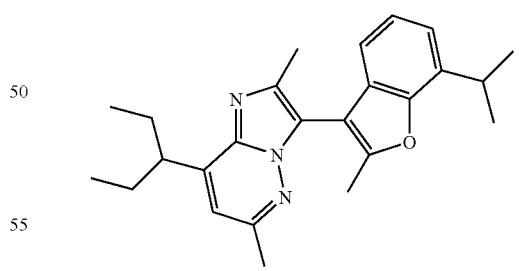

Using a procedure analogous to Example 50, from 8-(1-ethyl-propyl)-3-(7-isopropenyl-2-methyl-benzofuran-3-yl)-2,6-dimethyl-imidazo[1,2-b]pyridazine (0.12 g, 0.31 mmol) gives the title compound (77.4 mg, 0.20 mmol, 64%). $^1$H NMR (CDCl$_3$): δ 0.79-1.01 (m, 6H), 1.43 (d, J=7.0 Hz, 6H), 1.76-2.00 (m, 4H), 2.45 (s, 3H), 2.56 (s, 3H), 2.63 (s, 3H), 3.46-3.56 (m, 1H), 3.60-3.79 (m, 1H), 6.86-7.20 (m, 4H) ppm. ES-MS (m/z): calcd for C$_{25}$H$_{31}$N$_3$O (M+1)$^+$: 390.6. found: 390.3.

Example 92

Preparation of 3-(7-tert-butyl-2-methyl-benzo[b]thiophen-3-yl)-8-(1-ethyl-propyl)-2,6-dimethyl-imidazo[1,2-b]pyridazine

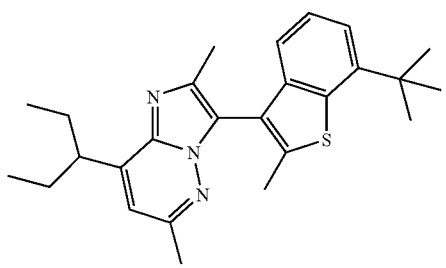

A. 1-tert-Butyl-2-(2-chloro-allylsulfanyl)-benzene

A solution of 2-tert-butyl-benzenethiol (5.0 g, 24.09 mmol) in acetone (25 mL) is reacted with 2,3-dichloro-propene (2.2 mL, 24.09 mmol) and $K_2CO_3$ (4.3 g, 31.32 mmol) at reflux overnight. It is cooled to rt and filtered and washed with EtOAc, and concentrated. The crude material is purified by chromatography gives the title compound (5.66 g, 23.58 mmol, 98%). $^1$H NMR (CDCl$_3$): δ 1.52 (s, 9H), 3.77 (s, 2H), 5.27 (bs, 1H), 5.31 (bs, 1H), 7.11-7.20 (m, 2H), 7.36-7.43 (m, 1H) ppm. ES-MS (m/z): calcd for $C_{13}H_{17}ClS$ M$^+$: 240.8. found: 240.9.

B. 7-tert-Butyl-2-methyl-benzo[b]thiophene

A solution of 1-tert-Butyl-2-(2-chloro-allylsulfanyl)-benzene (5.66 g, 23.58 mmol) in PhNEt2 (50 mL) is refluxed overnight. It is cooled to rt, diluted with EtOAc (100 mL), washed with 1.0 M HCl (3×100 mL); dried with Na$_2$SO$_4$; filtered and concentrated. The resulting crude material is purified by chromatography gives the title compound (4.69 g, 23.01 mmol, 98%). $^1$H NMR (CDCl$_3$): δ 1.54 (s, 9H), 2.59 (d, J=1.3 Hz, 3H), 6.99 (q, J=1.3 Hz, 1H), 7.21-7.29 (m, 2H), 7.53 (dd. J=7.4, 1.3 Hz, 1H) ppm. ES-MS (m/z): calcd for $C_{13}H_{16}S$ (M+1)$^+$: 205.3. found: 205.0.

C. 3-Bromo-7-tert-butyl-2-methyl-benzo[b]thiophene

A solution of 7-tert-butyl-2-methyl-benzo[b]thiophene 94.69 g, 23.0 mmol) in CH$_2$Cl$_2$ (100 mL) is cooled to 0° C. It is treated with Br$_2$ (1.18 mL, 23.0 mmol). The resulting reaction mixture is stirred at rt overnight. It is washed with 10% Na$_2$SO$_3$ (2×50 mL); brine (50 mL); dried with Na$_2$SO$_4$, filtered and concentrated gives the title compound (4.99 g, 17.57 mmol, 76%). $^1$H NMR (CDCl$_3$): δ 1.53 (s, 9H), 2.56 (s, 3H), 7.32 (dd, J=7.5, 1.3 Hz, 1H), 7.38 (t, J=7.5 Hz, 1H), 7.63 (dd, J=7.5 Hz, 1.3 Hz, 1H) ppm. ES-MS (m/z): calcd for $C_{13}H_{15}BrS$ (M+1)$^+$: 284.2. found: 284.9.

D. 3-(7-tert-butyl-2-methyl-benzo[b]thiophen-3-yl)-8-(1-ethyl-propyl)-2,6-dimethyl-imidazo[1,2-b]pyridazine Using a procedure analogous to Example 16B, from 3-bromo-7-tert-butyl-2-methyl-benzo[b]thiophene (0.4172 g, 1.47 mmol) and 8-(1-ethyl-propyl)-3-iodo-2,6-dimethyl-imidazo[1,2-b]pyridazine (0.3217 g, 1.47 mmol) gives the title compound (0.4262 g, 1.02 mmol, 69%). $^1$H NMR (CDCl$_3$): δ 0.94 (t, J=7.6 Hz, 3H), 0.95 (t, J=7.6 Hz, 3H), 1.62 (s, 9H), 1.79-1.99 (m, 4H), 2.41 (s, 3H), 2.45 (s, 3H), 2.47 (s, 3H), 3.36-3.48 (m, 1H), 6.70 (s, 1H), 7.11 (dd, J=7.5, 0.9 Hz, 1H), 7.25 (t, J=7.5 Hz, 1H), 7.27-7.33 (m, 1H) ppm. ES-MS (m/z): calcd for $C_{26}H_{33}N_3S$ (M+1)$^+$: 420.6. found: 420.3.

Example 93

Preparation of cyclopropyl-{3-[8-(1-ethyl-propyl)-2,6-dimethyl-imidazo[1,2-b]pyridazin-3-yl]-2-methyl-imidazo[1,2-a]pyridin-8-yl}-methanol

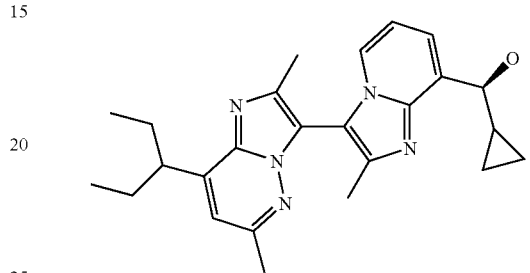

Using a procedure analogous to Example 41, from 3-[8-(1-ethyl-propyl)-2,6-dimethyl-imidazo[1,2-b]pyridazin-3-yl]-2-methyl-imidazo[1,2-a]pyridine-8-carbaldehyde (0.2977 g, 0.79 mmol) and cyclopropylmagnesium bromide (0.5 M, 1.9 mL, 0.95 mmol) gives the title compound (0.2623 g, 0.63 mmol, 79%). $^1$H NMR (CDCl$_3$): δ 0.40-0.55 (m, 1H), 0.60-0.70 (m, 1H), 0.71-0.80 (m, 1H), 0.90 (t, J=7.5 Hz, 3H), 0.91 (t, J=7.5 Hz, 3H), 1.48-1.59 (m, 1H), 1.78-1.94 (m, 5H), 2.38-2.46 (m, 9H), 3.30-3.41 (m, 1H), 4.11 (q, J=7.1 Hz, 1H), 5.42 (t, J=5.7 Hz, 1H), 6.70-6.76 (m, 2H), 7.23-7.28 (m, 1H), 7.44 (dd, J=6.5, 2.2 Hz, 1H) ppm. ES-MS (m/z): calcd for $C_{25}H_{31}N_5O$ (M+1)$^+$: 418.6. found: 418.2.

Example 94

Preparation of cyclopropyl-{3-[8-(1-ethyl-propyl)-2,6-dimethyl-imidazo[1,2-b]pyridazin-3-yl]-2-methyl-imidazo[1,2-a]pyridin-8-yl}-methanone

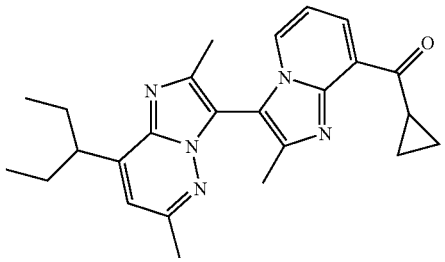

Using a procedure analogous to Example 43, from cyclopropyl-{3-[8-(1-ethyl-propyl)-2,6-dimethyl-imidazo[1,2-b]pyridazin-3-yl]-2-methyl-imidazo[1,2-a]pyridin-8-yl}-methanol (0.2082 g, 0.50 mmol) gives the title compound (0.1843 g, 0.44 mmol, 88%). $^1$H NMR (CDCl$_3$): δ 0.89 (t, J=7.1 Hz, 3H), 0.90 (t, J=7.1 Hz, 3H), 1.13-1.27 (m, 2H), 1.31-1.42 (m, 2H), 1.75-1.94 (m, 4H), 2.40 (s, 3H), 2.42 (s, 3H), 2.45 (s, 3H), 3.30-3.40 (m, 1H), 4.02-4.12 (m, 1H), 6.73 (s, 1H), 6.82 (t, J=6.9 Hz, 1H), 7.65 (dd, J=6.9, 1.3 Hz, 1H), 7.90 (dd, J=7.5, 1.3 Hz, 1H) ppm. ES-MS (m/z): calcd for C$_{25}$H$_{29}$N$_5$O (M+1)$^+$: 416.5. found: 416.2.

Example 95

Preparation of 1-{3-[8-(1-ethyl-propyl)-2,6-dimethyl-imidazo[1,2-b]pyridazin-3-yl]-2-methyl-imidazo[1,2-a]pyridin-8-yl}-2-methyl-propan-1-ol

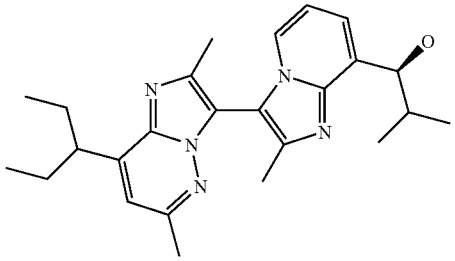

Using a procedure analogous to Example 41, from 3-[8-(1-ethyl-propyl)-2,6-dimethyl-imidazo[1,2-b]pyridazin-3-yl]-2-methyl-imidazo[1,2-a]pyridine-8-carbaldehyde (0.2513 g, 0.67 mmol) and iPrMgBr (2.0 M, 0.40 mL, 0.80 mmol) gives the title compound (0.1524 g, 0.36 mmol, 54%). $^1$H NMR (CDCl$_3$): δ 0.86-0.96 (m, 9H), 1.17 (d, J=6.5 Hz, 3H), 1.62-1.75 (m, 1H), 1.78-1.94 (m, 4H), 2.38 (s, 3H), 2.42 (s, 3H), 2.45 (s, 3H), 3.30-3.42 (m, 1H), 4.60 (t, J=8.4 Hz, 1H), 6.66-6.78 (m, 2H), 7.05 (d, J=6.6 Hz, 1H), 7.42 (dd, J=10.6, 6.6 Hz, 1H) ppm. ES-MS (m/z): calcd for C$_{25}$H$_{33}$N$_5$O (M+1)$^+$: 420.6. found: 420.2.

Example 96

Preparation of 1-{3-[8-(1-ethyl-propyl)-2,6-dimethyl-imidazo[1,2-b]pyridazin-3-yl]-2-methyl-imidazo[1,2-a]pyridin-8-yl}-2-methyl-propan-1-one

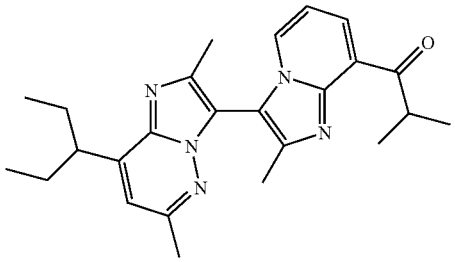

Using a procedure analogous to Example 43, from 1-{3-[8-(1-ethyl-propyl)-2,6-dimethyl-imidazo[1,2-b]pyridazin-3-yl]-2-methyl-imidazo[1,2-a]pyridin-8-yl}-2-methyl-propan-1-ol (0.13 g, 0.31 mmol) gives the title compound (95.8 mg, 0.23 mmol, 74%). $^1$H NMR (CDCl$_3$): δ 0.90 (t, J=7.5 Hz, 3H), 0.91 (t, J=7.5 Hz, 3H), 1.29 (d, J=6.6 Hz, 6H), 1.79-1.94 (m, 4H), 2.42 (s, 3H), 2.44 (s, 3H), 2.45 (s, 3H), 3.31-3.41 (m, 1H), 4.52-4.63 (m, 1H), 6.75 (s, 1H), 6.82 (t, J=7.1 Hz, 1H), 7.65 (dd, J=6.6, 1.3 Hz, 1H), 7.84 (dd, J=7.1, 1.3 Hz, 1H) ppm. ES-MS (m/z): calcd for C$_{25}$H$_{31}$N$_5$O (M+1)$^+$: 418.6; found: 418.2.

Example 97

Preparation of 1-{3-[8-(1-ethyl-propyl)-2,6-dimethyl-imidazo[1,2-b]pyridazin-3-yl]-2-methyl-imidazo[1,2-a]pyridin-8-yl}-propan-1-ol

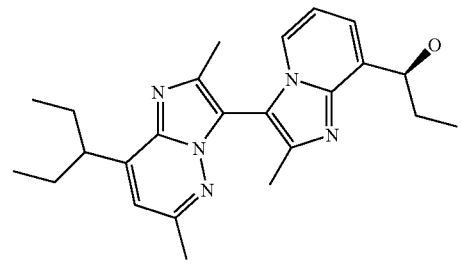

Using a procedure analogous to Example 41, from 3-[8-(1-ethyl-propyl)-2,6-dimethyl-imidazo[1,2-b]pyridazin-3-yl]-2-methyl-imidazo[1,2-a]pyridine-8-carbaldehyde (0.2675 g, 0.71 mmol) and EtMgBr (3.0 M, 0.29 mL, 0.87 mmol) gives the title compound (0.1963 g, 0.48 mmol, 68%). $^1$H NMR (CDCl$_3$): δ 0.85-0.96 (m, 6H), 1.08 (t, J=7.5 Hz, 1.5H), 1.09 (t, J=7.5 hz, 1.5H), 1.78-1.94 (m, 4H), 2.01-2.15 (m, 2H), 2.39 (s, 3H), 2.41 (s, 1.5H), 2.42 (s, 1.5H), 2.44 (s, 3H), 3.30-3.41 (m, 1H), 4.95-5.60 (m, 1H), 6.68-6.74 (m, 2H), 7.09 (d, J=6.6 Hz, 1H), 7.42 (t, J=7.0 Hz, 1H) ppm. ES-MS (m/z): calcd for C$_{24}$H$_{31}$N$_5$O (M+1)$^+$: 406.6. found: 406.2.

Example 98

Preparation of 1-{3-[8-(1-ethyl-propyl)-2,6-dimethyl-imidazo[1,2-b]pyridazin-3-yl]-2-methyl-imidazo[1,2-a]pyridin-8-yl}-propan-1-one

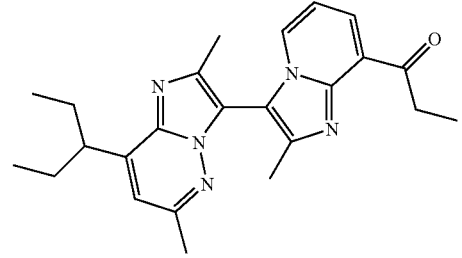

Using a procedure analogous to Example 43, from 11-{3-[8-(1-ethyl-propyl)-2,6-dimethyl-imidazo[1,2-b]pyridazin-3-yl]-2-methyl-imidazo[1,2-a]pyridin-8-yl}-propan-1-ol. (0.1728 g, 0.43 mmol) gives the title compound (0.1245 g, 0.31 mmol, 72%). $^1$H NMR (CDCl$_3$): δ 0.90 (t, J=7.5 Hz, 3H), 0.91 (t, J=7.5 Hz, 3H), 1.30 (t, J=7.1 Hz, 3H), 1.80-1.92 (m, 4H), 2.42 (s, 3H), 2.43 (s, 3H), 2.46 (s, 3H), 3.30-3.42 (m, 1H), 3.65 (q, J=7.1 Hz, 2H), 6.75 (s, 1H), 6.82 (t, J=7.1 Hz, 1H), 7.65 (dd, J=6.6, 1.3 Hz, 1H), 7.90 (dd, J=7.1, 1.3 Hz, 1H) ppm. ES-MS (m/z): calcd for C$_{24}$H$_{29}$N$_5$O (M+1)$^+$: 404.5. found: 404.2.

Example 99

Preparation of 8-(1-ethyl-propyl)-3-(8-isopropenyl-2-methyl-imidazo[1,2-a]pyridin-3-yl)-2,6-dimethyl-imidazo[1,2-b]pyridazine

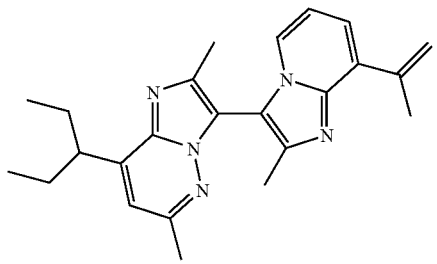

A. 1-{3-[8-(1-Ethyl-propyl)-2,6-dimethyl-imidazo[1,2-b]pyridazin-3-yl]-2-methyl-imidazo[1,2-a]pyridin-8-yl}-2,2-dimethyl-propan-1-ol Using a procedure analogous to Example 41, 3-[8-(1-ethyl-propyl)-2,6-dimethyl-imidazo[1,2-b]pyridazin-3-yl]-2-methyl-imidazo[1,2-a]pyridine-8-carbaldehyde (0.20 g, 0.53 mmol) and t-BuMgBr (2.0 M, 0.32 mL, 0.64 mmol) give the title compound (91.9 mg, 0.21 mmol, 66%). $^1$H NMR (CDCl$_3$): δ 0.87-0.95 (m, 6H), 1.06 (s, 4.5H), 1.07 (s, 4.5H), 1.79-1.94 (m, 4H), 2.38 (s, 3H), 2.42 (s, 3H), 2.46 (s, 3H), 3.30-3.41 (m, 1H), 4.65-5.80 (m, 1H), 6.69-6.76 (m, 2H), 7.05 (bs, 1H), 7.43 (dd, J=13.7, 7.1 Hz, 1H) ppm. ES-MS (m/z): calcd for $C_{26}H_{35}N_5O$ (M+1)$^+$: 434.6. found: 434.5.

B. 8-(1-Ethyl-propyl)-3-(8-isopropenyl-2-methyl-imidazo[1,2-a]pyridin-3-yl)-2,6-dimethyl-imidazo[1,2-b]pyridazine Using a procedure analogous to Example 49B, from 2-{3-[8-(1-ethyl-propyl)-2,6-dimethyl-imidazo[1,2-b]pyridazin-3-yl]-2-methyl-imidazo[1,2-a]pyridin-8-yl}-propan-2-ol (0.1647 g, 0.41 mmol) gives the title compound (72.9 mg, 0.19 mmol, 46%). $^1$H NMR (CDCl$_3$): δ 0.90 (t, J=7.4 Hz, 3H), 0.91 (t, J=7.4 Hz, 3H), 1.77-1.95 (m, 4H), 2.35 (s, 3H), 2.40 (s, 3H), 2.42 (s, 3H), 2.43 (s, 3H), 3.32-3.41 (m, 1H), 5.51 (bs, 1H), 6.28 (s, 1H), 6.70 (t, J=7.1 Hz, 1H), 6.72 (s, 1H), 7.18 (dd, J=7.1, 0.9 Hz, 1H), 7.43 (dd, J=6.6, 0.9 Hz, 1H) ppm. ES-MS (m/z): calcd for $C_{24}H_{29}N_5$ (M+1)$^+$: 388.5. found: 388.3.

Example 100

Preparation of 8-(1-Ethyl-propyl)-3-(8-isopropyl-2-methyl-imidazo[1,2-a]pyridin-3-yl)-2,6-dimethyl-imidazo[1,2-b]pyridazine

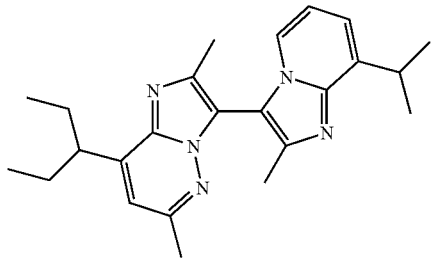

Using a procedure analogous to Example 50, from 8-(1-Ethyl-propyl)-3-(8-isopropenyl-2-methyl-imidazo[1,2-a]pyridin-3-yl)-2,6-dimethyl-imidazo[1,2-b]pyridazine (62.0 mg, 0.16 mmol) gives the title compound (50.4 mg, 0.13 mmol, 91%). $^1$H NMR (CDCl$_3$): δ 0.90 (t, J=7.5 Hz, 3H), 0.91 (t, J=7.5 Hz, 3H), 1.42 (d, J=1.7 Hz, 3H), 1.43 (d, J=1.7 Hz, 3H), 1.77-1.93 (m, 4H), 2.40 (s, 3H), 2.43 (s, 3H), 2.44 (s, 3H), 3.32-3.42 (m, 1H), 3.78-3.89 (m, 1H), 6.70 (t, J=6.7 Hz, 1H), 6.72 (s, 1H), 7.07 (t, J=7.1 Hz, 1H), 7.38 (dd, J=6.7, 0.8 Hz, 1H) ppm. ES-MS (m/z): calcd for $C_{24}H_{31}N_5$ (M+1)$^+$: 390.5. found: 390.2.

Example 101

Preparation of 3-[8-(1-ethyl-propyl)-2,6-dimethyl-imidazo[1,2-b]pyridazin-3-yl]-2-methyl-benzo[b]thiophene-7-carboxylic Acid Dimethylamide

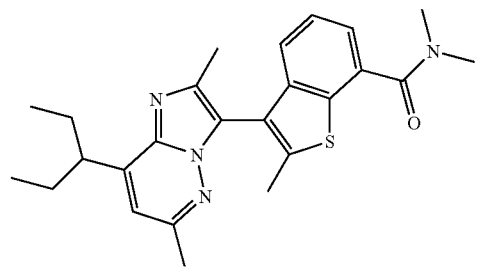

A. 3-[8-(1-Ethyl-propyl)-2,6-dimethyl-imidazo[1,2-b]pyridazin-3-yl]-2-methyl-benzo[b]thiophene-7-carboxylic Acid Using a procedure similar to Example 47 C, from 3-bromo-2-methyl-benzo[b]thiophene-7-carboxylic acid methyl ester (2.00 g, 9.13 mmol) and 8-(1-ethyl-propyl)-2,6-dimethyl-imidazo[1,2-a]pyridine (2.60 g, 9.13 mmol) at 140-145° C. gives the title compound (0.4435 g, 1.09 mmol, 12%). Note: in contrast with Example 47C, higher temperatures produce greater hydrolysis of the formed ester to the acid. ES-MS (m/z): calcd for $C_{23}H_{25}N_3O_2S$ (M+H)+: 408.5. found: 408.3.

B. 3-[8-(1-ethyl-propyl)-2,6-dimethyl-imidazo[1,2-b]pyridazin-3-yl]-2-methyl-benzo[b]thiophene-7-carboxylic Acid Dimethylamide 3-[8-(1-Ethyl-propyl)-2,6-dimethyl-imidazo[1,2-b]pyridazin-3-yl]-2-methyl-benzo[b]thiophene-7-carboxylic acid (0.22 g, 0.53 mmol) is reacted with oxalyl chloride (5 mL) at rt for 2 h. The excess reagent is removed in vacuo, and the resulting residue is dissolved in CH$_2$Cl$_2$ (5 mL). It is treated with Et$_3$N (0.6 mL) and 2.0 M NH(CH$_3$)$_3$ (1.0 mL). The reaction is stirred at rt for 10 min, then diluted with EtOAc (50 mL); washed with H$_2$O (2×20 mL); dried with Na$_2$SO$_4$; filtered and concentrated. Purification of the crude material by chromatography gives the title compound (83.6 mg, 0.19 mmol, 36%). $^1$H NMR (CDCl$_3$): δ 0.90 (t, J=7.4 Hz, 3H), 0.91 (t, J=7.4 Hz, 3H), 1.75-1.95 (m, 4H), 2.38 (s, 3H), 2.42 (s, 3H), 2.44 (s, 3H), 3.15 (bs, 6H), 3.35-3.45 (m, 1H), 6.69 (s, 1H), 7.27-7.33 (m, 3H) ppm. ES-MS (m/z): calcd for $C_{25}H_{30}N_4OS$ (M+1)$^+$: 435.6. found: 435.2.

Example 102

Preparation of 3-[8-(1-ethyl-propyl)-2,6-dimethyl-imidazo[1,2-b]pyridazin-3-yl]-2-methyl-benzo[b]thiophene-7-carboxylic Acid Methylamide

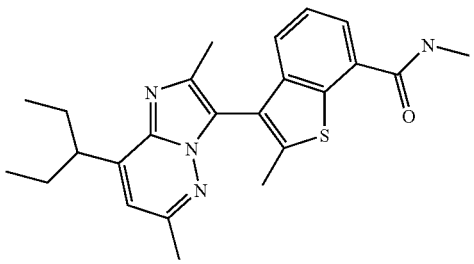

Using a procedure analogous to Example 101 B., from 3-[8-(1-ethyl-propyl)-2,6-dimethyl-imidazo[1,2-b]pyridazin-3-yl]-2-methyl-benzo[b]thiophene-7-carboxylic acid (0.23 g, 0.57 mmol) and $NH_2CH_3 \cdot HCl$ (58 mg, 0.85 mmol) gives the title compound (51.8 mg, 0.12 mmol, 21%). $^1H$ NMR ($CDCl_3$): δ 0.90 (t, J=7.5 Hz, 3H), 0.91 (t, J=7.5 Hz, 3H), 1.76-1.94 (m, 4H), 2.37 (s, 3H), 2.42 (s, 3H), 2.44 (s, 3H), 3.11 (d, J=4.8 Hz, 3H), 3.33-3.43 (m, 1H), 6.39 (q, J=4.8 Hz, 1H), 6.68 (s, 1H), 7.27-7.36 (m, 2H), 7.52 (dd, J=7.1, 0.9 Hz, 1H) ppm. ES-MS (m/z): calcd for $C_{24}H_{28}N_4OS$ $(M+1)^+$: 421.6. found: 421.3.

Example 103

Preparation of 1-{3-[8-(1-ethyl-propyl)-2,6-dimethyl-imidazo[1,2-b]pyridazin-3-yl]-2-methyl-benzo[b]thiophen-7-yl}-ethanone

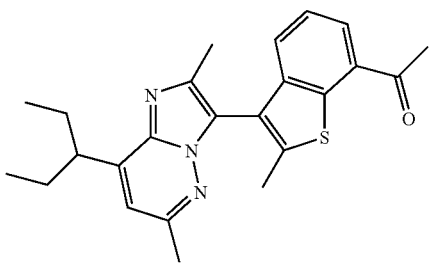

A. 3-Bromo-2-methyl-benzo[b]thiophene-7-carboxylic Acid methoxy-methyl-amide 3-Bromo-2-methyl-benzo[b]thiophene-7-carboxylic acid methyl ester 7.82 g, 27.43 mmol) was treated with NaOH (5 M, 28 mL, 140 mmol) and $H_2O$ (100 mL). It is refluxed for 4 h; cooled to 0° C., and acidified to pH (3-4) using 5 M HCl. The resulting precipitate is collected by filtration, washed with $H_2O$ (50 mL), and dried in a vac-oven. The material obtained is then treated with oxalyl chloride (2M, 27 mL) with a few drops of DMF. The reaction is stirred at 0° C. for 10 min, and at rt for 4 h. The excess reagent and solvent are removed in vacuo. The residue is finally treated with N,O-dimethyl hydroxylamine hydrochloride (4.00 g, 41.14 mmol) and $Et_3N$ (9.6 mL, 68.58 mmol) and $CH_2Cl_2$ (200 mL), and the resulting reaction mixture is stirred at rt for 2 h. It is diluted with $CH_2Cl_2$ (200 mL), washed with 0.1 M HCl (3×300 mL); dried with $Na_2SO_4$, filtered and concentrated. Purification of the crude material by chromatography gives the title compound (6.87 g, 21.89 mmol, 53%). $^1H$ NMR ($CDCl_3$): δ. 2.56 (s, 3H), 3.42 (s, 3H), 3.59 (s, 3H), 7.45 (t, J=7.9 Hz, 2H), 7.81-7.87 (m, 1H) ppm. ES-MS (m/z): calcd for $C_{12}H_{12}BrNO_2S$ $(M)^+$: 314.1. found: 314.2.

B. 1-(3-Bromo-2-methyl-benzo[b]thiophen-7-yl)-ethanone

A solution of 3-bromo-2-methyl-benzo[b]thiophene-7-carboxylic acid methoxy-methyl-amide (2.02 g, 6.43 mmol) in THF (65 mL) is cooled to 0° C., treated with $CH_3MgBr$ (3.0 M, 2.4 mL, 7.1 mmol). The reaction is stirred at 0° C. for 10 min, then at rt for 10 min. It is cooled to 0° C., quenched with sat. $NH_4C$ (10 mL); diluted with $H_2O$ (20 mL); treated with 0.1 M HCl (20 mL); extracted with EtOAc (2×40 mL). The combined organic layers are dried with $Na_2SO_4$, filtered and concentrated. Purification of the crude material by chromatography gives the title compound (1.39 g, 5.18 mmol, 81%). $^1H$ NMR ($CDCl_3$): δ. 2.58 (s, 3H), 2.75 (s, 3H), 7.53 (t, J=7.9 Hz, 1H), 7.96 (d, J=7.9 Hz, 1H), 7.99 (d, J=7.5 Hz, 1H) ppm. ES-MS (m/z): calcd for $C_{11}H_9BrOS$ $(M+1)^+$: 270.2. found: 270.0.

C. 1-{3-[8-(1-Ethyl-propyl)-2,6-dimethyl-imidazo[1,2-b]pyridazin-3-yl]-2-methyl-benzo[b]thiophen-7-yl}-ethanone Using a procedure analogous to Example 16B, from 8-(1-ethyl-propyl)-2,6-dimethyl-imidazo[1,2-b]pyridazine (1.13 g, 5.17 mmol) and 1-(3-bromo-2-methyl-benzo[b]thiophen-7-yl)-ethanone (1.39 g, 5.17 mmol) gives the title compound (0.30 g, 0.74 mmol, 14%). $^1H$ NMR ($CDCl_3$): δ 0.90 (t, J=7.5 Hz, 3H), 0.91 (t, J=7.5 Hz, 3H), 1.79-1.94 (m, 4H), 2.36 (s, 3H), 2.42 (s, 3H), 2.45 (s, 3H), 2.77 (s, 3H), 3.34-3.43 (m, 1H), 6.68 (s, 1H), 7.39 (t, J=7.4 Hz, 1H), 7.44-7.48 (m, 1H), 7.97 (dd, J=7.5, 0.9 Hz, 1H) ppm. ES-MS (m/z): calcd for $C_{24}H_{27}N_3OS$ $(M+1)^+$: 406.6. found: 406.4.

Example 104

Preparation of 1-{3-[8-(1-ethyl-propyl)-2,6-dimethyl-imidazo[1,2-b]pyridazin-3-yl]-2-methyl-benzo[b]thiophen-6-yl}-ethanone

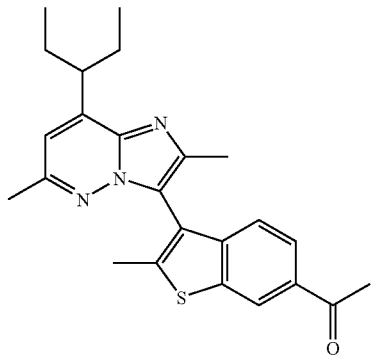

A. 6-Bromobenzo[b]thiophene

Into a stirred solution of 3-bromothiophenol (50.09 g, 264.9 mmol) and $K_2CO_3$ (36.61 g, 264.9 mmol) in acetone (361 mL) is added bromoacetaldehyde diethyl acetal (39.85 mL, 264.9 mmol) in a dropwise manner. After stirring for 2 h, the resulting slurry is filtered through a sintered glass funnel and the filtrate is concentrated under reduced pressure. The resulting precipitate is diluted with $CH_2Cl_2$ (200 mL), dried over MgSO₄, filtered and concentrated under reduced pressure to give 3-bromobenzenethio-acetaldehyde diethyl acetal as a yellow oil used in the next step as is (76.83 g, 95%).

Into a mixture of polyphosphoric acid (160 g) in chlorobenzene (1 L) at reflux is added a solution of the crude 3-bromobenzenethioacetaldehyde diethyl acetal (60.06 g, 196.76 mmol) in chlorobenzene (500 mL) via an addition funnel over a 1.5 h period. Upon complete addition, the mixture is heated at reflux for an additional 2 h and is then allowed to cool to room temperature. The chlorobenzene layer is decanted from the mixture and washed with saturated aqueous NaCl (500 mL). The aqueous layer is used to dilute the PPA, which is then extracted with Et₂O (3×500 mL). The combined organic layers are dried over MgSO₄, filtered and concentrated under reduced pressure. The residue is then purified by silica gel chromatography (100% hexanes). The purified fractions are combined and concentrated under reduced pressure to give 6-bromobenzo[b]thiophene as a white crystal (11.59 g, 27%). mp 54.8-58.3° C. IR (KBr) 3017, 1586, 1448, 1067, 814 cm⁻¹. Ion Spray MS 211.9, 213.9 (M)⁺.

B. 6-Bromo-2-methylbenzo[b]thiophene

Into a stirred solution of diisopropylamine (1.45 mL, 10.3 mmol) and TMEDA (3.4 mL, 22.5 mmol) in THF (30 mL, freshly distilled) at −78° C. is added 1.6 M n-BuLi (7.0 mL, 11.2 mmol) via a syringe. The solution is warmed to 0° C. for 30 min and re-cooled to −78° C. A solution of 6-bromobenzo[b]thiophene 2.0 g, 9.38 mmol) in THF (10 mL) is added via a cannula. After stirring for 30 min, a solution of CH₃I (14.0 mL, 28.1 mmol, 2.0 M in tert-butyl methyl ether) is added via a cannula. The solution is stirred overnight, while allowed to warm to room temperature, and diluted with saturated aqueous NaHCO₃ (50 mL). The mixture is extracted with Et₂O (3×50 mL). The organic layers are combined, dried over MgSO₄, filtered and concentrated under reduced pressure to give the title compound as a tan solid (2.0177 g, 95%).

C. 2-Methyl-benzo[b]thiophene-6-carboxylic Acid Methyl Ester

Using a procedure analogous to Example 23 (a), from 6-bromo-2-methyl-benzo[b]thiophene (1.35 g, 5.95 mmol) gives the title compound (0.84 g, 4.08 mmol, 69%). ¹H NMR (CDCl₃): δ. 2.62 (d, J=0.9 Hz, 3H), 3.94 (s, 3H), 7.03 (s, 1H), 7.67 (d, J=8.3 Hz, 1H), 7.96 (dd, J=8.4, 1.3 Hz, 1H), 8.46 (d, J=0.9 Hz, 1H) ppm. ES-MS (m/z): calcd for C₁₁H₁₀N₃O₂S (M+1)⁺: 207.3. found: 207.0.

D. 2-Methyl-benzo[b]thiophene-6-carboxylic Acid

2-Methyl-benzo[b]thiophene-6-carboxylic acid methyl ester (0.83 g, 4.0 mmol) is reacted with NaOH (0.80 g, 20 mmol) in H₂O (20 mL). at reflux for 2 h. The reaction is cooled to 0° C. and acidified with 1.0 M HCl to pH (3~4). It is extracted with EtOAc (3×100 mL); dried with Na₂SO₄ filtered and concentrated gives the title compound (0.78 g, 4.0 mmol, quant.). ¹H NMR (CDCl₃): δ 2.64 (d, J=0.89 Hz, 3H), 7.06 (s, 1H), 7.71 (d, J=8.3 Hz, 1H), 8.03 (dd, J=8.3, 1.7 Hz, 1H), 8.54 (d, J=0.8 Hz, 1H) ppm. ES-MS (m/z): calcd for C₁₀H₈O₂S (M−H)⁻: 191.2. found: 191.0.

E. 2-Methyl-benzo[b]thiophene-6-carboxylic Acid methoxy-methyl-amide

Using a procedure analogous to Example 103 A, from 2-methyl-benzo[b]thiophene-6-carboxylic acid (0.78 g, 4.04 mmol) gives the title compound (0.95 g, 4.04 mmol, quant.). ¹H NMR (CDCl₃): δ. 2.61 (d, J=1.3H, 3H), 3.39 (s, 3H), 3.56 (s, 3H), 7.01 (t, J=1.1H, 1H), 7.64 (s, 1H) 7.65 (s, 1H), 8.13 (d, J=0.8 Hz, 1H) ppm. ES-MS (m/z): calcd for C₁₂H₁₃NO₂S (M+H)+: 236.3. found: 236.2.

F. 3-Bromo-2-methyl-benzo[b]thiophene-6-carboxylic Acid methoxy-methyl-amide Using a procedure analogous to Example 47B, from 2-methyl-benzo[b]thiophene-6-carboxylic acid methoxy-methyl-amide (0.95 g, 4.04 mmol) gives the title compound (1.08 g, 3.43 mmol, 85%). ¹H NMR (CDCl₃): δ 2.58 (s, 3H), 3.40 (s, 3H), 3.55 (s, 3H), 7.70-7.78 (m, 1H), 8.12 (S, 1H) ppm. ES-MS (m/z): calcd for C₁₂H₁₂BrNO₂S M⁺: 314.2. found: 314.1.

G. 3-[8-(1-Ethyl-propyl)-2,6-dimethyl-imidazo[1,2-b]pyridazin-3-yl]-2-methyl-benzo[b]thiophene-6-carboxylic Acid methoxy-methyl-amide Using a procedure analogous to Example 16B, from 8-(1-ethyl-propyl)-2,6-dimethyl-imidazo[1,2-b]pyridazine (0.75 g, 3.41 mmol) and 3-bromo-2-methyl-benzo[b]thiophene-6-carboxylic acid methoxy-methyl-amide (1.07 g, 3.41 mmol) gives the title compound (0.17 g, 0.38 mmol, 11%). ¹H NMR (CDCl₃): δ 0.90 (t, J=7.5 Hz, 3H), 0.91 (t, J=7.5 Hz, 3H), 1.77-1.94 (m, 4H), 2.38 (s, 3H), 2.43 (s, 3H), 2.45 (s, 3H), 3.32-3.41 (m, 1H), 3.39 (s, 3H), 3.57 (s, 3H), 6.68 (s, 1H), 7.65 (d, J=1.3 Hz, 1H), 8.20-8.22 (m, 2H) ppm. ES-MS (m/z): calcd for C₂₅H₃₀N₄O₂S (M+H)⁺: 451.6. found: 451.4.

H. 1-{3-[8-(1-Ethyl-propyl)-2,6-dimethyl-imidazo[1,2-b]pyridazin-3-yl]-2-methyl-benzo[b]thiophen-6-yl}-ethanone Using a procedure analogous to Example 103 B, from 3-[8-(1-ethyl-propyl)-2,6-dimethyl-imidazo[1,2-b]pyridazin-3-yl]-2-methyl-benzo[b]thiophene-6-carboxylic acid methoxy-methyl-amide (0.17 g, 0.38 mmol) and 3.0 M CH₃MgBr (0.14 mL, 0.41 mmol) gives the title compound (104.3 mg, 0.26 mmol, 68%). ¹H NMR (CDCl₃): δ. 0.91 (t, J=7.5 Hz, 3H), 0.92 (t, J=7.5 Hz, 3H), 1.77-1.94 (m, 4H), 2.38 (s, 3H), 2.39 (s, 3H), 2.43 (s, 3H), 2.47 (s, 3H), 3.34-3.43 (m, 1H), 6.69 (s, 1H), 7.28 (d, J=8.4 Hz, 1H), 7.87 (dd, J=8.4, 1.8 Hz, 1H), 8.45 (d, J=1.3 Hz, 1H) ppm. ES-MS (m/z): calcd for C₂₄H₂₇N₃OS (M+H)⁺: 406.6. found: 406.4.

Example 105

Preparation of 8-(1-ethyl-propyl)-3-(5-fluoro-3-methyl-benzo[b]thiophen-2-yl)-6-methoxy-2-methyl-imidazo[1,2-b]pyridazine

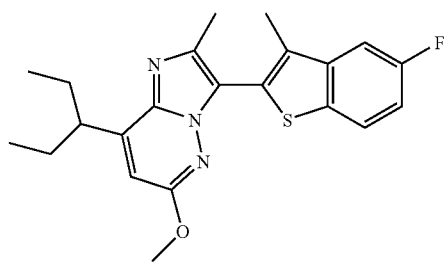

A. N-(6-Methoxy-pyridazin-3-yl)-2,2-dimethyl-propionamide

3-Chloro-6-methoxy-pyridazine (10.0 g, 69. 18 mmol) is mixed with 2,2-dimethyl-propionamide (8.40 g, 83.01 mmol), BINAP (2.15 g, 3.46 mmol), $Cs_2CO_3$ (33.8 g, 103.8 mmol) in dioxane (150 mL). It is degassed by passing $N_2$ through for 10 min at rt. $Pd_2(dba)_3$ (3.16 g, 3.46 mmol) is then added and the resulting reaction is refluxed overnight. The reaction is cooled to rt, diluted with EtOAc (150 mL); filtered through silica gel; washed with EtOAc (2×150 mL). The filtrate is washed with $H_2O$ (2×300 mL); dried with $MgSO_4$; filtered and concentrated. Purification of the crude material by chromatography gives the title compound (6.59 g, 31.53 mmol, 46%). $^1H$ NMR ($CDCl_3$): δ. 1.35 (s, 9H), 4.08 (s, 3H), 7.01 (d, J=9.7 Hz, 1H), 8.41 (d, J=9.7 Hz, 1H), 8.44 (bs, 1H) ppm. ES-MS (m/z): calcd for $C_{10}H_{15}N_3O_2$ $(M+H)^+$: 210.3. found: 210.1.

B. N-[4-(1-Ethyl-propyl)-6-methoxy-pyridazin-3-yl]-2,2-dimethyl-propionamide Using a procedure analogous to Example 17B, from N-(6-methoxy-pyridazin-3-yl)-2,2-dimethyl-propionamide (6.09 g, 29.14 mmol) and Grignard reagent prepared from 3-pentyl bromide (18.1 mL, 160.3 mmol) and Mg (3.84 g, 160.26 mmol) gives the title compound (5.32 g, 19.1 mmol, 65%). $^1H$ NMR ($CDCl_3$): δ. 0.84 (t, J=7.5 Hz, 6H), 1.36 (s, 9H), 1.50-1.72 (m, 4H), 3.50-3.70 (m, 1H), 4.07 (s, 3H), 6.96 (s, 1H) ppm. ES-MS (m/z): calcd for $C_{15}H_{25}N_3O_2$ $(M+H)^+$: 280.4. found: 280.2.

C. 8-(1-Ethyl-propyl)-3-(5-fluoro-3-methyl-benzo[b]thiophen-2-yl)-6-methoxy-2-methyl-imidazo[1,2-b]pyridazine and 1-[8-(1-ethyl-propyl)-3-(5-fluoro-3-methyl-benzo[b]thiophen-2-yl)-6-methoxy-2-methyl-imidazo[1,2-b]pyridazin-7-yl]-ethanone A solution of N-[4-(1-ethyl-propyl)-6-methoxy-pyridazin-3-yl]-2,2-dimethyl-propionamide (5.32 g, 19.08 mmol) in EtOH (250 mL) is treated with $ZnCl_2$ (26.0 g, 190.8 mmol) and refluxed for 48 h. The reaction is cooled to rt and concentrated. The residue is taken up with EtOAc (250 mL), and $H_2O$ (100 mL). It is washed with $H_2O$ (2×100 mL); dried with $Na_2SO_4$; filtered and concentrated. The residue is then dissolved in EtOAc (80 mL), reacted with chloroacetone (1.6 mL, 20.03 mmoL) at reflux overnight. While it is hot, $NaHCO_3$ (8.10 g) is added and the reaction is refluxed for 1 h. It is cooled to rt and filtered through silica gel washed with EtOAc and concentrated. The resulting mixture containing the desired product is dissolved in $CH_3CN$ (8 mL), treated with NIS (0.56 g, 2.47 mmol) and stirred at rt overnight. The reaction is diluted with EtOAc (100 mL), washed with 10% $Na_2SO_3$ (2×50 mL); dried with $Na_2SO_4$; filtered and concentrated. The baseline material is removed by chromatography, and the fraction containing the iodinated imidazo[1,2-b]pyridazine is collected and concentrated. The resulting material (0.4265 g) is then dissolved in a stock solution of $DME:H_2O$:EtOH=7:3:2 (20 mL); treated with 2 M $Na_2CO_3$ (1.2 mL) and boronic acid, 5-fluoro-3-methyl-benzo[b]thiophene-2-yl (299 mg, 1.43 mmol). The mixture is purged with $N_2$ for 5 min. tetrakis-triphenyl-phosphine palladium (0) (69 mg, 0.06 mmol) then refluxed overnight. The reaction is cooled to rt; diluted with $H_2O$ 950 mL); extracted with EtOAc (3×50 mL); dried with $Na_2SO_4$; filtered and concentrated. Purification of the crude material by silica gel chromatography gives the title compound (0.1572 g, 0.40 mmol, 2%). $^1H$ NMR ($CDCl_3$): δ. 0.91 (t, J=7.0 Hz, 6H), 1.75-1.92 (m, 4H), 2.32 (s, 3H), 2.48 (s, 3H), 3.28-3.38 (m, 1H), 3.88 (s, 3H), 6.49 (s, 1H), 7.15 (dt, J=8.9, 2.3 Hz, 1H), 7.44 (dd, J=9.7, 2.7 Hz, 1H), 7.79 (dd, J=8.9, 4.8 Hz, 1H) ppm. ES-MS (m/z): calcd for $C_{22}H_{24}FN_3OS$ $(M+H)^+$: 398.5. found: 398.2.

Example 106 & 107

Preparation of 3-[8-(1-Ethyl-propyl)-2,6-dimethyl-imidazo[1,2-b]pyridazin-3-yl]-2-methyl-benzofuran-7-carboxylic Acid methoxy-methyl-amide and 3-[8-(1-ethyl-propyl)-2,6-dimethyl-imidazo[1,2-b]pyridazin-3-yl]-2-methyl-benzofuran-7-carboxylic Acid Methylamide

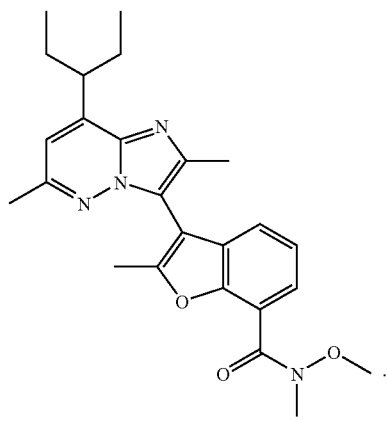

106

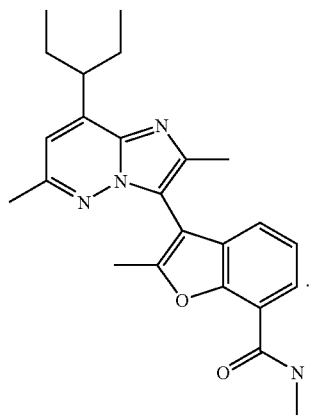

107

A. 3-Bromo-2-methyl-benzofuran-7-carboxylic Acid methoxy-methyl-amide

Using a procedure analogous to Example 103 A., from 3-bromo-2-methyl-benzofuran-7-carboxylic acid methyl ester (4.4876 g, 16.68 mmol) gives the title compound (3.71 g, 12.42 mmol, 75%). $^1H$ NMR ($CDCl_3$): 8.2.50 (s, 3H), 3.39 (s, 3H), 3.58 (s, 3H), 7.30 (t, J=7.5 Hz, 1H), 7.42 (dd, J=7.9, 1.3, Hz, 1H), 7.50 (dd, J=7.5, 1.3 hz, 1H). ES-MS (m/z): calcd for $C_{12}H_{12}BrNO_3$ $(M+H)^+$: 299.1. found: 300.0.

B. 3-[8-(1-Ethyl-propyl)-2,6-dimethyl-imidazo[1,2-b]pyridazin-3-yl]-2-methyl-benzofuran-7-carboxylic Acid methoxy-methyl-amide and 3-[8-(1-ethyl-propyl)-2,6-dimethyl-imidazo[1,2-b]pyridazin-3-yl]-2-methyl-benzofuran-7-carboxylic Acid Methylamide Using a procedure analogous to Example 16B, from 3-bromo-2-methyl-benzofuran-7-carboxylic acid methoxy-methyl-amide (3.71 g, 12.46 mmol) and 8-(1-ethyl-propyl)-2,6-dimethyl-imidazo[1,2-b]pyridazine (2.73 g, 12.46 mmol) gives 3-[8-(1-ethyl-propyl)-2,6-dimethyl-imidazo[1,2-b]pyridazin-3-yl]-2-methyl-benzofuran-7-carboxylic acid methoxy-methyl-amide (1.79 g, 4.14 mmol, 33%). $^1$H NMR (CDCl$_3$): δ. 0.87-0.93 (m, 6H), 1.76-1.94 (m, 4H), 2.45 (s, 3H), 2.46 (s, 3H), 2.47 (s, 3H), 3.30-3.41 (m, 1H), 3.44 (s, 3H), 3.70 (s, 3H), 6.69 (s, 1H), 7.21 (t, J=7.5 Hz, 1H), 7.31-7.34 (m, 1H), 7.41 (dd, J=7.9, 2.3 Hz, 1H). ES-MS (m/z): calcd for C$_{25}$H$_{30}$N$_4$O$_3$ (M+H)$^+$: 435.5. found: 435.4 and 3-[8-(1-ethyl-propyl)-2,6-dimethyl-imidazo[1,2-b]pyridazin-3-yl]-2-methyl-benzofuran-7-carboxylic acid methylamide (0.98 g, 2.42 mmol, 19%) $^1$H NMR (CDCl$_3$): δ. 0.89 (t, J=7.4 Hz, 3H), 0.90 (t, J=7.4 Hz, 3H), 1.77-1.94 (m, 4H), 2.45 (s, 3H), 2.47 (s, 3H), 2.50 (s, 3H), 3.16 (d, J=4.8 Hz, 3H), 3.32-3.41 (m, 1H), 6.70 (s, 1H), 7.29 (t, J=7.5 Hz, 1H), 7.38 (dd, J=7.5, 1.4 Hz, 1H), 7.46 (q, J=4.8 Hz, 1H), 8.09 (dd, J=7.5, 1.4 Hz, 1H). ES-MS (m/z): calcd for C$_{24}$H$_{28}$N$_4$O$_2$ (M+H)$^+$: 405.5; found: 405.4.

Example 108

Preparation of 1-{3-[8-(1-Ethyl-propyl)-2,6-dimethyl-imidazo[1,2-b]pyridazin-3-yl]-2-methyl-benzofuran-7-yl}-ethanone

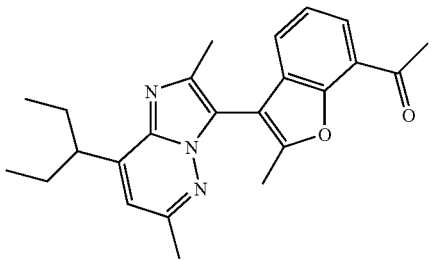

Using a procedure analogous to Example 103 B. from 3-[8-(1-ethyl-propyl)-2,6-dimethyl-imidazo[1,2-b]pyridazin-3-yl]-2-methyl-benzofuran-7-carboxylic acid methoxy-methyl-amide (1.79 g, 4.12 mmol) gives the title compound (1.28 g, 3.28 mmol, 80%). $^1$H NMR (CDCl$_3$): δ. 0.90 (t, J=7.5 Hz, 3H), 0.91 (t, J=7.5 Hz, 3H), 1.77-1.95 (m, 4H), 2.46 (s, 3H), 2.47 (s, 3H), 2.51 (s, 3H), 2.91 (s, 3H), 3.31-3.42 (m, 1H), 6.70 (s, 1H), 7.26 (t, J=7.7 Hz, 1H), 7.45 (dd, J=8.0, 1.4 Hz, 1H), 7.87 (dd, J=7.7, 1.4 Hz, 1H) ppm. ES-MS (m/z): calcd for C$_{24}$H$_{27}$N$_3$O$_2$ (M+H)$^+$: 390.5. found: 390.4.

Example 109

Preparation of 1-{3-[8-(1-ethyl-propyl)-2,6-dimethyl-imidazo[1,2-b]pyridazin-3-yl]-2-methyl-benzofuran-7-yl}-ethanol

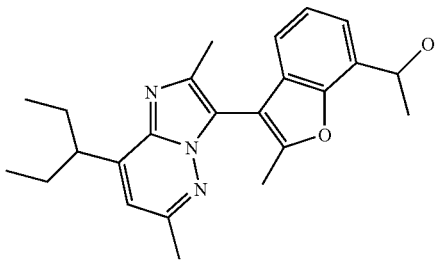

Using a procedure analogous to Example 39, from 1-{3-[8-(1-ethyl-propyl)-2,6-dimethyl-imidazo[1,2-b]pyridazin-3-yl]-2-methyl-benzofuran-7-yl}-ethanone (99.3 mg, 0.25 mmol) gives the title compound (97.6 mg, 0.25 mmol, quant.). $^1$H NMR (CDCl$_3$): δ. 0.90 (t, J=7.4 Hz, 3H), 0.91 (t, J=7.4 Hz, 3H), 1.71 (d, J=4.0 Hz, 1.5H), 1.73 (d, J=4.0 Hz, 1.5H), 1.78-1.94 (m, 4H), 2.43-2.50 (m, 9H), 3.39 (bs, 1H), 5.39-5.49 (m, 1H), 6.69 (s, 1H), 7.18 (s, 1H), 7.19 (bs, 1H), 7.28-7.33 (m, 1H) ppm. ES-MS (m/z): calcd for C$_{24}$H$_{29}$N$_3$O$_2$ (M+H)$^+$: 392.5. found: 392.4.

Example 110

(S)-8-(1-Ethyl-propyl)-3-[7-(1-methoxy-ethyl)-2-methyl-benzofuran-3-yl]-2,6-dimethyl-imidazo[1,2-b]pyridazine

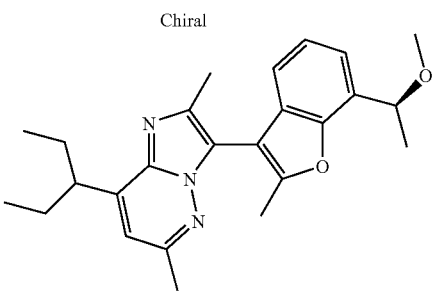

A. 3-Bromo-2-methyl-benzofuran-7-yl)-ethanone

Using a procedure analogous to Example 103 B, from 3-bromo-2-methyl-benzofuran-7-carboxylic acid methoxy-methyl-amide (4.90 g, 16.44 g) gives the title compound (3.99 g, 15.8 mmol, 96%). $^1$H NMR (CDCl$_3$): δ. 2.55 (s, 3H), 2.82 (s, 3H), 7.35 (t, J=7.4 Hz, 1H), 7.63 (dd, J=7.5, 0.6 Hz, 1H), 7.88 (dd, J=7.5, 1.3 Hz, 1H) ppm. ES-MS (m/z): calcd for C$_{11}$H$_9$BrO$_2$ (M+H)$^+$: 254.1. found: 254.9.

B. Racemic 1-(3-bromo-2-methyl-benzofuran-7-yl)-ethanol

Using a procedure analogous to Example 39., from 1-(3-bromo-2-methyl-benzofuran-7-yl)-ethanone (3.99 g, 15.8 mmol) gives the title compound (3.06 g, 12.0 mmol, 76%). $^1$H NMR (CDCl$_3$): δ. 1.64 (d, J=6.6 Hz, 3H), 2.49 (s, 3H), 5.36 (q, J=6.6 Hz, 1H), 7.26 (t, J=5.0 Hz, 1H), 7.31-7.37 (m, 2H) ppm. ES-MS (m/z): calcd for C$_{11}$H$_{11}$BrO$_2$ (M+H)$^+$: 255.1. found: 255.2.

C. (S) and (R)-1-(3-Bromo-2-methyl-benzofuran-7-yl)-ethanol

A racemic mixture of 1-(3-bromo-2-methyl-benzofuran-7-yl)-ethanol (3.06) is chromatographed (ChiralPak OJ-H, 4.6× 150 mm; 10% iPrOH/Hept, 0.6 mL/min, UV: 250 nm) gives enantiomer 1 (1.39 g, 45%, rt=5.9 min) and enantiomer 2 (1.36 g, 45%, rt=8.4 min). The assignment of absolute stereochemistry is based on work published in Cho, B. T. and Chun, Y. S., *Tetrahedron Asymmetry*, 10, p 1843, 1999.

(enantiomer 1)

NMR & ES-MS: equivalent to the racemate, Example 109 C.

(enantiomer 2)

NMR & ES-MS: equivalent to the racemate, Example 109 C.

D. (S)-[1-(3-Bromo-2-methyl-benzofuran-7-yl)-ethoxy]-tert-butyl-dimethyl-silane

A solution of (S)-1-(3-bromo-2-methyl-benzofuran-7-yl)-ethanol (1.39 g, 5.47 mmol) in CH$_2$Cl$_2$ (50 mL) is treated with imidazol (0.56 g, 8.21 mmol) and TBSCl (0.91 g, 6.02 mmol). The reaction is stirred at rt overnight. It is diluted with CH$_2$Cl$_2$ (50 mL); washed with 0.1 M HCl (3×30 mL); dried with Na₂SO₄; filtered and concentrated. The resulting crude material is purified by chromatography gives the title compound (1.92 g, 5.19 mmol, 95%). ¹H NMR (CDCl₃): δ. −0.02 (s, 3H), 0.07 (s, 3H), 0.91 (s, 3H), 2.48 (s, 3H), 1.52 (d, J=6.2 Hz, 3H), 5.38 (q, J=6.2 Hz, 1H), 7.25 (t, J=8.0 Hz, 1H), 7.30 (dd, J=8.0, 1.7 Hz, 1H), 7.40 (d, J=8.0 Hz, 1H) ppm.

E. (S)-1-{3-[8-(1-Ethyl-propyl)-2,6-dimethyl-imidazo[1,2-b]pyridazin-3-yl]-2-methyl-benzofuran-7-yl}-ethanol Using a procedure analogous to Example 16B, from (S)-[1-(3-bromo-2-methyl-benzofuran-7-yl)-ethoxy]-tert-butyl-dimethyl-silane (0.75 g, 2.03 mmol) and 8-(1-ethyl-propyl)-2,6-dimethyl-imidazo[1,2-b]pyridazine (0.44 g, 2.03 mmol) gives the crude coupling product, which is then dissolved in THF (50 mL), reacted with 1.0 M TBAF (2.2.2 mL, 2.2 mmol). The reaction is stirred at rt for 4 h. It is diluted with H₂O (50 mL), extracted with EtOAc (2×50 mL). The combined organic layers are dried with Na₂SO₄, filtered and concentrated. The resulting crude material is purified by chromatography gives the title compound (0.36 g, 0.91 mmol, 45%). ¹H NMR (CDCl₃): δ. 0.89 (t, J=7.5 Hz, 3H), 0.90 (t, J=7.5 Hz, 3H), 1.71 (d, J=3.5 Hz, 1.5H), 1.73 (d, J=3.5 Hz, 1.5H), 1.78-1.92 (m, 4H), 2.45-2.54 (m, 9H), 3.32-3.42 (m, 1H), 5.39-5.48 (m, 1H), 6.68 (s, 1H), 7.18 (d, J=3.9 Hz, 1H), 7.28-7.34 (m, 2H) ppm. ES-MS (m/z): calcd for C₂₄H₂₉N₃O₂ (M+H)⁺: 392.5. found: 392.3.

F. (S)-8-(1-Ethyl-propyl)-3-[7-(1-methoxy-ethyl)-2-methyl-benzofuran-3-yl]-2,6-dimethyl-imidazo[1,2-b]pyridazine A solution of (S)-1-{3-[8-(1-ethyl-propyl)-2,6-dimethyl-imidazo[1,2-b]pyridazin-3-yl]-2-methyl-benzofuran-7-yl}-ethanol (0.19 g, 0.50 mmol) in THF (5 mL) is cooled to 0° C., treated with 60% NaH (23 mg, 0.56 mmol). The mixture is stirred at 0° C. for 30 min. CH₃I (47 uL, 0.76 mmol) is added and the resulting mixture is stirred at 0° C. for 1 h and gradually warmed to rt. and stirred at rt overnight. The excess reagent is removed in vacuo. The residue is taked up with H₂O (20 mL) and EtOAc (50 mL). It is washed with sat. NH₄Cl (2×30 mL). The organic lay is dried with Na₂SO₄, filtered and concentrated. Purification of the crude material by chromatography gives the title compound (0.17 g, 0.41 mmol, 82%). ¹H NMR (CDCl₃): δ. 0.90 (t, J=7.5 Hz, 3H), 0.90 (t, J=7.5 Hz, 3H), 1.63 (d, J=4.0 Hz, 1.5H), 1.64 (d, J=4.0 Hz, 1.5H), 1.78-1.92 (m, 4H), 2.44 (s, 3H), 2.46 (s, 3H), 2.48 (s, 3H), 3.34-3.42 (m, 1H), 4.90-4.98 (m, 1H), 6.68 (s, 1H), 7.17-7.19 (m, 1H), 7.26-7.29 (m, 2H) ppm. ES-MS (m/z): calcd for C₂₅H₃₁N₃O₂ (M+H)⁺: 406.5. found: 406.2.

Example 111

Preparation of (R)-8-(1-Ethyl-propyl)-3-[7-(1-methoxy-ethyl)-2-methyl-benzofuran-3-yl]-2,6-dimethyl-imidazo[1,2-b]pyridazine

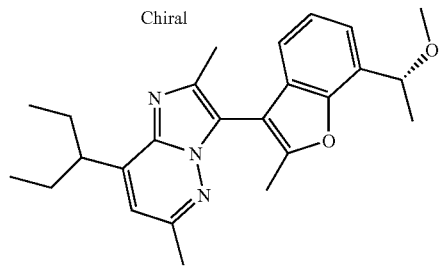

A. (R)-[1-(3-Bromo-2-methyl-benzofuran-7-yl)-ethoxy]-tert-butyl-dimethyl-silane Using a procedure analogous to Example 110 D, from (R)-1-(3-bromo-2-methyl-benzofuran-7-yl)-ethanol, Example 114C, (1.37 g, 5.36 mmol) gives the title compound (1.88 g, 5.09 mmol, 95%). ¹H NMR (CDCl₃): δ. −0.02 (s, 3H), 0.07 (s, 3H), 0.91 (s, 3H), 2.48 (s, 3H), 1.52 (d, J=6.2 Hz, 3H), 5.38 (q, J=6.2 Hz, 1H), 7.25 (t, J=8.0 Hz, 1H), 7.30 (dd, J=8.0, 1.7 Hz, 1H), 7.40 (d, J=8.0 Hz, 1H) ppm.

B. (R)-1-{3-[8-(1-Ethyl-propyl)-2,6-dimethyl-imidazo[1,2-b]pyridazin-3-yl]-2-methyl-benzofuran-7-yl}-ethanol Using a procedure analogous to Example 110 E., from (R)-[1-(3-bromo-2-methyl-benzofuran-7-yl)-ethoxy]-tert-butyl-dimethyl-silane (0.75 g, 2.03 mmol) and 8-(1-ethyl-propyl)-2,6-dimethyl-imidazo[1,2-b]pyridazine (0.44 g, 2.03 mmol) gives the title compound (0.43 g, 1.09 mmol, 54%). ¹H NMR (CDCl₃): δ. 0.89 (t, J=7.5 Hz, 3H), 0.90 (t, J=7.5 Hz, 3H), 1.71 (d, J=3.5 Hz, 1.5H), 1.73 (d, J=3.5 Hz, 1.5H), 1.78-1.92 (m, 4H), 2.45-2.54 (m, 9H), 3.32-3.42 (m, 1H), 5.39-5.48 (m, 1H), 6.68 (s, 1H), 7.18 (d, J=3.9 Hz, 1H), 7.28-7.34 (m, 2H) ppm. ES-MS (m/z): calcd for C₂₄H₂₉N₃O₂ (M+H)⁺: 392.5. found: 392.3.

C. (R)-8-(1-Ethyl-propyl)-3-[7-(1-methoxy-ethyl)-2-methyl-benzofuran-3-yl]-2,6-dimethyl-imidazo[1,2-b]pyridazine Using a procedure analogous to Example 110 F, from (R)-1-{3-[8-(1-Ethyl-propyl)-2,6-dimethyl-imidazo[1,2-b]pyridazin-3-yl]-2-methyl-benzofuran-7-yl}-ethanol (0.24 g, 0.61 mmol) gives the title compound (0.17 g, 0.41 mmol, 68%). ¹H NMR (CDCl₃): δ. 0.90 (t, J=7.5 Hz, 3H), 0.90 (t, J=7.5 Hz, 3H), 1.63 (d, J=4.0 Hz, 1.5H), 1.64 (d, J=4.0 Hz, 1.5H), 1.78-1.92 (m, 4H), 2.44 (s, 3H), 2.46 (s, 3H), 2.48 (s, 3H), 3.34-3.42 (m, 1H), 4.90-4.98 (m, 1H), 6.68 (s, 1H), 7.17-7.19 (m, 1H), 7.26-7.29 (m, 2H) ppm. ES-MS (m/z): calcd for C₂₅H₃₁N₃O₂ (M+H)⁺: 406.5. found: 406.2.

Example 112

Preparation of 8-(1-Ethyl-propyl)-2,6-dimethyl-3-(2-methyl-7-vinyl-benzofuran-3-yl)-imidazo[1,2-b]pyridazine

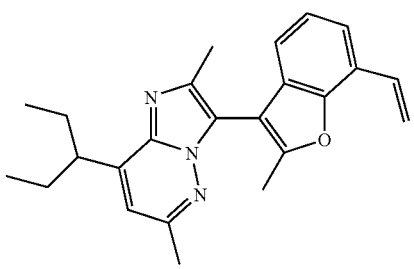

1-{3-[8-(1-Ethyl-propyl)-2,6-dimethyl-imidazo[1,2-b]pyridazin-3-yl]-2-methyl-benzofuran-7-yl}-ethanol (0.64 g, 1.63 mmol) is dissolved in CH₂Cl₂ (20 mL), treated with Et₃N (0.27 mL, 1.95 mmol) and MsCl (0.14 mL, 1.79 mmol). The reaction is stirred at rt overnight. It is diluted with CH₂Cl₂ (40 mL), washed with H₂O (2×40 mL); dried with Na₂SO₄; filtered and concentrated. The resulting crude material is dissolved in acetone (20 mL), refluxed with NaI (0.31 g, 2.04 mmol) overnight. The organic solvent is removed in vacuo, the residue is taken up with H$_2$O (30 mL) and extracted with EtOAc (2×30 mL); the combined organic layers are dried with Na$_2$SO$_4$; filtered and concentrated. Purification of the crude material by chromatography gives the title compound (0.28 g, 0.75 mmol, 46%). $^1$H NMR (CDCl$_3$): δ. 0.90 (t, J=7.0 Hz, 3H), 0.91 (t, J=7.0 Hz, 3H), 1.76-1.95 (m, 4H), 2.45 (s, 3H), 2.46 (s, 3H), 2.47 (s, 3H), 3.32-3.44 (m, 1H), 5.52 (dd, J=11.5, 1.3 Hz, 1H), 6.23 (dd, J=19.0, 1.3 Hz, 1H), 6.68 (s, 1H), 7.04 (dd, J=19.0, 11.5 Hz, 1H), 7.15 (d, J=1.3 Hz, 1H), 7.16 (s, 1H), 7.29 (t, J=4.8 Hz, 1H) ppm. ES-MS (m/z): calcd for C$_{24}$H$_{27}$N$_3$O (M+H)$^+$: 374.5. found: 374.2.

Example 113

(S)-8-(1-Ethyl-propyl)-3-[7-(1-methoxy-ethyl)-2-methyl-benzo[b]thiophen-3-yl]-2,6-dimethyl-imidazo[1,2-b]pyridazine

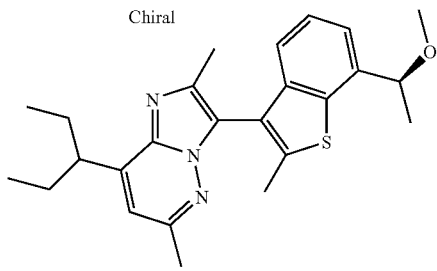

A. 1-(3-Bromo-2-methyl-benzo[b]thiophen-7-yl)-ethanol

Using a procedure analogous to Example 39, from 1-(3-bromo-2-methyl-benzo[b]thiophen-7-yl)-ethanone (0.15 g, 0.54 mmol) gives the title compound (0.13 g, 0.48 mmol, 89%). $^1$H NMR (CDCl$_3$): δ. 1.61 (d, J=6.6 Hz, 3H), 2.56 (s, 3H), 5.18 (q, J=6.6 Hz, 1H), 7.34 (d, J=7.0 Hz, 1H), 7.41 (t, J=7.4 Hz, 1H), 7.64 (dd, J=7.9, 1.3 Hz, 1H) ppm. ES-MS (m/z): calcd for C$_{11}$H$_{11}$BrOS M$^+$: 271.2. found: 271.2.

B. (S) and (R)-1-(3-Bromo-2-methyl-benzo[b]thiophen-7-yl)-ethanol

A racemic mixture of 1-(3-bromo-2-methyl-benzo[b]thiophen-7-yl)-ethanol (1.21 g) is chromatographed (Chiral-Pak OJ-H, 4.6×150 mm; 20% iPrOH/Hept, 0.6 mL/min, UV: 260 nm) gives enantiomer 1 (0.59 g, 49%, rt=7.8 min) and enantiomer 2 (0.59 g, 49%, rt=10.4 min).

(enantiomer 1)

NMR & ES-MS: equivalent to the racemate, Example 113 A.

(enantiomer 2)

NMR & ES-MS: equivalent to the racemate, Example 113 A.

C. (S)-[1-(3-Bromo-2-methyl-benzothiophen-7-yl)-ethoxy]-tert-butyl-dimethyl-silane Using a procedure analogous to Example 112 D, from (S)-1-(3-bromo-2-methyl-benzothiophen-7-yl)-ethanol (0.59 g, 2.17 mmol) gives the title compound (0.80 g, 2.08 mmol, 96%). $^1$H NMR (CDCl$_3$): δ. −0.04 (s, 3H), 0.06 (s, 3H), 0.91 (s, 3H), 1.51 (d, J=6.3 Hz, 3H), 2.56 (s, 3H), 5.11 (q, J=6.3 Hz, 1H), 7.30 (t, J=7.0 Hz, 1H), 7.38 (t, J=7.6 Hz, 1H), 7.60 (d, J=7.9 Hz, 1H) ppm.

D. (S)-1-{3-[8-(1-Ethyl-propyl)-2,6-dimethyl-imidazo[1,2-b]pyridazin-3-yl]-2-methyl-benzothiophen-7-yl}-ethanol Using a procedure analogous to Example 16B, from (S)-[1-(3-bromo-2-methyl-benzothiophene-7-yl)-ethoxy]-tert-butyl-dimethyl-silane (0.80 g, 2.07 mmol) and 8-(1-Ethyl-propyl)-2,6-dimethyl-imidazo[1,2-b]pyridazine (0.45 g, 2.07 mmol) gives the crude coupling product, which is then dissolved in THF (50 mL), reacted with 1.0 M TBAF (2.2.2 mL, 2.2 mmol). The reaction is stirred at rt for 4 h. It is diluted with H$_2$O (50 mL), extracted with EtOAc (2×50 mL). The combined organic layers are dried with Na$_2$SO$_4$, filtered and concentrated. The resulting crude material is purified by chromatography gives the title compound (0.35 g, 0.87 mmol, 42%). $^1$H NMR (CDCl$_3$): δ. 0.90 (t, J=7.5 Hz, 3H), 0.91 (t, J=7.5 Hz, 3H), 1.69 (d, J=6.6 Hz, 3H), 1.75-1.95 (m, 4H), 2.15 (d, J=1.8 Hz, 1H), 2.37 (s, 3H), 2.42 (s, 3H), 2.43 (s, 3H), 3.34-3.44 (m, 1H), 5.27 (dq, J=6.6, 1.8 Hz, 1H), 6.67 (s, 1H), 7.15 (d, J=7.5 Hz, 1H), 7.27 (t, J=7.9 Hz, 1H), 7.34 (d, J=7.1 Hz, 1H) ppm. ES-MS (m/z): calcd for C$_{24}$H$_{29}$N$_3$OS (M+H)$^+$: 408.6. found: 408.3.

E. (S)-8-(1-Ethyl-propyl)-3-[7-(1-methoxy-ethyl)-2-methyl-benzothiophen-3-yl]-2,6-dimethyl-imidazo[1,2-b]pyridazine Using a procedure analogous to Example 110 F, from (S)-1-{3-[8-(1-ethyl-propyl)-2,6-dimethyl-imidazo[1,2-b]pyridazin-3-yl]-2-methyl-benzothiophen-7-yl}-ethanol (0.21 g, 0.51 mmol) gives the title compound (0.17 g, 0.50 mmol, 98%). $^1$H NMR (CDCl$_3$): δ. 0.91 (t, J=7.2 Hz, 6H), 1.61 (d, J=6.6 Hz, 3H), 1.75-1.95 (m, 4H), 2.38 (s, 3H), 2.42 (s, 3H), 2.44 (s, 3H), 3.35 (d, J=4.5 Hz, 3H), 3.36-3.45 (m, 1H), 4.66 (q, J=6.6 Hz, 1H), 6.67 (s, 1H), 7.15 (dt, J=7.4, 1.8 Hz, 1H), 7.20-7.28 (m, 2H) ppm. ES-MS (m/z): calcd for C$_{25}$H$_{31}$N$_3$OS (M+H)$^+$: 422.6. found: 422.2.

Example 114

Preparation of (R)-8-(1-Ethyl-propyl)-3-[7-(1-methoxy-ethyl)-2-methyl-benzo[b]thiophen-3-yl]-2,6-dimethyl-imidazo[1,2-b]pyridazine

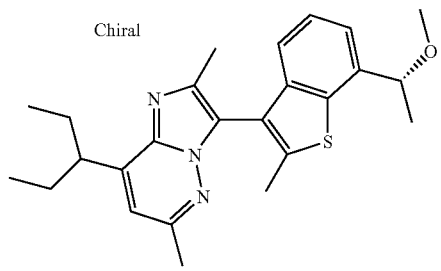

A. (R)-[1-(3-Bromo-2-methyl-benzothiophen-7-yl)-ethoxy]-tert-butyl-dimethyl-silane Using a procedure analogous to Example 110 D, from (R)-1-(3-bromo-2-methyl-benzothiophen-7-yl)-ethanol (0.59 g, 2.17 mmol) gives the title compound (0.73 g, 1.91 mmol, 88%). $^1$H NMR (CDCl$_3$): δ. −0.04 (s, 3H), 0.06 (s, 3H), 0.91 (s, 3H), 1.51 (d, J=6.3 Hz, 3H), 2.56 (s, 3H), 5.11 (q, J=6.3 Hz, 1H), 7.30 (t, J=7.0 Hz, 1H), 7.38 (t, J=7.6 Hz, 1H), 7.60 (d, J=7.9 Hz, 1H) ppm.

B. (R)-1-{3-[8-(1-Ethyl-propyl)-2,6-dimethyl-imidazo[1,2-b]pyridazin-3-yl]-2-methyl-benzothiophen-7-yl}-ethanol Using a procedure analogous to Example 16B, from (R)-[1-(3-bromo-2-methyl-benzothiophene-7-yl)-ethoxy]-tert-butyl-dimethyl-silane (0.73 g, 1.91 mmol) and 8-(1-Ethyl-propyl)-2,6-dimethyl-imidazo[1,2-b]pyridazine (0.41 g, 1.91 mmol) gives the crude coupling product, which is then dissolved in THF (50 mL), reacted with 1.0 M TBAF (2.2 mL, 2.2 mmol). The reaction is stirred at rt for 4 h. It is diluted with H$_2$O (50 mL), extracted with EtOAc (2×50 mL). The combined organic layers are dried with Na$_2$SO$_4$, filtered and concentrated. The resulting crude material is purified by chromatography gives the title compound (0.43 g, 1.05 mmol, 55%). $^1$H NMR (CDCl$_3$): δ. 0.90 (t, J=7.5 Hz, 3H), 0.91 (t, J=7.5 Hz, 3H), 1.69 (d, J=6.6 Hz, 3H), 1.75-1.95 (m, 4H), 2.15 (d, J=1.8 Hz, 1H), 2.37 (s, 3H), 2.42 (s, 3H), 2.43 (s, 3H), 3.34-3.44 (m, 1H), 5.27 (dq, J=6.6, 1.8 Hz, 1H), 6.67 (s, 1H), 7.15 (d, J=7.5 Hz, 1H), 7.27 (t, J=7.9 Hz, 1H), 7.34 (d, J=7.1 Hz, 1H) ppm. ES-MS (m/z): calcd for C$_{24}$H$_{29}$N$_3$OS (M+H)$^+$: 408.6. found: 408.3.

C. (R)-8-(1-Ethyl-propyl)-3-[7-(1-methoxy-ethyl)-2-methyl-benzothiophen-3-yl]-2,6-dimethyl-imidazo[1,2-b]pyridazine Using a procedure analogous to Example 110 F, from (R)-1-{3-[8-(1-ethyl-propyl)-2,6-dimethyl-imidazo[1,2-b]pyridazin-3-yl]-2-methyl-benzothiophen-7-yl}-ethanol (0.32 g, 0.79 mmol) gives the title compound (0.26 g, 0.62 mmol, 78%). $^1$H NMR (CDCl$_3$): δ. 0.91 (t, J=7.2 Hz, 6H), 1.61 (d, J=6.6 Hz, 3H), 1.75-1.95 (m, 4H), 2.38 (s, 3H), 2.42 (s, 3H), 2.44 (s, 3H), 3.35 (d, J=4.5 Hz, 3H), 3.36-3.45 (m, 1H), 4.66 (q, J=6.6 Hz, 1H), 6.67 (s, 1H), 7.15 (dt, J=7.4, 1.8 Hz, 1H), 7.20-7.28 (m, 2H) ppm. ES-MS (m/z): calcd for C$_{25}$H$_{31}$N$_3$OS (M+H)$^+$: 422.6. found: 422.2.

Example 115

Preparation of 3-Benzo[b]thiophen-3-yl-8-(1-ethyl-propyl)-2,6-dimethyl-imidazo[1,2-b]pyridazine

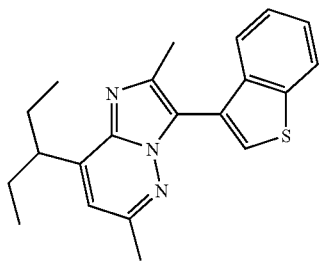

Using a procedure analoguous to Example 1H, from 0.100 g (0.291 mmol) of 8-(1-ethyl-propyl)-3-iodo-2,6-dimethyl-imidazo[1,2-b]pyridazine, 0.130 g (0.728 mmol) of thianaphthene-3-boronic acid, 0.202 g (0.175 mmol) to obtain the title compound 0.080 g, 78% yield. MS, ES+=350.2 (M+1); $^1$H NMR (DMSO d6)=8.082-8.062 (d, 1H); 7.979 (s, 1H); 7.428-7.388 (m, 1H); 7.350-7.337 (m, 2H); 6.941 (s, 1H); 3.129-3.093 (m, 1H); 2.343 (s, 3H); 2.320 (s, 3H); 1.888-1.754 (m, 4H); 0.802-0.766 (m, 6H) ppm.

Example 116

Preparation of 3-Benzofuran-2-yl-2,6-dimethyl-8-(1-propyl-butyl)-imidazo[1,2-b]pyridazine

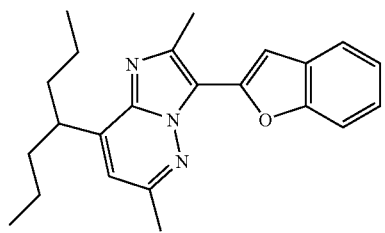

A. 2,2 Dimethyl-N-[6-methyl-4-(1-propyl-butyl)-pyridazin-3-yl]-propionamide

Using a procedure analoguous to Example 1C, from 0.630 g (25.9 mmol) of activated Magnesium, 4.64 g (25.9 mmol) of 4-bromoheptane, 0.500 g (2.59 mmol) of 2,2-dimethyl-N-(6-methyl-pyridazin-3yl)-propionamide to obtain the title compound 0.215 g (29%). MS, ES+=292.3 (M+1); $^1$H NMR (DMSO-d6)=9.78 (s, 1H); 7.466 (s, 1H); 3.40-3.33 (m, 1H); 2.57 (s, 3H); 1.48-1.46 (m, 4H); 1.23 (s, 9H); 1.19-1.02 (m, 4H); 0.80-0.77 (m, 6H) ppm.

B. 6-Methyl-4-(1-propyl-butyl)-pyridazin-3-ylamine

Using a procedure analoguous to Example 1D, from 0.200 g (0.686 mmol) of 2,2 Dimethyl-N-[6-methyl-4-(1-propyl-butyl)-pyridazin-3-yl]-propionamide to obtain 0.142 g of the title compound, quantitative yield. MS, ES+=208.3 (M+1); $^1$H NMR (DMSO-d6)=7.495 (s, 1H); 7.347 (s, 2H); 2.920-2.825 (m, 1H); 2.397 (s, 3H); 1.595-1.440 (m, 4H); 1.242-1.040 (m, 4H); 0.822-0.785 (m, 6H) ppm.

C. 2,6-Dimethyl-8-(1-propyl-butyl)-imidazo[1,2-b]pyridazine

Using a procedure analoguous to Example 1F, from 0.142 g (0.685 mmol) of 6-Methyl-4-(1-propyl-butyl)-pyridazin-3-ylamine, 0.054 mL (0.685 mmol) of chloroacetone to obtain 0.088 g of the title compound, 52% yield. MS, ES+=246.8 (M+1); $^1$H NMR (DMSO-d6)=7.84 (s, 1H); 6.86 (s, 1H); 3.23-3.15 (m, 1H); 2.430 (s, 3H); 2.32 (s, 3H); 1.82-1.72 (m, 2H); 1.69-1.60 (m, 2H); 1.20-1.01 (m, 4H); 0.81-0.78 (m, 6H) ppm.

D. 3-Iodo-2,6-dimethyl-8-(1-propyl-butyl)-imidazo[1,2-b]pyridazine

In an oven dried nitrogen purged 25 mL round bottom flask, 0.088 g (0.359 mmol) of 2,6-Dimethyl-8-(1-propyl-butyl)-imidazo[1,2-b]pyridazine, in 5 mL of dry acetonitrile is cooled to 0 C. 0.0.81 g (0.359 mmol) of NIS is added and the bath is allowed to expire. TLC in 1:1 Hexanes:Ethyl Acetate indicates SM is gone. Remove solvents to obtain 0.133 g of the title compound, quantitative yield. MS; $^1$H NMR (DMSO-d6)=6.985 (s, 1H); 3.262-3.190 (m, 1H);

2.502 (s, 3H); 2.480 (s, 3H); 1.823-1.600 (m, 4H); 1.182-0.985 (m, 4H); 0.804-0.768 (m, 6H) ppm.

E. 3-Benzofuran-2-yl-2,6-dimethyl-8-(1-propyl-butyl)-imidazo[1,2-b]pyridazine

Using a procedure analoguous to Example 11H, from 0.050 g (0.135 mmol) of 3-iodo-2,6-dimethyl-8-(1-propyl-butyl)-imidazo[1,2-b]pyridazine, 0.029 g (0.162 mmol) of benzofuran-2-boronic acid, 0.008 g (0.00675 mmol) to obtain 0.030 g of the title compound in 61% yield. MS, ES+=362.2 (M+1); $^1$H NMR (DMSO-d6)=7.738-7.719 (m, 2H); 7.655-7.657 (m, 2H); 7.317-7.274 (m, 2H); 7.122 (s, 1H); 2.773 (s, 3H); 2.618 (s, 3H); 1.831-1.685 (m, 4H); 1.205-1.077 (m, 4H); 0.831-0.795 (m, 6H) ppm.

Example 117

Preparation of 8-(1-Ethyl-propyl)-3-(6-methoxy-3-methyl-benzo[b]thiophen-2-yl)-2,6-dimethyl-imidazo[1,2-b]pyridazine

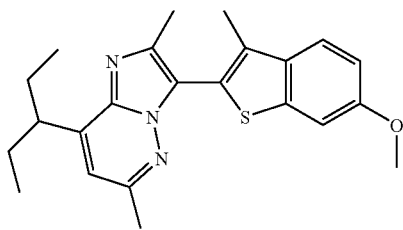

Using a procedure analoguous to Example 1H, from 0.100 g (0.383 mmol) of boronic acid, 8-(1-ethyl-propyl)-2,6-dimethyl-imidazo[1,2-b]pyridazine-3-yl, 0.040 g (0.153 mmol) of 2-bromo-6-methoxy-3-methyl-benzo[b]thiophene, (Campaigne, E.; Dinner, A.; Neiss, E. S. J. Heterocycl. Chem. 1970, 7, 695), to obtain the title compound 0.030 g, 50% yield. MS, ES+=394.2 (M+1); $^1$H NMR (DMSO-d6)=7.744-7.722 (d, 1H); 7.572 (s, 1H); 7.079-7.058 (d, 1H); 6.985 (s, 1H0; 3.835 (s, 3H); 3.099 (m, 1H); 2.430 (s, 3H); 2.345 (s, 3H); 2.169 (s, 3H); 1.838-1.782 (m, 4H); 0.799-0.764 (m, 6H) ppm.

Example 118

Preparation of 2-[8-(1-Ethyl-propyl)-2,6-dimethyl-imidazo[1,2-b]pyridazin-3-yl]-3-methyl-benzo[b]thiophen-5-ol

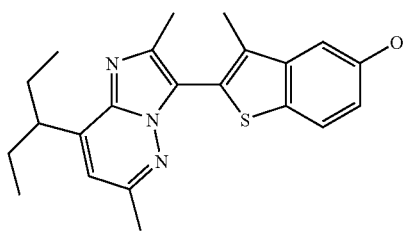

In an oven dried, nitrogen purged pressure tube, 0.040 g (0.105 mmol) of 8-(1-ethyl-propyl)-3-(5-fluoro-3-methyl-benzo[b]thiophen-2-yl)-2,6-dimethyl-imidazo[1,2-b]pyridazine, 0.012 g (0.21 mmol) of KOH, and 0.019 g (0.210 mmol) of N,N-dimethylethanolamine are combined in 1 mL of dry DMSO and heated at 90° C. After approximately 24 hours, the reaction mixture is diluted with 20 mL of ethyl acetate and 20 mL of water. The layers are separated and the aqueous is extracted 3×50 mL of ethyl acetate, dried (MgSO$_4$), and concentrated under vacuum. The crude mixture is purified by chromatography using Hexane/Ethyl Acetate. The product containing fractions are combined to obtain 0.010 g of the title compound, 25% yield. MS, ES+=380.1 (M+1); $^1$H NMR (DMSO-d6)=9.518 (s, 1H); 7.760-7.730 (s, 1H); 7.129 (s, 1H); 6.980 (s, 1H); 3.150-3.050 (m, 1H); 2.421 (s, 3H); 2.336 (s, 3H); 2.103 (s, 3H); 1.850-1.760 (m, 4H); 0.789-0.753 (m, 6H) ppm.

Example 119

Preparation of 3-(1,5-dimethyl-1H-indol-3-yl)-8-(1-ethyl-propyl)-2,6-dimethyl-imidazo[1,2-b]pyridazine

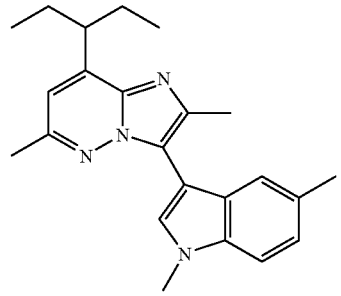

Using a procedure similar to Examples 30 and 31, 1,5-dimethyl-1H-indole gives the title compound 9%. MS/ES+= 361 (100%, M+1). $^1$H-NMR (CDCl$_3$): 7.24 (s, 1H); 7.21 (m, 2H); 7.01 (m, 1H); 6.53 (s, 1H); 3.79 (s, 3H); 3.29 (m, 1H); 2.44 (s, 3H); 2.40 (s, 3H); 1.74 (m, 4H); 0.81 (m, 6H) ppm.

Example 120

Preparation of 4-[3-(5-fluoro-3-methyl-benzo[b]thiophen-2-yl)-2,6-dimethyl-imidazo[1,2-b]pyridazin-8-yl]-heptan-4-ol

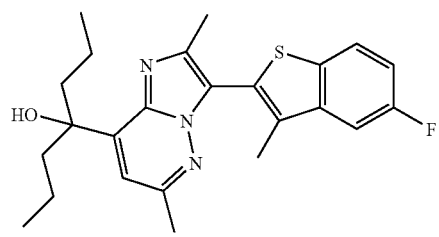

A. 3-(5-Fluoro-3-methyl-benzo[b]thiophen-2-yl)-2,6-dimethyl-imidazo[1,2-b]pyridazine-8-carboxylic Acid methoxy-methyl-amide The solution of 3-(5-fluoro-3-methyl-benzo[b]thiophen-2-yl)-2,6-dimethyl-imidazo[1,2-b]pyridazine (2.09 g, 6.73 mmol) in THF (56 mL) is stirred at −78° C. Ethyl N-methoxy-N-methylcarbamate (4.48 g, 33.7 mmol) is added. LDA (10 mL, 20.1 mmol) is added dropwise to maintain reaction temperature at −75° C. The reaction is stirred at −78° C. for 1 hour. The reaction is quenched with H₂O, filtered through celite with CH₂Cl₂. The collect solution is washed with H₂O, dried over Na₂SO₄, filtered and concentrated. The crude is purified by ISCO (50-100% EtOAc/Hexane) to give the title compound (0.85 g, 31%). ¹H NMR (CDCl₃): δ 7.8 (dd, J=4.8, 8.5 Hz, 1H), 7.5 (dd, J=2.5, 9.7 Hz, 1H), 7.2 (m, 1H), 7.0 (s, 1H), 3.7 (s, 3H), 3.5 (s, 3H), 2.6 (s, 3H), 2.55 (s, 3H), 2.3 (s, 3H) ppm. MS (m/e): 399 (100%, M+1).

B. 1-[3-(5-Fluoro-3-methyl-benzo[b]thiophen-2-yl)-2,6-dimethyl-imidazo[1,2-b]pyridazin-8-yl]-butan-1-one N-Propylmagnesium bromide (0.303 g, 2.06 mmol) is added dropwise to a solution of 3-(5-fluoro-3-methyl-benzo[b]thiophen-2-yl)-2,6-dimethyl-imidazo[1,2-b]pyridazine-8-carboxylic acid methoxy-methyl-amide (0.21 g, 0.52 mmol) in THF (5 mL) at 0° C. The reaction is stirred at room temperature overnight. The mixture is quenched with H₂O, extracted with CH₂Cl₂, dried over sodium sulfate, filtered, and concentrated to dryness. The crude is purified through an ISCO column (5-10% EtOAc/Hexane) to give the title compound (0.92 g, 42%). ¹H NMR (CDCl₃): δ 7.8 (dd, J=4.8, 8.5 Hz, 1H), 7.5 (dd, J=2.5, 9.7 Hz, 1H), 7.4 (s, 1H), 7.2 (m, 1H), 3.6 (t, J=5.7, 2H), 2.6 (s, 3H), 2.55 (s, 3H), 2.3 (s, 3H), 1.9 (m, 2H), 1.1 (t, J=7.5, 3H) ppm. MS (m/e): 382 (M+1).

C. 4-[3-(5-Fluoro-3-methyl-benzo[b]thiophen-2-yl)-2,6-dimethyl-imidazo[1,2-b]pyridazin-8-yl]-heptan-4-ol N-Propylmagnesium bromide (0.601 g, 4.09 mmol) is added dropwise to a solution of 1-[3-(5-fluoro-3-methyl-benzo[b]thiophen-2-yl)-2,6-dimethyl-imidazo[1,2-b]pyridazin-8-yl]-butan-1-one (1.08 g, 2.72 mmol) in THF (27 mL) at 0° C. The reaction is stirred at room temperature overnight. The mixture is quenched with ammonium chloride, extracted with ethylacetate, dried over sodium sulfate, filtered, and concentrated to dryness. The crude is purified by ISCO (5% EtOAc/Hexane) to give the title compound (280 mg, 24%). ¹H NMR (CDCl₃): δ 7.8 (dd, J=4.8, 8.5 Hz, 1H), 7.5 (dd, J=2.5, 9.7 Hz, 1H), 7.2 (m, 1H), 6.7 (s, 1H), 6.4 (s, 1H), 2.6 (s, 3H), 2.5 (s, 3H), 2.3 (s, 3H), 2.0 (m, 3H), 1.5 (m, 1H), 1.3 (m, 4H), 0.9 (t, J=7.3, 6H) ppm. Mass spectrum (m/e): 426 (M+1).

Example 121

Preparation of 8-(1-Ethyl-propyl)-3-(5-fluoro-3-methyl-benzo[b]thiophen-2-yl)-2-methyl-6-trifluoromethyl-imidazo[1,2-b]pyridazine

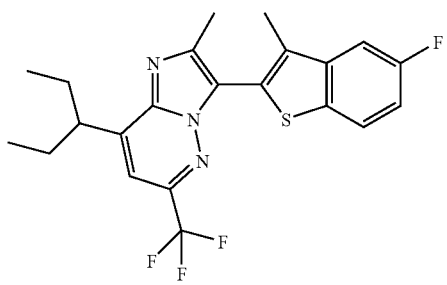

Using a procedure analogous to Example 1H, from 8-(1-ethyl-propyl)-3-iodo-2-methyl-6-trifluoromethyl-imidazo[1,2-b]pyridazine (0.13 g, 0.33 mmol) and boronic acid, 5-fluoro-3-methyl-benzo[b]thiophene-2-yl (69 mg, 0.33 mmol) to give the title compound (47.5 mg, 0.11 mmol, 33%). ¹H NMR (CDCl₃): δ. 0.92 (t, J=7.3 Hz, 6H), 1.82-2.00 (m, 4H), 2.28 (s, 3H), 2.59 (s, 3H), 3.42-3.51 (m, 1H), 7.12 (s, 1H), 7.18 (dt, J=8.8, 2.2 Hz, 1H), 7.47 (dd, J=9.2, 2.2 Hz, 1H), 7.87 (dd, J=8.8, 4.8 Hz, 1H). ES-MS (m/z): calcd for C₂₂H₂₁F₄N₃S (M+H)⁺: 436.5. found: 436.2.

General Procedure for the Preparation of 8-(1-Ethyl-propyl)-2,6-dimethyl-3-(1-alkyl-1H-benzoimidazol-2-yl)-imidazo[1,2-b]pyridazine A mixture of 8-(1-ethyl-propyl)-2,6-dimethyl-imidazo[1,2-b]pyridazine-3-boronic acid (1 mmol), barium hydroxide (0.3 mmol), Pd2dba3 (0.05 mmol), PPh3 (0.2 mmol) and the corresponding 2-iodo-1-alkyl-1H-benzoimidazole (0.9 mmol) in 2 ml of a mixture of dimethoxyethane/water (2/1) are added to a pressure tube with a stirring bar. The mixture is degassed for 30 min. After heating for 16 h at 90° C., the mixture is cooled, diluted with diethylether and washed with saturated aqueous ammonium chloride solution. The organic layer is dried over anhydrous magnesium sulfate, filtered, and solvent removed in vacuo. The residue is purified by silica gel column chromatography using mixtures of hexane-ethyl acetate as eluent.

Example 122

Preparation of 8-(1-ethyl-propyl)-3-(5-fluoro-1-isopropyl-1H-benzoimidazol-2-yl)-2,6-dimethyl-imidazo[1,2-b]pyridazine

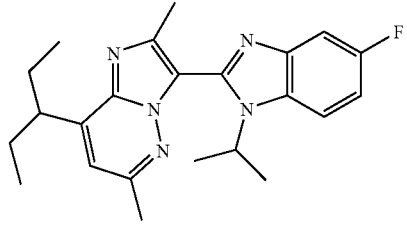

Using the general procedure for benzimidazoles above, 5-fluoro-2-iodo-1-isopropyl-1H-benzimidazole gives the title compound Yield 23%. MS/ES+=394 (100%, M+1). ¹H-NMR (CDCl₃): 7.37 (m, 2H); 6.96 (m, 1H); 6.68 (s, 1H); 4.24 (s, 1H); 3.22 (m, 1H); 2.45 (s, 3H); 2.37 (s, 3H); 1.74 (m, 4H); 1.54 (m, 6H); 0.76 (m, 6H) ppm.

Example 123

Preparation of 8-(1-ethyl-propyl)-3-(6-fluoro-1-isopropyl-1H-benzoimidazol-2-yl)-2,6-dimethyl-imidazo[1,2-b]pyridazine

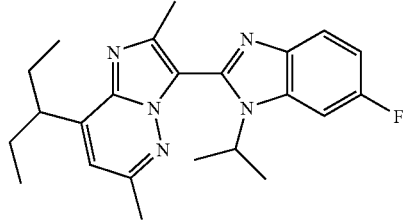

Using the general procedure for benzimidazoles above, 6-fluoro-2-iodo-1-isopropyl-1H-benzimidazole gives the title compound Yield 20%. MS/ES+=394 (100%, M+1). ¹H-NMR (CDCl₃): 7.70 (m, 1H); 7.28 (m, 1H); 6.95 (m, 1H);

6.64 (s, 1H); 4.24 (s, 1H); 3.25 (m, 1H); 2.45 (s, 3H); 2.37 (s, 3H); 1.77 (m, 4H); 1.55 (m, 6H); 0.76 (m, 6H) ppm.

Example 124

Preparation of 8-(1-ethyl-propyl)-3-(5-fluoro-1-methyl-1H-benzoimidazol-2-yl)-2,6-dimethyl-imidazo[1,2-b]pyridazine

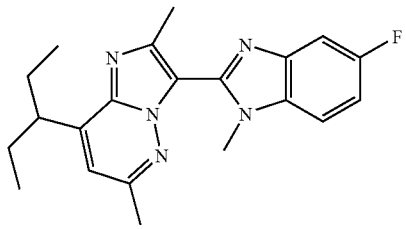

Using the general procedure for benzimidazoles above, 5-fluoro-2-iodo-1-methyl-1H-benzimidazole gives the title compound Yield 11%. MS/ES+=366 (100%, M+1). $^1$H-NMR (CDCl$_3$): 7.78 (m, 1H); 7.1 (m, 2H); 6.74 (s, 1H); 3.68 (s, 3H); 3.35 (m, 1H); 2.59 (s, 3H); 2.50 (s, 3H); 1.83 (m, 4H); 0.84 (m, 6H) ppm.

Example 125

Preparation of 8-(1-ethyl-propyl)-3-(6-fluoro-1-methyl-1H-benzoimidazol-2-yl)-2,6-dimethyl-imidazo[1,2-b]pyridazine

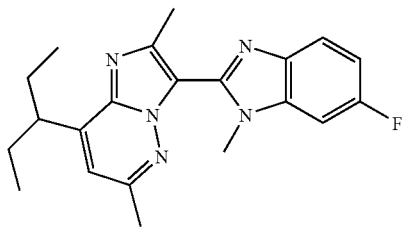

Using the general procedure for benzimidazoles above, 6-fluoro-2-iodo-1-methyl-1H-benzimidazole gives the title compound Yield 12%. MS/ES+=366 (100%, M+1). $^1$H-NMR (CDCl$_3$): 7.55 (m, 1H); 7.38 (m, 1H); 7.15 (m, 1H); 6.74 (s, 1H); 3.72 (s, 3H); 3.35 (m, 1H); 2.59 (s, 3H); 2.50 (s, 3H); 1.83 (m, 4H); 0.85 (m, 6H) ppm.

Example 126

Preparation of 8-(1-ethyl-propyl)-3-(5-chloro-1-methyl-1H-benzoimidazol-2-yl)-2,6-dimethyl-imidazo[1,2-b]pyridazine

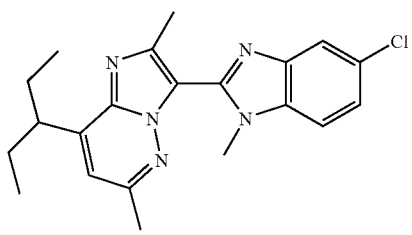

Using the general procedure for benzimidazoles above, 5-chloro-2-iodo-1-methyl-1H-benzimidazole gives the title compound Yield 14%. MS/ES+=382 (100%, M+1). $^1$H-NMR (CDCl$_3$): 7.76 (m, 1H); 7.28 (m, 2H); 6.68 (s, 1H); 3.65 (s, 3H); 3.25 (m, 1H); 2.51 (s, 3H); 2.42 (s, 3H); 1.77 (m, 4H); 0.78 (m, 6H) ppm.

Example 127

Preparation of 8-(1-ethyl-propyl)-3-(6-chloro-1-methyl-1H-benzoimidazol-2-yl)-2,6-dimethyl-imidazo[1,2-b]pyridazine

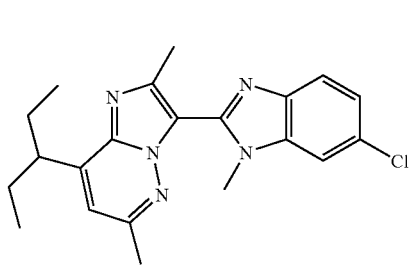

Using the general procedure for benzimidazoles above, 6-chloro-2-iodo-1-methyl-1H-benzimidazole gives the title compound Yield 11%. MS/ES+=382 (100%, M+1). $^1$H-NMR (CDCl$_3$): 7.90 (m, 1H); 7.50 (m, 2H); 6.68 (s, 1H); 3.71 (s, 3H); 3.25 (m, 1H); 2.51 (s, 3H); 2.42 (s, 3H); 1.77 (m, 4H); 0.78 (m, 6H) ppm.

Example 128

Preparation of Z/E-'3-(5-Fluoro-3-methyl-benzo[b]thiophen-2-yl)-2,6-dimethyl-8-(1-propyl-but-1-enyl)-imidazo[1,2-b]pyridazine

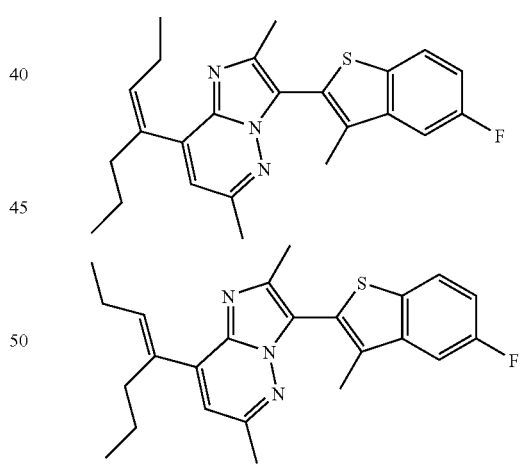

A solution of 4-[3-(5-fluoro-3-methyl-benzo[b]thiophen-2-yl)-2,6-dimethyl-imidazo[1,2-b]pyridazin-8-yl]-heptan-4-ol (380 mg, 0.89 mmol) in CH$_2$Cl$_2$ (9 mL) and Et$_3$N (9 mL) is stirred at 0° C. Methanesulfonyl chloride (614 mg, 5.36 mmol) is added. After 10 minutes, the ice bath is removed and the reaction is stirred at room temperature overnight. The mixture is quenched with 0.1 N HCl, extracted with CH$_2$Cl$_2$, dried over Na$_2$SO$_4$, filtered, and concentrated to dryness. The crude is purified through an ISCO column (5% EtOAc/Hexane) to give the title compound (128 mg, 35%). $^1$H NMR (CDCl$_3$): δ 7.8 (dd, J=4.8, 8.5 Hz, 1H), 7.5 (dd, J=2.5, 9.7 Hz, 1H), 7.2 (m, 1H), 6.8 (s, 1H), 6.48 (t, J=5.8, 1H), 2.8 (t, J=8.5, 2H), 2.6 (t, J=7.7, 2H), 2.54 (s, 3H), 2.53 (s, 3H), 2.4 (m, 2H), 2.3 (s, 3H), 1.4 (m, 2H), 1.15 (t, J=7.1, 3H), 0.93 (t, J=8.1, 3H) ppm. Mass spectrum (m/e): 408 (M+1).

Example 129

Preparation of 3-(5-fluoro-3-methyl-benzo[b]thiophen-2-yl)-2,6-dimethyl-8-(1-propyl-butyl)-imidazo[1,2-b]pyridazine

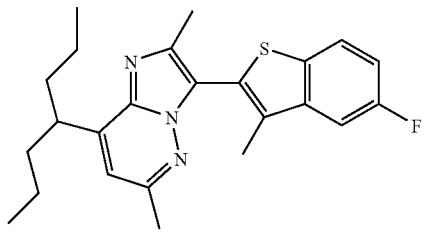

A solution of 3-(5-fluoro-3-methyl-benzo[b]thiophen-2-yl)-2,6-dimethyl-8-(1-propyl-but-1-enyl)-imidazo[1,2-b]pyridazine (23 mg, 0.06 mmol), MeOH (19 mL), and 10% Pd—C (69 mg) is hydrogenated at 30 psi at room temperature for 2 hours. The mixture is filtered through celite, washed with EtOAC and concentrated to dryness to give the title compound (20.5 mg, 89%) %). $^1$H NMR (CDCl$_3$): δ 7.8 (dd, J=4.8, 8.5 Hz, 1H), 7.5 (dd, J=2.5, 9.7 Hz, 1H), 7.2 (m, 1H), 6.9 (s, 1H), 3.69 (s, 1H), 2.62 (s, 3H), 2.58 (s, 3H), 2.4 (m, 2H), 2.3 (s, 3H), 1.8 (m, 4H), 1.29 (m, 4H), 0.93 (t, J=7.1, 6H) ppm. Mass spectrum (m/e): 410 (M+1).

Example 130

Preparation of 5-[3-(5-fluoro-3-methyl-benzo[b]thiophen-2-yl)-2,6-dimethyl-imidazo[1,2-b]pyridazin-8-yl]-nona-1,8-dien-5-ol

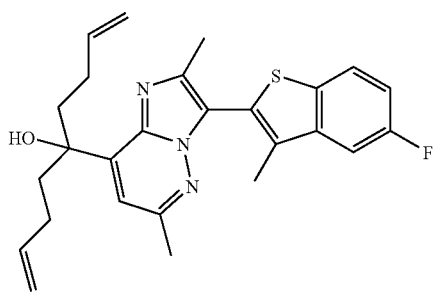

A. 1-[3-(5-Fluoro-3-methyl-benzo[b]thiophen-2-yl)-2,6-dimethyl-imidazo[1,2-b]pyridazin-8-yl]-pent-4-en-1-one Using a procedure similar to example 120 B, from 3-(5-fluoro-3-methyl-benzo[b]thiophen-2-yl)-2,6-dimethyl-imidazo[1,2-b]pyridazine-8-carboxylic acid methoxy-methyl-amide (0.370 g, 0.93 mmol) and 3-butenylmagnesium bromide (0.29 g, 1.86 mmol) to give the title compound (0.16 g, 45%). $^1$H NMR (CDCl$_3$): δ 7.8 (dd, J=4.8, 8.5 Hz, 1H), 7.5 (dd, J=2.5, 9.7 Hz, 1H), 7.2 (m, 1H), 6.0 (m, 1H), 5.3 (s, 1H), 5.18 (dd, J=16, 2H), 3.73 (t, J=7.1, 2H), 2.62 (s, 3H), 2.57 (s, 3H), 2.29 (s, 3H), 1.8-1.5 (m, 2H) ppm. Mass spectrum (m/e): 394 (M+1).

B. 5-[3-(5-Fluoro-3-methyl-benzo[b]thiophen-2-yl)-2,6-dimethyl-imidazo[1,2-b]pyridazin-8-yl]-nona-1,8-dien-5-ol Using a procedure similar to example 120 C, from 1-[3-(5-fluoro-3-methyl-benzo[b]thiophen-2-yl)-2,6-dimethyl-imidazo[1,2-b]pyridazin-8-yl]-pent-4-en-1-one (2.50 g, 6.35 mmol) and 3-butenylmagnesium bromide (3.03 g, 19.1 mmol) to give the title compound (0.54 g, 23%). $^1$H NMR (CDCl$_3$): δ 7.8 (dd, J=4.8, 8.5 Hz, 1H), 7.5 (dd, J=2.5, 9.7 Hz, 1H), 7.2 (m, 1H), 6.72 (s, 1H), 5.5 9s, 1H), 5.8 (m, 2H), 4.97 (dd, J=16, 4H), 2.53 (s, 3H), 2.46 (s, 3H), 2.26 (s, 3H), 2.2-1.9 (m, 8H) ppm. Mass spectrum (m/e): 450 (M+1).

Example 131

Preparation of Z/E-8-(1-But-3-enyl-penta-1,4-dienyl)-3-(5-fluoro-3-methyl-benzo[b]thiophen-2-yl)-2,6-dimethyl-imidazo[1,2-b]pyridazine

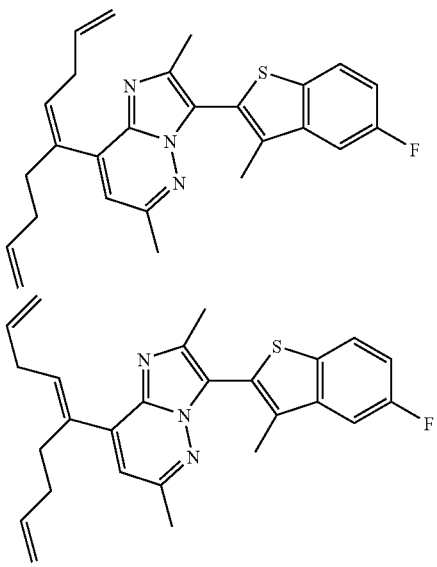

Using a procedure similar to example 130, from 5-[3-(5-fluoro-3-methyl-benzo[b]thiophen-2-yl)-2,6-dimethyl-imidazo[1,2-b]pyridazin-8-yl]-nona-1,8-dien-5-ol (0.40 g, 0.89 mmol) gives the title compound (0.90 g, 23%). Mass spectrum (m/e): 432 (M+1).

Example 132

Preparation of '8-(1-But-3-enyl-1-chloro-pent-4-enyl)-3-(5-fluoro-3-methyl-benzo[b]thiophen-2-yl)-2,6-dimethyl-imidazo[1,2-b]pyridazine

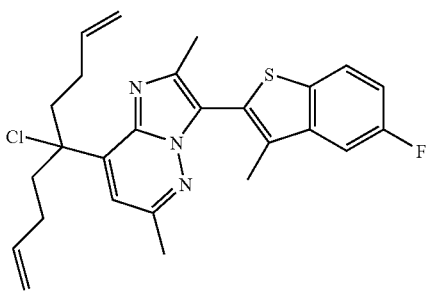

Using a procedure similar to example 128, from 5-[3-(5-fluoro-3-methyl-benzo[b]thiophen-2-yl)-2,6-dimethyl-imidazo[1,2-b]pyridazin-8-yl]-nona-1,8-dien-5-ol (0.40 g, 0.89 mmol) gives the title compound as a minor side product (0.10 g, 2.6%). $^1$H NMR (CDCl$_3$): δ 7.8 (dd, J=4.8, 8.5 Hz, 1H), 7.5 (dd, J=2.5, 9.7 Hz, 1H), 7.2 (m, 1H), 7.28 (s, 1H), 5.73 (m, 2H), 4.92 (dd, J=16, 4H), 3.2 (m, 2H), 2.53 (s, 3H), 2.46 (s, 3H), 2.26 (s, 3H), 2.2-1.9 (m, 4H); 1.8 (m, 4H) ppm. Mass spectrum (m/e): 469 (M+1).

Example A

In Vivo Potency Assessment Using Ex Vivo Binding

To assess in vivo potency, a compound of the present invention is evaluated using ex vivo binding. Using the procedures as provided in D. R. Gehlert et al., *EJP* 509: 145-153 (2005), a compound is administered to a rat via the oral route. The binding of $^{125}$I-sauvagine to the cerebellum is then assessed ex vivo as described in Gehlert et al. For example, Example 34 provides an ED$_{50}$ result of 5.5 mg/kg.

Example B

CRF1 Filter Binding Assay

The limitations of plasmid-based human CRF1 expression, in terms of generating a recombinant cell line with sufficient receptor density to develop a binding assay, are overcome by using a Phoenix retroviral expression system licensed from Stanford. The stable HEK-hCRF1 cell line is used to prepare membranes and binding reactions (200 μl) are set up as follows: 50 μl of $^{125}$I-sauvagine (0.2 nM final), 50 μl compound and 100 μL CRF1 membrane (25 μg/reaction). The reactions are incubated at room temperature for 2 hours and then terminated by filtration through pre-treated FB Millipore glass fiber filter plates (96 well). The plates are wash twice with ice-cold assay buffer (50 mM tris, 12.5 mM NaCl, 1 mM EDTA, 10 mM MgCl$_2$, 0.05% BSA, pH 7.2), air dried over night and counted with 100 μl Microscint 40 in a MicroBeta counter. Non-specific binding (NSB) is determined in the presence of 0.5 μM non-labeled sauvagine. Triplicate determinations are typically run and the median data points plotted by Graph Pad Prism.

Using this assay, the claimed exemplified compounds of the present invention inhibit the binding of $^{125}$I-Sauvagine (4 nM) in roller/adherent cells with a Ki (inhibition constant) below 10 μM. For example, Example 88 exhibits a Ki of 19.2±4.8 nM.

In addition, it has been discovered that the 5,6-bicycloaromatic imidazo[1,2-b]pyridazines exhibit surprisingly different inhibition constants in the CRF1 filter binding assay when substituted by 8-alkyl groups. For example, see Example 1 (16.3 nM) as compared to substitutions with 8-alkylamino groups (120 nM):

Example 1

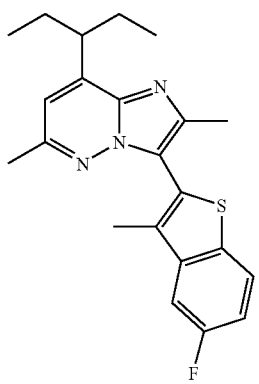

-continued

8-Alkylamino

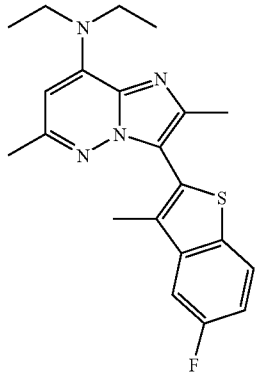

Example C

CRF2 Filter Binding Assay

The limitations of plasmid-based human CRF2 expression, in terms of generating a recombinant cell line with sufficient receptor density to develop a binding assay, are overcome by using a Phoenix retroviral expression system licensed from Stanford. The stable HEK-hCRF2 cell line is used to prepare membranes and binding reactions (200 A1) are set up as follows: 50 ul of $^{125}$I-sauvagine (0.2 nM final concentration), 50l compound and 100 μl CRF2 membrane (25 μg/reaction). The reactions are incubated at room temperature for 2 hours and then terminated by filtration through pre-treated FB Millipore glass fiber filter plates (96 well). The plates are washed twice with ice-cold assay buffer (50 mM tris, 12.5 mM NaCl, 1 mM EDTA, 10 mM MgCl$_2$, 0.05% BSA, pH 7.2), air dried over night and counted with 100 μl Microscint 40 in a Micro-Beta counter. Non-specific binding (NSB) is determined in the presence of 0.5 μM non-labeled sauvagine. Alternatively, compounds are evaluated using a Scintillation Proximity assay. This assay is set up as follows: 50 ul of $^{125}$I-Sauvagine (0.2 nM final concentration), 50 μl compound or non-labelled sauvagine (NSB) and 100 μl containing 250 μg wheat germ agglutinin (WGA) SPA beads and CRF2 membrane (1.5 μg/reaction). Plates are incubated for 4-5 hours at room temperature and then centrifuged at 200×g for 10 minutes. Bound radioactivity is assessed using a Wallac Trilux scintillation counter. Binding is assessed typically using triplicate determinations and the median data points plotted by Graph Pad Prism. Compounds are initially screened at a fixed concentration and, if sufficient activity is noted, subsequent concentration-response curves are generated.

Compounds of the present invention are tested in the CRF2 binding assay and exhibit weak affinity for the CRF2 receptor. For example, Example 88 exhibits a percent inhibition at 50 μM of 27±3. These results suggest that the compounds of the present invention are highly selective for the CRF1 receptor.

Example D

Bioavailability and Pharmacokinetic Properties

The compounds of Formula I are antagonists of CRF1, and possess surprisingly useful properties related to their pharmacokinetics and bioavailability The volume of distribution (Vdist) relates the amount of the drug in the body to the concentration of the drug in the blood or plasma. The volume of distribution refers to the fluid volume that would be required to contain the total amount of the drug in the body at the same concentration as in the blood or plasma: Vdist=amount of drug in the body/concentration of drug in blood or plasma (Goodman and Gillman's). For a 10 mg dose and a plasma concentration of 10 mg/L, the volume of distribution would be 1 liter. The volume of distribution reflects the extent to which the drug is present in the extravascular tissue. A large volume of distribution reflects the tendency of a compound to bind to the tissue components compared with plasma protein binding. In a clinical setting, Vdist can be used to determine a loading dose achieve a steady state concentration.

To test for volume of distribution, Male Sprague Dawley rats (N=3) are administered a single 3 mg/kg intravenous dose of compound. Multiple plasma samples are collected at time points from 0.08 to 24 hours post-dose. The plasma samples are analyzed by LC/MS/MS to determine the plasma concentrations. Plasma pharmacokinetic calculations are performed to determine the pharmacokinetic parameters including Vdist and plasma clearance (Clp).

An overwhelming majority of commercial CNS and cardiovascular drugs exhibit a human Vdist of <10 L/Kg. In comparison with CRF antagonists CP154526 (Schulz et al., *Proc. Natl. Acad. Sci. (USA)*, 93:10477 (1996)) and NBI30775 (Chen et al., *Drug Development Research*, 65:216 (2005)) which exhibit a rat Vdist of 114 L/Kg and 76 L/Kg, respectively, following a single intravenous dose, benzothiophene examples 1 and 2 of the present invention exhibits a rat Vdist of only 8 and 10 L/Kg, respectively. Similarly, indole examples 8 and 34 of the present invention exhibit a rat Vdist of only 17 and 15 L/kg, respectively.

Further, the plasma clearance (CLp) is a measure of the rate of removal of the drug from the body. Following an intravenous dose and first-order kinetics, the plasma clearance may be determined using the following equation: CLp=Dose/AUC, where AUC is the total area under the curve that describes the concentration of the drug in the plasma as a function of time from zero to infinity. The reference CRF antagonists CP154526 and NBI37582 exhibit rat clearance (CLp) of 83 and 306 mL/min/kg, respectively, following a single intravenous dose. Benzothiophene examples 1 and 2 of the present invention exhibit a rat CLp of only 9 and 12 mL/min/kg, respectively. Indole examples 8 and 34, of the present invention exhibit a rat CLp of only 29 and 14 mL/min/kg, respectively.

We claim:

1. A compound of formula I

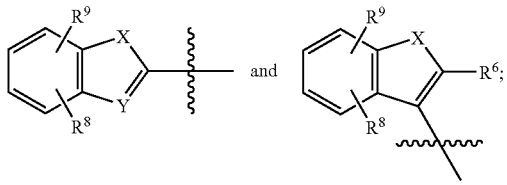

Formula I wherein:
R$^1$ and R$^3$ are independently methyl, trifluoromethyl, or methoxy;
R$^1$ is selected from the group consisting of:

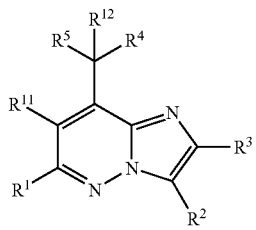

R$^4$ and R$^5$ are independently straight-chained (C$_2$-C$_4$)alkyl or straight-chained (C$_2$-C$_4$) alkenyl;
R$^6$ is methyl;
R$^8$ is hydrogen, halo, (C$_1$-C$_2$)alkoxy, (C$_1$-C$_5$)alkyl or (C$_3$) alkyl substituted with hydroxyl;
R$^9$ is hydrogen;
R$^{11}$ hydrogen;
R$^{12}$ is hydrogen, hydroxy, or halo;
X is —S— or —O—; and
Y is CR$^6$;
or pharmaceutically acceptable salts thereof.

2. The compound of claim 1 wherein R$^1$ and R$^3$ are methyl, R$^4$ and R$^5$ are ethyl, and R$^{11}$ and R$^{12}$ are hydrogen, or a pharmaceutically acceptable salt thereof.

3. The compound according to claim 2, wherein R$^2$ is selected from the group consisting of

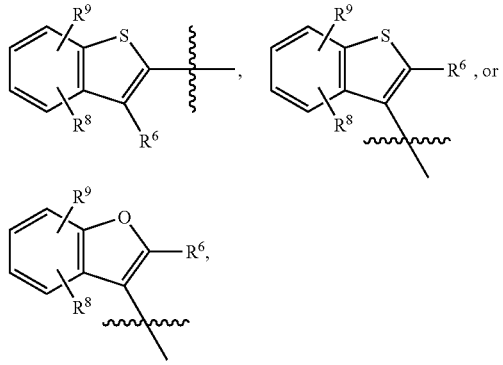

or a pharmaceutically acceptable salt thereof.

4. A compound according to claim 1 which is 2-{3-[8-(1-ethyl-propyl)-2,6-dimethyl-imidazo [1,2-b]pyridazin-3-yl]-2-methyl-benzofuran-7-yl}-propan-2-ol, or a pharmaceutically acceptable salt thereof.

5. A compound which is selected from the group consisting of
8-(1-ethyl-propyl)-2,6-dimethyl-3-[2-methyl-7-(1-methyl-cyclopropyl)-benzo[b]thiophen-3-yl]-imidazo[1,2-b]pyridazine,
8-(1-ethyl-propyl)-3-(7-isopropenyl-2-methyl-benzo[b]thiophen-3-yl]-2,6-dimethyl-imidazo[1,2-b]pyridazine,
8-(1-ethyl-propyl)-2,6-dimethyl-3-(2-methyl-7-vinyl-benzofuran-3-yl)-imidazo[1,2-b]pyridazine,
2-[8-(1-ethyl-propyl)-2,6-dimethyl-imidazo[1,2-b]pyridazin-3-yl]-3-methyl-benzo[b]thiophen-5-ol,
1-{3-[8-(1-ethyl-propyl)-2,6-dimethyl-imidazo[1,2-b]pyridazin-3-yl]-2-methyl-benzofuran-7-yl}-ethanol,
8-(1-ethyl-propyl)-3-[7-(1-methoxy-ethyl)-2-methyl-benzofuran-3-yl]-2,6-dimethyl-imidazo [1,2-b]pyridazine,
8-(1-ethyl-propyl)-3-[7-(1-methoxy-ethyl)-2-methyl-benzo [b]thiophen-3-yl]-2,6-dimethyl-imidazo[1,2-b]pyridazine,
8-(1-ethyl-propyl)-3-[7-(2-methoxy-1-methyl-ethyl)-2-methyl-benzo [b]thiophen-3-yl]-2,6-dimethyl-imidazo [1,2-b]pyridazine,
8-(1-ethyl-propyl)-3-(7-isopropenyl-2-methyl-benzofuran-3-yl)-2,6-dimethyl-imidazo[1,2-b]pyridazine,
1-{3-[8-(1-ethyl-propyl)-2,6-dimethyl-imidazo[1,2-b]pyridazin-3-yl]-2-methyl-benzofuran-7-yl}-ethanone,
1-{3-[8-(1-ethyl-propyl)-2,6-dimethyl-imidazo[1,2-b]pyridazin-3-yl]-2-methyl-benzo[b]thiophen-7-yl}-ethanone,
1-{3-[8-(1-ethyl-propyl)-2,6-dimethyl-imidazo[1,2-b]pyridazin-3-yl]-2-methyl-benzo[b]thiophen-6-yl}-ethanone,
3-[8-(1-ethyl-propyl)-2,6-dimethyl-imidazo[1,2-b]pyridazin-3-yl]-2-methyl-benzo[b]thiophen-7-carboxylic acid methyl ester, 3-[8-(1-ethyl-propyl)-2,6-dimethyl-imidazo[1,2-b]pyridazin-3-yl]-2-methyl-benzofuran-7-carboxylic acid methyl ester,
3-[8-(1-ethyl-propyl)-2,6-dimethyl-imidazo[1,2-b]pyridazin-3-yl]-2-methyl-benzo[b]thiophene-7-carboxylic acid methylamide,
3-[8-(1-ethyl-propyl)-2,6-dimethyl-imidazo[1,2-b]pyridazin-3-yl]-2-methyl-benzo [b]thiophene-7-carboxylic acid dimethylamide,
3-[8-(1-ethyl-propyl)-2,6-dimethyl-imidazo[1,2-b]pyridazin-3-yl]-2-methyl-benzofuran-7-carboxylic acid methylamide, and
3-[8-(1-ethyl-propyl)-2,6-dimethyl-imidazo[1,2-b]pyridazin-3-yl]-2-methyl-benzofuran-7-carboxylic acid methoxy-methyl-amide,
or a pharmaceutically acceptable salt thereof.

6. A pharmaceutical composition comprising a compound according to formula I, or a pharmaceutically acceptable salt thereof, and at least one pharmaceutically acceptable carrier, diluent or excipient, Formula I

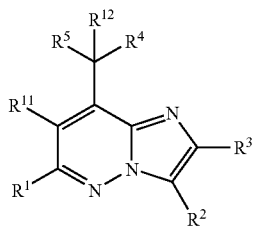

wherein:

$R^1$ and $R^3$ are independently methyl, trifluoromethyl, or methoxy;

$R^2$ is selected from the group consisting of:

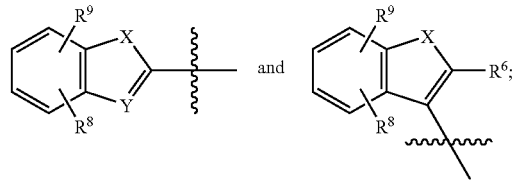

$R^4$ and $R^5$ are independently straight-chained ($C_2$-$C_4$alkyl or straight-chained ($C_2$-$C_4$) alkenyl;

$R^6$ is methyl;

$R^8$ is hydrogen, halo, ($C_1$-$C_2$)alkoxy, ($C_1$-$C_5$)alkyl or ($C_3$) alkyl substituted with hydroxyl;

$R^9$ is hydrogen;

$R^{11}$ is hydrogen;

$R^{12}$ is hydrogen, hydroxy, or halo;

X is —S— or —O—; and

Y is $CR^6$.

* * * * *